US008106253B2

(12) United States Patent
Davies et al.

(10) Patent No.: US 8,106,253 B2
(45) Date of Patent: Jan. 31, 2012

(54) GENERATION OF PLANTS WITH ALTERED PROTEIN, FIBER, OR OIL CONTENT

(75) Inventors: John P. Davies, Portland, OR (US); Hein Tsoeng (Medard) Ng, Charlottesville, VA (US); D. Ry Wagner, Pleasant Hill, OR (US)

(73) Assignee: Agrigenetics, Inc., Indianapolis, IN (US)

( * ) Notice: Subject to any disclaimer, the term of this patent is extended or adjusted under 35 U.S.C. 154(b) by 933 days.

(21) Appl. No.: 11/940,248

(22) Filed: Nov. 14, 2007

(65) Prior Publication Data

US 2008/0213457 A1 Sep. 4, 2008

Related U.S. Application Data

(60) Provisional application No. 60/866,053, filed on Nov. 15, 2006.

(51) Int. Cl.

*C12N 15/82* (2006.01)
*C12N 15/09* (2006.01)
*C12N 15/00* (2006.01)

(52) U.S. Cl. ..... 800/281; 800/278; 800/287; 435/320.1; 435/468; 536/23.1; 536/23.6

(58) Field of Classification Search ........................ None
See application file for complete search history.

(56) References Cited

U.S. PATENT DOCUMENTS

| | | | | |
|---|---|---|---|---|
| 5,322,783 | A | 6/1994 | Tomes et al. | |
| 5,538,880 | A | 7/1996 | Lundquist et al. | |
| 5,550,318 | A | 8/1996 | Adams et al. | |
| 5,563,055 | A | 10/1996 | Townsend et al. | |
| 5,610,042 | A | 3/1997 | Chang et al. | |
| 5,639,790 | A | 6/1997 | Voelker et al. | |
| 5,704,160 | A | 1/1998 | Bergquist et al. | |
| 5,952,544 | A | 9/1999 | Browse et al. | |
| 6,229,033 | B1 | 5/2001 | Knowlton | |
| 6,248,939 | B1 | 6/2001 | Leto et al. | |
| 6,750,046 | B2 * | 6/2004 | Moloney et al. | 435/69.7 |
| 7,566,816 | B2 * | 7/2009 | Lightner et al. | 800/298 |
| 2003/0046723 | A1 | 3/2003 | Heard et al. | |
| 2004/0019927 | A1 | 1/2004 | Sherman et al. | |
| 2004/0025202 | A1 | 2/2004 | Laurie et al. | |
| 2006/0048240 | A1 | 3/2006 | Alexandrov et al. | |
| 2006/0107345 | A1 * | 5/2006 | Alexandrov et al. | 800/278 |
| 2006/0150283 | A1 | 7/2006 | Alexandrov et al. | |
| 2006/0277630 | A1 | 12/2006 | Lightner et al. | |

FOREIGN PATENT DOCUMENTS

| | | |
|---|---|---|
| EP | 1033405 | 9/2000 |
| WO | 94/11516 | 5/1994 |
| WO | 95/06128 | 3/1995 |
| WO | WO9837755 * | 9/1998 |
| WO | WO 2004/035798 | 4/2004 |
| WO | 2004/093528 | 11/2004 |
| WO | WO 2004/093532 | 11/2004 |
| WO | 2005/047516 | 5/2005 |
| WO | 2005/107437 | 11/2005 |
| WO | 2007/053482 | 5/2007 |

OTHER PUBLICATIONS

Zou et al., "Modification of Seed Oil Content and Acyl Composition in the Brassicaceae by Expression of a Yeast *sn*-2 Acyltransferase Gene," *The Plant Cell*, 9:909-923 (1997).

Bateman et al., "Pfam 3.1: 1313 multiple alignments and profile HMMs match the majority of proteins," *Nucleic Acids Res.*, 27:260-262 (1999).

Bert et al., "Comparative genetic analysis of quantitative traits in sunflower (*Helianthus annuus* L.). 2. Characterisation of QTL involved in developmental and agronomic traits," *Theor. Appl. Genet.*, 107:181-9 (2003).

Browse et al., "Fluxes through the prokaryotic and eukaryotic pathways of lipid synthesis in the '16:3' plant *Arabidopsis thaliana*," *Biochem J.* 235:25-31 (1986).

Chapple and Carpita, "Plant cell walls as targets for biotechnology," *Current Opinion in Plant Biology*, 1:179-185 (1998).

Christensen et al., 9th *International Conference on Arabidopsis Research*, Univ. of Wisconsin-Madison, Jun. 24-28, Abstract 165 (1998).

Christou et al., "Inheritance and expression of foreign genes in transgenic soybean plants," *Proc. Natl. Acad. Sci. USA*, 86:7500-7504 (1989).

Colbert et al., "High-throughput screening for induced point mutations," *Plant Physiol.* 126:480-484 (2001).

De Block et al., "Transformation of *Brassica napus* and *Brassica oleracea* Using *Agrobacterium tumefaciens* and the Expression of the bar and neo Genes in the Transgenic Plants," *Plant Physiol.*, 91:694-701 (1989).

Douglas et al., "Nutritional evaluation of low phytate and high protein corns," *Poultry Sci.* 79:1586-1591 (2000).

Edwards et al., "Protein and energy evaluation of soybean meals processed from genetically modified high-protein soybeans," *Poultry Sci.* 79:525-527 (1999).

Everett et al., "Genetic engineering of sunflower (*Helianthus annuus L.*)," *Bio/Technology*, 5:1201 (1987).

Falco et al., "Transgenic canola and soybean seeds with increased lysine," *Bio/Technology*, 13:577-582 (1995).

Feldmann et al., "A Dwarf Mutant of *Arabidopsis* Generated by T-DNA Insertion Mutagenesis," *Science*, 243:1351-1354 (1989).

Focks and Benning, "wrinkled1: A novel, low-seed-oil mutant of *Arabidopsis* with a deficiency in the seed-specific regulation of carbohydrate metabolism," *Plant Physiol.*, 118:91-101 (1998).

Fridborg et al., "The *Arabidopsis* dwarf mutant *shi* exhibits reduced gibberellin responses conferred by overexpression of a new putative zinc finger protein," *Plant Cell*, 11:1019-1032 (1999).

Hayashi et al., "Activation of a plant gene by T-DNA tagging: auxin-independent growth in vitro," *Science*, 258:1350-1353 (1992).

(Continued)

*Primary Examiner* — Brent T Page

(74) *Attorney, Agent, or Firm* — Marcia J. Rosenfeld; Klarquist Sparkman LLP

(57) ABSTRACT

The present invention is directed to plants that display an improved oil quantity phenotype or an improved meal quality phenotype due to altered expression of an IMQ nucleic acid. The invention is further directed to methods of generating plants with an improved oil quantity phenotype or improved meal quality phenotype.

13 Claims, No Drawings

OTHER PUBLICATIONS

Honig and Rackis, "Determination of the total pepsin-pancreatin indigestible content (dietary fiber) of soybean products, wheat bran, and corn bran," *J. Agri. Food Chem.*, 27:1262-1266 (1979).
Jako et al., "Seed-specific over-expression of an *Arabidopsis* cDNA encoding a diacylglycerol acyltransferase enhances seed oil content and seed weight," *Plant Physiol.*, 126(2):861-74 (2001).
James and Dooner, "Isolation of EMS-induced mutants in *Arabidopsis* altered in seed fatty acid composition," *Theor. Appl. Genet.*, 80:241-245 (1990).
Kardailsky et al., "Activation tagging of the floral inducer FT," *Science*, 286:1962-1965 (1999).
Katavic et al., "Alteration of seed fatty acid composition by an ethyl methanesulfonate-induced mutation in *Arabidopsis thaliana* affecting diacylglycerol acyltransferase activity," *Plant Physiol.*, 108:399-409 (1995).
Klein et al., "High velocity microprojectiles for delivering nucleic acids into living cells," *Nature*, 327:70-73 (1987).
Lemieux et al., "Mutants of *Arabidopsis* with alterations in seed lipid fatty acid composition," *Theor. Appl. Genet.*, 80:234-240 (1990).
Lionneton et al., "Development of an AFLP-based linkage map and localization of QTLs for seed fatty acid content in condiment mustard (*Brassica juncea*)," *Genome*, 45:1203-15 (2002).
McCallum et al., "Targeted screening for induced mutations," *Nature Biotechnology*, 18:455-457 (2000).
Moore et al., "Chromatography of Amino Acids on Sulfonated Polystyrene Resins," *Anal. Chem.*, 30:1185-1190 (1958).
Mulder et al., "The InterPro Database, 2003 brings increased coverage and new features," *Nucleic Acids Res.*, 31:315-318, 2003.
Okuley et al., "*Arabidopsis FAD2* gene encodes the enzyme that is essential for polyunsaturated lipid synthesis," *Plant Cell*, 6:147-158 (1994).
Parsons et al., "Nutritional evaluation of soybean meals varying in oligosaccharide content," *Poultry Sci.*, 79:1127-1131 (2000).
Schaffer et al., "The late elongated hypocotyl mutation of *Arabidopsis* disrupts circadian rhythms and the photoperiodic control of flowering," *Cell*, 93:1219-1229 (1998).
Shewry, "Seed storage proteins: structures and biosynthesis," *Plant Cell*, 7:945-956 (1995).
Weigel et al., "Activation tagging in *Arabidopsis," Plant Physiology*, 122:1003-1013 (2000).
Wilson et al., "A Dissociation insertion causes a semidominant mutation that increases expression of TINY, an *Arabidopsis* gene related to APETALA2," *Plant Cell*, 8:659-671 (1996).
Yadav et al., "Cloning of higher plant omega-3 fatty acid desaturases," *Plant Physiol.*, 103:467-476 (1993).
Anoop et al., "Modulation of citrate metabolism alters aluminum tolerance in yeast and transgenic canola overexpressing a mitochondrial citrate synthase," *Plant Physiol.*, 132:2205-2217, 2003.
Beisson et al., "*Arabidopsis* genes involved in acyl lipid metabolism. A 2003 census of the candidates, a study of the distribution of expressed sequence tags in organs, and a web-based database," *Plant Physiol.*, 132:681-697, 2003.
Dehesh et al., "Overexpression of 3-ketoacyl-acyl-carrier protein synthase IIIs in plants reduces the rate of lipid synthesis," *Plant Physiol.*, 125:1103-1114, 2001.
Eastmond and Graham, "Re-examining the role of glyoxylate cycle in oilseeds," *Trends Plant Sci.*, 6(2):72-77, 2001.
Eccleston and Ohlrogge, "Expression of lauroyl-acyl carrier protein thioesterase in *brassica napus* seeds induces pathways for both fatty acid oxidation and biosynthesis and implies a set point for triacylglycerol accumulation," *Plant Cell.* 10:613-621, 1998.
Fatland et al., "Molecular biology of cytosolic acetyl-CoA generation," *Biochem. Soc. Trans.*, 28(6):593-595, 2000.
Fatland et al., "Reverse genetic characterization of cytosolic acetyl-CoA generation by ATP-citrate lyase in *Arabidopsis*," *Plant Cell*, 17:182-203, 2005.
Focks and Benning, "*wrinkled1*: A novel, low-seed-oil mutant of *Arabidopsis* with a deficiency in the seed-specific regulation of carbohydrate metabolism," *Plant Physiol.*, 118:91-101, 1998.
Girke et al., "Microarray analysis of developing *Arabidopsis* seeds," *Plant Physiol.*, 124:1570-1581, 2000.
Katavic et al., "Utility of the *Arabidopsis FAE1* and yeast *SLC1-1* genes for improvements in erucic acid and oil content in rapeseed," *Biochem Soc. Trans.*, 28(6):935-937, 2000.
Larson et al., "Acyl CoA profiles of transgenic plants that accumulate medium-chain fatty acids indicate inefficient storage lipid synthesis in developing oilseeds," *Plant J.*, 32:519-527, 2002.
Lin et al., "The Pex16p Homolog SSE1 and Storage Organelle Formation in *Arabidopsis* Seeds," *Science*, 284:328-330, 1999.
Liu and Butow, "A transcriptional switch in the expression of yeast tricarboxylic acid cycle genes in response to a reduction or loss of respiratory function," *Mol. Cell. Biol.*, 19:6720-6728, 1999.
Mekhedov et al., "Toward a Functional Catalog of the Plant Genome. A Survey of Genes for Lipid Biosynthesis," *Plant Physiology*, 122:389-401, 2000.
Moire et al., "Impact of Unusual Fatty Acid Synthesis on Futile Cycling through β-Oxidation and on Gene Expression in Transgenic Plants," *Plant Physiology*, 134:432-442, 2004.
Neuhaus et al., "Nonphotosynthetic Metabolism in Plastids," *Annu. Rev. Plant Physiol. Plant Mol.*, 51:111-140, 2000.
O'Hara et al., "Fatty Acid and Lipid Biosynthetic Genes Are Expressed at Constant Molar Ratios But Different Absolute Levels during Embryogenesis," *Plant Physiology*, 129:310-320, 2002.
Pritchard et al., "Germination and storage reserve mobilization are regulated independently in *Arabidopsis*," *The Plant Journal*, 31(5):639-647, 2002.
Rangasamy and Ratledge, "Genetic enhancement of fatty acid synthesis by targeting rat liver ATP:citrate lyase into plastids of tobacco," *Plant Physiol.*, 122:1231-1238, 2000.
Rangasamy et al., "Compartmentation of ATP:Citrate Lyase in Plants," *Plant Physiology*, 122:1225-1230, 2000.
Ratledge et al., "Correlation of ATP/Citrate Lyase Activity with Lipid Accumulation in Developing Seeds of *Brassica napus* L.," Lipids, 32(1):7-12, 1997.
Rawsthorne, Stephen, "Carbon flux and fatty acid synthesis in plants," *Progress in Lipid Research*, 41:182-196 (2002).
Ruuska et al., "Contrapuntal Networks of Gene Expression during *Arabidopsis* Seed Filling," *The Plant Cell*, 14:1191-1206, 2002.
Rylott et al., "Co-ordinate regulation of genes involved in storage lipid mobilization in *Arabidopsis thaliana," Biochem Soc. Trans.*, 29:283-287, 2001.
Schnarrenberger and Martin, "Evolution of the enzymes of the citric acid cycle and the glyoxylate cycle of higher plants, A case study of endosymbiotic gene transfer," *Eur. J. Biochem.*, 269:868-883, 2002.
Schnurr et al., "Characterization of an acyl-CoA synthetase from *Arabidopsis thaliana," Biochem Soc.Trans.*, 28(6):957-958, 2000.
Shockey et al., "Characterization of the AMP-binding protein gene family in *Arabidopsis thaliana*: will the real acyl-CoA synthetases please stand up?" *Biochem Soc. Trans.*, 28(6):955-957, 2000.
Thelen et al., "Biotin carboxyl carrier protein isoforms in Brassicaceae oilseeds," *Biochem. Soc. Trans.*, 28(6):595-598, 2000.
White et al., "A new set of *Arabidopsis* expressed sequence tags from developing seeds. The metabolic pathway from carbohydrates to seed oil," *Plant Physiol.*, 124:1582-1594, 2000.

* cited by examiner

SEQUENCE LISTING

<160> NUMBER OF SEQ ID NOS: 100

<210> SEQ ID NO 1
<211> LENGTH: 2888
<212> TYPE: DNA
<213> ORGANISM: Arabidopsis thaliana

<400> SEQUENCE: 1

```
agtgtccctc tcgcaccatt taatttcatt gcaccctctc aattctctct gtcattactc     60
tctcatctct cttcctccaa gatttgcacc tacctttcaa accttttgct cgccaacaaa    120
accgcgcttc acaaaaccat cagcggtttt ccgagaaaca aatctcagac cagacaccgc    180
tctactcttc tctctctctc cctctagggt ttcgtcgctt cttcctatat cccagttcag    240
agatgaaacc ttcaagaaaa caataaagag gaaagattaa agggtttgct ttcagtttcc    300
ggagtataag aaaagatgtt cgagccaaat atgctgcttg cggctatgaa caacgcagac    360
agcaataacc acaactacaa ccatgaagac aacaataatg aaggatttct tcgggacgat    420
gaattcgaca gtccgaatac taaatcggga agtgagaatc aagaaggagg atcaggaaac    480
gaccaagatc ctcttcatcc taacaagaag aaacgatatc atcgacacac ccaacttcag    540
atccaggaga tggaagcgtt cttcaaagag tgtcctcacc cagatgacaa gcaaaggaaa    600
cagctaagcc gtgaattgaa tttggaacct cttcaggtca aattctggtt ccaaaacaaa    660
cgtacccaaa tgaagaatca tcacgagcgg catgagaact cacatcttcg ggcggagaac    720
gaaaagcttc gaaacgacaa cctaagatat cgagaggctc ttgcaaatgc ttcgtgtcct    780
aattgtggtg gtccaacagc tatcggagaa atgtcattcg acgaacacca actccgtctc    840
gaaaatgctc gattaaggga agagatcgac cgtatatccg caatcgcagc taaatacgta    900
ggcaagccag tctcaaacta tccacttatg tctcctcctc ctcttcctcc acgtccacta    960
gaactcgcca tgggaaatat tggaggagaa gcttatggaa acaatccaaa cgatctcctt   1020
aagtccatca ctgcaccaac agaatctgac aaacctgtca tcatcgactt atccgtggct   1080
gcaatggaag agctcatgag gatggttcaa gtagacgagc ctctgtggaa gagtttggtt   1140
ttagacgaag aagaatatgc aaggaccttt cctagaggga tcggacctag accggctgga   1200
tatagatcag aagcttcgcg agaaagcgcg gttgtgatca tgaatcatgt taacatcgtt   1260
gagattctca tggatgtgaa tcaatggtcg acgattttcg cggggatggt ttctagagca   1320
atgacattag cggttttatc gacaggagtt gcaggaaact ataatggagc tcttcaagtg   1380
atgagtgcag agtttcaagt tccatctcca ttagtcccaa cacgtgaaac ctatttcgca   1440
cgttactgta aacaacaagg agatggttcg tgggcggttg tcgatatttc gttggatagt   1500
ctccaaccaa atcccccggc tagatgcagg cggcgagctt caggatgttt gattcaagaa   1560
ttgccaaatg gatattctaa ggtgacttgg gtggagcatg tggaagttga tgacagagga   1620
gttcataact tatacaaaca catggttagt actggtcatg cctttggtgc taaacgctgg   1680
gtagccattc ttgaccgcca atgcgagcgg ttagctagtg tcatggctac aaacatttcc   1740
tctggagaag ttggcgtgat aaccaaccaa gaagggagga ggagtatgct gaaattggca   1800
gagcggatgg ttataagctt ttgtgcagga gtgagtgctt caaccgctca cacgtggact   1860
acattgtccg gtacaggagc tgaagatgtt agagtgatga ctaggaagag tgtggatgat   1920
ccaggaaggc ctcctggtat tgttcttagt gcagccactt ctttttggat ccctgttcct   1980
ccaaagcgag tctttgactt cctcagagac gagaattcaa gaaatgagtg ggatattctg   2040
```

```
tctaatggag gagttgtgca agaaatggca catattgcta acgggaggga taccggaaac   2100

tgtgtttctc ttcttcgggt aaatagtgca aactctagcc agagcaatat gctgatccta   2160

caagagagct gcactgatcc tacagcttcc tttgtgatct atgctccagt cgatattgta   2220

gctatgaaca tagtgcttaa tggaggtgat ccagactatg tggctctgct tccatcaggt   2280

tttgctattc ttcctgatgg taatgccaat agtggagccc ctggaggaga tggagggtcg   2340

ctcttgactg ttgcttttca gattctggtt gactcagttc ctacggctaa gctgtctctt   2400

ggctctgttg caactgtcaa caatctaata gcttgcactg ttgagagaat caaagcttca   2460

atgtcttgtg agactgcttg aaaaccatcc attaggaaat aacaaaatgg tgatgatgga   2520

aaaaagagag agatttcagt ttgagaaaag cggaggagtc aagatcgaac ctcacaagag   2580

aataccattg agtgtttgtt agtgttaagt tttggtctgc ttatttgatg aaactaagca   2640

gtgaaaaact ttttacttga aagtgaatat gtagatggtt ttacgaggtt cgggaatttg   2700

acttcccctg tcacatactg aattagacaa aaacaaaaac taggttagaa agaatgcttt   2760

cggatttctt tttgtgttac agttactgtt tttctttcct tcttgtggtt agatggacca   2820

tcatcaggaa tttggagttt gtctttcttt tgtataaata tcttatacaa gtattttggt   2880

acttttgt                                                            2888
```

```
<210> SEQ ID NO 2
<211> LENGTH: 721
<212> TYPE: PRT
<213> ORGANISM: Arabidopsis thaliana

<400> SEQUENCE: 2

Met Phe Glu Pro Asn Met Leu Leu Ala Ala Met Asn Asn Ala Asp Ser
1               5                   10                  15

Asn Asn His Asn Tyr Asn His Glu Asp Asn Asn Asn Glu Gly Phe Leu
            20                  25                  30

Arg Asp Asp Glu Phe Asp Ser Pro Asn Thr Lys Ser Gly Ser Glu Asn
        35                  40                  45

Gln Glu Gly Gly Ser Gly Asn Asp Gln Asp Pro Leu His Pro Asn Lys
    50                  55                  60

Lys Lys Arg Tyr His Arg His Thr Gln Leu Gln Ile Gln Glu Met Glu
65                  70                  75                  80

Ala Phe Phe Lys Glu Cys Pro His Pro Asp Asp Lys Gln Arg Lys Gln
                85                  90                  95

Leu Ser Arg Glu Leu Asn Leu Glu Pro Leu Gln Val Lys Phe Trp Phe
            100                 105                 110

Gln Asn Lys Arg Thr Gln Met Lys Asn His His Glu Arg His Glu Asn
        115                 120                 125

Ser His Leu Arg Ala Glu Asn Glu Lys Leu Arg Asn Asp Asn Leu Arg
    130                 135                 140

Tyr Arg Glu Ala Leu Ala Asn Ala Ser Cys Pro Asn Cys Gly Gly Pro
145                 150                 155                 160

Thr Ala Ile Gly Glu Met Ser Phe Asp Glu His Gln Leu Arg Leu Glu
                165                 170                 175

Asn Ala Arg Leu Arg Glu Glu Ile Asp Arg Ile Ser Ala Ile Ala Ala
            180                 185                 190

Lys Tyr Val Gly Lys Pro Val Ser Asn Tyr Pro Leu Met Ser Pro Pro
        195                 200                 205

Pro Leu Pro Pro Arg Pro Leu Glu Leu Ala Met Gly Asn Ile Gly Gly
    210                 215                 220
```

```
Glu Ala Tyr Gly Asn Asn Pro Asn Asp Leu Leu Lys Ser Ile Thr Ala
225                 230                 235                 240

Pro Thr Glu Ser Asp Lys Pro Val Ile Ile Asp Leu Ser Val Ala Ala
                245                 250                 255

Met Glu Glu Leu Met Arg Met Val Gln Val Asp Glu Pro Leu Trp Lys
            260                 265                 270

Ser Leu Val Leu Asp Glu Glu Glu Tyr Ala Arg Thr Phe Pro Arg Gly
        275                 280                 285

Ile Gly Pro Arg Pro Ala Gly Tyr Arg Ser Glu Ala Ser Arg Glu Ser
    290                 295                 300

Ala Val Val Ile Met Asn His Val Asn Ile Val Glu Ile Leu Met Asp
305                 310                 315                 320

Val Asn Gln Trp Ser Thr Ile Phe Ala Gly Met Val Ser Arg Ala Met
                325                 330                 335

Thr Leu Ala Val Leu Ser Thr Gly Val Ala Gly Asn Tyr Asn Gly Ala
            340                 345                 350

Leu Gln Val Met Ser Ala Glu Phe Gln Val Pro Ser Pro Leu Val Pro
        355                 360                 365

Thr Arg Glu Thr Tyr Phe Ala Arg Tyr Cys Lys Gln Gln Gly Asp Gly
    370                 375                 380

Ser Trp Ala Val Val Asp Ile Ser Leu Asp Ser Leu Gln Pro Asn Pro
385                 390                 395                 400

Pro Ala Arg Cys Arg Arg Arg Ala Ser Gly Cys Leu Ile Gln Glu Leu
                405                 410                 415

Pro Asn Gly Tyr Ser Lys Val Thr Trp Val Glu His Val Glu Val Asp
            420                 425                 430

Asp Arg Gly Val His Asn Leu Tyr Lys His Met Val Ser Thr Gly His
        435                 440                 445

Ala Phe Gly Ala Lys Arg Trp Val Ala Ile Leu Asp Arg Gln Cys Glu
    450                 455                 460

Arg Leu Ala Ser Val Met Ala Thr Asn Ile Ser Ser Gly Glu Val Gly
465                 470                 475                 480

Val Ile Thr Asn Gln Glu Gly Arg Arg Ser Met Leu Lys Leu Ala Glu
                485                 490                 495

Arg Met Val Ile Ser Phe Cys Ala Gly Val Ser Ala Ser Thr Ala His
            500                 505                 510

Thr Trp Thr Thr Leu Ser Gly Thr Gly Ala Glu Asp Val Arg Val Met
        515                 520                 525

Thr Arg Lys Ser Val Asp Asp Pro Gly Arg Pro Pro Gly Ile Val Leu
    530                 535                 540

Ser Ala Ala Thr Ser Phe Trp Ile Pro Val Pro Pro Lys Arg Val Phe
545                 550                 555                 560

Asp Phe Leu Arg Asp Glu Asn Ser Arg Asn Glu Trp Asp Ile Leu Ser
                565                 570                 575

Asn Gly Gly Val Val Gln Glu Met Ala His Ile Ala Asn Gly Arg Asp
            580                 585                 590

Thr Gly Asn Cys Val Ser Leu Leu Arg Val Asn Ser Ala Asn Ser Ser
        595                 600                 605

Gln Ser Asn Met Leu Ile Leu Gln Glu Ser Cys Thr Asp Pro Thr Ala
    610                 615                 620

Ser Phe Val Ile Tyr Ala Pro Val Asp Ile Val Ala Met Asn Ile Val
625                 630                 635                 640

Leu Asn Gly Gly Asp Pro Asp Tyr Val Ala Leu Leu Pro Ser Gly Phe
                645                 650                 655
```

```
Ala Ile Leu Pro Asp Gly Asn Ala Asn Ser Gly Ala Pro Gly Gly Asp
            660                 665                 670

Gly Gly Ser Leu Leu Thr Val Ala Phe Gln Ile Leu Val Asp Ser Val
        675                 680                 685

Pro Thr Ala Lys Leu Ser Leu Gly Ser Val Ala Thr Val Asn Asn Leu
    690                 695                 700

Ile Ala Cys Thr Val Glu Arg Ile Lys Ala Ser Met Ser Cys Glu Thr
705                 710                 715                 720

Ala


<210> SEQ ID NO 3
<211> LENGTH: 2679
<212> TYPE: DNA
<213> ORGANISM: Arabidopsis thaliana

<400> SEQUENCE: 3

gtatgatctt caagaagaaa gataaacgac tccgaagaaa gatttaagtt attgttgttc     60

atacaaaaag aagggtttgc tttcagtttc cggagtataa gaaaagatgt tcgagccaaa    120

tatgctgctt gcggctatga acaacgcaga cagcaataac cacaactaca accatgaaga    180

caacaataat gaaggatttc ttcgggacga tgaattcgac agtccgaata ctaaatcggg    240

aagtgagaat caagaaggag gatcaggaaa cgaccaagat cctcttcatc ctaacaagaa    300

gaaacgatat catcgacaca cccaacttca gatccaggag atggaagcgt tcttcaaaga    360

gtgtcctcac ccagatgaca agcaaaggaa acagctaagc cgtgaattga atttggaacc    420

tcttcaggtc aaattctggt tccaaaacaa acgtacccaa atgaagaatc atcacgagcg    480

gcatgagaac tcacatcttc gggcggagaa cgaaaagctt cgaaacgaca acctaagata    540

tcgagaggct cttgcaaatg cttcgtgtcc taattgtggt ggtccaacag ctatcggaga    600

aatgtcattc gacgaacacc aactccgtct cgaaaatgct cgattaaggg aagagatcga    660

ccgtatatcc gcaatcgcag ctaaatacgt aggcaagcca gtctcaaact atccacttat    720

gtctcctcct cctcttcctc cacgtccact agaactcgcc atgggaaata ttggaggaga    780

agcttatgga aacaatccaa acgatctcct taagtccatc actgcaccaa cagaatctga    840

caaacctgtc atcatcgact tatccgtggc tgcaatggaa gagctcatga ggatggttca    900

agtagacgag cctctgtgga agagtttggt tttagacgaa gaagaatatg caaggacctt    960

tcctagaggg atcggaccta gaccggctgg atatagatca gaagcttcgc gagaaagcgc   1020

ggttgtgatc atgaatcatg ttaacatcgt tgagattctc atggatgtga atcaatggtc   1080

gacgattttc gcggggatgg tttctagagc aatgacatta gcggttttat cgacaggagt   1140

tgcaggaaac tataatggag ctcttcaagt gatgagtgca gagtttcaag ttccatctcc   1200

attagtccca acacgtgaaa cctatttcgc acgttactgt aaacaacaag gagatggttc   1260

gtgggcggtt gtcgatattt cgttggatag tctccaacca aatcccccgg ctagatgcag   1320

gcggcgagct tcaggatgtt tgattcaaga attgccaaat ggatattcta aggtgacttg   1380

ggtggagcat gtggaagttg atgacagagg agttcataac ttatacaaac acatggttag   1440

tactggtcat gcctttggtg ctaaacgctg ggtagccatt cttgaccgcc aatgcgagcg   1500

gttagctagt gtcatggcta caaacatttc ctctggagaa gttggcgtga taaccaacca   1560

agaagggagg aggagtatgc tgaaattggc agagcggatg gttataagct tttgtgcagg   1620

agtgagtgct tcaaccgctc acacgtggac tacattgtcc ggtacaggag ctgaagatgt   1680

tagagtgatg actaggaaga gtgtggatga tccaggaagg cctcctggta ttgttcttag   1740
```

```
tgcagccact tctttttgga tccctgttcc tccaaagcga gtctttgact tcctcagaga   1800

cgagaattca agaaatgagt gggatattct gtctaatgga ggagttgtgc aagaaatggc   1860

acatattgct aacgggaggg ataccggaaa ctgtgtttct cttcttcggg taaatagtgc   1920

aaactctagc cagagcaata tgctgatcct acaagagagc tgcactgatc ctacagcttc   1980

ctttgtgatc tatgctccag tcgatattgt agctatgaac atagtgctta atggaggtga   2040

tccagactat gtggctctgc ttccatcagg ttttgctatt cttcctgatg gtaatgccaa   2100

tagtggagcc cctggaggag atggagggtc gctcttgact gttgcttttc agattctggt   2160

tgactcagtt cctacggcta agctgtctct tggctctgtt gcaactgtca acaatctaat   2220

agcttgcact gttgagagaa tcaaagcttc aatgtcttgt gagactgctt gaaaaccatc   2280

cattaggaaa taacaaaatg gtgatgatgg aaaaaagaga gagatttcag tttgagaaaa   2340

gcggaggagt caagatcgaa cctcacaaga gaataccatt gagtgtttgt tagtgttaag   2400

ttttggtctg cttatttgat gaaactaagc agtgaaaaac tttttacttg aaagtgaata   2460

tgtagatggt tttacgaggt tcgggaattt gacttcccct gtcacatact gaattagaca   2520

aaaacaaaaa ctaggttaga aagaatgctt tcggatttct ttttgtgtta cagttactgt   2580

ttttctttcc ttcttgtggt tagatggacc atcatcagga atttggagtt tgtctttctt   2640

ttgtataaat atcttataca agtattttgg tacttttgt                          2679
```

<210> SEQ ID NO 4
<211> LENGTH: 721
<212> TYPE: PRT
<213> ORGANISM: Arabidopsis thaliana

<400> SEQUENCE: 4

```
Met Phe Glu Pro Asn Met Leu Leu Ala Ala Met Asn Asn Ala Asp Ser
1               5                   10                  15

Asn Asn His Asn Tyr Asn His Glu Asp Asn Asn Asn Glu Gly Phe Leu
            20                  25                  30

Arg Asp Asp Glu Phe Asp Ser Pro Asn Thr Lys Ser Gly Ser Glu Asn
        35                  40                  45

Gln Glu Gly Gly Ser Gly Asn Asp Gln Asp Pro Leu His Pro Asn Lys
    50                  55                  60

Lys Lys Arg Tyr His Arg His Thr Gln Leu Gln Ile Gln Glu Met Glu
65                  70                  75                  80

Ala Phe Phe Lys Glu Cys Pro His Pro Asp Asp Lys Gln Arg Lys Gln
                85                  90                  95

Leu Ser Arg Glu Leu Asn Leu Glu Pro Leu Gln Val Lys Phe Trp Phe
            100                 105                 110

Gln Asn Lys Arg Thr Gln Met Lys Asn His His Glu Arg His Glu Asn
        115                 120                 125

Ser His Leu Arg Ala Glu Asn Glu Lys Leu Arg Asn Asp Asn Leu Arg
    130                 135                 140

Tyr Arg Glu Ala Leu Ala Asn Ala Ser Cys Pro Asn Cys Gly Gly Pro
145                 150                 155                 160

Thr Ala Ile Gly Glu Met Ser Phe Asp Glu His Gln Leu Arg Leu Glu
                165                 170                 175

Asn Ala Arg Leu Arg Glu Glu Ile Asp Arg Ile Ser Ala Ile Ala Ala
            180                 185                 190

Lys Tyr Val Gly Lys Pro Val Ser Asn Tyr Pro Leu Met Ser Pro Pro
        195                 200                 205
```

```
Pro Leu Pro Pro Arg Pro Leu Glu Leu Ala Met Gly Asn Ile Gly Gly
    210                 215                 220

Glu Ala Tyr Gly Asn Asn Pro Asn Asp Leu Leu Lys Ser Ile Thr Ala
225                 230                 235                 240

Pro Thr Glu Ser Asp Lys Pro Val Ile Ile Asp Leu Ser Val Ala Ala
                245                 250                 255

Met Glu Glu Leu Met Arg Met Val Gln Val Asp Glu Pro Leu Trp Lys
            260                 265                 270

Ser Leu Val Leu Asp Glu Glu Glu Tyr Ala Arg Thr Phe Pro Arg Gly
        275                 280                 285

Ile Gly Pro Arg Pro Ala Gly Tyr Arg Ser Glu Ala Ser Arg Glu Ser
    290                 295                 300

Ala Val Val Ile Met Asn His Val Asn Ile Val Glu Ile Leu Met Asp
305                 310                 315                 320

Val Asn Gln Trp Ser Thr Ile Phe Ala Gly Met Val Ser Arg Ala Met
                325                 330                 335

Thr Leu Ala Val Leu Ser Thr Gly Val Ala Gly Asn Tyr Asn Gly Ala
            340                 345                 350

Leu Gln Val Met Ser Ala Glu Phe Gln Val Pro Ser Pro Leu Val Pro
        355                 360                 365

Thr Arg Glu Thr Tyr Phe Ala Arg Tyr Cys Lys Gln Gln Gly Asp Gly
    370                 375                 380

Ser Trp Ala Val Val Asp Ile Ser Leu Asp Ser Leu Gln Pro Asn Pro
385                 390                 395                 400

Pro Ala Arg Cys Arg Arg Arg Ala Ser Gly Cys Leu Ile Gln Glu Leu
                405                 410                 415

Pro Asn Gly Tyr Ser Lys Val Thr Trp Val Glu His Val Glu Val Asp
            420                 425                 430

Asp Arg Gly Val His Asn Leu Tyr Lys His Met Val Ser Thr Gly His
        435                 440                 445

Ala Phe Gly Ala Lys Arg Trp Val Ala Ile Leu Asp Arg Gln Cys Glu
    450                 455                 460

Arg Leu Ala Ser Val Met Ala Thr Asn Ile Ser Ser Gly Glu Val Gly
465                 470                 475                 480

Val Ile Thr Asn Gln Glu Gly Arg Arg Ser Met Leu Lys Leu Ala Glu
                485                 490                 495

Arg Met Val Ile Ser Phe Cys Ala Gly Val Ser Ala Ser Thr Ala His
            500                 505                 510

Thr Trp Thr Thr Leu Ser Gly Thr Gly Ala Glu Asp Val Arg Val Met
        515                 520                 525

Thr Arg Lys Ser Val Asp Asp Pro Gly Arg Pro Pro Gly Ile Val Leu
    530                 535                 540

Ser Ala Ala Thr Ser Phe Trp Ile Pro Val Pro Pro Lys Arg Val Phe
545                 550                 555                 560

Asp Phe Leu Arg Asp Glu Asn Ser Arg Asn Glu Trp Asp Ile Leu Ser
                565                 570                 575

Asn Gly Gly Val Val Gln Glu Met Ala His Ile Ala Asn Gly Arg Asp
            580                 585                 590

Thr Gly Asn Cys Val Ser Leu Leu Arg Val Asn Ser Ala Asn Ser Ser
        595                 600                 605

Gln Ser Asn Met Leu Ile Leu Gln Glu Ser Cys Thr Asp Pro Thr Ala
    610                 615                 620

Ser Phe Val Ile Tyr Ala Pro Val Asp Ile Val Ala Met Asn Ile Val
625                 630                 635                 640
```

```
Leu Asn Gly Gly Asp Pro Asp Tyr Val Ala Leu Leu Pro Ser Gly Phe
                645                 650                 655

Ala Ile Leu Pro Asp Gly Asn Ala Asn Ser Gly Ala Pro Gly Gly Asp
            660                 665                 670

Gly Gly Ser Leu Leu Thr Val Ala Phe Gln Ile Leu Val Asp Ser Val
        675                 680                 685

Pro Thr Ala Lys Leu Ser Leu Gly Ser Val Ala Thr Val Asn Asn Leu
    690                 695                 700

Ile Ala Cys Thr Val Glu Arg Ile Lys Ala Ser Met Ser Cys Glu Thr
705                 710                 715                 720

Ala


<210> SEQ ID NO 5
<211> LENGTH: 1258
<212> TYPE: DNA
<213> ORGANISM: Arabidopsis thaliana

<400> SEQUENCE: 5

atctccaaag ctcgttctca ccttacttgg caaacactca acgaagaaag gagagagaga      60

cggtaatggc gatcaagaac attctcgccc ttgtggttct tcttagcgtg gttggagttt     120

ctgtcgccat tccacagttg cttgacctcg actactaccg gtctaagtgt cccaaggcag     180

aggaaattgt tcgtggtgtc acagtacaat atgtttctcg ccagaaaacc cttgccgcta     240

aacttctaag gatgcatttc catgattgtt tcgtcagagg atgtgatggt tccgttcttc     300

tgaaatctgc aaagaatgat gcggaaagag acgctgtccc caacctgacc ctgaaaggtt     360

atgaagtggt ggatgcggcc aagacagcgc tggagaggaa gtgtcctaat ctcatttctt     420

gcgctgatgt tcttgccttg gtcgccagag atgccgtggc agtgatcggg ggaccatggt     480

ggccggttcc attgggccgc agggatggac gcatctcgaa attgaacgat gcattgctaa     540

atttaccatc tcctttcgcc gacataaaga cgctgaagaa gaactttgcc aacaagggtc     600

ttaacgctaa agaccttgtg gttctctcag gggtcacac cattggaatc tctagttgcg      660

ctctcgtcaa cagtcgtctc tacaacttca caggaaaggg cgattctgac ccatccatga     720

accctagcta cgtgagggaa ttgaagagaa agtgcccgcc tacagatttc agaacctcac     780

tgaacatgga cccaggcagt gcgttgacat tcgacactca ctacttcaag gtcgtggctc     840

agaagaaagg gctcttcaca tctgactcta cgcttctcga tgacattgag accaaaaact     900

acgttcagac tcaggccatt ctccctcctg tgtttcttc tttcaataaa gatttctccg      960

attccatggt caaacttggt ttcgtccaaa ttcttaccgg caaaaatggt gagatcagga    1020

agagatgcgc cttccctaac taatttggat cgatcagacc gggtttcgga tgattttgag    1080

tctacacgtt tttctctgct tattttcttt ctttttcttt tttctttcac ggaagtttga    1140

gctttggtgt tgtcttcttc tgtttcttcc atgaataatt gttttttgtt gagtaacttt    1200

acatttgtat tctttacggt gactgtgttt tgtaatggaa aaagtttgtt tcgaattc      1258


<210> SEQ ID NO 6
<211> LENGTH: 325
<212> TYPE: PRT
<213> ORGANISM: Arabidopsis thaliana

<400> SEQUENCE: 6

Met Ala Ile Lys Asn Ile Leu Ala Leu Val Val Leu Leu Ser Val Val
1               5                   10                  15

Gly Val Ser Val Ala Ile Pro Gln Leu Leu Asp Leu Asp Tyr Tyr Arg
```

```
            20                  25                  30

Ser Lys Cys Pro Lys Ala Glu Glu Ile Val Arg Gly Val Thr Val Gln
        35                  40                  45

Tyr Val Ser Arg Gln Lys Thr Leu Ala Ala Lys Leu Leu Arg Met His
    50                  55                  60

Phe His Asp Cys Phe Val Arg Gly Cys Asp Gly Ser Val Leu Leu Lys
65                  70                  75                  80

Ser Ala Lys Asn Asp Ala Glu Arg Asp Ala Val Pro Asn Leu Thr Leu
                85                  90                  95

Lys Gly Tyr Glu Val Val Asp Ala Ala Lys Thr Ala Leu Glu Arg Lys
            100                 105                 110

Cys Pro Asn Leu Ile Ser Cys Ala Asp Val Leu Ala Leu Val Ala Arg
        115                 120                 125

Asp Ala Val Ala Val Ile Gly Gly Pro Trp Trp Pro Val Pro Leu Gly
    130                 135                 140

Arg Arg Asp Gly Arg Ile Ser Lys Leu Asn Asp Ala Leu Leu Asn Leu
145                 150                 155                 160

Pro Ser Pro Phe Ala Asp Ile Lys Thr Leu Lys Lys Asn Phe Ala Asn
                165                 170                 175

Lys Gly Leu Asn Ala Lys Asp Leu Val Val Leu Ser Gly Gly His Thr
            180                 185                 190

Ile Gly Ile Ser Ser Cys Ala Leu Val Asn Ser Arg Leu Tyr Asn Phe
        195                 200                 205

Thr Gly Lys Gly Asp Ser Asp Pro Ser Met Asn Pro Ser Tyr Val Arg
    210                 215                 220

Glu Leu Lys Arg Lys Cys Pro Pro Thr Asp Phe Arg Thr Ser Leu Asn
225                 230                 235                 240

Met Asp Pro Gly Ser Ala Leu Thr Phe Asp Thr His Tyr Phe Lys Val
                245                 250                 255

Val Ala Gln Lys Lys Gly Leu Phe Thr Ser Asp Ser Thr Leu Leu Asp
            260                 265                 270

Asp Ile Glu Thr Lys Asn Tyr Val Gln Thr Gln Ala Ile Leu Pro Pro
        275                 280                 285

Val Phe Ser Ser Phe Asn Lys Asp Phe Ser Asp Ser Met Val Lys Leu
    290                 295                 300

Gly Phe Val Gln Ile Leu Thr Gly Lys Asn Gly Glu Ile Arg Lys Arg
305                 310                 315                 320

Cys Ala Phe Pro Asn
                325
```

<210> SEQ ID NO 7
<211> LENGTH: 1346
<212> TYPE: DNA
<213> ORGANISM: Arabidopsis thaliana

<400> SEQUENCE: 7

```
ccttacttgg caaacactca acgaagaaag gagagagaga cggtaatggc gatcaagaac      60

attctcgccc ttgtggttct tcttagcgtg gttggagttt ctgtcgccat tccacagttg     120

cttgacctcg actactaccg gtctaagtgt cccaaggcag aggaaattgt tcgtggtgtc     180

acagtacaat atgtttctcg ccagaaaacc cttgccgcta aacttctaag gatgcatttc     240

catgattgtt tcgtcagagg atgtgatggt tccgttcttc tgaaatctgc aaagaatgat     300

gcggaaagag acgctgtccc caacctgacc ctgaaaggtt atgaagtggt ggatgcggcc     360

aagacagcgc tggagaggaa gtgtcctaat ctcatttctt gcgctgatgt tcttgccttg     420
```

```
gtcgccagag atgccgtggc agtgatcggg ggaccatggt ggccggttcc attgggccgc    480
agggatggac gcatctcgaa attgaacgat gcattgctaa atttaccatc tcctttcgcc    540
gacataaaga cgctgaagaa gaactttgcc aacaagggtc ttaacgctaa agaccttgtg    600
gttctctcag gggtcacac cattggaatc tctagttgcg ctctcgtcaa cagtcgtctc    660
tacaacttca caggaaaggg cgattctgac ccatccatga accctagcta cgtgagggaa    720
ttgaagagaa agtgcccgcc tacagatttc agaacctcac tgaacatgga cccaggcagt    780
gcgttgacat tcgacactca ctacttcaag gtcgtggctc agaagaaagg gctcttcaca    840
tctgactcta cgcttctcga tgacattgag accaaaaact acgttcagac tcaggccatt    900
ctccctcctg tgttttcttc tttcaataaa gatttctccg attccatggt caaacttggt    960
ttcgtccaaa ttcttaccgg caaaaatggt gagatcagga agagatgcgc cttccctaac   1020
taatttggat cgatcagacc gggtttcgga tgattttgag tctacacgtt tttctctgct   1080
tattttcttt ctttttcttt tttctttcac ggaagtttga gctttggtgt tgtcttcttc   1140
tgtttcttcc atgaataatt gtttttgtt gagtaacttt acatttgtat tctttacggt   1200
gactgtgttt tgtaatggaa aaagtttgtt tcgaattcat ccgttaaacg taaacctaaa   1260
ttaaacaaaa attataattg gaaagcaaaa cattttgtaa gcttcgtggt gtttttacta   1320
tgaattaata tttatgtttg tttttc                                         1346
```

<210> SEQ ID NO 8
<211> LENGTH: 325
<212> TYPE: PRT
<213> ORGANISM: Arabidopsis thaliana

<400> SEQUENCE: 8

```
Met Ala Ile Lys Asn Ile Leu Ala Leu Val Val Leu Leu Ser Val Val
1               5                   10                  15

Gly Val Ser Val Ala Ile Pro Gln Leu Leu Asp Leu Asp Tyr Tyr Arg
            20                  25                  30

Ser Lys Cys Pro Lys Ala Glu Glu Ile Val Arg Gly Val Thr Val Gln
        35                  40                  45

Tyr Val Ser Arg Gln Lys Thr Leu Ala Ala Lys Leu Leu Arg Met His
    50                  55                  60

Phe His Asp Cys Phe Val Arg Gly Cys Asp Gly Ser Val Leu Leu Lys
65                  70                  75                  80

Ser Ala Lys Asn Asp Ala Glu Arg Asp Ala Val Pro Asn Leu Thr Leu
                85                  90                  95

Lys Gly Tyr Glu Val Val Asp Ala Ala Lys Thr Ala Leu Glu Arg Lys
            100                 105                 110

Cys Pro Asn Leu Ile Ser Cys Ala Asp Val Leu Ala Leu Val Ala Arg
        115                 120                 125

Asp Ala Val Ala Val Ile Gly Gly Pro Trp Trp Pro Val Pro Leu Gly
    130                 135                 140

Arg Arg Asp Gly Arg Ile Ser Lys Leu Asn Asp Ala Leu Leu Asn Leu
145                 150                 155                 160

Pro Ser Pro Phe Ala Asp Ile Lys Thr Leu Lys Lys Asn Phe Ala Asn
                165                 170                 175

Lys Gly Leu Asn Ala Lys Asp Leu Val Val Leu Ser Gly Gly His Thr
            180                 185                 190

Ile Gly Ile Ser Ser Cys Ala Leu Val Asn Ser Arg Leu Tyr Asn Phe
        195                 200                 205
```

```
Thr Gly Lys Gly Asp Ser Asp Pro Ser Met Asn Pro Ser Tyr Val Arg
    210                 215                 220

Glu Leu Lys Arg Lys Cys Pro Pro Thr Asp Phe Arg Thr Ser Leu Asn
225                 230                 235                 240

Met Asp Pro Gly Ser Ala Leu Thr Phe Asp Thr His Tyr Phe Lys Val
                245                 250                 255

Val Ala Gln Lys Lys Gly Leu Phe Thr Ser Asp Ser Thr Leu Leu Asp
            260                 265                 270

Asp Ile Glu Thr Lys Asn Tyr Val Gln Thr Gln Ala Ile Leu Pro Pro
        275                 280                 285

Val Phe Ser Ser Phe Asn Lys Asp Phe Ser Asp Ser Met Val Lys Leu
    290                 295                 300

Gly Phe Val Gln Ile Leu Thr Gly Lys Asn Gly Glu Ile Arg Lys Arg
305                 310                 315                 320

Cys Ala Phe Pro Asn
                325
```

<210> SEQ ID NO 9
<211> LENGTH: 1208
<212> TYPE: DNA
<213> ORGANISM: Arabidopsis thaliana

<400> SEQUENCE: 9

```
acacaacata atcctcccaa acagagagag tctcaaaaat taaaccaaca aatttaaaga     60

tgaattgctt gatagctata gctctttcag tctctttctt tcttgtggga attgttggac    120

cgatccaagc tcaattgcag atgaatttct atgccaattc ttgtcctaat gctgaaaaga    180

ttgttcaaga ttttgtttca aaccacgttt ctaatgctcc ttctcttgct gctgctctca    240

ttagaatgca tttccatgac tgttttgtcc gaggttgtga tggatcagtg cttataaact    300

caacgtcagg aaacgcagag agagacgcga ctcctaacct aacggttcga gggtttggct    360

tcatcgacgc aattaaatct gtgcttgaag ctcaatgccc tggaattgtc tcttgcgctg    420

atattatcgc tctagcttct cgcgacgctg tcgttttcac cggaggaccg aattggagtg    480

taccgaccgg aagaagagac gggaggatat caaacgcagc ggaggcatta gccaacattc    540

ctcctccaac cagtaatatc accaatcttc agacactctt tgcaaaccaa ggacttgatc    600

ttaaggacct cgttttacta tccggggctc acactattgg tgtatctcac tgctcgtctt    660

tcacaaaccg tctctacaat tttacgggtc gtggaggcca agatccggct ttggacagcg    720

agtacgcagc caatctcaag tctagaaaat gtcctagcct caacgataac aagaccatcg    780

tagagatgga tccagggagc cgcaaaacat ttgatctaag ttattaccag ctcgtactca    840

agcgtagagg tctgtttcaa tcagactctg ctctcaccac taaccccaca acactttcaa    900

acataaaccg gatcttgacg ggttcggtgg ggagtttctt ctctgagttt gccaagtcaa    960

tggagaaaat gggtcggatc aatgtcaaga ctggttcagc tggagtggtt aggaggcaat   1020

gttccgttgc aaatagttaa ggggtggaaa tgtaaaagat ttgggagctt gtgggggtag   1080

ttgtgataat aattaataag gatgattgtg aatttatgat gtggcctttt gggatttgtg   1140

tgtatggatt ttgttacaga cttcgtcaat aaagaaataa aaagatttta ctgctttttt   1200

tttaacat                                                             1208
```

<210> SEQ ID NO 10
<211> LENGTH: 326
<212> TYPE: PRT
<213> ORGANISM: Arabidopsis thaliana

<400> SEQUENCE: 10

```
Met Asn Cys Leu Ile Ala Ile Ala Leu Ser Val Ser Phe Phe Leu Val
1               5                   10                  15

Gly Ile Val Gly Pro Ile Gln Ala Gln Leu Gln Met Asn Phe Tyr Ala
            20                  25                  30

Asn Ser Cys Pro Asn Ala Glu Lys Ile Val Gln Asp Phe Val Ser Asn
        35                  40                  45

His Val Ser Asn Ala Pro Ser Leu Ala Ala Ala Leu Ile Arg Met His
    50                  55                  60

Phe His Asp Cys Phe Val Arg Gly Cys Asp Gly Ser Val Leu Ile Asn
65                  70                  75                  80

Ser Thr Ser Gly Asn Ala Glu Arg Asp Ala Thr Pro Asn Leu Thr Val
                85                  90                  95

Arg Gly Phe Gly Phe Ile Asp Ala Ile Lys Ser Val Leu Glu Ala Gln
            100                 105                 110

Cys Pro Gly Ile Val Ser Cys Ala Asp Ile Ile Ala Leu Ala Ser Arg
        115                 120                 125

Asp Ala Val Val Phe Thr Gly Gly Pro Asn Trp Ser Val Pro Thr Gly
    130                 135                 140

Arg Arg Asp Gly Arg Ile Ser Asn Ala Ala Glu Ala Leu Ala Asn Ile
145                 150                 155                 160

Pro Pro Pro Thr Ser Asn Ile Thr Asn Leu Gln Thr Leu Phe Ala Asn
                165                 170                 175

Gln Gly Leu Asp Leu Lys Asp Leu Val Leu Leu Ser Gly Ala His Thr
            180                 185                 190

Ile Gly Val Ser His Cys Ser Ser Phe Thr Asn Arg Leu Tyr Asn Phe
        195                 200                 205

Thr Gly Arg Gly Gly Gln Asp Pro Ala Leu Asp Ser Glu Tyr Ala Ala
    210                 215                 220

Asn Leu Lys Ser Arg Lys Cys Pro Ser Leu Asn Asp Asn Lys Thr Ile
225                 230                 235                 240

Val Glu Met Asp Pro Gly Ser Arg Lys Thr Phe Asp Leu Ser Tyr Tyr
                245                 250                 255

Gln Leu Val Leu Lys Arg Arg Gly Leu Phe Gln Ser Asp Ser Ala Leu
            260                 265                 270

Thr Thr Asn Pro Thr Thr Leu Ser Asn Ile Asn Arg Ile Leu Thr Gly
        275                 280                 285

Ser Val Gly Ser Phe Phe Ser Glu Phe Ala Lys Ser Met Glu Lys Met
    290                 295                 300

Gly Arg Ile Asn Val Lys Thr Gly Ser Ala Gly Val Val Arg Arg Gln
305                 310                 315                 320

Cys Ser Val Ala Asn Ser
                325
```

<210> SEQ ID NO 11
<211> LENGTH: 747
<212> TYPE: DNA
<213> ORGANISM: Arabidopsis thaliana

<400> SEQUENCE: 11

```
aaacccacca ttcaaacaaa acacaaaaac aacaaaaaaa ccatttcccc aaaaaaaaaa      60

aaacaaaaac agaggatgaa acaaaaccag agcaagttct tgagaataat ctcaacacct     120

ctaagagctt taggcaaggc acgtgatttc tacgtgagaa gcatcaccgg ttgcgcagct     180

cgtactcaat attcctcctc cgcctccgtc tccgctcctt ttccaagaag ccggagctcc     240
```

```
tcctccgccg ccttctcctc ctccgcatca tcccggagaa ccaccgattt cgggatagat    300

gaagattaca gcgagctagt gagagctgcg tcggtgagga gtttagggca caagaatgag    360

atagacatgt tgatacaaga gaagctgcaa cagcagaagc aacagaagca aggagggttg    420

cctaagagct cgagtgctgg gatggcgagg atagaggaag aggaagaaac agaggaagga    480

tctgtgaatc cgaaggtgaa gaagactaag aaagtctctg atcttttgta tcctcgtagc    540

aaatcttacg ccgttactac tagtacccct atcttgtaac ttctcttctt ctttttcttt    600

cttcttaatt ttagtatttt gtggattgat tatcattttt ctagctcgat ttttcgtgca    660

ctgtgaaata ctattttctt agcttgattt taataatttt gtggattgat tagaaataaa    720

taactaaacc tactctagct tcgaatc                                        747
```

<210> SEQ ID NO 12
<211> LENGTH: 167
<212> TYPE: PRT
<213> ORGANISM: Arabidopsis thaliana

<400> SEQUENCE: 12

```
Met Lys Gln Asn Gln Ser Lys Phe Leu Arg Ile Ile Ser Thr Pro Leu
1               5                   10                  15

Arg Ala Leu Gly Lys Ala Arg Asp Phe Tyr Val Arg Ser Ile Thr Gly
            20                  25                  30

Cys Ala Ala Arg Thr Gln Tyr Ser Ser Ser Ala Ser Val Ser Ala Pro
        35                  40                  45

Phe Pro Arg Ser Arg Ser Ser Ser Ser Ala Ala Phe Ser Ser Ser Ala
    50                  55                  60

Ser Ser Arg Arg Thr Thr Asp Phe Gly Ile Asp Glu Asp Tyr Ser Glu
65                  70                  75                  80

Leu Val Arg Ala Ala Ser Val Arg Ser Leu Gly His Lys Asn Glu Ile
                85                  90                  95

Asp Met Leu Ile Gln Glu Lys Leu Gln Gln Gln Lys Gln Gln Lys Gln
            100                 105                 110

Gly Gly Leu Pro Lys Ser Ser Ser Ala Gly Met Ala Arg Ile Glu Glu
        115                 120                 125

Glu Glu Glu Thr Glu Glu Gly Ser Val Asn Pro Lys Val Lys Lys Thr
    130                 135                 140

Lys Lys Val Ser Asp Leu Leu Tyr Pro Arg Ser Lys Ser Tyr Ala Val
145                 150                 155                 160

Thr Thr Ser Thr Pro Ile Leu
                165
```

<210> SEQ ID NO 13
<211> LENGTH: 1791
<212> TYPE: DNA
<213> ORGANISM: Arabidopsis thaliana

<400> SEQUENCE: 13

```
cgttttgttg tttatccaac ttgtcattca tcgatgtctc tctcttccag cctttcttga     60

atctctcacc tctcacgcca atttcatttt catgcatcgc tatttcccct tatcttcttc    120

ttcttcttct tatctcccaa ctaaattatc tgtctccatt catgttatta tggtcaacaa    180

cagaatctga atcccatttc cccattttcg gatcacaata actaacaaac cctagatttc    240

tatctatagt ccttcgatct gtttctgtgt ctccttaaag ctgtgatttt tgcaattggg    300

gtttgtgaga ttcgatcaat taattgtgtt tgttgaatgg accttcttcg attgagagaa    360
```

```
aagggtatat tttatctca gagaagaagg aaatggctga tttttatggc gatctctgga    420

gtttctggct atggagctta caaggtttat catttgccat ctgttgccag aaaaaggaag    480

cgtcttttta agcttttcgg agccattgtc tctgtagctg aattgatctc tgattcagct    540

gagaccttaa gtatggtatc acgagacgtg aaggattttc tcaattcaga ttcagatgaa    600

atccctaaca gcttgaagca gatcgcgaag atcacaactt cgaatgagtt tacggattcg    660

ctttctaggg tttctcaggc tgtgactatt ggtgcctttc gtgggtacaa atccgaatcg    720

tctattggtg attcaggaat tgagaaatca tcagactcga gtgttgttga tagagtgatt    780

gataaggttt tctcagaggc tggaactggt tttgtttcag ttgttgttgg tagctttgct    840

aagaatcttg ttcttggatt ttactctggt aaggtagaga gtggtgtgaa atgtgagggt    900

tctgattctt ctgagacacc tagatgggtg actttgcttg gtgatgacaa gtgtagagag    960

cttttagctg attgtattga gagattcacc agcactgcaa ttggtgtgta tcttgacaag   1020

acgatggata tcaatactta tgatcaaatc tttgaaggct tgacgaatcc gaaacatcag   1080

gatagtgtca aggacgttct tgtttcggtt tgtaacggtg ctctcgagac tattgttagg   1140

acatctcacg acgtgtttac atcttcaagg tctaagaatg tgatagaaga gatcgaagat   1200

gatgatttca agagtaatgg ttccgcgaga agcaagatgg tttcggaatc aggagatggg   1260

gtcaagagta atgggtggac tgaggctatt gcaactacat tggcagttcc gagcaatcgg   1320

aggtttatgt ttgatgtaac aggaagagta acactagaaa cgacgagatc aatcatcgca   1380

tttataatgg tgaagacatt tcaagggttc agaaaaagta tcaatgtggt tcatgaagag   1440

gttacagaca gaggacgcca agcagttgaa tatgttggag ccaaatcttc tgttataatc   1500

actgtatgcc ttgcgttgta cttgcacatc ataagcggct gtgttcggaa ttctcccata   1560

ggcgtaagcc agcattttta gttcttcaga tgaagaagag atcatcgatt tggttggata   1620

taggataata tttgttaggt acacaagatt tatcagctcg ttgtttatag ttggagctga   1680

gaatattgta aagattgtgt gcgtgtatta gcacaacttg attcttattg atggatcatg   1740

gatcttatat atatatacat attgaaaagg ttcttggggc attgatcttt g            1791
```

<210> SEQ ID NO 14
<211> LENGTH: 414
<212> TYPE: PRT
<213> ORGANISM: Arabidopsis thaliana

<400> SEQUENCE: 14

```
Met Asp Leu Leu Arg Leu Arg Glu Lys Gly Ile Phe Leu Ser Gln Arg
1               5                   10                  15

Arg Arg Lys Trp Leu Ile Phe Met Ala Ile Ser Gly Val Ser Gly Tyr
            20                  25                  30

Gly Ala Tyr Lys Val Tyr His Leu Pro Ser Val Ala Arg Lys Arg Lys
        35                  40                  45

Arg Leu Phe Lys Leu Phe Gly Ala Ile Val Ser Val Ala Glu Leu Ile
    50                  55                  60

Ser Asp Ser Ala Glu Thr Leu Ser Met Val Ser Arg Asp Val Lys Asp
65                  70                  75                  80

Phe Leu Asn Ser Asp Ser Asp Glu Ile Pro Asn Ser Leu Lys Gln Ile
                85                  90                  95

Ala Lys Ile Thr Thr Ser Asn Glu Phe Thr Asp Ser Leu Ser Arg Val
            100                 105                 110

Ser Gln Ala Val Thr Ile Gly Ala Phe Arg Gly Tyr Lys Ser Glu Ser
        115                 120                 125
```

```
Ser Ile Gly Asp Ser Gly Ile Glu Lys Ser Ser Asp Ser Ser Val Val
    130                 135                 140

Asp Arg Val Ile Asp Lys Val Phe Ser Glu Ala Gly Thr Gly Phe Val
145                 150                 155                 160

Ser Val Val Val Gly Ser Phe Ala Lys Asn Leu Val Leu Gly Phe Tyr
                165                 170                 175

Ser Gly Lys Val Glu Ser Gly Val Lys Cys Glu Gly Ser Asp Ser Ser
            180                 185                 190

Glu Thr Pro Arg Trp Val Thr Leu Leu Gly Asp Asp Lys Cys Arg Glu
        195                 200                 205

Leu Leu Ala Asp Cys Ile Glu Arg Phe Thr Ser Thr Ala Ile Gly Val
    210                 215                 220

Tyr Leu Asp Lys Thr Met Asp Ile Asn Thr Tyr Asp Gln Ile Phe Glu
225                 230                 235                 240

Gly Leu Thr Asn Pro Lys His Gln Asp Ser Val Lys Asp Val Leu Val
                245                 250                 255

Ser Val Cys Asn Gly Ala Leu Glu Thr Ile Val Arg Thr Ser His Asp
            260                 265                 270

Val Phe Thr Ser Ser Arg Ser Lys Asn Val Ile Glu Glu Ile Glu Asp
        275                 280                 285

Asp Asp Phe Lys Ser Asn Gly Ser Ala Arg Ser Lys Met Val Ser Glu
    290                 295                 300

Ser Gly Asp Gly Val Lys Ser Asn Gly Trp Thr Glu Ala Ile Ala Thr
305                 310                 315                 320

Thr Leu Ala Val Pro Ser Asn Arg Arg Phe Met Phe Asp Val Thr Gly
                325                 330                 335

Arg Val Thr Leu Glu Thr Thr Arg Ser Ile Ile Ala Phe Ile Met Val
            340                 345                 350

Lys Thr Phe Gln Gly Phe Arg Lys Ser Ile Asn Val Val His Glu Glu
        355                 360                 365

Val Thr Asp Arg Gly Arg Gln Ala Val Glu Tyr Val Gly Ala Lys Ser
    370                 375                 380

Ser Val Ile Ile Thr Val Cys Leu Ala Leu Tyr Leu His Ile Ile Ser
385                 390                 395                 400

Gly Cys Val Arg Asn Ser Pro Ile Gly Val Ser Gln His Phe
                405                 410
```

```
<210> SEQ ID NO 15
<211> LENGTH: 555
<212> TYPE: DNA
<213> ORGANISM: Arabidopsis thaliana

<400> SEQUENCE: 15

atgtctgtcc aaaaagctgt caagagttct cactacgagg cagaatccaa catggaacaa      60

gatattgtta gaaaagcatg ggtctttaag ccaagtggtc ttaatttcat atggggaggt     120

gattctcggt attgggtcat ccctaacgaa gacaggacgc ctgctgaact aaagaaagtg     180

agttggttag aagtaaccgg ttcgtacgac aagatagaac caggcaaaac ataccgaatt     240

ggttttaaaa tctcgttcac agctgatgca accggatggg accaagctcc agttttcatg     300

tcagcaaaaa ttggaaagaa agggaggaca atttggaaga ggatcaaatc ggttaacaat     360

aactttgaca aactcaaagg cggaaccgga ccggttaaca taccagatga gactgatggt     420

cggtttgaga tctttgtaag tcccaaggta gcaataaacc aagacaccaa gctccaattt     480

ggtttgtatg aagtgtggac cggaaaatgg aaaacaggct tgttgatcta tgaagctttt     540
```

```
gttgaagaag tgtaa                                                   555


<210> SEQ ID NO 16
<211> LENGTH: 184
<212> TYPE: PRT
<213> ORGANISM: Arabidopsis thaliana

<400> SEQUENCE: 16

Met Ser Val Gln Lys Ala Val Lys Ser Ser His Tyr Glu Ala Glu Ser
1               5                   10                  15

Asn Met Glu Gln Asp Ile Val Arg Lys Ala Trp Val Phe Lys Pro Ser
            20                  25                  30

Gly Leu Asn Phe Ile Trp Gly Gly Asp Ser Arg Tyr Trp Val Ile Pro
        35                  40                  45

Asn Glu Asp Arg Thr Pro Ala Glu Leu Lys Lys Val Ser Trp Leu Glu
    50                  55                  60

Val Thr Gly Ser Tyr Asp Lys Ile Glu Pro Gly Lys Thr Tyr Arg Ile
65                  70                  75                  80

Gly Phe Lys Ile Ser Phe Thr Ala Asp Ala Thr Gly Trp Asp Gln Ala
                85                  90                  95

Pro Val Phe Met Ser Ala Lys Ile Gly Lys Lys Gly Arg Thr Ile Trp
            100                 105                 110

Lys Arg Ile Lys Ser Val Asn Asn Asn Phe Asp Lys Leu Lys Gly Gly
        115                 120                 125

Thr Gly Pro Val Asn Ile Pro Asp Glu Thr Asp Gly Arg Phe Glu Ile
    130                 135                 140

Phe Val Ser Pro Lys Val Ala Ile Asn Gln Asp Thr Lys Leu Gln Phe
145                 150                 155                 160

Gly Leu Tyr Glu Val Trp Thr Gly Lys Trp Lys Thr Gly Leu Leu Ile
                165                 170                 175

Tyr Glu Ala Phe Val Glu Glu Val
            180


<210> SEQ ID NO 17
<211> LENGTH: 2295
<212> TYPE: DNA
<213> ORGANISM: Arabidopsis thaliana

<400> SEQUENCE: 17

atggacgatg agtcattacc cacaaccaat tccacttccg atcacagagg cttctataaa     60

gagattctct ttgggatgaa gaagattggg ttccgcgagt ttcttcacgg gtatcacttt    120

cgaggtttgg tttcggaatt gaggcatgtt catgtcgaag aaatcatgga tgaattgatg    180

tctgaaagct cagatctttc tgtttggttt ttcaaagagc tgagagatat ctatgcgttt    240

cgtcattcga gtttttccac attgttggtt tcacatgttt tagctggtca aagacgtttc    300

aaagagcttc aagtgattct ggaacaattg cttcaagaag aaggcacatt gagaatggtt    360

gatgattctc tttatatctt gaaaaagatg aaggatcaga acttgaatgt gtcgacacag    420

tcgtacaact ccgttttgta tcattttaga gagacggata agatgtggga tgtgtacaag    480

gaaatcaagg ataagaacga gcacacgtac tcaacagttg tagatggttt gtgtaggcaa    540

caaaagctag aggatgcagt tttgttcctt cgaacttcag agtggaagga tattggtccc    600

tctgtagttt ctttcaatag tataatgtca ggttactgta aattgggttt tgtagatatg    660

gcgaagtcgt tttctgtac agttttgaaa tgtgggttgg ttcctagtgt atatagtcac    720

aatatactca tcaatggact ctgtctagtt ggttctatcg cagaagcttt agagttggct    780
```

```
agtgacatga ataagcatgg agtggaacct gattctgtga catacaatat tcttgcgaaa    840

gggtttcatc ttctcggtat gatcagtggg gcttgggagg taattcgaga tatgttggat    900

aaaggattga gtcctgatgt tattacatac acaattttac tatgtggaca atgtcagtta    960

ggaaatattg acatgggttt agtattgctg aaggatatgt tgtcgagggg atttgagtta   1020

aacagtatca tcccatgcag tgtaatgctc agtggtttat gtaaaacagg aagaatagat   1080

gaagctttgt cgttattcaa tcaaatgaaa gccgatggtc tgagccctga tcttgtagca   1140

tattctattg tgattcatgg cctctgcaag ttaggaaaat ttgatatggc tctttggctt   1200

tacgacgaga tgtgtgacaa aagaattctt ccgaattcga ggactcatgg tgctcttttg   1260

ctcggtttat gtcagaaagg gatgttactt gaggcaagat cgcttttgga ttctctgatt   1320

tcaagtggag agacactgga tattgttctg tacaatatcg taattgacgg gtatgcaaag   1380

tctggttgca ttgaggaggc gttagagtta ttcaaagtag tcattgagac tgggataact   1440

cctagcgttg caacttttaa ttctttgata tacgggtatt gcaaaaccca gaatatagct   1500

gaggctagaa aaatcttaga tgtcatcaag ttatatggat tggctccaag tgttgtgagt   1560

tatacaactc tgatggatgc atatgcaaat tgtggaaata ccaaaagcat agatgaattg   1620

cgcagggaaa tgaaagcaga aggaatccca ccaaccaatg tcacgtactc agtgattttt   1680

aaaggacttt gcagaggctg gaaacatgaa aattgcaacc atgtactcag ggaaaggata   1740

ttcgaaaaat gcaagcaggg actcagggac atggaatctg aaggtatacc tccagatcag   1800

atcacatata atacaattat tcagtatcta tgcagagtta aacatttatc tggagcattt   1860

gtgtttctcg aaataatgaa atctcgaaat cttgatgctt catctgctac ttataatatt   1920

ctaatcgaca gcctttgtgt ctacggttac ataaggaaag ctgacagttt tatctattcg   1980

ctccaggagc agaatgttag tttgtccaaa tttgcttata ccacactgat caaggcacat   2040

tgtgtaaagg gtgaccctga aatggcagtg aagctatttc atcaactgct gcacagagga   2100

ttcaatgttt ccattaggga ctatagcgcg gtgatcaacc gtttgtgtag gagacatttg   2160

gtaaacgaga gcaaattctt cttctgtcta atgttatccc agggtatttc gcctgactta   2220

gacatttgtg aagtgatgat caagtcagat gaattgcttt cctggacaat caaatggggt   2280

ttgttgcctg attag                                                    2295
```

<210> SEQ ID NO 18
<211> LENGTH: 764
<212> TYPE: PRT
<213> ORGANISM: Arabidopsis thaliana

<400> SEQUENCE: 18

```
Met Asp Asp Glu Ser Leu Pro Thr Thr Asn Ser Thr Ser Asp His Arg
1               5                   10                  15

Gly Phe Tyr Lys Glu Ile Leu Phe Gly Met Lys Lys Ile Gly Phe Arg
            20                  25                  30

Glu Phe Leu His Gly Tyr His Phe Arg Gly Leu Val Ser Glu Leu Arg
        35                  40                  45

His Val His Val Glu Glu Ile Met Asp Glu Leu Met Ser Glu Ser Ser
    50                  55                  60

Asp Leu Ser Val Trp Phe Phe Lys Glu Leu Arg Asp Ile Tyr Ala Phe
65                  70                  75                  80

Arg His Ser Ser Phe Ser Thr Leu Leu Val Ser His Val Leu Ala Gly
                85                  90                  95

Gln Arg Arg Phe Lys Glu Leu Gln Val Ile Leu Glu Gln Leu Leu Gln
            100                 105                 110
```

```
Glu Glu Gly Thr Leu Arg Met Val Asp Asp Ser Leu Tyr Ile Leu Lys
        115                 120                 125

Lys Met Lys Asp Gln Asn Leu Asn Val Ser Thr Gln Ser Tyr Asn Ser
    130                 135                 140

Val Leu Tyr His Phe Arg Glu Thr Asp Lys Met Trp Asp Val Tyr Lys
145                 150                 155                 160

Glu Ile Lys Asp Lys Asn Glu His Thr Tyr Ser Thr Val Val Asp Gly
                165                 170                 175

Leu Cys Arg Gln Gln Lys Leu Glu Asp Ala Val Leu Phe Leu Arg Thr
            180                 185                 190

Ser Glu Trp Lys Asp Ile Gly Pro Ser Val Val Ser Phe Asn Ser Ile
        195                 200                 205

Met Ser Gly Tyr Cys Lys Leu Gly Phe Val Asp Met Ala Lys Ser Phe
    210                 215                 220

Phe Cys Thr Val Leu Lys Cys Gly Leu Val Pro Ser Val Tyr Ser His
225                 230                 235                 240

Asn Ile Leu Ile Asn Gly Leu Cys Leu Val Gly Ser Ile Ala Glu Ala
                245                 250                 255

Leu Glu Leu Ala Ser Asp Met Asn Lys His Gly Val Glu Pro Asp Ser
            260                 265                 270

Val Thr Tyr Asn Ile Leu Ala Lys Gly Phe His Leu Leu Gly Met Ile
        275                 280                 285

Ser Gly Ala Trp Glu Val Ile Arg Asp Met Leu Asp Lys Gly Leu Ser
    290                 295                 300

Pro Asp Val Ile Thr Tyr Thr Ile Leu Leu Cys Gly Gln Cys Gln Leu
305                 310                 315                 320

Gly Asn Ile Asp Met Gly Leu Val Leu Leu Lys Asp Met Leu Ser Arg
                325                 330                 335

Gly Phe Glu Leu Asn Ser Ile Ile Pro Cys Ser Val Met Leu Ser Gly
            340                 345                 350

Leu Cys Lys Thr Gly Arg Ile Asp Glu Ala Leu Ser Leu Phe Asn Gln
        355                 360                 365

Met Lys Ala Asp Gly Leu Ser Pro Asp Leu Val Ala Tyr Ser Ile Val
    370                 375                 380

Ile His Gly Leu Cys Lys Leu Gly Lys Phe Asp Met Ala Leu Trp Leu
385                 390                 395                 400

Tyr Asp Glu Met Cys Asp Lys Arg Ile Leu Pro Asn Ser Arg Thr His
                405                 410                 415

Gly Ala Leu Leu Leu Gly Leu Cys Gln Lys Gly Met Leu Leu Glu Ala
            420                 425                 430

Arg Ser Leu Leu Asp Ser Leu Ile Ser Ser Gly Glu Thr Leu Asp Ile
        435                 440                 445

Val Leu Tyr Asn Ile Val Ile Asp Gly Tyr Ala Lys Ser Gly Cys Ile
    450                 455                 460

Glu Glu Ala Leu Glu Leu Phe Lys Val Val Ile Glu Thr Gly Ile Thr
465                 470                 475                 480

Pro Ser Val Ala Thr Phe Asn Ser Leu Ile Tyr Gly Tyr Cys Lys Thr
                485                 490                 495

Gln Asn Ile Ala Glu Ala Arg Lys Ile Leu Asp Val Ile Lys Leu Tyr
            500                 505                 510

Gly Leu Ala Pro Ser Val Val Ser Tyr Thr Thr Leu Met Asp Ala Tyr
        515                 520                 525

Ala Asn Cys Gly Asn Thr Lys Ser Ile Asp Glu Leu Arg Arg Glu Met
```

```
    530                 535                 540

Lys Ala Glu Gly Ile Pro Pro Thr Asn Val Thr Tyr Ser Val Ile Phe
545                 550                 555                 560

Lys Gly Leu Cys Arg Gly Trp Lys His Glu Asn Cys Asn His Val Leu
                565                 570                 575

Arg Glu Arg Ile Phe Glu Lys Cys Lys Gln Gly Leu Arg Asp Met Glu
            580                 585                 590

Ser Glu Gly Ile Pro Pro Asp Gln Ile Thr Tyr Asn Thr Ile Ile Gln
        595                 600                 605

Tyr Leu Cys Arg Val Lys His Leu Ser Gly Ala Phe Val Phe Leu Glu
    610                 615                 620

Ile Met Lys Ser Arg Asn Leu Asp Ala Ser Ser Ala Thr Tyr Asn Ile
625                 630                 635                 640

Leu Ile Asp Ser Leu Cys Val Tyr Gly Tyr Ile Arg Lys Ala Asp Ser
                645                 650                 655

Phe Ile Tyr Ser Leu Gln Glu Gln Asn Val Ser Leu Ser Lys Phe Ala
            660                 665                 670

Tyr Thr Thr Leu Ile Lys Ala His Cys Val Lys Gly Asp Pro Glu Met
        675                 680                 685

Ala Val Lys Leu Phe His Gln Leu Leu His Arg Gly Phe Asn Val Ser
    690                 695                 700

Ile Arg Asp Tyr Ser Ala Val Ile Asn Arg Leu Cys Arg Arg His Leu
705                 710                 715                 720

Val Asn Glu Ser Lys Phe Phe Phe Cys Leu Met Leu Ser Gln Gly Ile
                725                 730                 735

Ser Pro Asp Leu Asp Ile Cys Glu Val Met Ile Lys Ser Asp Glu Leu
            740                 745                 750

Leu Ser Trp Thr Ile Lys Trp Gly Leu Leu Pro Asp
        755                 760
```

<210> SEQ ID NO 19
<211> LENGTH: 2481
<212> TYPE: DNA
<213> ORGANISM: Arabidopsis thaliana

<400> SEQUENCE: 19

```
aaaaaagcgt cgttgagagg ttagagacga aggaaggagg cagaggatag agagatagcg      60

aggctaatgg atcagtgact cactgagtca gattttaccg attcattgcc tccattgaag     120

cctcttttct cagattctac gcttcactgt ctcttctcca tgtgcgtctc ctcctcctcc     180

gtttcttcag atcttgcttt ccggtgacgg ttttaatctt cttctctctg gtaacacgta     240

taaagcatgg cttacctgat gtagacatgt agtgttaggc taaagactcc tcttttcact     300

tctgtcttgt tgagtttgtg ttggtttaag gctttaagcc aaaggcgttg ttggtctgac     360

aagatggcaa tggcggtgtt taaggctcct ctaaaagggg aatttcatgg ggctagaaag     420

atggaaggga agcaatataa gcaccatctg cttcagcaac agtctacagg gagaagacgt     480

gtgttcgtgc aaaccgatac tggctgtgtg ttgggagttg agttggatcg taatgacaat     540

gttcatactg tgaagaaaag gcttcagatt gcgtttaact ttcctactga ggaaagctct     600

ttgacctttg gggatatggt gttgaagaat gacttgagtg ctgtgaggaa tgattctccg     660

cttctcttaa agcgtaactt aatgcacaga agctcttcta ctccgtgtct ttcacctact     720

gggaatgatc tgcagaggaa agatcgaagt ggtcctattg agatacttag tcactcgccc     780

tgttttctgt ctttgaagca aacagcgaat gacattgtta aggcgatgaa gatgggtgtt     840
```

```
gaaccaatcc ctgttaatgg tgggcttgga ggggcatact attttaggga tgaaaagggt    900
caaagtgttg ctattgtcaa gcctacggat gaagagccgt ttgcccctaa caatcctaaa    960
ggcttcgtag ggaaagcgct tgggcagcct ggtttaaagc cttctgtgcg ggttggggaa   1020
accgggttta gagaagttgc tgcatacctt cttgattatg atcactttgc taatgttcct   1080
cctacggctc ttgtgaagat aacacactct gttttcaatg tcaatgatgg aatggatggg   1140
aacaaatctc gtgagaagaa gaagctggtc agcagcaaga ttgcttcgtt ccagaagttt   1200
gtacctcatg attttgatgc cagtgatcac gggacttcaa gcttccctgt cgcttctgtg   1260
caccgcattg ggattttgga cataaggatt ctcaacacag accggcatgg tggaaatctt   1320
ttggtgaaga agcttgatga tggtggtgtt gggaggtttg gtcaagtgga gcttattcca   1380
atagatcatg gtctttgctt accagaaaca ctcgaagatc cttacttcga atggattcat   1440
tggcctcagg cttcaatacc tttctctgaa gaagaacttg actacataca aagtcttgat   1500
ccagtgaaag attgtgaaat gcttcgaaga gagcttccga tgattcgaga ggcttgtctc   1560
agggttctag ttctctgtac cgttttcctt aaagaagctg ctgtttttgg actttgtctt   1620
gcagagatcg gtgagatgat gactcgagaa tttcgtgcag gagaagagga accaagtgaa   1680
ctagaaatgt tgtgtatcga agccaagaga ttaaccactg aacaagacgt tttgtctccc   1740
aagtcagatg gagaaggaga gacagagttt cagtttgata tagactacaa tgagctagac   1800
tcggtttatg gctctgagac agaaaccgat gagttcttcg ccaagaaccc attttcaaac   1860
ggacgttctt cacttggaga gctcaaagag agcattgctg aagaagaaga agatgacgaa   1920
gaggaggcaa aacttactct atctctctca aagctttcca catcaatgaa gaacaatcta   1980
agcaacacca tgggatccgg atacctgaaa cctccgaaag acaaccaaac cgacaaagca   2040
ttggtaagtc acaagagcgc gaacgtgcag ctcccgctta gcgtaaactt tgtgaagtta   2100
gccgacatga aagaagttga atgggttgtg ttcttggaga ggtttcagga gttgctttac   2160
tcggcttttg cagaacgcaa gaccatgacg ttgaggaaca cacagagact tggtacatcg   2220
tgcaagtttt gagatcatac gagttcacat aagagaagac caaagatttc acttttacga   2280
gttttgaagc aattacttgt tagctacgtt aagattagtt tacttttgta gcgaccacga   2340
gcacttgcaa tgtgaagaaa tgtttatttt gcctgtaaat attctttacc attttttttt   2400
ccctaacttc catttccttc ttttgtttca aatcgttttg cattgtcttt acaagaataa   2460
gttgaatgaa aatagttgcc t                                              2481
```

<210> SEQ ID NO 20
<211> LENGTH: 622
<212> TYPE: PRT
<213> ORGANISM: Arabidopsis thaliana

<400> SEQUENCE: 20

```
Met Ala Met Ala Val Phe Lys Ala Pro Leu Lys Gly Glu Phe His Gly
1               5                   10                  15

Ala Arg Lys Met Glu Gly Lys Gln Tyr Lys His His Leu Leu Gln Gln
            20                  25                  30

Gln Ser Thr Gly Arg Arg Arg Val Phe Val Gln Thr Asp Thr Gly Cys
        35                  40                  45

Val Leu Gly Val Glu Leu Asp Arg Asn Asp Asn Val His Thr Val Lys
    50                  55                  60

Lys Arg Leu Gln Ile Ala Phe Asn Phe Pro Thr Glu Glu Ser Ser Leu
65                  70                  75                  80

Thr Phe Gly Asp Met Val Leu Lys Asn Asp Leu Ser Ala Val Arg Asn
```

```
                85                  90                  95

Asp Ser Pro Leu Leu Leu Lys Arg Asn Leu Met His Arg Ser Ser Ser
            100                 105                 110

Thr Pro Cys Leu Ser Pro Thr Gly Asn Asp Leu Gln Arg Lys Asp Arg
        115                 120                 125

Ser Gly Pro Ile Glu Ile Leu Ser His Ser Pro Cys Phe Leu Ser Leu
    130                 135                 140

Lys Gln Thr Ala Asn Asp Ile Val Lys Ala Met Lys Met Gly Val Glu
145                 150                 155                 160

Pro Ile Pro Val Asn Gly Gly Leu Gly Gly Ala Tyr Tyr Phe Arg Asp
                165                 170                 175

Glu Lys Gly Gln Ser Val Ala Ile Val Lys Pro Thr Asp Glu Glu Pro
            180                 185                 190

Phe Ala Pro Asn Asn Pro Lys Gly Phe Val Gly Lys Ala Leu Gly Gln
        195                 200                 205

Pro Gly Leu Lys Pro Ser Val Arg Val Gly Glu Thr Gly Phe Arg Glu
    210                 215                 220

Val Ala Ala Tyr Leu Leu Asp Tyr Asp His Phe Ala Asn Val Pro Pro
225                 230                 235                 240

Thr Ala Leu Val Lys Ile Thr His Ser Val Phe Asn Val Asn Asp Gly
                245                 250                 255

Met Asp Gly Asn Lys Ser Arg Glu Lys Lys Lys Leu Val Ser Ser Lys
            260                 265                 270

Ile Ala Ser Phe Gln Lys Phe Val Pro His Asp Phe Asp Ala Ser Asp
        275                 280                 285

His Gly Thr Ser Ser Phe Pro Val Ala Ser Val His Arg Ile Gly Ile
    290                 295                 300

Leu Asp Ile Arg Ile Leu Asn Thr Asp Arg His Gly Gly Asn Leu Leu
305                 310                 315                 320

Val Lys Lys Leu Asp Asp Gly Gly Val Gly Arg Phe Gly Gln Val Glu
                325                 330                 335

Leu Ile Pro Ile Asp His Gly Leu Cys Leu Pro Glu Thr Leu Glu Asp
            340                 345                 350

Pro Tyr Phe Glu Trp Ile His Trp Pro Gln Ala Ser Ile Pro Phe Ser
        355                 360                 365

Glu Glu Glu Leu Asp Tyr Ile Gln Ser Leu Asp Pro Val Lys Asp Cys
    370                 375                 380

Glu Met Leu Arg Arg Glu Leu Pro Met Ile Arg Glu Ala Cys Leu Arg
385                 390                 395                 400

Val Leu Val Leu Cys Thr Val Phe Leu Lys Glu Ala Ala Val Phe Gly
                405                 410                 415

Leu Cys Leu Ala Glu Ile Gly Glu Met Met Thr Arg Glu Phe Arg Ala
            420                 425                 430

Gly Glu Glu Glu Pro Ser Glu Leu Glu Met Leu Cys Ile Glu Ala Lys
        435                 440                 445

Arg Leu Thr Thr Glu Gln Asp Val Leu Ser Pro Lys Ser Asp Gly Glu
    450                 455                 460

Gly Glu Thr Glu Phe Gln Phe Asp Ile Asp Tyr Asn Glu Leu Asp Ser
465                 470                 475                 480

Val Tyr Gly Ser Glu Thr Glu Thr Asp Glu Phe Phe Ala Lys Asn Pro
                485                 490                 495

Phe Ser Asn Gly Arg Ser Ser Leu Gly Glu Leu Lys Glu Ser Ile Ala
            500                 505                 510
```

```
Glu Glu Glu Glu Asp Asp Glu Glu Glu Ala Lys Leu Thr Leu Ser Leu
        515                 520                 525

Ser Lys Leu Ser Thr Ser Met Lys Asn Asn Leu Ser Asn Thr Met Gly
    530                 535                 540

Ser Gly Tyr Leu Lys Pro Pro Lys Asp Asn Gln Thr Asp Lys Ala Leu
545                 550                 555                 560

Val Ser His Lys Ser Ala Asn Val Gln Leu Pro Leu Ser Val Asn Phe
                565                 570                 575

Val Lys Leu Ala Asp Met Lys Glu Val Glu Trp Val Val Phe Leu Glu
            580                 585                 590

Arg Phe Gln Glu Leu Leu Tyr Ser Ala Phe Ala Glu Arg Lys Thr Met
        595                 600                 605

Thr Leu Arg Asn Thr Gln Arg Leu Gly Thr Ser Cys Lys Phe
    610                 615                 620
```

<210> SEQ ID NO 21
<211> LENGTH: 1189
<212> TYPE: DNA
<213> ORGANISM: Arabidopsis thaliana

<400> SEQUENCE: 21

```
cagagcaaaa aaacactagt taagagattc aggttacctt caagttacaa attgagacaa      60

tcttgttctt tgtttgttag attaccttct attcttgatt gtgttttccg aagatttttt     120

agaaccaatc cacttgtttt tcctaataca ggggtggtgt tttcgtggtg gtaaaaggat     180

aaaatttctt gagaatgcct gcatacattt ctgaggagaa gttgttcttc aacaagaaac     240

ctttcggatc caaaatctca gacaacaacg aaattgaaga acttgatcaa gagaatttgg     300

ttgtgacaag acaagaagtt aatgatgatt ccaaagtggc accgagagat gtagtagcta     360

catcaacaag tgtctctaag aaggctttaa ccttgggaga tattttatca ttggaggatt     420

cccaaagccc acccaacaaa aacaacacta atggacctga agaaaacatg gtccatcata     480

acccacatct ggagataaca gaggaatcag aagcagacaa ctcttgtgat gacaacaatc     540

tcttgaaaag gaatctccca aatggtttcg gggaaataag tttctgtgaa gcaaagtcga     600

gtttagatta tattacttac tgtggaccac tctcaggctc cgaaaacctc tctattcgtt     660

ctgatggaac cagcgcaagc tcttttgctc tcccaatact gcaatcggag tggaacagca     720

gtcctgtaag aatggggaaa gctgaggaga cgcaacttcg aatggtgata gctgaggaga     780

gaaaagttcg aaaggataaa gctgagaaga cacaacttcg aaaggagaaa gctgaggagt     840

cacaacttcg agaggtgaaa gctgaggaga ctcaacttcg aatggtgaaa gctgaggaga     900

ctcaacttcg aaaggagaaa gctgaggaaa cacaacttcg aatggtgata gctgaggaga     960

gacaacttcg aaaggagaaa gatgagaaga gacaacttcg aaaggggaag aaaggatgga    1020

gacattactc ttctcttctc tgttgtagat tctgatggat tctatcagag gatttttaac    1080

ctttttaggc tttgcattca atatacaaag accgttcgaa taagaacaga aaatagtggt    1140

ttttctgtaa tgtattattt cgtagacctc aaatacttta tattcaatt                1189
```

<210> SEQ ID NO 22
<211> LENGTH: 286
<212> TYPE: PRT
<213> ORGANISM: Arabidopsis thaliana

<400> SEQUENCE: 22

```
Met Pro Ala Tyr Ile Ser Glu Glu Lys Leu Phe Phe Asn Lys Lys Pro
1               5                   10                  15
```

```
Phe Gly Ser Lys Ile Ser Asp Asn Asn Glu Ile Glu Glu Leu Asp Gln
            20                  25                  30

Glu Asn Leu Val Val Thr Arg Gln Glu Val Asn Asp Asp Ser Lys Val
        35                  40                  45

Ala Pro Arg Asp Val Val Ala Thr Ser Thr Ser Val Ser Lys Lys Ala
    50                  55                  60

Leu Thr Leu Gly Asp Ile Leu Ser Leu Glu Asp Ser Gln Ser Pro Pro
65                  70                  75                  80

Asn Lys Asn Asn Thr Asn Gly Pro Glu Glu Asn Met Val His His Asn
                85                  90                  95

Pro His Leu Glu Ile Thr Glu Glu Ser Glu Ala Asp Asn Ser Cys Asp
            100                 105                 110

Asp Asn Asn Leu Leu Lys Arg Asn Leu Pro Asn Gly Phe Gly Glu Ile
        115                 120                 125

Ser Phe Cys Glu Ala Lys Ser Ser Leu Asp Tyr Ile Thr Tyr Cys Gly
    130                 135                 140

Pro Leu Ser Gly Ser Glu Asn Leu Ser Ile Arg Ser Asp Gly Thr Ser
145                 150                 155                 160

Ala Ser Ser Phe Ala Leu Pro Ile Leu Gln Ser Glu Trp Asn Ser Ser
                165                 170                 175

Pro Val Arg Met Gly Lys Ala Glu Glu Thr Gln Leu Arg Met Val Ile
            180                 185                 190

Ala Glu Glu Arg Lys Val Arg Lys Asp Lys Ala Glu Lys Thr Gln Leu
        195                 200                 205

Arg Lys Glu Lys Ala Glu Glu Ser Gln Leu Arg Glu Val Lys Ala Glu
    210                 215                 220

Glu Thr Gln Leu Arg Met Val Lys Ala Glu Glu Thr Gln Leu Arg Lys
225                 230                 235                 240

Glu Lys Ala Glu Glu Thr Gln Leu Arg Met Val Ile Ala Glu Glu Arg
                245                 250                 255

Gln Leu Arg Lys Glu Lys Asp Glu Lys Arg Gln Leu Arg Lys Gly Lys
            260                 265                 270

Lys Gly Trp Arg His Tyr Ser Ser Leu Leu Cys Cys Arg Phe
        275                 280                 285
```

<210> SEQ ID NO 23
<211> LENGTH: 1579
<212> TYPE: DNA
<213> ORGANISM: Arabidopsis thaliana

<400> SEQUENCE: 23

```
cagagcaaaa aaacactagt taagagattc aggttacctt caagttacaa attgagacaa      60

tcttgttctt tgtttgttag attaccttct attcttgatt gtgttttccg aagatttttt     120

agaaccaatc cacttgtttt tcctaataca ggggtggtgt tttcgtggtg gtaaaaggat     180

aaaatttctt gagaatgcct gcatacattt ctgaggtttg gtttgtaatt atttgcaaaa     240

tcaaacggca ataaactgtt tttcattgtt tttgttatta tatatgctca aattaaatgc     300

agagattttg gttgctgaaa ctcattgaca tttcaacgat ttttttggat tcttgtacta     360

tatgtttttc tattggataa acagtaaaac catctcgctt tagattctag tataattcat     420

tctttgacga atactcttat ttagattcta gttgttagag acattgacat gtgactccat     480

ggctttatac atcaataaaa taatccagtt gttatgaaat aatccaatta tttaatgatc     540

ttcatgttag gatatatgtt aaggtgtaat agtttaatgg aaagcttgtg taacttacga     600

tgcaggagaa gttgttcttc aacaagaaac ctttcggatc caaaatctca gacaacaacg     660
```

```
aaattgaaga acttgatcaa gagaatttgg ttgtgacaag acaagaagtt aatgatgatt    720

ccaaagtggc accgagagat gtagtagcta catcaacaag tgtctctaag aaggctttaa    780

ccttgggaga tattttatca ttggaggatt cccaaagccc acccaacaaa aacaacacta    840

atggacctga agaaaacatg gtccatcata acccacatct ggagataaca gaggaatcag    900

aagcagacaa ctcttgtgat gacaacaatc tcttgaaaag gaatctccca aatggtttcg    960

gggaaataag tttctgtgaa gcaaagtcga gtttagatta tattacttac tgtggaccac   1020

tctcaggctc cgaaaacctc tctattcgtt ctgatggaac cagcgcaagc tcttttgctc   1080

tcccaatact gcaatcggag tggaacagca gtcctgtaag aatgggggaaa gctgaggaga  1140

cgcaacttcg aatggtgata gctgaggaga gaaaagttcg aaaggataaa gctgagaaga   1200

cacaacttcg aaaggagaaa gctgaggagt cacaacttcg agaggtgaaa gctgaggaga   1260

ctcaacttcg aatggtgaaa gctgaggaga ctcaacttcg aaaggagaaa gctgaggaaa   1320

cacaacttcg aatggtgata gctgaggaga gacaacttcg aaaggagaaa gatgagaaga   1380

gacaacttcg aaaggggaag aaaggatgga gacattactc ttctcttctc tgttgtagat   1440

tctgatggat tctatcagag gatttttaac ctttttaggc tttgcattca atatacaaag   1500

accgttcgaa taagaacaga aaatagtggt ttttctgtaa tgtattattt cgtagacctc   1560

aaatacttta tattcaatt                                                 1579
```

<210> SEQ ID NO 24
<211> LENGTH: 281
<212> TYPE: PRT
<213> ORGANISM: Arabidopsis thaliana

<400> SEQUENCE: 24

```
Met Gln Glu Lys Leu Phe Phe Asn Lys Lys Pro Phe Gly Ser Lys Ile
1               5                   10                  15

Ser Asp Asn Asn Glu Ile Glu Glu Leu Asp Gln Glu Asn Leu Val Val
            20                  25                  30

Thr Arg Gln Glu Val Asn Asp Asp Ser Lys Val Ala Pro Arg Asp Val
        35                  40                  45

Val Ala Thr Ser Thr Ser Val Ser Lys Lys Ala Leu Thr Leu Gly Asp
    50                  55                  60

Ile Leu Ser Leu Glu Asp Ser Gln Ser Pro Pro Asn Lys Asn Asn Thr
65                  70                  75                  80

Asn Gly Pro Glu Glu Asn Met Val His His Asn Pro His Leu Glu Ile
                85                  90                  95

Thr Glu Glu Ser Glu Ala Asp Asn Ser Cys Asp Asp Asn Asn Leu Leu
            100                 105                 110

Lys Arg Asn Leu Pro Asn Gly Phe Gly Glu Ile Ser Phe Cys Glu Ala
        115                 120                 125

Lys Ser Ser Leu Asp Tyr Ile Thr Tyr Cys Gly Pro Leu Ser Gly Ser
    130                 135                 140

Glu Asn Leu Ser Ile Arg Ser Asp Gly Thr Ser Ala Ser Ser Phe Ala
145                 150                 155                 160

Leu Pro Ile Leu Gln Ser Glu Trp Asn Ser Ser Pro Val Arg Met Gly
                165                 170                 175

Lys Ala Glu Glu Thr Gln Leu Arg Met Val Ile Ala Glu Glu Arg Lys
            180                 185                 190

Val Arg Lys Asp Lys Ala Glu Lys Thr Gln Leu Arg Lys Glu Lys Ala
        195                 200                 205
```

```
Glu Glu Ser Gln Leu Arg Glu Val Lys Ala Glu Glu Thr Gln Leu Arg
    210                 215                 220

Met Val Lys Ala Glu Glu Thr Gln Leu Arg Lys Glu Lys Ala Glu Glu
225                 230                 235                 240

Thr Gln Leu Arg Met Val Ile Ala Glu Glu Arg Gln Leu Arg Lys Glu
                245                 250                 255

Lys Asp Glu Lys Arg Gln Leu Arg Lys Gly Lys Lys Gly Trp Arg His
            260                 265                 270

Tyr Ser Ser Leu Leu Cys Cys Arg Phe
        275                 280
```

<210> SEQ ID NO 25
<211> LENGTH: 1269
<212> TYPE: DNA
<213> ORGANISM: Arabidopsis thaliana

<400> SEQUENCE: 25

```
ctctcttttt ctctctttac tattttcttc cttaccaaat atagcaacaa caaaaaaacg     60

ttttctgtga tggaggtccc gattataaac agaataggcg attttgacat ggggataaac    120

tcgataaacg acccgtcgta tttatctcga gctttggcag tctccggtgt cggaaagtta    180

catcaagctt atagtttttg gaaatggggc gccttattgc tacttgcatt ttttgcttca    240

tttacatcgt taactacaag aatcaagact ttagtcttta gattaagaaa tgtaaacgtg    300

tctctacctt cccaaactct tttatgtaat tacgacagcg actccgattg gtctttctcg    360

tcagactctt cagacgaaga gaaagatgag gacgataaca aagaagatga ctcggtcaat    420

ggcgattcac gcgttcaaag atttggttat taccatgatg atgatgataa gggtattagt    480

ggaagtgtcc cctggttgcg gcggtgcagt ggtagcttcg gagatttgtt agatttaggc    540

tcaagcggag tcgtgaagct ttgggacaat cttgatttca acggagaagg aagtccggtg    600

gcttcttttt tcagcaaatg cggctcatac tcgttattgt catcggcggt tttattagcg    660

gcggagaaga aaggatccga cggcttggaa gtgagtgcgt gggatgcacg cgttggtttt    720

ggggtgcccg cgttgctcgc ggaatggaag cagccgggaa ggttactcgg gaagatcatt    780

agggttgacg taggtgacgt ggacaagatc tacgtcggtg atgacgtcga aggagagatt    840

actgtgggag acatgaggat ggttaacggt gcgttgacgg aactgacgga atcagaggtt    900

gagaggatgg tgagaagacg cagacgccgt cattgaggct gacggtgccg ttggggagat    960

gtattgatga taaatgattg attggcatgg tagggtctaa taaagactga aaagttcaac   1020

gcaaatgcaa gtgacgaaca ttttttttatt tttgtaaata atttgtctgt cttgtatttt   1080

tttcaattta ggttttcaat tttttggcaa aaaaagaaag aaagaaatct cttattttgt   1140

tcttcgaaat aaagaaattc aacctcctgt tgtcgtgtat tttggatttc atgttgtaag   1200

tagacttgga aatgtaaggt aactctattt tttttggtta attattacat taataataat   1260

gtttaaatt                                                           1269
```

<210> SEQ ID NO 26
<211> LENGTH: 288
<212> TYPE: PRT
<213> ORGANISM: Arabidopsis thaliana

<400> SEQUENCE: 26

```
Met Glu Val Pro Ile Ile Asn Arg Ile Gly Asp Phe Asp Met Gly Ile
1               5                   10                  15

Asn Ser Ile Asn Asp Pro Ser Tyr Leu Ser Arg Ala Leu Ala Val Ser
            20                  25                  30
```

```
Gly Val Gly Lys Leu His Gln Ala Tyr Ser Phe Trp Lys Trp Gly Ala
        35                  40                  45

Leu Leu Leu Leu Ala Phe Phe Ala Ser Phe Thr Ser Leu Thr Thr Arg
    50                  55                  60

Ile Lys Thr Leu Val Phe Arg Leu Arg Asn Val Asn Val Ser Leu Pro
65                  70                  75                  80

Ser Gln Thr Leu Leu Cys Asn Tyr Asp Ser Asp Ser Asp Trp Ser Phe
                85                  90                  95

Ser Ser Asp Ser Ser Asp Glu Glu Lys Asp Glu Asp Asp Asn Lys Glu
            100                 105                 110

Asp Asp Ser Val Asn Gly Asp Ser Arg Val Gln Arg Phe Gly Tyr Tyr
        115                 120                 125

His Asp Asp Asp Asp Lys Gly Ile Ser Gly Ser Val Pro Trp Leu Arg
    130                 135                 140

Arg Cys Ser Gly Ser Phe Gly Asp Leu Leu Asp Leu Gly Ser Ser Gly
145                 150                 155                 160

Val Val Lys Leu Trp Asp Asn Leu Asp Phe Asn Gly Glu Gly Ser Pro
                165                 170                 175

Val Ala Ser Phe Phe Ser Lys Cys Gly Ser Tyr Ser Leu Leu Ser Ser
            180                 185                 190

Ala Val Leu Leu Ala Ala Glu Lys Lys Gly Ser Asp Gly Leu Glu Val
        195                 200                 205

Ser Ala Trp Asp Ala Arg Val Gly Phe Gly Val Pro Ala Leu Leu Ala
    210                 215                 220

Glu Trp Lys Gln Pro Gly Arg Leu Leu Gly Lys Ile Ile Arg Val Asp
225                 230                 235                 240

Val Gly Asp Val Asp Lys Ile Tyr Val Gly Asp Asp Val Glu Gly Glu
                245                 250                 255

Ile Thr Val Gly Asp Met Arg Met Val Asn Gly Ala Leu Thr Glu Leu
            260                 265                 270

Thr Glu Ser Glu Val Glu Arg Met Val Arg Arg Arg Arg Arg Arg His
        275                 280                 285
```

<210> SEQ ID NO 27
<211> LENGTH: 1029
<212> TYPE: DNA
<213> ORGANISM: Arabidopsis thaliana

<400> SEQUENCE: 27

```
atgcaacaac tcatgacctt gttatcacca ccactctctc attcttctct ccttcccacc      60

gtcactacca aattcgggtc accacgatta gtcactacgt gcatgggcca tgcagggcgt     120

aaaaatatca aggataaggt ggttctcatc acaggtacaa caggcacagg caagtcacgc     180

ctctcagtcg atcttgccac ccgttttttt cccgccgaga tcataaactc ggacaaaatg     240

caaatctaca agggattcga gattgtcaca aatctaatcc cactgcatga gcaaggagga     300

gtcccgcacc atcttctagg tcagttccac ccacaagacg gtgaactcac ccctgcagag     360

ttccgttctt tggcgacact gtccatctct aaactaattt ctagcaagaa actcccgatt     420

gtagttggtg gatccaactc cttcaatcac gctctactcg ccgagcgttt tgacccggat     480

attgatccat tctctcccgg atcgagtctt tcaacgatct gctctgacct aaggtacaaa     540

tgttgcatct tatgggttga tgttttagag ccggttctgt tccaacactt gtgcaatcgt     600

gtcgaccaaa tgatcgagtc gggattggtc gagcagcttg ccgaattgta cgaccctgtt     660

gtagattcgg gtcgacgact aggggttcgg aagacgatag gagtagagga gttcgaccga     720
```

```
tactttagag tataccctaa ggagatggac aagggaattt gggacttagc gagaaaggcg    780

gcgtacgagg agacagtgaa ggggatgaaa gagaggacat gtcggttggt gaagaagcag    840

aaagagaaga tcatgaagct gataagaggt ggttgggaga ttaagaggct tgacgctacg    900

gcggcaatta tggctgagct gaatcaaagt acggcaaagg gagaaggaaa gaatgggaga    960

gagatttggg aaaaacacat tgtggatgaa agtgtcgaga ttgtcaagaa gtttttgttg   1020

gaagtttag                                                           1029
```

```
<210> SEQ ID NO 28
<211> LENGTH: 342
<212> TYPE: PRT
<213> ORGANISM: Arabidopsis thaliana

<400> SEQUENCE: 28

Met Gln Gln Leu Met Thr Leu Leu Ser Pro Pro Leu Ser His Ser Ser
1               5                   10                  15

Leu Leu Pro Thr Val Thr Thr Lys Phe Gly Ser Pro Arg Leu Val Thr
            20                  25                  30

Thr Cys Met Gly His Ala Gly Arg Lys Asn Ile Lys Asp Lys Val Val
        35                  40                  45

Leu Ile Thr Gly Thr Thr Gly Thr Gly Lys Ser Arg Leu Ser Val Asp
    50                  55                  60

Leu Ala Thr Arg Phe Phe Pro Ala Glu Ile Ile Asn Ser Asp Lys Met
65                  70                  75                  80

Gln Ile Tyr Lys Gly Phe Glu Ile Val Thr Asn Leu Ile Pro Leu His
                85                  90                  95

Glu Gln Gly Gly Val Pro His His Leu Leu Gly Gln Phe His Pro Gln
            100                 105                 110

Asp Gly Glu Leu Thr Pro Ala Glu Phe Arg Ser Leu Ala Thr Leu Ser
        115                 120                 125

Ile Ser Lys Leu Ile Ser Ser Lys Lys Leu Pro Ile Val Val Gly Gly
    130                 135                 140

Ser Asn Ser Phe Asn His Ala Leu Leu Ala Glu Arg Phe Asp Pro Asp
145                 150                 155                 160

Ile Asp Pro Phe Ser Pro Gly Ser Ser Leu Ser Thr Ile Cys Ser Asp
                165                 170                 175

Leu Arg Tyr Lys Cys Cys Ile Leu Trp Val Asp Val Leu Glu Pro Val
            180                 185                 190

Leu Phe Gln His Leu Cys Asn Arg Val Asp Gln Met Ile Glu Ser Gly
        195                 200                 205

Leu Val Glu Gln Leu Ala Glu Leu Tyr Asp Pro Val Val Asp Ser Gly
    210                 215                 220

Arg Arg Leu Gly Val Arg Lys Thr Ile Gly Val Glu Glu Phe Asp Arg
225                 230                 235                 240

Tyr Phe Arg Val Tyr Pro Lys Glu Met Asp Lys Gly Ile Trp Asp Leu
                245                 250                 255

Ala Arg Lys Ala Ala Tyr Glu Glu Thr Val Lys Gly Met Lys Glu Arg
            260                 265                 270

Thr Cys Arg Leu Val Lys Lys Gln Lys Glu Lys Ile Met Lys Leu Ile
        275                 280                 285

Arg Gly Gly Trp Glu Ile Lys Arg Leu Asp Ala Thr Ala Ala Ile Met
    290                 295                 300

Ala Glu Leu Asn Gln Ser Thr Ala Lys Gly Glu Gly Lys Asn Gly Arg
305                 310                 315                 320
```

Glu Ile Trp Glu Lys His Ile Val Asp Glu Ser Val Glu Ile Val Lys
325 330 335

Lys Phe Leu Leu Glu Val
340

<210> SEQ ID NO 29
<211> LENGTH: 1299
<212> TYPE: DNA
<213> ORGANISM: Arabidopsis thaliana

<400> SEQUENCE: 29

```
atctccaacc tccaccgcat tgattcctct gcttccggtt caatgtcgct gctaaaccaa     60
ctcttcaacc gtgggatctt tggcgccaaa tgcaagacaa gcttgaactt ggcgatagct    120
cgaatgaaat tgctgcaaaa caagagagat atgcagctta aacatatgaa gaaggagata    180
gctcacttct tgcaagctgg acaagaaccc attgctcgaa ttcgggtttg atctcattct    240
gatttctgta tgttacttct tacaatcaac atcaatctct tatgttcttg tctgagattt    300
aggtggagca tgtgatcaga gaaatgaatt tatgggcagc ttatgagata ttggagctat    360
tctgcgagtt tatacttgct cgtgttccaa ttcttgaaag tgaaaaggaa tgcccgagag    420
agttgagaga ggctattgct agcattatct ttgctgctcc aaggtgctct gaagtacctg    480
atcttcttca aataaagaat ctgtttggta caaaatatgg aaaagaattt atcatggttg    540
cttctgagct tcgtccggat tctggtgtca atcgtactat cattgagaag ctttctccta    600
ccagtccatc tggagcggca aggctcaaga tgttaaagga aattgcgcag gagtacagtt    660
tgaattggga ttcttctgcc acggaagcag agttcatgaa gagccatgaa gacctactgg    720
gtggagctaa gcaaatacat cgtcaagatg gtatctctga atctcgaccg tcccaacaag    780
gctacggtca gtcttcggtt tctagggaag ttgaaagtct gcctgcagag gccacacaga    840
gattccaaaa gcttcaagct caaaacccag tgagcaaaag catgccatca tctaagctga    900
cttcagcctt tcaagctcct cctgatacta gacggaatca gactgatgta atggagatag    960
ctcgagctgc cctagctagc gctgatcgtg caacagcagc tgctcgtgct gctgcgcaac   1020
tagtgaatgt ctcttatggg gctactacac ccacagtagc agcagaaggg aagcccttaa   1080
acttaatgta gttgccacgt cgtcatttgt gaataaaagc aactgtattt gcttcataca   1140
cagaaagaag gataacgatg ttttctttgg tacttcatag gtttggaaaa atgagtatgc   1200
taaagagtat tggtagatta tgctcgagtg ttgtgacctt aggttgattc aaaagacagt   1260
gatgtttaaa tgtgacatac agatataact ctgaagttt                          1299
```

<210> SEQ ID NO 30
<211> LENGTH: 255
<212> TYPE: PRT
<213> ORGANISM: Arabidopsis thaliana

<400> SEQUENCE: 30

Met Asn Leu Trp Ala Ala Tyr Glu Ile Leu Glu Leu Phe Cys Glu Phe
1 5 10 15

Ile Leu Ala Arg Val Pro Ile Leu Glu Ser Glu Lys Glu Cys Pro Arg
20 25 30

Glu Leu Arg Glu Ala Ile Ala Ser Ile Ile Phe Ala Ala Pro Arg Cys
35 40 45

Ser Glu Val Pro Asp Leu Leu Gln Ile Lys Asn Leu Phe Gly Thr Lys
50 55 60

Tyr Gly Lys Glu Phe Ile Met Val Ala Ser Glu Leu Arg Pro Asp Ser

```
65                  70                  75                  80

Gly Val Asn Arg Thr Ile Ile Glu Lys Leu Ser Pro Thr Ser Pro Ser
                85                  90                  95

Gly Ala Ala Arg Leu Lys Met Leu Lys Glu Ile Ala Gln Glu Tyr Ser
            100                 105                 110

Leu Asn Trp Asp Ser Ser Ala Thr Glu Ala Glu Phe Met Lys Ser His
        115                 120                 125

Glu Asp Leu Leu Gly Gly Ala Lys Gln Ile His Arg Gln Asp Gly Ile
    130                 135                 140

Ser Glu Ser Arg Pro Ser Gln Gln Gly Tyr Gly Gln Ser Ser Val Ser
145                 150                 155                 160

Arg Glu Val Glu Ser Leu Pro Ala Glu Ala Thr Gln Arg Phe Gln Lys
                165                 170                 175

Leu Gln Ala Gln Asn Pro Val Ser Lys Ser Met Pro Ser Ser Lys Leu
            180                 185                 190

Thr Ser Ala Phe Gln Ala Pro Pro Asp Thr Arg Arg Asn Gln Thr Asp
        195                 200                 205

Val Met Glu Ile Ala Arg Ala Ala Leu Ala Ser Ala Asp Arg Ala Thr
    210                 215                 220

Ala Ala Ala Arg Ala Ala Ala Gln Leu Val Asn Val Ser Tyr Gly Ala
225                 230                 235                 240

Thr Thr Pro Thr Val Ala Ala Glu Gly Lys Pro Leu Asn Leu Met
                245                 250                 255
```

<210> SEQ ID NO 31
<211> LENGTH: 1421
<212> TYPE: DNA
<213> ORGANISM: Arabidopsis thaliana

<400> SEQUENCE: 31

```
ttcctctgct tccggttcaa tgtcgctgct aaaccaactc ttcaaccgtg ggatctttgg     60

cgccaaatgg tttcttcgtc ttcttctttt ctcttatacg ttgatttggg ttttgattga    120

agctagggtt tcttcaataa tttgatgcca tcgattactc ttttgcttca atttgaaatt    180

agagtttgtt atgctcttaa ttgtccataa aactgagaaa ttgaagtaaa tgttggcagc    240

aagacaagct tgaacttggc gatagctcga atgaaattgc tgcaaaacaa gagagatatg    300

cagcttaaac atatgaagaa ggagatagct cacttcttgc aagctggaca agaacccatt    360

gctcgaattc gggtttgatc tcattctgat ttctgtatgt tacttcttac aatcaacatc    420

aatctcttat gttcttgtct gagatttagg tggagcatgt gatcagagaa atgaatttat    480

gggcagctta tgagatattg gagctattct gcgagtttat acttgctcgt gttccaattc    540

ttgaaagtga aaaggaatgc ccgagagagt tgagagaggc tattgctagc attatctttg    600

ctgctccaag gtgctctgaa gtacctgatc ttcttcaaat aaagaatctg tttggtacaa    660

aatatggaaa agaatttatc atggttgctt ctgagcttcg tccggattct ggtgtcaatc    720

gtactatcat tgagaagctt tctcctacca gtccatctgg agcggcaagg ctcaagatgt    780

taaaggaaat tgcgcaggag tacagtttga attgggattc ttctgccacg gaagcagagt    840

tcatgaagag ccatgaagac ctactgggtg gagctaagca aatacatcgt caagatggta    900

tctctgaatc tcgaccgtcc caacaaggct acggtcagtc ttcggtttct agggaagttg    960

aaagtctgcc tgcagaggcc acacagagat tccaaaagct tcaagctcaa aacccagtga   1020

gcaaaagcat gccatcatct aagctgactt cagcctttca agctcctcct gatactagac   1080

ggaatcagac tgatgtaatg gagatagctc gagctgccct agctagcgct gatcgtgcaa   1140
```

cagcagctgc tcgtgctgct gcgcaactag tgaatgtctc ttatggggct actacaccca 1200
cagtagcagc agaagggaag cccttaaact taatgtagtt gccacgtcgt catttgtgaa 1260
taaaagcaac tgtatttgct tcatacacag aaagaaggat aacgatgttt tctttggtac 1320
ttcataggtt tggaaaaatg agtatgctaa agagtattgg tagattatgc tcgagtgttg 1380
tgaccttagg ttgattcaaa agacagtgat gtttaaatgt g 1421

<210> SEQ ID NO 32
<211> LENGTH: 255
<212> TYPE: PRT
<213> ORGANISM: Arabidopsis thaliana

<400> SEQUENCE: 32

Met Asn Leu Trp Ala Ala Tyr Glu Ile Leu Glu Leu Phe Cys Glu Phe
1 5 10 15

Ile Leu Ala Arg Val Pro Ile Leu Glu Ser Glu Lys Glu Cys Pro Arg
20 25 30

Glu Leu Arg Glu Ala Ile Ala Ser Ile Ile Phe Ala Ala Pro Arg Cys
35 40 45

Ser Glu Val Pro Asp Leu Leu Gln Ile Lys Asn Leu Phe Gly Thr Lys
50 55 60

Tyr Gly Lys Glu Phe Ile Met Val Ala Ser Glu Leu Arg Pro Asp Ser
65 70 75 80

Gly Val Asn Arg Thr Ile Ile Glu Lys Leu Ser Pro Thr Ser Pro Ser
85 90 95

Gly Ala Ala Arg Leu Lys Met Leu Lys Glu Ile Ala Gln Glu Tyr Ser
100 105 110

Leu Asn Trp Asp Ser Ser Ala Thr Glu Ala Glu Phe Met Lys Ser His
115 120 125

Glu Asp Leu Leu Gly Gly Ala Lys Gln Ile His Arg Gln Asp Gly Ile
130 135 140

Ser Glu Ser Arg Pro Ser Gln Gln Gly Tyr Gly Gln Ser Ser Val Ser
145 150 155 160

Arg Glu Val Glu Ser Leu Pro Ala Glu Ala Thr Gln Arg Phe Gln Lys
165 170 175

Leu Gln Ala Gln Asn Pro Val Ser Lys Ser Met Pro Ser Ser Lys Leu
180 185 190

Thr Ser Ala Phe Gln Ala Pro Pro Asp Thr Arg Arg Asn Gln Thr Asp
195 200 205

Val Met Glu Ile Ala Arg Ala Ala Leu Ala Ser Ala Asp Arg Ala Thr
210 215 220

Ala Ala Ala Arg Ala Ala Gln Leu Val Asn Val Ser Tyr Gly Ala
225 230 235 240

Thr Thr Pro Thr Val Ala Ala Glu Gly Lys Pro Leu Asn Leu Met
245 250 255

<210> SEQ ID NO 33
<211> LENGTH: 1305
<212> TYPE: DNA
<213> ORGANISM: Arabidopsis thaliana

<400> SEQUENCE: 33
atcttcttcg ttttcctttt tcctcaatcg acgacgatca atctccaacc tccaccgcat 60
tgattcctct gcttccggtt caatgtcgct gctaaaccaa ctcttcaacc gtgggatctt 120
tggcgccaaa tgcaagacaa gcttgaactt ggcgatagct cgaatgaaat tgctgcaaaa 180

```
caagagagat atgcagctta aacatatgaa gaaggagata gctcacttct tgcaagctgg    240

acaagaaccc attgctcgaa ttcgggtgga gcatgtgatc agagaaatga atttatgggc    300

agcttatgag atattggagc tattctgcga gtttatactt gctcgtgttc caattcttga    360

aagtgaaaag gaatgcccga gagagttgag agaggctatt gctagcatta tctttgctgc    420

tccaaggtgc tctgaagtac ctgatcttct tcaaataaag aatctgtttg gtacaaaata    480

tggaaaagaa tttatcatgg ttgcttctga gcttcgtccg gattctggtg tcaatcgtac    540

tatcattgag aagctttctc ctaccagtcc atctggagcg gcaaggctca agatgttaaa    600

ggaaattgcg caggagtaca gtttgaattg ggattcttct gccacggaag cagagttcat    660

gaagagccat gaagacctac tgggtggagc taagcaaata catcgtcaag atggtatctc    720

tgaatctcga ccgtcccaac aaggctacgg tcagtcttcg gtttctaggg aagttgaaag    780

tctgcctgca gaggccacac agagattcca aaagcttcaa gctcaaaacc cagtgagcaa    840

aagcatgcca tcatctaagc tgacttcagc ctttcaagct cctcctgata ctagacggaa    900

tcagactgat gtaatggaga tagctcgagc tgccctagct agcgctgatc gtgcaacagc    960

agctgctcgt gctgctgcgc aactagtgaa tgtctcttat ggggctacta cacccacagt   1020

agcagcagaa gggaagccct taaacttaat gtagttgcca cgtcgtcatt tgtgaataaa   1080

agcaactgta tttgcttcat acacagaaag aaggataacg atgttttctt tggtacttca   1140

taggtttgga aaaatgagta tgctaaagag tattggtaga ttatgctcga gtgttgtgac   1200

cttaggttga ttcaaaagac agtgatgttt aaatgtgaca tacagatata actctgaagt   1260

ttgttggttt tacaaaatct atgcagaaaa aacaacatta tcatg                   1305
```

```
<210> SEQ ID NO 34
<211> LENGTH: 323
<212> TYPE: PRT
<213> ORGANISM: Arabidopsis thaliana

<400> SEQUENCE: 34

Met Ser Leu Leu Asn Gln Leu Phe Asn Arg Gly Ile Phe Gly Ala Lys
1               5                   10                  15

Cys Lys Thr Ser Leu Asn Leu Ala Ile Ala Arg Met Lys Leu Leu Gln
            20                  25                  30

Asn Lys Arg Asp Met Gln Leu Lys His Met Lys Lys Glu Ile Ala His
        35                  40                  45

Phe Leu Gln Ala Gly Gln Glu Pro Ile Ala Arg Ile Arg Val Glu His
    50                  55                  60

Val Ile Arg Glu Met Asn Leu Trp Ala Ala Tyr Glu Ile Leu Glu Leu
65                  70                  75                  80

Phe Cys Glu Phe Ile Leu Ala Arg Val Pro Ile Leu Glu Ser Glu Lys
                85                  90                  95

Glu Cys Pro Arg Glu Leu Arg Glu Ala Ile Ala Ser Ile Ile Phe Ala
            100                 105                 110

Ala Pro Arg Cys Ser Glu Val Pro Asp Leu Leu Gln Ile Lys Asn Leu
        115                 120                 125

Phe Gly Thr Lys Tyr Gly Lys Glu Phe Ile Met Val Ala Ser Glu Leu
    130                 135                 140

Arg Pro Asp Ser Gly Val Asn Arg Thr Ile Ile Glu Lys Leu Ser Pro
145                 150                 155                 160

Thr Ser Pro Ser Gly Ala Ala Arg Leu Lys Met Leu Lys Glu Ile Ala
                165                 170                 175
```

```
Gln Glu Tyr Ser Leu Asn Trp Asp Ser Ser Ala Thr Glu Ala Glu Phe
            180                 185                 190

Met Lys Ser His Glu Asp Leu Leu Gly Gly Ala Lys Gln Ile His Arg
        195                 200                 205

Gln Asp Gly Ile Ser Glu Ser Arg Pro Ser Gln Gln Gly Tyr Gly Gln
    210                 215                 220

Ser Ser Val Ser Arg Glu Val Glu Ser Leu Pro Ala Glu Ala Thr Gln
225                 230                 235                 240

Arg Phe Gln Lys Leu Gln Ala Gln Asn Pro Val Ser Lys Ser Met Pro
                245                 250                 255

Ser Ser Lys Leu Thr Ser Ala Phe Gln Ala Pro Pro Asp Thr Arg Arg
            260                 265                 270

Asn Gln Thr Asp Val Met Glu Ile Ala Arg Ala Ala Leu Ala Ser Ala
        275                 280                 285

Asp Arg Ala Thr Ala Ala Ala Arg Ala Ala Ala Gln Leu Val Asn Val
    290                 295                 300

Ser Tyr Gly Ala Thr Thr Pro Thr Val Ala Ala Glu Gly Lys Pro Leu
305                 310                 315                 320

Asn Leu Met


<210> SEQ ID NO 35
<211> LENGTH: 1527
<212> TYPE: DNA
<213> ORGANISM: Arabidopsis thaliana

<400> SEQUENCE: 35

aggtcgcaac accgcaatag atcttttccc caagtttcag acaaacataa agcagcagag     60

aaaattttca agtttcaaag agcttttccc tcaccaagca aaatttggat atttgtcagc    120

aaaatctgca gctaaattgg gacttgtctt gttagttcaa agattgaaac ttttttggtt    180

aattgtttgg cggaagaaga tttacaatgg gagaggagca tccgagaaag cggtctagac    240

aacattttga agcggaggcg agaaacgtat cgttgtttga atcccctcaa tgcgaaacct    300

ccaagtggta tttcagcagg gaagagattg agcgtttctc tccatccaga aaagatggga    360

ttgatcttgt gaaggagtcg tttttacggt cttcgtattg caccttcctg caaagacttg    420

gcatgaagct tcatgtgtcc caggttacaa tatcatgtgc aatggtgatg tgccacaggt    480

tttacatgcg ccaatctcat gcaaaaaatg actggcagac aatagcgact tccagtctgt    540

tcctcgcttg caaagctgaa gatgagccat gtcaactgtc cagtgtcgtt gtagcgtctt    600

atgaaataat ttatgagtgg gatccttctg cctcaattag aatccatcaa actgagtgtt    660

atcatgaatt taaagaaatt attttgtccg ggaaagtctt tctgctgagc acaagtgctt    720

tccatttaga cattgaactt ccctacaaac ctctggctgc ggctttgaat agactgaacg    780

cttggcctga ccttgcaaca gctgcatgga attttgtgca tgactggatt cgaaccacac    840

tatgcttgca gtacaaaccc catgttattg caacagccac tgtgcaccta gctgctacgt    900

ttcagaatgc gaaagtaggc agcaggagag attggtggtt ggagtttgga gttacaacta    960

agctattaaa agaggtaatc caggagatgt gcacactgat agaagtggac agaaggagga   1020

atatgccacc tccacctcca cctccaagaa gagagttaag ttgggcaata cctgcagccg   1080

taaagccggt ccatatggct agagcttatc cgtttcacag ctaccctttg cagtcctata   1140

gacaggctgg catctggtga gccattgttg agcagcatga agatgtaatc tctcttagag   1200

tcttgagttg gtttagcaat aaaagatttc cgtagagact catgagagag gcagtgtagc   1260

attatataga gatccgagtg aggtgcttct gtctaagtta agcgtctcat gtatgaccaa   1320
```

```
agtggattct ctcgagattc ttggtctctg ttctcgatag agagagatta tgtatagaag   1380

tgtcccattc acatgttata atactagctg actttatatc gtttgtatat ctggaatcta   1440

tgtttttggt ttctttaaaa agtttaaagt tgttttgatt ttgactaatt ctctcattgt   1500

taagtaattt ggtttttgat gaagtgc                                        1527


<210> SEQ ID NO 36
<211> LENGTH: 317
<212> TYPE: PRT
<213> ORGANISM: Arabidopsis thaliana

<400> SEQUENCE: 36

Met Gly Glu Glu His Pro Arg Lys Arg Ser Arg Gln His Phe Glu Ala
1               5                   10                  15

Glu Ala Arg Asn Val Ser Leu Phe Glu Ser Pro Gln Cys Glu Thr Ser
            20                  25                  30

Lys Trp Tyr Phe Ser Arg Glu Glu Ile Glu Arg Phe Ser Pro Ser Arg
        35                  40                  45

Lys Asp Gly Ile Asp Leu Val Lys Glu Ser Phe Leu Arg Ser Ser Tyr
    50                  55                  60

Cys Thr Phe Leu Gln Arg Leu Gly Met Lys Leu His Val Ser Gln Val
65                  70                  75                  80

Thr Ile Ser Cys Ala Met Val Met Cys His Arg Phe Tyr Met Arg Gln
                85                  90                  95

Ser His Ala Lys Asn Asp Trp Gln Thr Ile Ala Thr Ser Ser Leu Phe
            100                 105                 110

Leu Ala Cys Lys Ala Glu Asp Glu Pro Cys Gln Leu Ser Ser Val Val
        115                 120                 125

Val Ala Ser Tyr Glu Ile Ile Tyr Glu Trp Asp Pro Ser Ala Ser Ile
    130                 135                 140

Arg Ile His Gln Thr Glu Cys Tyr His Glu Phe Lys Glu Ile Ile Leu
145                 150                 155                 160

Ser Gly Glu Ser Leu Leu Leu Ser Thr Ser Ala Phe His Leu Asp Ile
                165                 170                 175

Glu Leu Pro Tyr Lys Pro Leu Ala Ala Ala Leu Asn Arg Leu Asn Ala
            180                 185                 190

Trp Pro Asp Leu Ala Thr Ala Ala Trp Asn Phe Val His Asp Trp Ile
        195                 200                 205

Arg Thr Thr Leu Cys Leu Gln Tyr Lys Pro His Val Ile Ala Thr Ala
    210                 215                 220

Thr Val His Leu Ala Ala Thr Phe Gln Asn Ala Lys Val Gly Ser Arg
225                 230                 235                 240

Arg Asp Trp Trp Leu Glu Phe Gly Val Thr Thr Lys Leu Leu Lys Glu
                245                 250                 255

Val Ile Gln Glu Met Cys Thr Leu Ile Glu Val Asp Arg Arg Arg Asn
            260                 265                 270

Met Pro Pro Pro Pro Pro Pro Pro Arg Arg Glu Leu Ser Trp Ala Ile
        275                 280                 285

Pro Ala Ala Val Lys Pro Val His Met Ala Arg Ala Tyr Pro Phe His
    290                 295                 300

Ser Tyr Pro Leu Gln Ser Tyr Arg Gln Ala Gly Ile Trp
305                 310                 315


<210> SEQ ID NO 37
<211> LENGTH: 444
```

<212> TYPE: DNA
<213> ORGANISM: Arabidopsis thaliana

<400> SEQUENCE: 37

```
atggatataa aatcggaaac agagcaatac aaaagaaaag cagagataga gaaacacaca     60

aaggagccaa ataaacacag agacgaagca gtgctccaaa atagagctgg gaggcacaga    120

gaccgagccg taatagatca caaaagcgaa gaaagagaga gagaaagcgt acagaatgtt    180

acagagatga gtgggattga gagatctgag ggtgagtggt cgccgccggt ggaaggaatt    240

accgacgagg agctgccgtc tcactcgccg atggatgatc tagggtttgc tttgttcgcg    300

agttggggga gaaagacaga gagacagaga atgggatctc ctgacataag gatttatatt    360

tttaatccga taaaaaagat aataataatg gaaactagaa tccggtttgg tctagaatgg    420

aaaccaagcg gttttggttc ttga                                            444
```

<210> SEQ ID NO 38
<211> LENGTH: 147
<212> TYPE: PRT
<213> ORGANISM: Arabidopsis thaliana

<400> SEQUENCE: 38

```
Met Asp Ile Lys Ser Glu Thr Glu Gln Tyr Lys Arg Lys Ala Glu Ile
1               5                   10                  15

Glu Lys His Thr Lys Glu Pro Asn Lys His Arg Asp Glu Ala Val Leu
            20                  25                  30

Gln Asn Arg Ala Gly Arg His Arg Asp Arg Ala Val Ile Asp His Lys
        35                  40                  45

Ser Glu Glu Arg Glu Arg Glu Ser Val Gln Asn Val Thr Glu Met Ser
    50                  55                  60

Gly Ile Glu Arg Ser Glu Gly Glu Trp Ser Pro Pro Val Glu Gly Ile
65                  70                  75                  80

Thr Asp Glu Glu Leu Pro Ser His Ser Pro Met Asp Asp Leu Gly Phe
                85                  90                  95

Ala Leu Phe Ala Ser Trp Gly Arg Lys Thr Glu Arg Gln Arg Met Gly
            100                 105                 110

Ser Pro Asp Ile Arg Ile Tyr Ile Phe Asn Pro Ile Lys Lys Ile Ile
        115                 120                 125

Ile Met Glu Thr Arg Ile Arg Phe Gly Leu Glu Trp Lys Pro Ser Gly
    130                 135                 140

Phe Gly Ser
145
```

<210> SEQ ID NO 39
<211> LENGTH: 1381
<212> TYPE: DNA
<213> ORGANISM: Arabidopsis thaliana

<400> SEQUENCE: 39

```
attctctgtc tctctgtctt tctcccccaa ctcgcgaaca aagcaaaccc tagatcatcc     60

atcggcgagt gagacggcag ctcctcgtcg gtaattcctt ccaccggcgg cgaccactca    120

ccctcagatc tctcaatccc actcatctct gtaacattct ggtggaaatt ctgccatggc    180

ggagcatttg gcttcaatct ttggtactga gaaagacaga gtgaattgcc ctttctactt    240

caagattggc gcttgccgtc atggtgaccg gtgctcgcgt cttcacaacc gtcctaccat    300

ctccccaaca ctccttcttt caaacatgta ccaaaggcct gacatgatta cccctggtgt    360

tgacgctcag ggccaaccac tcgacccgcg taagattcag gagcactttg aggatttctt    420
```

```
tgaggatctt tttgaggagc ttggaaagtt tggcgagata gagagcctca acatttgtga    480

caaccttgct gaccacatga ttggcaacgt atatgttcag tttaaggaag aggatcaggc    540

tgcagctgct ttgcaggctc tgcaaggtag gttctattca ggacgtccca tcattgctga    600

tttctctcct gtgacggatt tccgcgaagc cacgtgtagg cagtatgaag aaaacaactg    660

caaccgtggt gggtactgta atttcatgca tgtgaagctt gtttcgaggg aactaaggag    720

aaaactcttt gggagatatc ggcgatcata ccgcagagga agtagaagca ggagcagaag    780

caggagtatt agccccagga acaagagaga taatgaccga cgtgatcctt ctcacaggga    840

attcagtcat cgggacagag atcgcgagtt ttaccgtcat ggaagtggaa aaaggagcag    900

tgagaggtcg gagaggcaag agagggacgg ttcaaggggt aggagacaag caagccctaa    960

acgaggaggg agcccgggtg gcgggaggga aggaagtgag gagaggaggg caaggattga   1020

gcaatggaac agagaacggg aggagaagga agagggagga gcataaaaac agttgtttac   1080

tcaaatcaca attgctgcta tgtggtttct gcgtctgctt ctctgcgttt attctgaaat   1140

cggtaaaatc tggtgatgga tttttcattt ggctgttcta atttggaact tgaaatgagt   1200

ggaatcaact tctttagatt ataaaatgtt tggggttact ttcttgtagt tttgattagg   1260

aaaaaccgct ctgtcccctt gttattgatt ttcaccagtg ttctttagaa ctttgtacta   1320

tcttctgttg gttaaaactt aaaagagttc tagtttaatt cgaagttgtc tattgttctt   1380

c                                                                   1381
```

```
<210> SEQ ID NO 40
<211> LENGTH: 296
<212> TYPE: PRT
<213> ORGANISM: Arabidopsis thaliana

<400> SEQUENCE: 40

Met Ala Glu His Leu Ala Ser Ile Phe Gly Thr Glu Lys Asp Arg Val
1               5                   10                  15

Asn Cys Pro Phe Tyr Phe Lys Ile Gly Ala Cys Arg His Gly Asp Arg
            20                  25                  30

Cys Ser Arg Leu His Asn Arg Pro Thr Ile Ser Pro Thr Leu Leu Leu
        35                  40                  45

Ser Asn Met Tyr Gln Arg Pro Asp Met Ile Thr Pro Gly Val Asp Ala
    50                  55                  60

Gln Gly Gln Pro Leu Asp Pro Arg Lys Ile Gln Glu His Phe Glu Asp
65                  70                  75                  80

Phe Phe Glu Asp Leu Phe Glu Glu Leu Gly Lys Phe Gly Glu Ile Glu
                85                  90                  95

Ser Leu Asn Ile Cys Asp Asn Leu Ala Asp His Met Ile Gly Asn Val
            100                 105                 110

Tyr Val Gln Phe Lys Glu Glu Asp Gln Ala Ala Ala Ala Leu Gln Ala
        115                 120                 125

Leu Gln Gly Arg Phe Tyr Ser Gly Arg Pro Ile Ile Ala Asp Phe Ser
    130                 135                 140

Pro Val Thr Asp Phe Arg Glu Ala Thr Cys Arg Gln Tyr Glu Glu Asn
145                 150                 155                 160

Asn Cys Asn Arg Gly Gly Tyr Cys Asn Phe Met His Val Lys Leu Val
                165                 170                 175

Ser Arg Glu Leu Arg Arg Lys Leu Phe Gly Arg Tyr Arg Arg Ser Tyr
            180                 185                 190

Arg Arg Gly Ser Arg Ser Arg Ser Arg Ser Arg Ser Ile Ser Pro Arg
```

```
        195                 200                 205

Asn Lys Arg Asp Asn Asp Arg Arg Asp Pro Ser His Arg Glu Phe Ser
    210                 215                 220

His Arg Asp Arg Asp Arg Glu Phe Tyr Arg His Gly Ser Gly Lys Arg
225                 230                 235                 240

Ser Ser Glu Arg Ser Glu Arg Gln Glu Arg Asp Gly Ser Arg Gly Arg
                245                 250                 255

Arg Gln Ala Ser Pro Lys Arg Gly Gly Ser Pro Gly Gly Gly Arg Glu
            260                 265                 270

Gly Ser Glu Glu Arg Arg Ala Arg Ile Glu Gln Trp Asn Arg Glu Arg
        275                 280                 285

Glu Glu Lys Glu Glu Gly Gly Ala
    290                 295


<210> SEQ ID NO 41
<211> LENGTH: 1824
<212> TYPE: DNA
<213> ORGANISM: Arabidopsis thaliana

<400> SEQUENCE: 41

gaaactcttc aaaaatcatc attctttttc atctttcttt acacacaaac acacatacac      60

acacatatat aatacagaga tcaggtataa taaatactta tatatatagc atcatcaact     120

ctcatacata tatggactct gctaatctcc atcagcttca agatcaatta cagcttgtgg     180

ggtcttcttc atcttcttct tccttagaca ataactctga cccttcttgc tatggagctt     240

catctgccca tcaatggagc ccaggaggta tttctttgaa tagtgtgagc ttgagtcata     300

attataacaa tgagatgtta aacacaagag ctcacaacaa caacaacaac aacaacacaa     360

gtgaatgtat gagtctctcc agcatccaca atcactcctt gatccaacaa caagactttc     420

ctttacaatg gcctcatgac caatcttcat atcaacatca tgaaggactt ctcaagatca     480

aagaagagct ttcctcatca actatctcag accatcaaga aggcatatcc aagttcacag     540

acatgttaaa tagtccagtg ataacaaact atttgaagat caatgaacat aaggactaca     600

ctgagaagct tcttctcaag agtatgtctt ctggattccc gatcaatgga gactatggta     660

gcagccttcc ctcttcttct tcttcctctt caccttcgtc tcagtcgcat agaggcaact     720

tcagtcagat ttacccaagc gtaaacatat cgagtttgag cgaatctcgg aagatgagca     780

tggacgacat gagtaacatc tcaagaccat ttgatataaa catgcaggtt tttgatggaa     840

gattgtttga aggaaatgta ttagttcctc cttttaacgc tcaagagatt agtagtcttg     900

ggatgagcag aggaagcctt ccttcttttg gcctcccttt tcatcatcat ctgcagcaaa     960

cacttcccca cctttcttct tcccctactc atcaaatgga aatgttcagc aatgaacctc    1020

aaacaagtga agggaagagg cataacttct tgatggcaac aaaagcagga gaaaatgctt    1080

ccaagaaacc gcgcgtggaa tcacgctcct cttgcccacc cttcaaggtg aggaaagaaa    1140

agttaggaga cagaatagca gctctgcagc agttggtttc acccttttggg aagacagata    1200

cagcatctgt gttaatggaa gcaattggat acatcaaatt cctacagagc cagatcgaga    1260

ctttaagcgt cccctacatg agagcatcta ggaaccgacc cggaaaagcc tcccagctgg    1320

tctcacaatc acaagaaggg gatgaggaag agacgagaga tcttagaagc cgtgggctat    1380

gtctagtgcc gttatcatgc atgacttatg ttaccggaga tggtggggat ggaggaggcg    1440

gtgttggtac tggtttttgg ccaacgccac ctggttttgg tggcggaact tagccgtgga    1500

cttaacaaac cgtaggacta tgatgagtac atttatcgga cttggaggta gagaataaga    1560
```

```
agaaatgtta aaggtggagt attagttctt taatctcttt tggttttggt ttattaattg   1620

aaattttcgg ttttgatagt ggagcaaagt tggtcgtcct gattagaaag aagtgttaca   1680

ggatagacca gctttgatcc atttaagatt agtagtgaga cttgacgata tgtttctact   1740

tacatgatgg gctgtggggg ctacataaaa tatcaaatag ctttggatta ttttgttaaa   1800

tctcttttgt agataatgtg tcaa                                          1824


<210> SEQ ID NO 42
<211> LENGTH: 453
<212> TYPE: PRT
<213> ORGANISM: Arabidopsis thaliana

<400> SEQUENCE: 42

Met Asp Ser Ala Asn Leu His Gln Leu Gln Asp Gln Leu Gln Leu Val
1               5                   10                  15

Gly Ser Ser Ser Ser Ser Ser Ser Leu Asp Asn Asn Ser Asp Pro Ser
            20                  25                  30

Cys Tyr Gly Ala Ser Ser Ala His Gln Trp Ser Pro Gly Gly Ile Ser
        35                  40                  45

Leu Asn Ser Val Ser Leu Ser His Asn Tyr Asn Asn Glu Met Leu Asn
    50                  55                  60

Thr Arg Ala His Asn Asn Asn Asn Asn Asn Asn Thr Ser Glu Cys Met
65                  70                  75                  80

Ser Leu Ser Ser Ile His Asn His Ser Leu Ile Gln Gln Gln Asp Phe
                85                  90                  95

Pro Leu Gln Trp Pro His Asp Gln Ser Ser Tyr Gln His His Glu Gly
            100                 105                 110

Leu Leu Lys Ile Lys Glu Glu Leu Ser Ser Ser Thr Ile Ser Asp His
        115                 120                 125

Gln Glu Gly Ile Ser Lys Phe Thr Asp Met Leu Asn Ser Pro Val Ile
    130                 135                 140

Thr Asn Tyr Leu Lys Ile Asn Glu His Lys Asp Tyr Thr Glu Lys Leu
145                 150                 155                 160

Leu Leu Lys Ser Met Ser Ser Gly Phe Pro Ile Asn Gly Asp Tyr Gly
                165                 170                 175

Ser Ser Leu Pro Ser Ser Ser Ser Ser Ser Ser Pro Ser Ser Gln Ser
            180                 185                 190

His Arg Gly Asn Phe Ser Gln Ile Tyr Pro Ser Val Asn Ile Ser Ser
        195                 200                 205

Leu Ser Glu Ser Arg Lys Met Ser Met Asp Asp Met Ser Asn Ile Ser
    210                 215                 220

Arg Pro Phe Asp Ile Asn Met Gln Val Phe Asp Gly Arg Leu Phe Glu
225                 230                 235                 240

Gly Asn Val Leu Val Pro Pro Phe Asn Ala Gln Glu Ile Ser Ser Leu
                245                 250                 255

Gly Met Ser Arg Gly Ser Leu Pro Ser Phe Gly Leu Pro Phe His His
            260                 265                 270

His Leu Gln Gln Thr Leu Pro His Leu Ser Ser Ser Pro Thr His Gln
        275                 280                 285

Met Glu Met Phe Ser Asn Glu Pro Gln Thr Ser Glu Gly Lys Arg His
    290                 295                 300

Asn Phe Leu Met Ala Thr Lys Ala Gly Glu Asn Ala Ser Lys Lys Pro
305                 310                 315                 320

Arg Val Glu Ser Arg Ser Ser Cys Pro Pro Phe Lys Val Arg Lys Glu
                325                 330                 335
```

```
Lys Leu Gly Asp Arg Ile Ala Ala Leu Gln Gln Leu Val Ser Pro Phe
            340                 345                 350

Gly Lys Thr Asp Thr Ala Ser Val Leu Met Glu Ala Ile Gly Tyr Ile
        355                 360                 365

Lys Phe Leu Gln Ser Gln Ile Glu Thr Leu Ser Val Pro Tyr Met Arg
    370                 375                 380

Ala Ser Arg Asn Arg Pro Gly Lys Ala Ser Gln Leu Val Ser Gln Ser
385                 390                 395                 400

Gln Glu Gly Asp Glu Glu Glu Thr Arg Asp Leu Arg Ser Arg Gly Leu
                405                 410                 415

Cys Leu Val Pro Leu Ser Cys Met Thr Tyr Val Thr Gly Asp Gly Gly
            420                 425                 430

Asp Gly Gly Gly Gly Val Gly Thr Gly Phe Trp Pro Thr Pro Pro Gly
        435                 440                 445

Phe Gly Gly Gly Thr
    450
```

<210> SEQ ID NO 43
<211> LENGTH: 1677
<212> TYPE: DNA
<213> ORGANISM: Arabidopsis thaliana

<400> SEQUENCE: 43

```
atggctcgtg tttacatgga gacgatgata caaaaatgcg tcagcttctc ccaaatcaaa     60

caactccaat ctcacttcct caccgccggc catttccaat cttcctttct ccgttctcgt    120

cttctcgaac gctgcgcaat ctcaccattc ggagaccttt ccttcgccgt acaaattttc    180

cggtacatcc ctaaaccttt aaccaatgat tggaacgcaa tcatccgcgg attcgccgga    240

agttctcatc cttcacttgc gttttcatgg tatcgttcca tgttgcagca atcttcgtca    300

tcgtcggcta tatgtagagt cgatgctttg acttgttctt ttactcttaa agcttgtgca    360

cgtgcgcttt gttcttccgc tatggatcaa cttcattgtc agattaaccg tcggggatta    420

tccgctgatt cgcttctttg tactacgttg cttgatgctt actctaaaaa cggagattta    480

attagtgcgt ataagttgtt cgatgaaatg cctgtgagag atgttgcgtc gtggaacgcg    540

ttgatcgcgg ggttagtgtc tggtaatcga gcgagtgagg cgatggagtt gtataagaga    600

atggaaacgg aaggaattag aagaagtgaa gtaactgttg ttgctgcttt aggagcttgt    660

tctcatttgg gtgatgttaa ggaaggtgaa aatatcttcc atggatacag taacgataat    720

gtgattgtta gtaacgcggc tattgatatg tattcgaaat gcgggtttgt tgataaagct    780

tatcaagtgt ttgaacaatt cactggtaag aagagtgttg ttacatggaa cactatgatt    840

acagggtttg cagtgcatgg agaagcacat agagcgttgg agatttttga caagttggag    900

gataatggta ttaagcctga tgatgtctcg tacttagctg ctttaactgc gtgtagacat    960

gcggggttag tggagtatgg tttgtctgta ttcaataata tggcttgtaa gggcgttgag   1020

cgtaacatga agcactatgg ttgtgtggtt gatctgttaa gccgtgcagg aaggttgaga   1080

gaagctcacg atatcatatg ttcaatgtcg atgattccgg atcctgtttt gtggcagagc   1140

cttcttggag cttcggagat ttatagtgat gttgaaatgg ctgagattgc ttctagggaa   1200

ataaaggaaa tgggagttaa caatgatggt gattttgtgt tgctatcgaa tgtttatgct   1260

gcgcagggac ggtggaaaga tgtaggacga gtgagagatg atatggaaag caaacaagtg   1320

aagaaaattc caggtcttag ctacatagaa gccaaaggaa cgattcatga attctacaac   1380

agtgacaaga gccatgaaca gtggagagag atttatgaga agatcgatga gatcaggttc   1440
```

aagataagag aggatggtta cgtggcgcag acaggacttg tgttgcacga cataggagag 1500
gaagagaaag agaacgcttt gtgctatcac agcgagaaat tggcggtggc ctacggactg 1560
atgatgatgg atggtgcgga cgaggagagt ccgttcggtt tcataggttc aaagatggtt 1620
cttgctcttg cagagatttt tggtaacgtt acaaaattaa gagggtggca attttaa 1677

<210> SEQ ID NO 44
<211> LENGTH: 558
<212> TYPE: PRT
<213> ORGANISM: Arabidopsis thaliana

<400> SEQUENCE: 44

```
Met Ala Arg Val Tyr Met Glu Thr Met Ile Gln Lys Cys Val Ser Phe
1               5                   10                  15

Ser Gln Ile Lys Gln Leu Gln Ser His Phe Leu Thr Ala Gly His Phe
            20                  25                  30

Gln Ser Ser Phe Leu Arg Ser Arg Leu Leu Glu Arg Cys Ala Ile Ser
        35                  40                  45

Pro Phe Gly Asp Leu Ser Phe Ala Val Gln Ile Phe Arg Tyr Ile Pro
    50                  55                  60

Lys Pro Leu Thr Asn Asp Trp Asn Ala Ile Ile Arg Gly Phe Ala Gly
65                  70                  75                  80

Ser Ser His Pro Ser Leu Ala Phe Ser Trp Tyr Arg Ser Met Leu Gln
                85                  90                  95

Gln Ser Ser Ser Ser Ser Ala Ile Cys Arg Val Asp Ala Leu Thr Cys
            100                 105                 110

Ser Phe Thr Leu Lys Ala Cys Ala Arg Ala Leu Cys Ser Ser Ala Met
        115                 120                 125

Asp Gln Leu His Cys Gln Ile Asn Arg Arg Gly Leu Ser Ala Asp Ser
    130                 135                 140

Leu Leu Cys Thr Thr Leu Leu Asp Ala Tyr Ser Lys Asn Gly Asp Leu
145                 150                 155                 160

Ile Ser Ala Tyr Lys Leu Phe Asp Glu Met Pro Val Arg Asp Val Ala
                165                 170                 175

Ser Trp Asn Ala Leu Ile Ala Gly Leu Val Ser Gly Asn Arg Ala Ser
            180                 185                 190

Glu Ala Met Glu Leu Tyr Lys Arg Met Glu Thr Glu Gly Ile Arg Arg
        195                 200                 205

Ser Glu Val Thr Val Val Ala Ala Leu Gly Ala Cys Ser His Leu Gly
    210                 215                 220

Asp Val Lys Glu Gly Glu Asn Ile Phe His Gly Tyr Ser Asn Asp Asn
225                 230                 235                 240

Val Ile Val Ser Asn Ala Ala Ile Asp Met Tyr Ser Lys Cys Gly Phe
                245                 250                 255

Val Asp Lys Ala Tyr Gln Val Phe Glu Gln Phe Thr Gly Lys Lys Ser
            260                 265                 270

Val Val Thr Trp Asn Thr Met Ile Thr Gly Phe Ala Val His Gly Glu
        275                 280                 285

Ala His Arg Ala Leu Glu Ile Phe Asp Lys Leu Glu Asp Asn Gly Ile
    290                 295                 300

Lys Pro Asp Asp Val Ser Tyr Leu Ala Ala Leu Thr Ala Cys Arg His
305                 310                 315                 320

Ala Gly Leu Val Glu Tyr Gly Leu Ser Val Phe Asn Asn Met Ala Cys
                325                 330                 335
```

```
Lys Gly Val Glu Arg Asn Met Lys His Tyr Gly Cys Val Val Asp Leu
            340                 345                 350

Leu Ser Arg Ala Gly Arg Leu Arg Glu Ala His Asp Ile Ile Cys Ser
        355                 360                 365

Met Ser Met Ile Pro Asp Pro Val Leu Trp Gln Ser Leu Leu Gly Ala
    370                 375                 380

Ser Glu Ile Tyr Ser Asp Val Glu Met Ala Glu Ile Ala Ser Arg Glu
385                 390                 395                 400

Ile Lys Glu Met Gly Val Asn Asn Asp Gly Asp Phe Val Leu Leu Ser
                405                 410                 415

Asn Val Tyr Ala Ala Gln Gly Arg Trp Lys Asp Val Gly Arg Val Arg
            420                 425                 430

Asp Asp Met Glu Ser Lys Gln Val Lys Lys Ile Pro Gly Leu Ser Tyr
        435                 440                 445

Ile Glu Ala Lys Gly Thr Ile His Glu Phe Tyr Asn Ser Asp Lys Ser
    450                 455                 460

His Glu Gln Trp Arg Glu Ile Tyr Glu Lys Ile Asp Glu Ile Arg Phe
465                 470                 475                 480

Lys Ile Arg Glu Asp Gly Tyr Val Ala Gln Thr Gly Leu Val Leu His
                485                 490                 495

Asp Ile Gly Glu Glu Glu Lys Glu Asn Ala Leu Cys Tyr His Ser Glu
            500                 505                 510

Lys Leu Ala Val Ala Tyr Gly Leu Met Met Met Asp Gly Ala Asp Glu
        515                 520                 525

Glu Ser Pro Phe Gly Phe Ile Gly Ser Lys Met Val Leu Ala Leu Ala
    530                 535                 540

Glu Ile Phe Gly Asn Val Thr Lys Leu Arg Gly Trp Gln Phe
545                 550                 555


<210> SEQ ID NO 45
<211> LENGTH: 1935
<212> TYPE: DNA
<213> ORGANISM: Arabidopsis thaliana

<400> SEQUENCE: 45

atggaaaata atggagaaat gaatgcacag cctgaattat cagttgatat aaccaagact     60

tatatgtatg agaaattatg gaacatatgt gctggacctt tgtgtgttct tccgaaacct    120

ggagaaaaag tttattactt tcctcaaggg cacatcgagc tcattgagaa ttctacaaga    180

gatgaattgg atcatatcag gccaattttt gatcttccat ctaagcttcg atgtcgtgtt    240

gtggctattg atcgtaaggt agacaaaaat acagatgaag tctatgctca gatttcgtta    300

atgcctgata caacagaagt tatgacccat aatactacta tggatactcg aagaccaata    360

gtttattttt ttagtaaaat tttaacggcg tctgacgtca gtttaagtgg tggattaatt    420

attcccaaac aatatgccat tgagtgtttt cctccgctgg atatgtccca accaatatcc    480

acacaaaatc ttgttgcaaa ggatctctat ggtcaagaat ggagtttcaa acatgtcttt    540

agaggtacac cgcagagaca tatgtttact agcggcggcg gctggagcgt atttgcaaca    600

acaaaaagat tgattgttgg ggatatattt gtactcctta gaggagagaa tggggagtta    660

cgatttggta ttaggcgagc aaagcatcaa caaggccaca taccttcatc agtaatatca    720

gcaaattgta tgcaacatgg agtaatagct tcagtagtga atgcttttaa aaccaaatgc    780

atgttcaatg tggtttataa gccaagttca agtcaatttg ttataagcta tgacaaattt    840

gttgatgcaa tgaacaataa ttacattgtt ggttcgagat ttaggatgca gtttgagggt    900
```

```
aaggattttt ctgaaaaaag atacgatggg acgattattg gtgtaaatga catgtctcct    960

cattggaagg attcagaatg gcgaagccta aaagtgcaat gggacgagct ttcaccattt   1020

ctaagaccta atcaggtttc accttgggac atcgagcatc taattccttc gtcagatatc   1080

tctcaatcaa gtttgaaaaa gaaaaaacat tggcttcaat tgaatgaaat tggtgcaaca   1140

ttatcgaatc tttggacatg ccaagaaatt ggacaacgga gcatgaattc tcctataagt   1200

gttcctgagt ttagttatcc caatgcaatt gaagattcaa agtttctttc tggtttgcta   1260

ctgaatcact cactcctagc catacctaat gaaaactata acagcgacca aatgattcaa   1320

ccaaggaaag aagatataac aactgaagca accactagtt gcctcttgtt tggagttgat   1380

ctgaccaaag tatcaaagag caaagattcc atctgtccaa ttgaatcatg caaaaaatca   1440

gaaatttcaa aactcaaaaa tcaaaaagca accactagtt gcctcaagat aaaaagtttg   1500

accaaaccca acctctgaga tcaccaaaag aggtccaaag cacggaattc aattttacta   1560

gaagtcgtat taaagttcat atgcaaggtg tagccataag tagagctgtg gatttaactg   1620

ctatgcatgg atacaatcag ctgatacaaa aactggaaga actctttgat ctcaaagacg   1680

agttacgaac tcgcaatcaa tgggaaatag tttttacaaa caatgaagga gctgagatgc   1740

ttgtcgggga tgatccatgg cctgagttct gcaatatggc gaaaagaata ttcatatgct   1800

caaaagagga gataaagaaa atgaagttga agaacaaatt ctttcaacct gaatcaaaag   1860

ctttaacatc ttcagacgta ccaccaaacg tcacagataa ctaacctttc ttataaagat   1920

aagagagctg aaaat                                                    1935
```

<210> SEQ ID NO 46
<211> LENGTH: 505
<212> TYPE: PRT
<213> ORGANISM: Arabidopsis thaliana

<400> SEQUENCE: 46

```
Met Glu Asn Asn Gly Glu Met Asn Ala Gln Pro Glu Leu Ser Val Asp
1               5                   10                  15

Ile Thr Lys Thr Tyr Met Tyr Glu Lys Leu Trp Asn Ile Cys Ala Gly
            20                  25                  30

Pro Leu Cys Val Leu Pro Lys Pro Gly Glu Lys Val Tyr Tyr Phe Pro
        35                  40                  45

Gln Gly His Ile Glu Leu Ile Glu Asn Ser Thr Arg Asp Glu Leu Asp
    50                  55                  60

His Ile Arg Pro Ile Phe Asp Leu Pro Ser Lys Leu Arg Cys Arg Val
65                  70                  75                  80

Val Ala Ile Asp Arg Lys Val Asp Lys Asn Thr Asp Glu Val Tyr Ala
                85                  90                  95

Gln Ile Ser Leu Met Pro Asp Thr Thr Glu Val Met Thr His Asn Thr
            100                 105                 110

Thr Met Asp Thr Arg Arg Pro Ile Val Tyr Phe Phe Ser Lys Ile Leu
        115                 120                 125

Thr Ala Ser Asp Val Ser Leu Ser Gly Gly Leu Ile Ile Pro Lys Gln
    130                 135                 140

Tyr Ala Ile Glu Cys Phe Pro Pro Leu Asp Met Ser Gln Pro Ile Ser
145                 150                 155                 160

Thr Gln Asn Leu Val Ala Lys Asp Leu Tyr Gly Gln Glu Trp Ser Phe
                165                 170                 175

Lys His Val Phe Arg Gly Thr Pro Gln Arg His Met Phe Thr Ser Gly
            180                 185                 190
```

```
Gly Gly Trp Ser Val Phe Ala Thr Thr Lys Arg Leu Ile Val Gly Asp
        195                 200                 205

Ile Phe Val Leu Leu Arg Gly Glu Asn Gly Glu Leu Arg Phe Gly Ile
    210                 215                 220

Arg Arg Ala Lys His Gln Gln Gly His Ile Pro Ser Ser Val Ile Ser
225                 230                 235                 240

Ala Asn Cys Met Gln His Gly Val Ile Ala Ser Val Val Asn Ala Phe
                245                 250                 255

Lys Thr Lys Cys Met Phe Asn Val Val Tyr Lys Pro Ser Ser Ser Gln
            260                 265                 270

Phe Val Ile Ser Tyr Asp Lys Phe Val Asp Ala Met Asn Asn Asn Tyr
        275                 280                 285

Ile Val Gly Ser Arg Phe Arg Met Gln Phe Glu Gly Lys Asp Phe Ser
    290                 295                 300

Glu Lys Arg Tyr Asp Gly Thr Ile Ile Gly Val Asn Asp Met Ser Pro
305                 310                 315                 320

His Trp Lys Asp Ser Glu Trp Arg Ser Leu Lys Val Gln Trp Asp Glu
                325                 330                 335

Leu Ser Pro Phe Leu Arg Pro Asn Gln Val Ser Pro Trp Asp Ile Glu
            340                 345                 350

His Leu Ile Pro Ser Ser Asp Ile Ser Gln Ser Ser Leu Lys Lys Lys
        355                 360                 365

Lys His Trp Leu Gln Leu Asn Glu Ile Gly Ala Thr Leu Ser Asn Leu
    370                 375                 380

Trp Thr Cys Gln Glu Ile Gly Gln Arg Ser Met Asn Ser Pro Ile Ser
385                 390                 395                 400

Val Pro Glu Phe Ser Tyr Pro Asn Ala Ile Glu Asp Ser Lys Phe Leu
                405                 410                 415

Ser Gly Leu Leu Leu Asn His Ser Leu Leu Ala Ile Pro Asn Glu Asn
            420                 425                 430

Tyr Asn Ser Asp Gln Met Ile Gln Pro Arg Lys Glu Asp Ile Thr Thr
        435                 440                 445

Glu Ala Thr Thr Ser Cys Leu Leu Phe Gly Val Asp Leu Thr Lys Val
    450                 455                 460

Ser Lys Ser Lys Asp Ser Ile Cys Pro Ile Glu Ser Cys Lys Lys Ser
465                 470                 475                 480

Glu Ile Ser Lys Leu Lys Asn Gln Lys Ala Thr Thr Ser Cys Leu Lys
                485                 490                 495

Ile Lys Ser Leu Thr Lys Pro Asn Leu
            500                 505
```

<210> SEQ ID NO 47
<211> LENGTH: 1857
<212> TYPE: DNA
<213> ORGANISM: Arabidopsis thaliana

<400> SEQUENCE: 47

```
atggaaaata atggagaaat gaatgcacag cctgaattat cagttgatat aaccaagact     60

tatatgtatg agaaattatg gaacatatgt gctggacctt tgtgtgttct tccgaaacct    120

ggagaaaaag tttattactt tcctcaaggg cacatcgagc tcattgagaa ttctacaaga    180

gatgaattgg atcatatcag gccaattttt gatcttccat ctaagcttcg atgtcgtgtt    240

gtggctattg atcgtaaggt agacaaaaat acagatgaag tctatgctca gatttcgtta    300

atgcctgata caacagaagt tatgacccat aatactacta tggatactcg aagaccaata    360
```

```
gtttattttt ttagtaaaat tttaacggcg tctgacgtca gtttaagtgg tggattaatt    420

attcccaaac aatatgccat tgagtgtttt cctccgctgg atatgtccca accaatatcc    480

acacaaaatc ttgttgcaaa ggatctctat ggtcaagaat ggagtttcaa acatgtcttt    540

agaggtacac cgcagagaca tatgtttact agcggcggcg gctggagcgt atttgcaaca    600

acaaaaagat tgattgttgg ggatatattt gtactcctta gaggagagaa tggggagtta    660

cgatttggta ttaggcgagc aaagcatcaa caaggccaca taccttcatc agtaatatca    720

gcaaattgta tgcaacatgg agtaatagct tcagtagtga atgcttttaa aaccaaatgc    780

atgttcaatg tggtttataa gccaaggatg cagtttgagg gtaaggattt ttctgaaaaa    840

agatacgatg ggacgattat tggtgtaaat gacatgtctc ctcattggaa ggattcagaa    900

tggcgaagcc taaaagtgca atgggacgag ctttcaccat ttctaagacc taatcaggtt    960

tcaccttggg acatcgagca tctaattcct tcgtcagata tctctcaatc aagtttgaaa   1020

aagaaaaaac attggcttca attgaatgaa attggtgcaa cattatcgaa tctttggaca   1080

tgccaagaaa ttggacaacg gagcatgaat tctcctataa gtgttcctga gtttagttat   1140

cccaatgcaa ttgaagattc aaagtttctt tctggtttgc tactgaatca ctcactccta   1200

gccataccta atgaaaacta taacagcgac caaatgattc aaccaaggaa agaagatata   1260

acaactgaag caaccactag ttgcctcttg tttggagttg atctgaccaa agtatcaaag   1320

agcaaagatt ccatctgtcc aattgaatca tgcaaaaaat cagaaatttc aaaactcaaa   1380

aatcaaaaag caaccactag ttgcctcaag ataaaaagtt tgaccaaacc caacctctga   1440

gatcaccaaa agaggtccaa agcacggaat tcaattttac tagaagtcgt attaaagttc   1500

atatgcaagg tgtagccata agtagagctg tggatttaac tgctatgcat ggatacaatc   1560

agctgataca aaaactggaa gaactctttg atctcaaaga cgagttacga actcgcaatc   1620

aatgggaaat agtttttaca aacaatgaag gagctgagat gcttgtcggg gatgatccat   1680

ggcctgagtt ctgcaatatg gcgaaaagaa tattcatatg ctcaaaagag gagataaaga   1740

aaatgaagtt gaagaacaaa ttctttcaac ctgaatcaaa agctttaaca tcttcagacg   1800

taccaccaaa cgtcacagat aactaacctt tcttataaag ataagagagc tgaaaat      1857
```

<210> SEQ ID NO 48
<211> LENGTH: 479
<212> TYPE: PRT
<213> ORGANISM: Arabidopsis thaliana

<400> SEQUENCE: 48

```
Met Glu Asn Asn Gly Glu Met Asn Ala Gln Pro Glu Leu Ser Val Asp
1               5                   10                  15

Ile Thr Lys Thr Tyr Met Tyr Glu Lys Leu Trp Asn Ile Cys Ala Gly
            20                  25                  30

Pro Leu Cys Val Leu Pro Lys Pro Gly Glu Lys Val Tyr Tyr Phe Pro
        35                  40                  45

Gln Gly His Ile Glu Leu Ile Glu Asn Ser Thr Arg Asp Glu Leu Asp
    50                  55                  60

His Ile Arg Pro Ile Phe Asp Leu Pro Ser Lys Leu Arg Cys Arg Val
65                  70                  75                  80

Val Ala Ile Asp Arg Lys Val Asp Lys Asn Thr Asp Glu Val Tyr Ala
                85                  90                  95

Gln Ile Ser Leu Met Pro Asp Thr Thr Glu Val Met Thr His Asn Thr
            100                 105                 110

Thr Met Asp Thr Arg Arg Pro Ile Val Tyr Phe Phe Ser Lys Ile Leu
```

```
        115                 120                 125

Thr Ala Ser Asp Val Ser Leu Ser Gly Gly Leu Ile Ile Pro Lys Gln
    130                 135                 140

Tyr Ala Ile Glu Cys Phe Pro Pro Leu Asp Met Ser Gln Pro Ile Ser
145                 150                 155                 160

Thr Gln Asn Leu Val Ala Lys Asp Leu Tyr Gly Gln Glu Trp Ser Phe
                165                 170                 175

Lys His Val Phe Arg Gly Thr Pro Gln Arg His Met Phe Thr Ser Gly
            180                 185                 190

Gly Gly Trp Ser Val Phe Ala Thr Thr Lys Arg Leu Ile Val Gly Asp
        195                 200                 205

Ile Phe Val Leu Leu Arg Gly Glu Asn Gly Glu Leu Arg Phe Gly Ile
    210                 215                 220

Arg Arg Ala Lys His Gln Gln Gly His Ile Pro Ser Ser Val Ile Ser
225                 230                 235                 240

Ala Asn Cys Met Gln His Gly Val Ile Ala Ser Val Val Asn Ala Phe
                245                 250                 255

Lys Thr Lys Cys Met Phe Asn Val Val Tyr Lys Pro Arg Met Gln Phe
            260                 265                 270

Glu Gly Lys Asp Phe Ser Glu Lys Arg Tyr Asp Gly Thr Ile Ile Gly
        275                 280                 285

Val Asn Asp Met Ser Pro His Trp Lys Asp Ser Glu Trp Arg Ser Leu
    290                 295                 300

Lys Val Gln Trp Asp Glu Leu Ser Pro Phe Leu Arg Pro Asn Gln Val
305                 310                 315                 320

Ser Pro Trp Asp Ile Glu His Leu Ile Pro Ser Ser Asp Ile Ser Gln
                325                 330                 335

Ser Ser Leu Lys Lys Lys Lys His Trp Leu Gln Leu Asn Glu Ile Gly
            340                 345                 350

Ala Thr Leu Ser Asn Leu Trp Thr Cys Gln Glu Ile Gly Gln Arg Ser
        355                 360                 365

Met Asn Ser Pro Ile Ser Val Pro Glu Phe Ser Tyr Pro Asn Ala Ile
    370                 375                 380

Glu Asp Ser Lys Phe Leu Ser Gly Leu Leu Leu Asn His Ser Leu Leu
385                 390                 395                 400

Ala Ile Pro Asn Glu Asn Tyr Asn Ser Asp Gln Met Ile Gln Pro Arg
                405                 410                 415

Lys Glu Asp Ile Thr Thr Glu Ala Thr Thr Ser Cys Leu Leu Phe Gly
            420                 425                 430

Val Asp Leu Thr Lys Val Ser Lys Ser Lys Asp Ser Ile Cys Pro Ile
        435                 440                 445

Glu Ser Cys Lys Lys Ser Glu Ile Ser Lys Leu Lys Asn Gln Lys Ala
    450                 455                 460

Thr Thr Ser Cys Leu Lys Ile Lys Ser Leu Thr Lys Pro Asn Leu
465                 470                 475


<210> SEQ ID NO 49
<211> LENGTH: 2019
<212> TYPE: DNA
<213> ORGANISM: Arabidopsis thaliana

<400> SEQUENCE: 49

atccaaaatc tatctaccgc cgatcaaaaa accctagaat ttcttccact gttatgtaag      60

tttgatcttg ttgtctccac taagaggcga agagagaaag agggttttag gttgtgtgtt     120
```

```
ctgtttcaaa gggtttactt ctcgttgacc ccgatcgaga tggttgattc ttctcgtgat    180

tcgtgtttca aagctggtaa gtttagtgct ccaggttttc gatttcaccc tactgatgaa    240

gagcttgtgg tttattatct taagaggaag atctgttgta aaaaacttcg agtcaatgcc    300

attggtgtcg ttgatgttta caaagtcgat ccttctgaat tgcctggtct atcgatgttg    360

aagacgggag atagacagtg gttctttttc actccaagga ataggaagta tcctaacgca    420

gctaggtcaa gtagaggtac tgcaactggt tattggaagg cgacaggaaa ggatcgagtc    480

attgagtaca attcaagatc tgttggactc aagaagactc ttgttttcta tagaggtcgt    540

gctcctaatg gtgagagaac tgactgggtg atgcatgagt acactatgga tgaagaagag    600

ctagggagat gtaagaacgc taaggagtat tatgctcttt ataagcttta taagaagagt    660

ggggctggtc ctaagaatgg tgaacagtat ggtgctccgt tccaagaaga agaatgggtt    720

gatagtgata gtgaagatgc agatagtgtc gctgtaccgg attatcccgt ggtccgttat    780

gagaatggtc cttgtgtgga tgatactaaa ttttgcaatc ctgtcaaact tcagttagag    840

gatattgaga agcttctcaa tgaaatccca gatgcacccg gggttaacca aagacagttt    900

gatgagtttg ttggtgttcc acagggtaat agtgcagaag tgatacagag cacattgctg    960

aataattctt ctggagagta tattgaccct cggacgaatg gaatgttctt gccaaatggc   1020

cagctataca acagggactc gagttttcag tcccatttga attcatttga ggctacctct   1080

ggtatggcac ctcttctaga taatgagaag gaggagtaca ttgaaatgaa tgatcttctg   1140

atccctgagc tcggtgcttc ttcaacagag aaatccacag agttcttgaa ccatggtgaa   1200

tttggtgatg ttaatgaata cgaccaattg ttcaatgaca tatctgtttt tcagggaact   1260

tctacagatc tgtcttgtct gagtaatttt actaataaca catcaggcca aagacagcaa   1320

ttactttatg aacagttcca gtaccagaca cctgagaacc agcttaataa ctacatgcat   1380

cctagtacca ctcttaatca gttcactgac aatatgtggt ttaaagatga tcaggctgct   1440

ctctatgttc aaccaccaca atcttcttct ggagcattca cttcacagtc aacaggtgtg   1500

atgcctgagt ctatgaatcc cactatgagt gtaaatcccc aatacaagga aggacaaaat   1560

ggtggtggaa caaggagcca gttctcatca gctctgtggg aattattgga atcaatacca   1620

tcaacaccag cctctgcctg tgagggtcct cttaaccaga cctttgtgcg tatgtctagc   1680

ttcagccgca tcaggttcaa tggaacgtca gtgactagta gaaaagtcac tgtagcaaag   1740

aagcgtatca gtaacagagg ttttcttctg ttatcaatta tgggtgcttt gtgtgctatc   1800

ttctgggtgt tcaaagccac cgttggagtt atgggaagac ctctcttgtc gtgacctaga   1860

ctcttgaatc ttgattcagc ataagttagc ctgatccaca tctttgatta tgtatagagt   1920

ttgaaagagt ttaattctta acaaaagatt tcttttttcc tggattctct gatggctttg   1980

aaattttgct tgcacttatc atattaagca gaatttttg                          2019
```

<210> SEQ ID NO 50
<211> LENGTH: 564
<212> TYPE: PRT
<213> ORGANISM: Arabidopsis thaliana

<400> SEQUENCE: 50

```
Met Val Asp Ser Ser Arg Asp Ser Cys Phe Lys Ala Gly Lys Phe Ser
1               5                   10                  15

Ala Pro Gly Phe Arg Phe His Pro Thr Asp Glu Glu Leu Val Val Tyr
            20                  25                  30

Tyr Leu Lys Arg Lys Ile Cys Cys Lys Lys Leu Arg Val Asn Ala Ile
        35                  40                  45
```

```
Gly Val Val Asp Val Tyr Lys Val Asp Pro Ser Glu Leu Pro Gly Leu
    50                  55                  60

Ser Met Leu Lys Thr Gly Asp Arg Gln Trp Phe Phe Phe Thr Pro Arg
65                  70                  75                  80

Asn Arg Lys Tyr Pro Asn Ala Ala Arg Ser Ser Arg Gly Thr Ala Thr
                85                  90                  95

Gly Tyr Trp Lys Ala Thr Gly Lys Asp Arg Val Ile Glu Tyr Asn Ser
            100                 105                 110

Arg Ser Val Gly Leu Lys Lys Thr Leu Val Phe Tyr Arg Gly Arg Ala
        115                 120                 125

Pro Asn Gly Glu Arg Thr Asp Trp Val Met His Glu Tyr Thr Met Asp
    130                 135                 140

Glu Glu Glu Leu Gly Arg Cys Lys Asn Ala Lys Glu Tyr Tyr Ala Leu
145                 150                 155                 160

Tyr Lys Leu Tyr Lys Lys Ser Gly Ala Gly Pro Lys Asn Gly Glu Gln
                165                 170                 175

Tyr Gly Ala Pro Phe Gln Glu Glu Glu Trp Val Asp Ser Asp Ser Glu
            180                 185                 190

Asp Ala Asp Ser Val Ala Val Pro Asp Tyr Pro Val Val Arg Tyr Glu
        195                 200                 205

Asn Gly Pro Cys Val Asp Asp Thr Lys Phe Cys Asn Pro Val Lys Leu
    210                 215                 220

Gln Leu Glu Asp Ile Glu Lys Leu Leu Asn Glu Ile Pro Asp Ala Pro
225                 230                 235                 240

Gly Val Asn Gln Arg Gln Phe Asp Glu Phe Val Gly Val Pro Gln Gly
                245                 250                 255

Asn Ser Ala Glu Val Ile Gln Ser Thr Leu Leu Asn Asn Ser Ser Gly
            260                 265                 270

Glu Tyr Ile Asp Pro Arg Thr Asn Gly Met Phe Leu Pro Asn Gly Gln
        275                 280                 285

Leu Tyr Asn Arg Asp Ser Ser Phe Gln Ser His Leu Asn Ser Phe Glu
    290                 295                 300

Ala Thr Ser Gly Met Ala Pro Leu Leu Asp Asn Glu Lys Glu Glu Tyr
305                 310                 315                 320

Ile Glu Met Asn Asp Leu Leu Ile Pro Glu Leu Gly Ala Ser Ser Thr
                325                 330                 335

Glu Lys Ser Thr Glu Phe Leu Asn His Gly Glu Phe Gly Asp Val Asn
            340                 345                 350

Glu Tyr Asp Gln Leu Phe Asn Asp Ile Ser Val Phe Gln Gly Thr Ser
        355                 360                 365

Thr Asp Leu Ser Cys Leu Ser Asn Phe Thr Asn Asn Thr Ser Gly Gln
    370                 375                 380

Arg Gln Gln Leu Leu Tyr Glu Gln Phe Gln Tyr Gln Thr Pro Glu Asn
385                 390                 395                 400

Gln Leu Asn Asn Tyr Met His Pro Ser Thr Thr Leu Asn Gln Phe Thr
                405                 410                 415

Asp Asn Met Trp Phe Lys Asp Asp Gln Ala Ala Leu Tyr Val Gln Pro
            420                 425                 430

Pro Gln Ser Ser Ser Gly Ala Phe Thr Ser Gln Ser Thr Gly Val Met
        435                 440                 445

Pro Glu Ser Met Asn Pro Thr Met Ser Val Asn Pro Gln Tyr Lys Glu
    450                 455                 460

Gly Gln Asn Gly Gly Gly Thr Arg Ser Gln Phe Ser Ser Ala Leu Trp
```

465 470 475 480

Glu Leu Leu Glu Ser Ile Pro Ser Thr Pro Ala Ser Ala Cys Glu Gly
485 490 495

Pro Leu Asn Gln Thr Phe Val Arg Met Ser Ser Phe Ser Arg Ile Arg
500 505 510

Phe Asn Gly Thr Ser Val Thr Ser Arg Lys Val Thr Val Ala Lys Lys
515 520 525

Arg Ile Ser Asn Arg Gly Phe Leu Leu Leu Ser Ile Met Gly Ala Leu
530 535 540

Cys Ala Ile Phe Trp Val Phe Lys Ala Thr Val Gly Val Met Gly Arg
545 550 555 560

Pro Leu Leu Ser

<210> SEQ ID NO 51
<211> LENGTH: 3452
<212> TYPE: DNA
<213> ORGANISM: Arabidopsis thaliana

<400> SEQUENCE: 51

```
atggcggaag agaatcgtaa ggatcgaggt gtttcttcta ctgttgcgat tccttctggt     60
ttgaaccgga tcaaaactcg gttagcttcg tcaggtccta gacctgaaga ttcctccgat    120
accgttctta aacctccgtt taatcggaat cagaagacta ttgttcctcg tggtcatggt    180
agaaccactg gctcttcgaa acaagagcgt aagggaacaa aattgtcaag gtggcttgct    240
tcctataaac ccaagtattc ttgtcaccct ccaaaatatg cttgctcgag tacaacgagt    300
agtgaggaga tcaagttaag aggcaagaac tctggtaaag acgaagagaa gatgattaag    360
atatctgaaa ctaaccctcc ctgttcaaag tcaatgggta taaagagctt ttcccatgaa    420
ttaggaccaa ggggtggtgt tcaaactccc taccctcgtc cgcacagcta taacgatctg    480
aaggaacttc tgggctcact tcactcaaga tttgatgttg ctaaagagac tgtggataag    540
aagctggatg tctttgtcag agatgtcaaa gaggctatgg agaaaatgga tccatcatgt    600
cctgaagatc gagaaatggc agagcagtta cttgatgtgg ctcgagcctg tatggagatg    660
acatctgctc aacttcgtgc tacttgtgaa tctattgtcc aagacttaac taggaaaagg    720
aaacagtgcc aagcaggact tgtgaagtgg ttgttctctc agttgctttt tatattgact    780
cattgtacaa gagttgtgat gtttcagaag gagactgagc caattgatga gagctccttt    840
cgcaaattta aggaatgttt agaacgcatc cctgctttgg aaacagattg gggttctact    900
cctagagttg atgattctgg ttctggttat cctgaatatc aaagaaatga agctgggcag    960
aaattcaaaa gacgagacaa agaatctttg gagtcagaga cagcacttga ttatgtggta   1020
ccaaatgatc atggcaataa tgctgctaga gaaggttatg cagctgctaa acaagaattt   1080
ccatcgcatg aacctcaatt tgatagtaaa gtggtagaac aaagatttta tttgagcgat   1140
gagtatgaag ataagatgtc aaatgagcct ggaaaagagt taggcggatc tgattatgta   1200
atctgcagga tatgtgagga ggaagttcct ctcttccatc tggaaccgca ctcttacata   1260
tgtgcatacg cagataaatg tgaaataaat tgtgtggatg ttgatgagcg ccttttgaaa   1320
ctggaggaga tactggaaca gataattgat tcacgaagtt taaattcctt cactcaagct   1380
ggtggcttgg aaaactctgt tctgcggaaa tctggagttg catctgaagg ttgttctccc   1440
aagataaacg aatggcggaa taaaggttta gagggaatgt ttgaggatct gcacgagatg   1500
gacactgcct tcatagacga gtcttacaca tatcctattc accttaagag ccatgtaggg   1560
gccaaatttt gccatcatgc cacttcatca tcaacaggta gcatcacgtc agtatcttca   1620
```

```
acaaataccc ccagaacaag tcactttgac tcctattggc tagaacggca ttgtccagag   1680

caagaggatc ttcgactgat gatggacctt tctgatattg cccgctgtgg agcaagcaca   1740

gatttctcga aagaggggtc ctgtgactat ataatggcat gcatgcaaga catacaagct   1800

gtcttgaagc agggcaagct caaagcactt gtaatagata ctttcggggg gcggatcgag   1860

aaacttctct gcgagaaata tttacatgct cgtgaattga ctgccgataa aagttcggtg   1920

ggtaacatta aagagagtga agatgtcttg gagcatgcat cggctactcc acagttactg   1980

ctgaaagata ggataagcat cgatgacttt gagatcatca aaccaataag tagaggtgcc   2040

tttggtaaag tctttcttgc acgcaaaaga acaactggag actttttttgc aataaaggta   2100

ctcaaaaagt tggatatgat aaggaaaaat gatatcgaga ggatactaca agagcgaaat   2160

atactaataa ctgtcagata ccccttttttg gttcgatttt tttactcatt cacctgcaga   2220

gataatctct acttggtaat ggaatatctt aatggtggtg atctatactc tctgctccag   2280

aaagttggct gtcttgacga agaaattgct cgtatataca tcgcggaact ggttcttgca   2340

ttggagtacc tccattctct gaagattgtc caccgtgatc taaagcctga taacctgtta   2400

atcgcctata atgggcacat caagctaaca gactttgggc tttcaaagat tggtcttata   2460

aacaacacaa ttgatttatc tggccatgag tcagatgtat ccccaagaac aaattctcat   2520

cattttcaga agaaccaaga agaagaaaga attcggcatt cggctgttgg gacacctgac   2580

tacttggcac cagagattct tcttggaact gaacacggtt atgctgcgga ttggtggtct   2640

gctggaattg tcttgtttga attattaact ggaattccac cttttaccgc atcccgccca   2700

gagaaaatat ttgacaacat cctcaatggt aaaatgccct ggccagatgt tcctggtgaa   2760

atgtcttatg aagctcagga tttgattaac aggcttcttg tccatgagcc ggaaaagcga   2820

ctgggggcga acggtgctgc agaggtaaag tcgcatccct tttttcaagg agttgactgg   2880

gagaatcttg ctttgcaaaa ggctgctttt gttccgcaac ctgagagtat aaatgacaca   2940

agctatttcg tatcacgctt tagtgaaagc agttgcagcg atactgaaac tggtaacaac   3000

agtgggtcaa atccagattc aggagacgag ttggatgaat gcaccaacct ggagaagttt   3060

gattctccgc cttattatct ctcgctcatt aacttttctt tcaagaattt gtcacaattg   3120

gcttcaatca atcatgatgt gctattgcaa aaggatccag ctaaaggagg aggagactca   3180

ccctttaaaa gccatggaac gtagagctct cctacaaccg tcaaaggtgg ccttagtccg   3240

ctgttttctc tggtttgcgc cctgctttga ccgttgtagc tgctgctgct actatgctga   3300

aattgttacc tcaaggtctt tgggtaatta ttttcagttt tgtcataaat tgatttggaa   3360

ccatttcaaa tgcaaatcca agtatttatt gcgtggcaac aacacacata tacatgtgta   3420

taagcttgtg tgtattgagg ctgatggaaa ta                                 3452
```

<210> SEQ ID NO 52
<211> LENGTH: 1067
<212> TYPE: PRT
<213> ORGANISM: Arabidopsis thaliana

<400> SEQUENCE: 52

```
Met Ala Glu Glu Asn Arg Lys Asp Arg Gly Val Ser Ser Thr Val Ala
1               5                   10                  15

Ile Pro Ser Gly Leu Asn Arg Ile Lys Thr Arg Leu Ala Ser Ser Gly
            20                  25                  30

Pro Arg Pro Glu Asp Ser Ser Asp Thr Val Leu Lys Pro Pro Phe Asn
        35                  40                  45
```

```
Arg Asn Gln Lys Thr Ile Val Pro Arg Gly His Gly Arg Thr Thr Gly
    50                  55                  60

Ser Ser Lys Gln Glu Arg Lys Gly Thr Lys Leu Ser Arg Trp Leu Ala
65                  70                  75                  80

Ser Tyr Lys Pro Lys Tyr Ser Cys His Pro Pro Lys Tyr Ala Cys Ser
                85                  90                  95

Ser Thr Thr Ser Ser Glu Glu Ile Lys Leu Arg Gly Lys Asn Ser Gly
            100                 105                 110

Lys Asp Glu Glu Lys Met Ile Lys Ile Ser Glu Thr Asn Pro Pro Cys
        115                 120                 125

Ser Lys Ser Met Gly Ile Lys Ser Phe Ser His Glu Leu Gly Pro Arg
    130                 135                 140

Gly Gly Val Gln Thr Pro Tyr Pro Arg Pro His Ser Tyr Asn Asp Leu
145                 150                 155                 160

Lys Glu Leu Leu Gly Ser Leu His Ser Arg Phe Asp Val Ala Lys Glu
                165                 170                 175

Thr Val Asp Lys Lys Leu Asp Val Phe Val Arg Asp Val Lys Glu Ala
            180                 185                 190

Met Glu Lys Met Asp Pro Ser Cys Pro Glu Asp Arg Glu Met Ala Glu
        195                 200                 205

Gln Leu Leu Asp Val Ala Arg Ala Cys Met Glu Met Thr Ser Ala Gln
    210                 215                 220

Leu Arg Ala Thr Cys Glu Ser Ile Val Gln Asp Leu Thr Arg Lys Arg
225                 230                 235                 240

Lys Gln Cys Gln Ala Gly Leu Val Lys Trp Leu Phe Ser Gln Leu Leu
                245                 250                 255

Phe Ile Leu Thr His Cys Thr Arg Val Val Met Phe Gln Lys Glu Thr
            260                 265                 270

Glu Pro Ile Asp Glu Ser Ser Phe Arg Lys Phe Lys Glu Cys Leu Glu
        275                 280                 285

Arg Ile Pro Ala Leu Glu Thr Asp Trp Gly Ser Thr Pro Arg Val Asp
    290                 295                 300

Asp Ser Gly Ser Gly Tyr Pro Glu Tyr Gln Arg Asn Glu Ala Gly Gln
305                 310                 315                 320

Lys Phe Lys Arg Arg Asp Lys Glu Ser Leu Glu Ser Glu Thr Ala Leu
                325                 330                 335

Asp Tyr Val Val Pro Asn Asp His Gly Asn Asn Ala Ala Arg Glu Gly
            340                 345                 350

Tyr Ala Ala Ala Lys Gln Glu Phe Pro Ser His Glu Pro Gln Phe Asp
        355                 360                 365

Ser Lys Val Val Glu Gln Arg Phe Tyr Leu Ser Asp Glu Tyr Glu Asp
    370                 375                 380

Lys Met Ser Asn Glu Pro Gly Lys Glu Leu Gly Gly Ser Asp Tyr Val
385                 390                 395                 400

Ile Cys Arg Ile Cys Glu Glu Glu Val Pro Leu Phe His Leu Glu Pro
                405                 410                 415

His Ser Tyr Ile Cys Ala Tyr Ala Asp Lys Cys Glu Ile Asn Cys Val
            420                 425                 430

Asp Val Asp Glu Arg Leu Leu Lys Leu Glu Glu Ile Leu Glu Gln Ile
        435                 440                 445

Ile Asp Ser Arg Ser Leu Asn Ser Phe Thr Gln Ala Gly Gly Leu Glu
    450                 455                 460

Asn Ser Val Leu Arg Lys Ser Gly Val Ala Ser Glu Gly Cys Ser Pro
465                 470                 475                 480
```

```
Lys Ile Asn Glu Trp Arg Asn Lys Gly Leu Glu Gly Met Phe Glu Asp
                485                 490                 495

Leu His Glu Met Asp Thr Ala Phe Ile Asp Glu Ser Tyr Thr Tyr Pro
            500                 505                 510

Ile His Leu Lys Ser His Val Gly Ala Lys Phe Cys His His Ala Thr
        515                 520                 525

Ser Ser Ser Thr Gly Ser Ile Thr Ser Val Ser Ser Thr Asn Thr Pro
    530                 535                 540

Arg Thr Ser His Phe Asp Ser Tyr Trp Leu Glu Arg His Cys Pro Glu
545                 550                 555                 560

Gln Glu Asp Leu Arg Leu Met Met Asp Leu Ser Asp Ile Ala Arg Cys
                565                 570                 575

Gly Ala Ser Thr Asp Phe Ser Lys Glu Gly Ser Cys Asp Tyr Ile Met
            580                 585                 590

Ala Cys Met Gln Asp Ile Gln Ala Val Leu Lys Gln Gly Lys Leu Lys
        595                 600                 605

Ala Leu Val Ile Asp Thr Phe Gly Gly Arg Ile Glu Lys Leu Leu Cys
    610                 615                 620

Glu Lys Tyr Leu His Ala Arg Glu Leu Thr Ala Asp Lys Ser Ser Val
625                 630                 635                 640

Gly Asn Ile Lys Glu Ser Glu Asp Val Leu Glu His Ala Ser Ala Thr
                645                 650                 655

Pro Gln Leu Leu Leu Lys Asp Arg Ile Ser Ile Asp Asp Phe Glu Ile
            660                 665                 670

Ile Lys Pro Ile Ser Arg Gly Ala Phe Gly Lys Val Phe Leu Ala Arg
        675                 680                 685

Lys Arg Thr Thr Gly Asp Phe Phe Ala Ile Lys Val Leu Lys Lys Leu
    690                 695                 700

Asp Met Ile Arg Lys Asn Asp Ile Glu Arg Ile Leu Gln Glu Arg Asn
705                 710                 715                 720

Ile Leu Ile Thr Val Arg Tyr Pro Phe Leu Val Arg Phe Phe Tyr Ser
                725                 730                 735

Phe Thr Cys Arg Asp Asn Leu Tyr Leu Val Met Glu Tyr Leu Asn Gly
            740                 745                 750

Gly Asp Leu Tyr Ser Leu Leu Gln Lys Val Gly Cys Leu Asp Glu Glu
        755                 760                 765

Ile Ala Arg Ile Tyr Ile Ala Glu Leu Val Leu Ala Leu Glu Tyr Leu
    770                 775                 780

His Ser Leu Lys Ile Val His Arg Asp Leu Lys Pro Asp Asn Leu Leu
785                 790                 795                 800

Ile Ala Tyr Asn Gly His Ile Lys Leu Thr Asp Phe Gly Leu Ser Lys
                805                 810                 815

Ile Gly Leu Ile Asn Asn Thr Ile Asp Leu Ser Gly His Glu Ser Asp
            820                 825                 830

Val Ser Pro Arg Thr Asn Ser His His Phe Gln Lys Asn Gln Glu Glu
        835                 840                 845

Glu Arg Ile Arg His Ser Ala Val Gly Thr Pro Asp Tyr Leu Ala Pro
    850                 855                 860

Glu Ile Leu Leu Gly Thr Glu His Gly Tyr Ala Ala Asp Trp Trp Ser
865                 870                 875                 880

Ala Gly Ile Val Leu Phe Glu Leu Leu Thr Gly Ile Pro Pro Phe Thr
                885                 890                 895

Ala Ser Arg Pro Glu Lys Ile Phe Asp Asn Ile Leu Asn Gly Lys Met
```

```
            900                 905                 910

Pro Trp Pro Asp Val Pro Gly Glu Met Ser Tyr Glu Ala Gln Asp Leu
        915                 920                 925

Ile Asn Arg Leu Leu Val His Glu Pro Glu Lys Arg Leu Gly Ala Asn
    930                 935                 940

Gly Ala Ala Glu Val Lys Ser His Pro Phe Phe Gln Gly Val Asp Trp
945                 950                 955                 960

Glu Asn Leu Ala Leu Gln Lys Ala Ala Phe Val Pro Gln Pro Glu Ser
                965                 970                 975

Ile Asn Asp Thr Ser Tyr Phe Val Ser Arg Phe Ser Glu Ser Ser Cys
            980                 985                 990

Ser Asp Thr Glu Thr Gly Asn Asn  Ser Gly Ser Asn Pro  Asp Ser Gly
        995                 1000                1005

Asp Glu  Leu Asp Glu Cys Thr  Asn Leu Glu Lys Phe  Asp Ser Pro
    1010                 1015                1020

Pro Tyr  Tyr Leu Ser Leu Ile  Asn Phe Ser Phe Lys  Asn Leu Ser
    1025                 1030                1035

Gln Leu  Ala Ser Ile Asn His  Asp Val Leu Leu Gln  Lys Asp Pro
    1040                 1045                1050

Ala Lys  Gly Gly Gly Asp Ser  Pro Phe Lys Ser His  Gly Thr
    1055                 1060                1065
```

<210> SEQ ID NO 53
<211> LENGTH: 991
<212> TYPE: DNA
<213> ORGANISM: Arabidopsis thaliana

<400> SEQUENCE: 53

```
ttttatacat ttttaagaag cccacgaaaa gcccaaattt gaaaacttca atgggtttta     60

tcctgaaaat tccgattgga ttctccgatt gattccatga tgaaggcttc tttcaaggga    120

aagttcgatg tcgacaagag cggtagcgtt gcttcgctta ccttcaacgc cggcaatgct    180

aagctacgag ccaccatgac tgatgcttcc ttcgtcgccg gtcctagctt taatggtctc    240

tctctcgccg ttgagaagcc tggcttcttc atcatcgact acaacgtccc taaaaaggat    300

gttaggtttc agtttatgaa cactatcaga attgcagaga agcctttgaa tctgacttac    360

attcatatga gaggagataa ccggacgatt gttgacggga gttttgtgat tgatccagca    420

aacaagttgt ctgctaatta catggtgggt acaaagaatt gtaagctgaa gtatacttat    480

gttcatggag ggatagctac atttgagcct tgttatgacg tggctaagaa tatgtgggac    540

tttgcgattt ctcataaact ttatggtggt gataatctca aggcaactta tcagacttct    600

agtaagatgc ttggtttgga atggtcgaac aactctaaat caactggatc tttcaaggta    660

tgtgcatcaa tgaatctagc tgaggaattg aagccgccaa aactgaccgc agaaactaca    720

tggaacctgg aactttagct cccaaaaagt ctcaattctt tcggttgttt gatgtggatt    780

caaaagtctt gacagaggaa tctagaacat ttctagtcgt ttccttgttt atcattgtga    840

agactataat gaccacaaaa attgctattc tagtattagt gagtccaatt agtagtaaaa    900

gaatacccaa aaatgtagag tttgtcaacg aaggtgtttt tattcaacat ttcgagctaa    960

tactcacaaa tacatgaaga atttgcattt a                                   991
```

<210> SEQ ID NO 54
<211> LENGTH: 213
<212> TYPE: PRT
<213> ORGANISM: Arabidopsis thaliana

<400> SEQUENCE: 54

```
Met Met Lys Ala Ser Phe Lys Gly Lys Phe Asp Val Asp Lys Ser Gly
1               5                   10                  15

Ser Val Ala Ser Leu Thr Phe Asn Ala Gly Asn Ala Lys Leu Arg Ala
            20                  25                  30

Thr Met Thr Asp Ala Ser Phe Val Ala Gly Pro Ser Phe Asn Gly Leu
        35                  40                  45

Ser Leu Ala Val Glu Lys Pro Gly Phe Phe Ile Ile Asp Tyr Asn Val
    50                  55                  60

Pro Lys Lys Asp Val Arg Phe Gln Phe Met Asn Thr Ile Arg Ile Ala
65                  70                  75                  80

Glu Lys Pro Leu Asn Leu Thr Tyr Ile His Met Arg Gly Asp Asn Arg
                85                  90                  95

Thr Ile Val Asp Gly Ser Phe Val Ile Asp Pro Ala Asn Lys Leu Ser
            100                 105                 110

Ala Asn Tyr Met Val Gly Thr Lys Asn Cys Lys Leu Lys Tyr Thr Tyr
        115                 120                 125

Val His Gly Gly Ile Ala Thr Phe Glu Pro Cys Tyr Asp Val Ala Lys
    130                 135                 140

Asn Met Trp Asp Phe Ala Ile Ser His Lys Leu Tyr Gly Gly Asp Asn
145                 150                 155                 160

Leu Lys Ala Thr Tyr Gln Thr Ser Ser Lys Met Leu Gly Leu Glu Trp
                165                 170                 175

Ser Asn Asn Ser Lys Ser Thr Gly Ser Phe Lys Val Cys Ala Ser Met
            180                 185                 190

Asn Leu Ala Glu Glu Leu Lys Pro Pro Lys Leu Thr Ala Glu Thr Thr
        195                 200                 205

Trp Asn Leu Glu Leu
    210
```

<210> SEQ ID NO 55
<211> LENGTH: 2151
<212> TYPE: DNA
<213> ORGANISM: Arabidopsis thaliana

<400> SEQUENCE: 55

```
atgcagggag agagggctag tcttggttct ttatcaaagg ctttgaactt tgagcgcggt     60

tctacgtcta gtaacgctgt ggtagatcag caaattcgtt gggagaatct tcacaattat    120

ggtgataatg atttgcagga ttacatgagt tcagctgctg atacaaatcc tacttttgca    180

aactcagttt atcatgagaa acggggcttg cagaggttta acattggtga ggctagctct    240

agtgggacga agaacgaagg ggcaagtctc actgaacaat ggaagggaat tggaaggttt    300

gaggaacaga ggaatgataa gcttgagttg agccctttgt ttgtgcaacc atctaatgga    360

agccgcgtgg ttcgtgatgt caatctaaat gcagaataca atgagcatct tgaggatatg    420

aatccggtta cagttcatcc tggtcatttt gaggttaatg gacttaggtc tgagttttta    480

ctagataaca gtgttagagc tggttcctct gttgatggac gtcgtgcatc ctgtaaaaga    540

aaagctcttg atgcaagcgg tggtcagtcc tcttcaactg gaggtttccg tgagttccag    600

cgtggagtat ccagttcttg gatctcaggt cctacgtatt acagcccagc aatgacagca    660

aatgatttaa acatatctct tgatcatggt cgaaggggtt tggtatctag cgctgttcca    720

aatctatctc ctcctaccat cacagagagc tctagtagaa attaccctgt ctgggttaat    780

cccacatatc aacaagaaac cgtaagcaat tttgctccat ccttgaactc accagggctt    840
```

```
atacctgcag atcaccagca gatcagcatg agatatggac atgcgttagg caattttgca    900

tctcagaacc caaatgctcc tgctactcat atgccccctg tttcaagaaa tacatttcaa    960

tggaacacaa gccccgtggc agcggttata tcatctagtt ctgctactcc tgttgacaga   1020

aatgttattc atcgaaatgc aaccagacaa agaagtaata ctctagagat tcccttgttt   1080

gtcccagctc ctgaactgag aaatgtggcc catggtcata ttagcagaaa tgcaagtggt   1140

gctagacatg ttgcatcgtc ttcatccagg acaagtgttc agccatcacc gtctagtcca   1200

gcattgactc cttaccagaa taactcacta cataatcaaa gaagattatc tgaaaacttt   1260

cgtaggtcat tgctttcttc ccttgttaca cagcagaggg ctgctcgttc attggcccat   1320

cctgcctctc caaatgagca cgtgcttcaa tctggtggtg ataacacctc tcaggtgcat   1380

aatcgagctt cctcgagagc aggtccaaga caagggcaag atgcaactgg catttctcat   1440

tctttgcgag gcttggcatc cacaagtcga ggaagaacca gaatgggggc atccgagatc   1500

cgtaacatct tggagcacat gcgtagagca gggaacttgc gtttggagga tgttatgctt   1560

ctcaatcagt ccataatgct aggtgcggct gatattcatg accgatatag agacatgcga   1620

cttgatgttg acaacatgac atatgaggag ctgttgtctc tagaagaacg gattggagat   1680

gtttgtaccg gtttgaacga ggaaaccata tcaaaccgat tgaagcagca gaagtacaaa   1740

agtagtacta gatcttcaca agaagtagaa ccatgctgtg tttgtcagga ggaatataag   1800

gaagaagaag aaataggaag gctggaatgt ggacacgact ttcatagtca atgcatcaaa   1860

gaatggctga agcagaagaa tctttgcccg atttgcaaaa caacaggatt aaacactgca   1920

aataagccac aaagataatg atcgaaagac tgttgggttc taaccatttg tcgaatcttc   1980

aataccattg aagcctcatc agaacactgc aggcaagttg gtgtctgctt ttggggttga   2040

ctgaagatag gaatgaaggg aaagtaactg agggggatag agagaacagg agaacctaag   2100

aaaaaacttt ggttcttctg aatttatttc tataagttaa ttttaccaat t            2151
```

```
<210> SEQ ID NO 56
<211> LENGTH: 645
<212> TYPE: PRT
<213> ORGANISM: Arabidopsis thaliana

<400> SEQUENCE: 56

Met Gln Gly Glu Arg Ala Ser Leu Gly Ser Leu Ser Lys Ala Leu Asn
1               5                   10                  15

Phe Glu Arg Gly Ser Thr Ser Ser Asn Ala Val Val Asp Gln Gln Ile
            20                  25                  30

Arg Trp Glu Asn Leu His Asn Tyr Gly Asp Asn Asp Leu Gln Asp Tyr
        35                  40                  45

Met Ser Ser Ala Ala Asp Thr Asn Pro Thr Phe Ala Asn Ser Val Tyr
    50                  55                  60

His Glu Lys Arg Gly Leu Gln Arg Phe Asn Ile Gly Glu Ala Ser Ser
65                  70                  75                  80

Ser Gly Thr Lys Asn Glu Gly Ala Ser Leu Thr Glu Gln Trp Lys Gly
                85                  90                  95

Ile Gly Arg Phe Glu Glu Gln Arg Asn Asp Lys Leu Glu Leu Ser Pro
            100                 105                 110

Leu Phe Val Gln Pro Ser Asn Gly Ser Arg Val Val Arg Asp Val Asn
        115                 120                 125

Leu Asn Ala Glu Tyr Asn Glu His Leu Glu Asp Met Asn Pro Val Thr
    130                 135                 140

Val His Pro Gly His Phe Glu Val Asn Gly Leu Arg Ser Glu Phe Leu
```

```
145                 150                 155                 160

Leu Asp Asn Ser Val Arg Ala Gly Ser Ser Val Asp Gly Arg Arg Ala
                165                 170                 175

Ser Cys Lys Arg Lys Ala Leu Asp Ala Ser Gly Gly Gln Ser Ser Ser
            180                 185                 190

Thr Gly Gly Phe Arg Glu Phe Gln Arg Gly Val Ser Ser Ser Trp Ile
        195                 200                 205

Ser Gly Pro Thr Tyr Tyr Ser Pro Ala Met Thr Ala Asn Asp Leu Asn
    210                 215                 220

Ile Ser Leu Asp His Gly Arg Arg Gly Leu Val Ser Ser Ala Val Pro
225                 230                 235                 240

Asn Leu Ser Pro Pro Thr Ile Thr Glu Ser Ser Ser Arg Asn Tyr Pro
                245                 250                 255

Val Trp Val Asn Pro Thr Tyr Gln Gln Glu Thr Val Ser Asn Phe Ala
            260                 265                 270

Pro Ser Leu Asn Ser Pro Gly Leu Ile Pro Ala Asp His Gln Gln Ile
        275                 280                 285

Ser Met Arg Tyr Gly His Ala Leu Gly Asn Phe Ala Ser Gln Asn Pro
    290                 295                 300

Asn Ala Pro Ala Thr His Met Pro Pro Val Ser Arg Asn Thr Phe Gln
305                 310                 315                 320

Trp Asn Thr Ser Pro Val Ala Ala Val Ile Ser Ser Ser Ser Ala Thr
                325                 330                 335

Pro Val Asp Arg Asn Val Ile His Arg Asn Ala Thr Arg Gln Arg Ser
            340                 345                 350

Asn Thr Leu Glu Ile Pro Leu Phe Val Pro Ala Pro Glu Leu Arg Asn
        355                 360                 365

Val Ala His Gly His Ile Ser Arg Asn Ala Ser Gly Ala Arg His Val
    370                 375                 380

Ala Ser Ser Ser Ser Arg Thr Ser Val Gln Pro Ser Pro Ser Ser Pro
385                 390                 395                 400

Ala Leu Thr Pro Tyr Gln Asn Asn Ser Leu His Asn Gln Arg Arg Leu
                405                 410                 415

Ser Glu Asn Phe Arg Arg Ser Leu Leu Ser Ser Leu Val Thr Gln Gln
            420                 425                 430

Arg Ala Ala Arg Ser Leu Ala His Pro Ala Ser Pro Asn Glu His Val
        435                 440                 445

Leu Gln Ser Gly Gly Asp Asn Thr Ser Gln Val His Asn Arg Ala Ser
    450                 455                 460

Ser Arg Ala Gly Pro Arg Gln Gly Gln Asp Ala Thr Gly Ile Ser His
465                 470                 475                 480

Ser Leu Arg Gly Leu Ala Ser Thr Ser Arg Gly Arg Thr Arg Met Gly
                485                 490                 495

Ala Ser Glu Ile Arg Asn Ile Leu Glu His Met Arg Arg Ala Gly Asn
            500                 505                 510

Leu Arg Leu Glu Asp Val Met Leu Leu Asn Gln Ser Ile Met Leu Gly
        515                 520                 525

Ala Ala Asp Ile His Asp Arg Tyr Arg Asp Met Arg Leu Asp Val Asp
    530                 535                 540

Asn Met Thr Tyr Glu Glu Leu Leu Ser Leu Glu Glu Arg Ile Gly Asp
545                 550                 555                 560

Val Cys Thr Gly Leu Asn Glu Glu Thr Ile Ser Asn Arg Leu Lys Gln
                565                 570                 575
```

```
Gln Lys Tyr Lys Ser Ser Thr Arg Ser Ser Gln Glu Val Glu Pro Cys
            580                 585                 590

Cys Val Cys Gln Glu Glu Tyr Lys Glu Glu Glu Glu Ile Gly Arg Leu
        595                 600                 605

Glu Cys Gly His Asp Phe His Ser Gln Cys Ile Lys Glu Trp Leu Lys
    610                 615                 620

Gln Lys Asn Leu Cys Pro Ile Cys Lys Thr Thr Gly Leu Asn Thr Ala
625                 630                 635                 640

Asn Lys Pro Gln Arg
                645


<210> SEQ ID NO 57
<211> LENGTH: 891
<212> TYPE: DNA
<213> ORGANISM: Arabidopsis thaliana

<400> SEQUENCE: 57

ataagtaatc aaattccaaa aaaaataaaa taatacaaat ctctcttttt ctctctaaaa      60

aatcttgata tggatcaaaa cgtaccaata agcaagaagc tatggaacat cgtacgtttt     120

ctcttgtaca tgatccgcaa aggcgtctca aaaaacaaac tcatcgctga cttcaacgcc     180

actctcaaac gtggcaagaa cctcatgttc caccaacgtc gtcgtgtcca cgccggttcc     240

accgcctcag ccgctctaaa cgctacttca gccaccgcgt catcgcgaca agagtacgag     300

tttagctgca gcaacactcc aaactattca ttccctttct ctaatatggc tttcatgagg     360

aaaaagagtc acaataatct cttcacgtgt ggtcaaacgc ctcagacgct tgacgacgac     420

gtagccgccg ctagagccgt tcttgagctt cttaacggcg ttggagagaa aggaaacgtc     480

acgccggcag atttaacggt ggctttgtct ccttatttcc ccggttttgg acagactcca     540

ttggttagac cgttaagagt aacggactca ccgtttccgt taacgccgga aaatggtgat     600

gtggctaatg gacacgttga caaagcagct gatgatttta taaagaagtt ttataagaac     660

ttgaatcagc agaaaaaaat gattgagttc agctaaatat taatccgaat tgtgtgtatc     720

ttcgtcatat ttctcttctt ccttaaatat ttttttaccc tttttctttt ctttcttttt     780

tttctctcgt tttgtgctga ttaaaatcca aagatgtaat gatattttgg ggggttttta     840

ttttcgattc ctaacacaat tggatattat gaataaaaaa atatcatcgg t              891


<210> SEQ ID NO 58
<211> LENGTH: 208
<212> TYPE: PRT
<213> ORGANISM: Arabidopsis thaliana

<400> SEQUENCE: 58

Met Asp Gln Asn Val Pro Ile Ser Lys Lys Leu Trp Asn Ile Val Arg
1               5                   10                  15

Phe Leu Leu Tyr Met Ile Arg Lys Gly Val Ser Lys Asn Lys Leu Ile
            20                  25                  30

Ala Asp Phe Asn Ala Thr Leu Lys Arg Gly Lys Asn Leu Met Phe His
        35                  40                  45

Gln Arg Arg Arg Val His Ala Gly Ser Thr Ala Ser Ala Ala Leu Asn
    50                  55                  60

Ala Thr Ser Ala Thr Ala Ser Ser Arg Gln Glu Tyr Glu Phe Ser Cys
65                  70                  75                  80

Ser Asn Thr Pro Asn Tyr Ser Phe Pro Phe Ser Asn Met Ala Phe Met
                85                  90                  95

Arg Lys Lys Ser His Asn Asn Leu Phe Thr Cys Gly Gln Thr Pro Gln
```

```
            100                 105                 110

Thr Leu Asp Asp Asp Val Ala Ala Ala Arg Ala Val Leu Glu Leu Leu
        115                 120                 125

Asn Gly Val Gly Glu Lys Gly Asn Val Thr Pro Ala Asp Leu Thr Val
    130                 135                 140

Ala Leu Ser Pro Tyr Phe Pro Gly Phe Gly Gln Thr Pro Leu Val Arg
145                 150                 155                 160

Pro Leu Arg Val Thr Asp Ser Pro Phe Pro Leu Thr Pro Glu Asn Gly
                165                 170                 175

Asp Val Ala Asn Gly His Val Asp Lys Ala Ala Asp Asp Phe Ile Lys
            180                 185                 190

Lys Phe Tyr Lys Asn Leu Asn Gln Gln Lys Lys Met Ile Glu Phe Ser
        195                 200                 205


<210> SEQ ID NO 59
<211> LENGTH: 3433
<212> TYPE: DNA
<213> ORGANISM: Arabidopsis thaliana

<400> SEQUENCE: 59

acatctcttc ttcatcctct cttctacttt cctctttcct ctttccttct tcgaataaat     60

ttctagggtt tttcttttct ctaaagtttt catttttatt tcaatgagag ctcgaagaag    120

gagaatatgg gtttgagaac tgataatatt atggcttcgt ttcgaggtgg aatcggggtt    180

tctaatggct gagtcaactc ggtgattctg tgttatagtc acgagcaaat ataaaaaagt    240

ttgtaacttt cttgtttttt taggtgtgtg tgttcagaga aaaggtcgaa tctttttcg    300

gtgtttgtaa aagggaaagt tgtaatctta aagtctgttt ttctttcttg tgttttggta    360

tttagctcat aaaagccgag gagtaatata aaggataggt tttgtctttg tgtgcccttt    420

tgagattgca tgaagaaaaa aagcctctag tgtgttttga aggaaacaga attcgatatt    480

tatgcggtaa tgtgatttgt gaagctactc caagtgctta ggatttgaga tggcttagat    540

ttggtagttg ttcaagctgt ggagtttgtg gtggactaag aagctctctg tctcctttgt    600

ttagtatgtt gtggttatct tctgtttaga aggatttagt tattcatctg gagggggtag    660

tagggtcatt tgtgagattc tgtgattgtg aaataagaag agttttgctg aggagtaatg    720

gcaatgtctt gcaaggatgg taagttggga tgtttggata atgggaagta tgtgaggtat    780

acacctgaac aagttgaagc acttgagagg ctttatcatg actgtcctaa accgagttct    840

attcgccgtc agcagttgat cagagagtgt cctattctct ctaacattga gcctaaacag    900

atcaaagtgt ggtttcagaa ccgaagatgt agagagaaac aaaggaaaga ggcttcacgg    960

cttcaagctg tgaatcggaa gttgacggca atgaacaagc tcttgatgga ggagaatgac   1020

aggttgcaga agcaagtgtc acagctggtc catgaaaaca gctacttccg tcaacatact   1080

ccaaatcctt cactcccagc taaagacaca agctgtgaat cggtggtgac gagtggtcag   1140

caccaattgg catctcaaaa tcctcagaga gatgctagtc ctgcaggact tttgtccatt   1200

gcagaagaaa ctttagcaga gtttctttca aaggcaactg gaaccgctgt tgagtgggtt   1260

cagatgcctg gaatgaagcc tggtccggat tccattggaa tcatcgctat ttctcatggt   1320

tgcactggtg tggcagcacg cgcctgtggc ctagtgggtc ttgagcctac aagggttgca   1380

gagattgtca aggatcgtcc ttcgtggttc cgcgaatgtc gagctgttga agttatgaac   1440

gtgttgccaa ctgccaatgg tggaaccgtt gagctgcttt atatgcagct ctatgcacca   1500

actacattgg ccccaccacg cgatttctgg ctgttacgtt acacctctgt tttagaagat   1560
```

```
ggcagccttg tggtgtgcga gagatctctt aagagcactc aaaatggtcc tagtatgcca   1620

ctggttcaga attttgtgag agcagagatg ctttccagtg ggtacttgat acggccttgt   1680

gatggtggtg gctcaatcat acacatagtg gatcatatgg atttggaggc ttgtagcgtg   1740

cctgaggtct tgcgcccgct ctatgagtca cccaaagtac ttgcacagaa gacaacaatg   1800

gcggcactgc gtcagctcaa gcaaatagct caggaggtta ctcagactaa tagtagtgtt   1860

aatgggtggg gacggcgtcc tgctgcctta agagctctca gccagaggct aagcagaggc   1920

ttcaatgaag ctgtaaatgg tttcactgat gaaggatggt cagtgatagg agatagcatg   1980

gatgatgtca caatcactgt aaactcttct ccagacaagc taatgggtct aaatcttaca   2040

tttgccaatg gctttgctcc tgtaagcaat gttgttttat gcgcaaaagc atcaatgctt   2100

ttacagaatg ttcctccggc gatcctgctt cggtttctga gggagcatag gtcagaatgg   2160

gctgacaaca acattgatgc gtatctagca gcagcagtta aagtagggcc ttgtagtgcc   2220

cgagttggag gatttggagg gcaggttata cttccacttg ctcatactat tgagcatgaa   2280

gagtttatgg aagtcatcaa attggaaggt cttggtcatt cccctgaaga tgcaatcgtt   2340

ccaagagata tcttccttct tcaactttgt agcggaatgg atgaaaatgc tgtaggaacc   2400

tgtgcggaac ttatatttgc tccaatcgat gcttcgtttg cggatgatgc acctctgctt   2460

ccttctggtt ttcgtattat ccctcttgat tccgcaaagc aggaagtatc tagcccaaac   2520

cgaaccttgg atcttgcttc ggcactggaa attggttcag ctggaacaaa agcctcaact   2580

gatcaatcag gaaactccac atgtgcaaga tctgtgatga caatagcatt tgagtttggt   2640

atcgagagcc atatgcaaga acatgtagca tccatggcta ggcagtatgt tcgaggtatc   2700

atatcatcgg tgcagagagt agcattggct ctttctcctt ctcatatcag ctcacaagtt   2760

ggtctacgca ctcctttggg tactcctgaa gcccaaacac ttgctcgttg gatttgccag   2820

agttacaggg gctacatggg tgttgagcta cttaaatcaa acagtgacgg caatgaatct   2880

attcttaaga atctttggca tcacactgat gctataatct gctgctcaat gaaggccttg   2940

cccgtcttca catttgcaaa ccaggcggga cttgacatgc tggagactac attagttgct   3000

cttcaagaca tctctttaga gaagatattt gatgacaatg gaagaaagac tctttgctct   3060

gagttcccac agatcatgca acagggcttc gcgtgccttc aaggcgggat atgtctctca   3120

agcatgggga gaccagtttc gtatgagaga gcagttgctt ggaaagtact caatgaagaa   3180

gaaaatgctc attgcatctg ctttgtgttc atcaattggt cctttgtgtg agatttattg   3240

tattttgtat tttcagacta agcttttgcc ttttggctgt attgtaaaac ggtcatgttg   3300

ttgttgttgt tgttgttgtt cttgatgttg ctgtgaacac gtaaaacagt gttttgtttc   3360

aaaactcaag aaatgcttgc ttaatttgta gtttgattaa gagtgataat gatgatcttt   3420

ttcttttctt gtt                                                      3433
```

<210> SEQ ID NO 60
<211> LENGTH: 837
<212> TYPE: PRT
<213> ORGANISM: Arabidopsis thaliana

<400> SEQUENCE: 60

```
Met Ala Met Ser Cys Lys Asp Gly Lys Leu Gly Cys Leu Asp Asn Gly
1               5                   10                  15

Lys Tyr Val Arg Tyr Thr Pro Glu Gln Val Glu Ala Leu Glu Arg Leu
            20                  25                  30

Tyr His Asp Cys Pro Lys Pro Ser Ser Ile Arg Arg Gln Gln Leu Ile
        35                  40                  45
```

```
Arg Glu Cys Pro Ile Leu Ser Asn Ile Glu Pro Lys Gln Ile Lys Val
    50                  55                  60

Trp Phe Gln Asn Arg Arg Cys Arg Glu Lys Gln Arg Lys Glu Ala Ser
65                  70                  75                  80

Arg Leu Gln Ala Val Asn Arg Lys Leu Thr Ala Met Asn Lys Leu Leu
                85                  90                  95

Met Glu Glu Asn Asp Arg Leu Gln Lys Gln Val Ser Gln Leu Val His
            100                 105                 110

Glu Asn Ser Tyr Phe Arg Gln His Thr Pro Asn Pro Ser Leu Pro Ala
        115                 120                 125

Lys Asp Thr Ser Cys Glu Ser Val Val Thr Ser Gly Gln His Gln Leu
    130                 135                 140

Ala Ser Gln Asn Pro Gln Arg Asp Ala Ser Pro Ala Gly Leu Leu Ser
145                 150                 155                 160

Ile Ala Glu Glu Thr Leu Ala Glu Phe Leu Ser Lys Ala Thr Gly Thr
                165                 170                 175

Ala Val Glu Trp Val Gln Met Pro Gly Met Lys Pro Gly Pro Asp Ser
            180                 185                 190

Ile Gly Ile Ile Ala Ile Ser His Gly Cys Thr Gly Val Ala Ala Arg
        195                 200                 205

Ala Cys Gly Leu Val Gly Leu Glu Pro Thr Arg Val Ala Glu Ile Val
    210                 215                 220

Lys Asp Arg Pro Ser Trp Phe Arg Glu Cys Arg Ala Val Glu Val Met
225                 230                 235                 240

Asn Val Leu Pro Thr Ala Asn Gly Gly Thr Val Glu Leu Leu Tyr Met
                245                 250                 255

Gln Leu Tyr Ala Pro Thr Thr Leu Ala Pro Pro Arg Asp Phe Trp Leu
            260                 265                 270

Leu Arg Tyr Thr Ser Val Leu Glu Asp Gly Ser Leu Val Val Cys Glu
        275                 280                 285

Arg Ser Leu Lys Ser Thr Gln Asn Gly Pro Ser Met Pro Leu Val Gln
    290                 295                 300

Asn Phe Val Arg Ala Glu Met Leu Ser Ser Gly Tyr Leu Ile Arg Pro
305                 310                 315                 320

Cys Asp Gly Gly Gly Ser Ile Ile His Ile Val Asp His Met Asp Leu
                325                 330                 335

Glu Ala Cys Ser Val Pro Glu Val Leu Arg Pro Leu Tyr Glu Ser Pro
            340                 345                 350

Lys Val Leu Ala Gln Lys Thr Thr Met Ala Ala Leu Arg Gln Leu Lys
        355                 360                 365

Gln Ile Ala Gln Glu Val Thr Gln Thr Asn Ser Ser Val Asn Gly Trp
    370                 375                 380

Gly Arg Arg Pro Ala Ala Leu Arg Ala Leu Ser Gln Arg Leu Ser Arg
385                 390                 395                 400

Gly Phe Asn Glu Ala Val Asn Gly Phe Thr Asp Glu Gly Trp Ser Val
                405                 410                 415

Ile Gly Asp Ser Met Asp Asp Val Thr Ile Thr Val Asn Ser Ser Pro
            420                 425                 430

Asp Lys Leu Met Gly Leu Asn Leu Thr Phe Ala Asn Gly Phe Ala Pro
        435                 440                 445

Val Ser Asn Val Val Leu Cys Ala Lys Ala Ser Met Leu Leu Gln Asn
    450                 455                 460

Val Pro Pro Ala Ile Leu Leu Arg Phe Leu Arg Glu His Arg Ser Glu
```

```
465                 470                 475                 480

Trp Ala Asp Asn Asn Ile Asp Ala Tyr Leu Ala Ala Ala Val Lys Val
                485                 490                 495

Gly Pro Cys Ser Ala Arg Val Gly Gly Phe Gly Gly Gln Val Ile Leu
            500                 505                 510

Pro Leu Ala His Thr Ile Glu His Glu Glu Phe Met Glu Val Ile Lys
        515                 520                 525

Leu Glu Gly Leu Gly His Ser Pro Glu Asp Ala Ile Val Pro Arg Asp
    530                 535                 540

Ile Phe Leu Leu Gln Leu Cys Ser Gly Met Asp Glu Asn Ala Val Gly
545                 550                 555                 560

Thr Cys Ala Glu Leu Ile Phe Ala Pro Ile Asp Ala Ser Phe Ala Asp
                565                 570                 575

Asp Ala Pro Leu Leu Pro Ser Gly Phe Arg Ile Ile Pro Leu Asp Ser
            580                 585                 590

Ala Lys Gln Glu Val Ser Ser Pro Asn Arg Thr Leu Asp Leu Ala Ser
        595                 600                 605

Ala Leu Glu Ile Gly Ser Ala Gly Thr Lys Ala Ser Thr Asp Gln Ser
    610                 615                 620

Gly Asn Ser Thr Cys Ala Arg Ser Val Met Thr Ile Ala Phe Glu Phe
625                 630                 635                 640

Gly Ile Glu Ser His Met Gln Glu His Val Ala Ser Met Ala Arg Gln
                645                 650                 655

Tyr Val Arg Gly Ile Ile Ser Ser Val Gln Arg Val Ala Leu Ala Leu
            660                 665                 670

Ser Pro Ser His Ile Ser Ser Gln Val Gly Leu Arg Thr Pro Leu Gly
        675                 680                 685

Thr Pro Glu Ala Gln Thr Leu Ala Arg Trp Ile Cys Gln Ser Tyr Arg
    690                 695                 700

Gly Tyr Met Gly Val Glu Leu Leu Lys Ser Asn Ser Asp Gly Asn Glu
705                 710                 715                 720

Ser Ile Leu Lys Asn Leu Trp His His Thr Asp Ala Ile Ile Cys Cys
                725                 730                 735

Ser Met Lys Ala Leu Pro Val Phe Thr Phe Ala Asn Gln Ala Gly Leu
            740                 745                 750

Asp Met Leu Glu Thr Thr Leu Val Ala Leu Gln Asp Ile Ser Leu Glu
        755                 760                 765

Lys Ile Phe Asp Asp Asn Gly Arg Lys Thr Leu Cys Ser Glu Phe Pro
    770                 775                 780

Gln Ile Met Gln Gln Gly Phe Ala Cys Leu Gln Gly Gly Ile Cys Leu
785                 790                 795                 800

Ser Ser Met Gly Arg Pro Val Ser Tyr Glu Arg Ala Val Ala Trp Lys
                805                 810                 815

Val Leu Asn Glu Glu Glu Asn Ala His Cys Ile Cys Phe Val Phe Ile
            820                 825                 830

Asn Trp Ser Phe Val
        835

<210> SEQ ID NO 61
<211> LENGTH: 3430
<212> TYPE: DNA
<213> ORGANISM: Arabidopsis thaliana

<400> SEQUENCE: 61

acatctcttc ttcatcctct cttctacttt cctctttcct ctttccttct tcgaataaat      60
```

```
ttctagggtt tttcttttct ctaaagtttt catttttatt tcaatgagag ctcgaagaag    120
gagaatatgg gtttgagaac tgataatatt atggcttcgt ttcgaggtgg aatcggggtt    180
tctaatggct gagtcaactc ggtgattctg tgttatagtc acgagcaaat ataaaaaagt    240
ttgtaacttt cttgtttttt taggtgtgtg tgttcagaga aaaggtcgaa tctttttttcg   300
gtgtttgtaa aagggaaagt tgtaatctta aagtctgttt ttctttcttg tgttttggta    360
tttagctcat aaaagccgag gagtaatata aaggataggt tttgtctttg tgtgcccttt    420
tgagattgca tgaagaaaaa aagcctctag tgtgttttga aggaaacaga attcgatatt    480
tatgcggtaa tgtgatttgt gaagctactc caagtgctta ggatttgaga tggcttagat    540
ttggtagttg ttcaagctgt ggagtttgtg gtggactaag aagctctctg tctcctttgt    600
ttagtatgtt gtggttatct tctgtttaga aggatttagt tattcatctg gagggggtag    660
tagggtcatt tgtgagattc tgtgattgtg aaataagaag agttttgctg aggagtaatg    720
gcaatgtctt gcaaggatgg taagttggga tgtttggata atgggaagta tgtgaggtat    780
acacctgaac aagttgaagc acttgagagg ctttatcatg actgtcctaa accgagttct    840
attcgccgtc agcagttgat cagagagtgt cctattctct ctaacattga gcctaaacag    900
atcaaagtgt ggtttcagaa ccgaagatgt agagagaaac aaaggaaaga ggcttcacgg    960
cttcaagctg tgaatcggaa gttgacggca atgaacaagc tcttgatgga ggagaatgac   1020
aggttgcaga agcaagtgtc acagctggtc catgaaaaca gctacttccg tcaacatact   1080
ccaaatcctt cactcccagc taaagacaca agctgtgaat cggtggtgac gagtggtcag   1140
caccaattgg catctcaaaa tcctcagaga gatgctagtc ctgcaggact tttgtccatt   1200
gcagaagaaa ctttagcaga gtttctttca aaggcaactg gaaccgctgt tgagtgggtt   1260
cagatgcctg gaatgaagcc tggtccggat tccattggaa tcatcgctat ttctcatggt   1320
tgcactggtg tggcagcacg cgcctgtggc ctagtgggtc ttgagcctac aagggttgca   1380
gagattgtca aggatcgtcc ttcgtggttc cgcgaatgtc gagctgttga agttatgaac   1440
gtgttgccaa ctgccaatgg tggaaccgtt gagctgcttt atatgcagct ctatgcacca   1500
actacattgg ccccaccacg cgatttctgg ctgttacgtt acacctctgt tttagaagat   1560
ggcagccttg tggtgtgcga gagatctctt aagagcactc aaaatggtcc tagtatgcca   1620
ctggttcaga attttgtgag agcagagatg ctttccagtg ggtacttgat acggccttgt   1680
gatggtggtg gctcaatcat acacatagtg gatcatatgg atttggaggc ttgtagcgtg   1740
cctgaggtct tgcgcccgct ctatgagtca cccaaagtac ttgcacagaa gacaacaatg   1800
gcggcactgc gtcagctcaa gcaaatagct caggaggtta ctcagactaa tagtagtgtt   1860
aatgggtggg gacggcgtcc tgctgcctta agagctctca gccagaggct aagcagaggc   1920
ttcaatgaag ctgtaaatgg tttcactgat gaaggatggt cagtgatagg agatagcatg   1980
gatgatgtca caatcactgt aaactcttct ccagacaagc taatgggtct aaatcttaca   2040
tttgccaatg gctttgctcc tgtaagcaat gttgttttat gcgcaaaagc atcaatgctt   2100
ttacagaatg ttcctccggc gatcctgctt cggtttctga gggagcatag gtcagaatgg   2160
gctgacaaca acattgatgc gtatctagca gcagcagtta aagtagggcc ttgtagtgcc   2220
cgagttggag gatttggagg gcaggttata cttccacttg ctcatactat tgagcatgaa   2280
gagtttatgg aagtcatcaa attggaaggt cttggtcatt cccctgaaga tgcaatcgtt   2340
ccaagagata tcttccttct tcaactttgt agcggaatgg atgaaaatgc tgtaggaacc   2400
tgtgcggaac ttatatttgc tccaatcgat gcttcgtttg cggatgatgc acctctgctt   2460
```

```
ccttctggtt ttcgtattat ccctcttgat tccgcaaagg aagtatctag cccaaaccga   2520

accttggatc ttgcttcggc actggaaatt ggttcagctg gaacaaaagc ctcaactgat   2580

caatcaggaa actccacatg tgcaagatct gtgatgacaa tagcatttga gtttggtatc   2640

gagagccata tgcaagaaca tgtagcatcc atggctaggc agtatgttcg aggtatcata   2700

tcatcggtgc agagagtagc attggctctt tctccttctc atatcagctc acaagttggt   2760

ctacgcactc ctttgggtac tcctgaagcc caaacacttg ctcgttggat ttgccagagt   2820

tacaggggct acatgggtgt tgagctactt aaatcaaaca gtgacggcaa tgaatctatt   2880

cttaagaatc tttggcatca cactgatgct ataatctgct gctcaatgaa ggccttgccc   2940

gtcttcacat ttgcaaacca ggcgggactt gacatgctgg agactacatt agttgctctt   3000

caagacatct ctttagagaa gatatttgat gacaatggaa gaaagactct ttgctctgag   3060

ttcccacaga tcatgcaaca gggcttcgcg tgccttcaag gcgggatatg tctctcaagc   3120

atggggagac cagtttcgta tgagagagca gttgcttgga aagtactcaa tgaagaagaa   3180

aatgctcatt gcatctgctt tgtgttcatc aattggtcct ttgtgtgaga tttattgtat   3240

tttgtatttt cagactaagc ttttgccttt tggctgtatt gtaaaacggt catgttgttg   3300

ttgttgttgt tgttgttctt gatgttgctg tgaacacgta aaacagtgtt ttgtttcaaa   3360

actcaagaaa tgcttgctta atttgtagtt tgattaagag tgataatgat gatctttttc   3420

ttttcttgtt                                                          3430

<210> SEQ ID NO 62
<211> LENGTH: 836
<212> TYPE: PRT
<213> ORGANISM: Arabidopsis thaliana

<400> SEQUENCE: 62

Met Ala Met Ser Cys Lys Asp Gly Lys Leu Gly Cys Leu Asp Asn Gly
1               5                   10                  15

Lys Tyr Val Arg Tyr Thr Pro Glu Gln Val Glu Ala Leu Glu Arg Leu
            20                  25                  30

Tyr His Asp Cys Pro Lys Pro Ser Ser Ile Arg Arg Gln Gln Leu Ile
        35                  40                  45

Arg Glu Cys Pro Ile Leu Ser Asn Ile Glu Pro Lys Gln Ile Lys Val
    50                  55                  60

Trp Phe Gln Asn Arg Arg Cys Arg Glu Lys Gln Arg Lys Glu Ala Ser
65                  70                  75                  80

Arg Leu Gln Ala Val Asn Arg Lys Leu Thr Ala Met Asn Lys Leu Leu
                85                  90                  95

Met Glu Glu Asn Asp Arg Leu Gln Lys Gln Val Ser Gln Leu Val His
            100                 105                 110

Glu Asn Ser Tyr Phe Arg Gln His Thr Pro Asn Pro Ser Leu Pro Ala
        115                 120                 125

Lys Asp Thr Ser Cys Glu Ser Val Val Thr Ser Gly Gln His Gln Leu
    130                 135                 140

Ala Ser Gln Asn Pro Gln Arg Asp Ala Ser Pro Ala Gly Leu Leu Ser
145                 150                 155                 160

Ile Ala Glu Glu Thr Leu Ala Glu Phe Leu Ser Lys Ala Thr Gly Thr
                165                 170                 175

Ala Val Glu Trp Val Gln Met Pro Gly Met Lys Pro Gly Pro Asp Ser
            180                 185                 190

Ile Gly Ile Ile Ala Ile Ser His Gly Cys Thr Gly Val Ala Ala Arg
```

```
        195                 200                 205

Ala Cys Gly Leu Val Gly Leu Glu Pro Thr Arg Val Ala Glu Ile Val
    210                 215                 220

Lys Asp Arg Pro Ser Trp Phe Arg Glu Cys Arg Ala Val Glu Val Met
225                 230                 235                 240

Asn Val Leu Pro Thr Ala Asn Gly Gly Thr Val Glu Leu Leu Tyr Met
                245                 250                 255

Gln Leu Tyr Ala Pro Thr Thr Leu Ala Pro Pro Arg Asp Phe Trp Leu
            260                 265                 270

Leu Arg Tyr Thr Ser Val Leu Glu Asp Gly Ser Leu Val Val Cys Glu
        275                 280                 285

Arg Ser Leu Lys Ser Thr Gln Asn Gly Pro Ser Met Pro Leu Val Gln
    290                 295                 300

Asn Phe Val Arg Ala Glu Met Leu Ser Ser Gly Tyr Leu Ile Arg Pro
305                 310                 315                 320

Cys Asp Gly Gly Gly Ser Ile Ile His Ile Val Asp His Met Asp Leu
                325                 330                 335

Glu Ala Cys Ser Val Pro Glu Val Leu Arg Pro Leu Tyr Glu Ser Pro
            340                 345                 350

Lys Val Leu Ala Gln Lys Thr Thr Met Ala Ala Leu Arg Gln Leu Lys
        355                 360                 365

Gln Ile Ala Gln Glu Val Thr Gln Thr Asn Ser Ser Val Asn Gly Trp
    370                 375                 380

Gly Arg Arg Pro Ala Ala Leu Arg Ala Leu Ser Gln Arg Leu Ser Arg
385                 390                 395                 400

Gly Phe Asn Glu Ala Val Asn Gly Phe Thr Asp Glu Gly Trp Ser Val
                405                 410                 415

Ile Gly Asp Ser Met Asp Asp Val Thr Ile Thr Val Asn Ser Ser Pro
            420                 425                 430

Asp Lys Leu Met Gly Leu Asn Leu Thr Phe Ala Asn Gly Phe Ala Pro
        435                 440                 445

Val Ser Asn Val Val Leu Cys Ala Lys Ala Ser Met Leu Leu Gln Asn
    450                 455                 460

Val Pro Pro Ala Ile Leu Leu Arg Phe Leu Arg Glu His Arg Ser Glu
465                 470                 475                 480

Trp Ala Asp Asn Asn Ile Asp Ala Tyr Leu Ala Ala Ala Val Lys Val
                485                 490                 495

Gly Pro Cys Ser Ala Arg Val Gly Gly Phe Gly Gly Gln Val Ile Leu
            500                 505                 510

Pro Leu Ala His Thr Ile Glu His Glu Glu Phe Met Glu Val Ile Lys
        515                 520                 525

Leu Glu Gly Leu Gly His Ser Pro Glu Asp Ala Ile Val Pro Arg Asp
    530                 535                 540

Ile Phe Leu Leu Gln Leu Cys Ser Gly Met Asp Glu Asn Ala Val Gly
545                 550                 555                 560

Thr Cys Ala Glu Leu Ile Phe Ala Pro Ile Asp Ala Ser Phe Ala Asp
                565                 570                 575

Asp Ala Pro Leu Leu Pro Ser Gly Phe Arg Ile Ile Pro Leu Asp Ser
            580                 585                 590

Ala Lys Glu Val Ser Ser Pro Asn Arg Thr Leu Asp Leu Ala Ser Ala
        595                 600                 605

Leu Glu Ile Gly Ser Ala Gly Thr Lys Ala Ser Thr Asp Gln Ser Gly
    610                 615                 620
```

```
Asn Ser Thr Cys Ala Arg Ser Val Met Thr Ile Ala Phe Glu Phe Gly
625                 630                 635                 640

Ile Glu Ser His Met Gln Glu His Val Ala Ser Met Ala Arg Gln Tyr
                645                 650                 655

Val Arg Gly Ile Ile Ser Ser Val Gln Arg Val Ala Leu Ala Leu Ser
            660                 665                 670

Pro Ser His Ile Ser Ser Gln Val Gly Leu Arg Thr Pro Leu Gly Thr
        675                 680                 685

Pro Glu Ala Gln Thr Leu Ala Arg Trp Ile Cys Gln Ser Tyr Arg Gly
    690                 695                 700

Tyr Met Gly Val Glu Leu Leu Lys Ser Asn Ser Asp Gly Asn Glu Ser
705                 710                 715                 720

Ile Leu Lys Asn Leu Trp His His Thr Asp Ala Ile Ile Cys Cys Ser
                725                 730                 735

Met Lys Ala Leu Pro Val Phe Thr Phe Ala Asn Gln Ala Gly Leu Asp
            740                 745                 750

Met Leu Glu Thr Thr Leu Val Ala Leu Gln Asp Ile Ser Leu Glu Lys
        755                 760                 765

Ile Phe Asp Asp Asn Gly Arg Lys Thr Leu Cys Ser Glu Phe Pro Gln
    770                 775                 780

Ile Met Gln Gln Gly Phe Ala Cys Leu Gln Gly Gly Ile Cys Leu Ser
785                 790                 795                 800

Ser Met Gly Arg Pro Val Ser Tyr Glu Arg Ala Val Ala Trp Lys Val
                805                 810                 815

Leu Asn Glu Glu Glu Asn Ala His Cys Ile Cys Phe Val Phe Ile Asn
            820                 825                 830

Trp Ser Phe Val
        835
```

<210> SEQ ID NO 63
<211> LENGTH: 2801
<212> TYPE: DNA
<213> ORGANISM: Arabidopsis thaliana

<400> SEQUENCE: 63

```
atggaacttg tgtcgtttgg agtagaaaag ctttgggacc gactgagcca agaatatgac      60

caatttaaag gagttgaaga tcaagtaact gagttaaaaa gtaacctaaa cttgttaaag     120

tcatttttga aagatgcaga tgccaagaaa catataagtg agatggtgcg acactgtgtg     180

gaagagatca aagatattgt ttatgacacg gaggacataa tcgaaacgtt tattctcaag     240

gaaaaagttg aaatgaaacg tggcatcatg aagcgtatca aaagatttgc ttcgactata     300

atggatcgta gggaacttgc gtctgatatt ggaggaataa gtaagcggat ctccaaggtg     360

atacaggata tgcaaagttt tggagtacaa cagataatta ctgatggcag ccgttcttca     420

catccactac aagaaagaca aagggagatg cggcacacgt ttctagggga ctccgaaaac     480

gattttgtgg gaatggaagc aaatgttaag aaattggttg gatatttggt ggagaaagat     540

gactatcaaa ttgtttcttt aaccgggatg ggtggtcttg gtaaaaccac ccttgctaga     600

caagttttta atcatgatgt tgtaaaagat cggtttgatg gattcgcatg ggtgagtgtt     660

tcgcaagagt ttactcggat atcggtgtgg caaacgatct tgcagaatct cacatctaaa     720

gagaggaaag atgaaatcca gaatatgaaa gaagctgacc ttcatgatga tctcttccga     780

ttgttggaat catctaaaac attaattgtg ctagatgaca tatggaaaga agaagattgg     840

gacttaatca agccaatatt tccacccaaa aaaggttgga aggtgctact tacttctcga     900
```

```
actgagagta tcgcgatgcg tggagataca acatatatta gctttaaacc aaaatgccta    960

tctatcccag acagttggac acttttccaa agcatagcaa tgccaaggaa agatacatcc   1020

gaatttaagg ttgatgagga aatggaaaat atgggtaaga agatgatcaa acattgtgga   1080

ggactatcat tggctgtcaa agtcttagga gggttgttag ctgcaaaata cacactgcat   1140

gattggaaaa gattatctga gaatattgga tctcatatcg tggaaagaac tagcggtaac   1200

aacagttcta ttgatcatgt attgtctgtg agctttgaag aattgcctaa ttatttgaag   1260

cattgtttcc tatacctcgc ccactttcca gaagatcatg agatagacgt agagaagttg   1320

cattattatt gggctgcaga aggaatatct gaacgtaggc gttacgatgg agagaccatt   1380

cgagatactg gagatagcta catagaggag ttggtgagaa gaaatatggt tatttctgaa   1440

agggacgtta tgacttccag atttgaaact tgtcgtttgc atgacatgat gagagaaatt   1500

tgtttgttta aagccaaaga agagaacttc ctacaaattg tcagtaacca ctccccgaca   1560

tcaaaccctc aaactcttgg tgcttctcgc agatttgtct tacataatcc tactacatta   1620

catgttgaga gatataaaaa taatccaaaa cttcgatcgc tcgtggttgt ctatgatgat   1680

attggaaata gaagatggat gctatcaggt tcaatcttta caagggtaaa acttctacgg   1740

gtgttagatc tcgttcaagc caagtttaaa ggagggaagt taccttctga cattggaaag   1800

ctcatccact taagatactt gagcttaaaa gatgccaagg tatctcatct accttcttct   1860

ctaagaaatc tagtcctgct aatctattta gatatacgca cagatttcac ggatatattc   1920

gtgcccaatg tcttcatggg gatgagagaa ttgagatatc ttgaactacc cagatttatg   1980

catgagaaga caaagttgga gttgagtaat ctagaaaaat tggaggcctt agagaatttc   2040

tcaacaaaga gtagcagctt ggaggatctc cgtggtatgg tcaggttgag gactcttgtg   2100

atcattttaa gtgaggggac tagtctacaa actctatctg catcagtatg tggactgaga   2160

cacttggaaa attttaaaat aatggaaaac gctggcgtta acaggatggg agaagagaga   2220

atggtattgg atttcactta tctcaaaaag ctcaccttga gtatagagat gccaaggctt   2280

cctaaaatac aacaccttcc ttctcacctt acggtcttag atctatctta ctgttgtttg   2340

gaggaagatc caatgccgat tctagagaaa ttactcgagt taaaagattt aagtttagat   2400

tatctatctt tctccgggag gaaaatggtt tgctcggctg gtgggtttcc tcaattgcgt   2460

aagctagctt tggatgaaca agaggagtgg gaagagtgga tagtagaaga aggctccatg   2520

tcacggcttc atactctaag tatttggagt tcaacattaa aggagcttcc tgatgggctg   2580

cgattcatat attctttaaa gaatctgatc atgggaaaga gctggatgga gagattatcg   2640

gaacgaggag aagaatttta caaagttcaa aacattcctt ttattaaatt cagttcttaa   2700

ttcttattat aatcttttga actctttgca ctgtttttgt atgggtgtct tttgttgtat   2760

aataacactt acagatttc ttgcaaaaat atattggttt t                         2801
```

<210> SEQ ID NO 64
<211> LENGTH: 899
<212> TYPE: PRT
<213> ORGANISM: Arabidopsis thaliana

<400> SEQUENCE: 64

```
Met Glu Leu Val Ser Phe Gly Val Glu Lys Leu Trp Asp Arg Leu Ser
1               5                   10                  15

Gln Glu Tyr Asp Gln Phe Lys Gly Val Glu Asp Gln Val Thr Glu Leu
            20                  25                  30

Lys Ser Asn Leu Asn Leu Leu Lys Ser Phe Leu Lys Asp Ala Asp Ala
        35                  40                  45
```

```
Lys Lys His Ile Ser Glu Met Val Arg His Cys Val Glu Glu Ile Lys
    50                  55                  60

Asp Ile Val Tyr Asp Thr Glu Asp Ile Ile Glu Thr Phe Ile Leu Lys
65                  70                  75                  80

Glu Lys Val Glu Met Lys Arg Gly Ile Met Lys Arg Ile Lys Arg Phe
                85                  90                  95

Ala Ser Thr Ile Met Asp Arg Arg Glu Leu Ala Ser Asp Ile Gly Gly
            100                 105                 110

Ile Ser Lys Arg Ile Ser Lys Val Ile Gln Asp Met Gln Ser Phe Gly
        115                 120                 125

Val Gln Gln Ile Ile Thr Asp Gly Ser Arg Ser Ser His Pro Leu Gln
    130                 135                 140

Glu Arg Gln Arg Glu Met Arg His Thr Phe Ser Arg Asp Ser Glu Asn
145                 150                 155                 160

Asp Phe Val Gly Met Glu Ala Asn Val Lys Lys Leu Val Gly Tyr Leu
                165                 170                 175

Val Glu Lys Asp Asp Tyr Gln Ile Val Ser Leu Thr Gly Met Gly Gly
            180                 185                 190

Leu Gly Lys Thr Thr Leu Ala Arg Gln Val Phe Asn His Asp Val Val
        195                 200                 205

Lys Asp Arg Phe Asp Gly Phe Ala Trp Val Ser Val Ser Gln Glu Phe
    210                 215                 220

Thr Arg Ile Ser Val Trp Gln Thr Ile Leu Gln Asn Leu Thr Ser Lys
225                 230                 235                 240

Glu Arg Lys Asp Glu Ile Gln Asn Met Lys Glu Ala Asp Leu His Asp
                245                 250                 255

Asp Leu Phe Arg Leu Leu Glu Ser Ser Lys Thr Leu Ile Val Leu Asp
            260                 265                 270

Asp Ile Trp Lys Glu Glu Asp Trp Asp Leu Ile Lys Pro Ile Phe Pro
        275                 280                 285

Pro Lys Lys Gly Trp Lys Val Leu Leu Thr Ser Arg Thr Glu Ser Ile
    290                 295                 300

Ala Met Arg Gly Asp Thr Thr Tyr Ile Ser Phe Lys Pro Lys Cys Leu
305                 310                 315                 320

Ser Ile Pro Asp Ser Trp Thr Leu Phe Gln Ser Ile Ala Met Pro Arg
                325                 330                 335

Lys Asp Thr Ser Glu Phe Lys Val Asp Glu Glu Met Glu Asn Met Gly
            340                 345                 350

Lys Lys Met Ile Lys His Cys Gly Gly Leu Ser Leu Ala Val Lys Val
        355                 360                 365

Leu Gly Gly Leu Leu Ala Ala Lys Tyr Thr Leu His Asp Trp Lys Arg
    370                 375                 380

Leu Ser Glu Asn Ile Gly Ser His Ile Val Glu Arg Thr Ser Gly Asn
385                 390                 395                 400

Asn Ser Ser Ile Asp His Val Leu Ser Val Ser Phe Glu Glu Leu Pro
                405                 410                 415

Asn Tyr Leu Lys His Cys Phe Leu Tyr Leu Ala His Phe Pro Glu Asp
            420                 425                 430

His Glu Ile Asp Val Glu Lys Leu His Tyr Tyr Trp Ala Ala Glu Gly
        435                 440                 445

Ile Ser Glu Arg Arg Arg Tyr Asp Gly Glu Thr Ile Arg Asp Thr Gly
    450                 455                 460

Asp Ser Tyr Ile Glu Glu Leu Val Arg Arg Asn Met Val Ile Ser Glu
```

```
465                 470                 475                 480

Arg Asp Val Met Thr Ser Arg Phe Glu Thr Cys Arg Leu His Asp Met
                485                 490                 495

Met Arg Glu Ile Cys Leu Phe Lys Ala Lys Glu Glu Asn Phe Leu Gln
            500                 505                 510

Ile Val Ser Asn His Ser Pro Thr Ser Asn Pro Gln Thr Leu Gly Ala
        515                 520                 525

Ser Arg Arg Phe Val Leu His Asn Pro Thr Thr Leu His Val Glu Arg
    530                 535                 540

Tyr Lys Asn Asn Pro Lys Leu Arg Ser Leu Val Val Val Tyr Asp Asp
545                 550                 555                 560

Ile Gly Asn Arg Arg Trp Met Leu Ser Gly Ser Ile Phe Thr Arg Val
                565                 570                 575

Lys Leu Leu Arg Val Leu Asp Leu Val Gln Ala Lys Phe Lys Gly Gly
            580                 585                 590

Lys Leu Pro Ser Asp Ile Gly Lys Leu Ile His Leu Arg Tyr Leu Ser
        595                 600                 605

Leu Lys Asp Ala Lys Val Ser His Leu Pro Ser Ser Leu Arg Asn Leu
    610                 615                 620

Val Leu Leu Ile Tyr Leu Asp Ile Arg Thr Asp Phe Thr Asp Ile Phe
625                 630                 635                 640

Val Pro Asn Val Phe Met Gly Met Arg Glu Leu Arg Tyr Leu Glu Leu
                645                 650                 655

Pro Arg Phe Met His Glu Lys Thr Lys Leu Glu Leu Ser Asn Leu Glu
            660                 665                 670

Lys Leu Glu Ala Leu Glu Asn Phe Ser Thr Lys Ser Ser Ser Leu Glu
        675                 680                 685

Asp Leu Arg Gly Met Val Arg Leu Arg Thr Leu Val Ile Ile Leu Ser
    690                 695                 700

Glu Gly Thr Ser Leu Gln Thr Leu Ser Ala Ser Val Cys Gly Leu Arg
705                 710                 715                 720

His Leu Glu Asn Phe Lys Ile Met Glu Asn Ala Gly Val Asn Arg Met
                725                 730                 735

Gly Glu Glu Arg Met Val Leu Asp Phe Thr Tyr Leu Lys Lys Leu Thr
            740                 745                 750

Leu Ser Ile Glu Met Pro Arg Leu Pro Lys Ile Gln His Leu Pro Ser
        755                 760                 765

His Leu Thr Val Leu Asp Leu Ser Tyr Cys Cys Leu Glu Glu Asp Pro
    770                 775                 780

Met Pro Ile Leu Glu Lys Leu Leu Glu Leu Lys Asp Leu Ser Leu Asp
785                 790                 795                 800

Tyr Leu Ser Phe Ser Gly Arg Lys Met Val Cys Ser Ala Gly Gly Phe
                805                 810                 815

Pro Gln Leu Arg Lys Leu Ala Leu Asp Glu Gln Glu Glu Trp Glu Glu
            820                 825                 830

Trp Ile Val Glu Glu Gly Ser Met Ser Arg Leu His Thr Leu Ser Ile
        835                 840                 845

Trp Ser Ser Thr Leu Lys Glu Leu Pro Asp Gly Leu Arg Phe Ile Tyr
    850                 855                 860

Ser Leu Lys Asn Leu Ile Met Gly Lys Ser Trp Met Glu Arg Leu Ser
865                 870                 875                 880

Glu Arg Gly Glu Glu Phe Tyr Lys Val Gln Asn Ile Pro Phe Ile Lys
                885                 890                 895
```

Phe Ser Ser

<210> SEQ ID NO 65
<211> LENGTH: 3967
<212> TYPE: DNA
<213> ORGANISM: Arabidopsis thaliana

<400> SEQUENCE: 65

```
cgtgtgctta tccaaagacg acgagaggag tcccaagaag tctagcggta tcaatcaaat     60
ctcttcttac tagaggagat tccttggaac catcaagagg aagcattatg gctggggaac    120
ttatttcgtt tggtatacaa aacctgtgga acctactgag tcaagaatgc gagctatttc    180
agggagtcga agatcaagta actgaactaa aaagggatct aaacttgtta agctcttttc    240
tgaaagatgc agatgcaaag aaacatacaa gtgcggtggt gaaaaactgt gttgaagaga    300
tcaaggaaat tatctatgat ggagaggata caatcgaaac atttgttctt gagcaaaacc    360
tgggaaaaac aagtggtatc aagaagagta tcagaagact tgcttgcatt attccagatc    420
gaaggagata tgcattaggt atcggaggct taagtaatag gatctccaag gtgatccgag    480
atatgcagag ttttggagtg caacaagcta tcgttgatgg tgggtataag caacctcaag    540
gtgataaaca aagggagatg cgaccaagat tttctaagga cgacgatagc gattttgtgg    600
ggttggaagc aaatgttaag aaattggttg gatatttggt ggacgaagca aacgttcaag    660
tggtttccat aaccgggatg ggtggtctag gtaaaaccac acttgctaaa caggttttta    720
accatgagga tgttaaacat cagtttgatg ggctctcatg ggtgtgtgtt tcacaagatt    780
ttacccgaat gaatgtatgg caaaagatct tgagggacct caaacccaaa gaggaagaaa    840
agaaaatcat ggagatgaca caagatacac tccaaggtga actaattcga ttgttggaaa    900
cgtctaagtc attaattgtc ctcgatgaca tatgggaaaa agaagattgg gaactaatca    960
agccaatatt tccaccgacc aaaggttgga aagtgttgct tacttctcga aacgagagtg   1020
tcgccatgcg tagaaataca tcatatatca actttaaacc agaatgccta accactgaag   1080
acagttggac actttttcag aggatagccc ttcctatgaa agatgcagct gaatttaaga   1140
ttgatgagga aaaggaagag ttgggtaagc taatgatcaa acactgtgga gggttaccat   1200
tggccatcag agtgttagga ggtatgttag ctgaaaaata cacatcgcat gattggagaa   1260
gattatctga gaatattgga tctcatctcg tgggaggaag aactaacttt aatgacgaca   1320
acaacaatac atgtaactat gtattgtctc taagctttga agaattgcca agttatttga   1380
agcattgttt cctctacttg gcccattttc cagatgatta tgagataaac gtaaagaatt   1440
tgtcatatta ctgggctgca gaaggaatat tccaacctag gcattacgat ggagaaatca   1500
ttcgagatgt tggagatgtc tacatagagg agctggtgag gaggaatatg gtcatttccg   1560
aaagagatgt aaagacttcg agatttgaaa cttgtcattt gcatgacatg atgagagaag   1620
tttgtttgtt aaaagccaaa gaagagaact tcctacagat taccagtagc cgcacttcaa   1680
ctggaaactc tctgtctatt gtcacatctc gcaggcttgt ctaccaatat cctattacat   1740
tagatgttga gaaagatata aacgatccaa aacttcgatc tctcgtggtt gttgccaata   1800
cttatatgtt ttggggaggt tggagttgga tgctgttagg ttcaagcttt ataaggttag   1860
aactactgag ggtattagat atccatagag ccaagttgaa aggagggaag ttagcttctt   1920
ccattggaca gctcatccac ttaagatact tgaacttaaa gcatgctgag gtaactcata   1980
taccttattc actaggaaat ctgaagttgt tgatctatct gaatttagtc attttagtct   2040
ccggatctac attggtgccc aatgtcttga aggagatgca acaactgaga taccttgcgt   2100
```

```
taccaaaaga tatggggagg aagacaaaac tagaattgag taatctagta aaattggaga   2160

ctttgaaaaa tttctcaaca aagaattgca gcttggagga tcttcgtggt atggtcaggc   2220

tgagaacgct caccatcgaa ttacgtaagg agacgagtct agaaactcta gctgcatcta   2280

taggcggatt gaaatacctc gaaagcctta caataactga tcttggttct gagatgagga   2340

cgaaggaagc gggaatcgta tttgatttcg tttatctcaa aacgctaacg ttgaaactgt   2400

atatgcctag gctttctaaa gaacaacact tcccttctca ccttacaacc ttatatctac   2460

aacattgtcg gttggaagag gatcccatgc cgattctaga gaagttgcat cagttgaaag   2520

agcttgaatt aaggcgtaaa tctttcagtg gaaaggaaat ggtttgctcg agcggtgggt   2580

ttcctcaatt gcagaagctt tcaataaaag gactagagga atgggaagat tggaaagtag   2640

aagaaagctc catgccagtt cttcatactc tcgatattcg ggattgtcga aaattaaagc   2700

agcttcctga tgaacacctt ccttctcacc ttacatccat atctctattt ttttgttgtt   2760

tggaggagga tccaatgccg actctagaga gattggttca cttgaaagag cttcaattat   2820

tgtttagatc tttcagtggg aggataatgg tttgcgctgg cagtgggttt cctcaactgc   2880

acaagctaaa attatctgaa ctagatgggt tggaagagtg gatagtagag gatggctcca   2940

tgccacagct tcatactctg gaaattcgtc ggtgtccaaa gttaaagaag cttcctaatg   3000

ggtttccaca attgcagaat cttgagttaa atgagctaga ggaatgggaa gagtggatag   3060

tagaggatgg ctccatgcca cttcttcata ctctaagaat ttggaattgt ccaaagttaa   3120

agcagctgcc tgatgggttg cgatttatct attcattaaa gaatttgact gtaccaaaga   3180

gatggaagaa gagattgtcg aaaggaggag aagattatta caaagtccaa cacattcctt   3240

ctgttgaatt ctactaggaa tgctctcagc aatcacagac tatgtatata tatgtacaca   3300

taaagagctg cattgatggt gttcgatgaa ttgtctaact gtgactatcc ttgacgagat   3360

atgtaatcat aagcctctgt ttccacccaa aatcaggtcg gaagatagtt gcaggtagga   3420

agctaatcaa acaagacacc ttatttttca cgacgagatg ttgaacccct gaagaatgtt   3480

ggacaccatt ttgatggata aaacattttc ataggagaaa tgatacttta tgggagtgtt   3540

gcggcgaagc tactgaacct ttttgaaagc ggtgttgcct atctttaaga gcgtcggagg   3600

tgatataact gggagactct tgatgagatg ttggcctatc tggaatactt cccagttggg   3660

agaccaacgg agatgaatac cgtcaacaat tcaccaacga cccatctcaa gagcttggac   3720

acgagggaga aggttggtgc ctggttcaaa cagtggtgca tccaaaacgc aggccgtgta   3780

gcattttgtt tcgggttcta catggccatg gcgaagaagg gtgaccagtt ggaaggtgca   3840

tacaccctaa atactataaa ggtttataga agtgattgat ttattccatt caacgattta   3900

caatatatat acacaagaga gacttgctga gcacacttat aatcaatgtg agtatataca   3960

atattac                                                             3967
```

<210> SEQ ID NO 66
<211> LENGTH: 1049
<212> TYPE: PRT
<213> ORGANISM: Arabidopsis thaliana

<400> SEQUENCE: 66

```
Met Ala Gly Glu Leu Ile Ser Phe Gly Ile Gln Asn Leu Trp Asn Leu
1               5                   10                  15

Leu Ser Gln Glu Cys Glu Leu Phe Gln Gly Val Glu Asp Gln Val Thr
            20                  25                  30

Glu Leu Lys Arg Asp Leu Asn Leu Leu Ser Ser Phe Leu Lys Asp Ala
        35                  40                  45
```

```
Asp Ala Lys Lys His Thr Ser Ala Val Val Lys Asn Cys Val Glu Glu
    50                  55                  60

Ile Lys Glu Ile Ile Tyr Asp Gly Glu Asp Thr Ile Glu Thr Phe Val
65                  70                  75                  80

Leu Glu Gln Asn Leu Gly Lys Thr Ser Gly Ile Lys Lys Ser Ile Arg
                85                  90                  95

Arg Leu Ala Cys Ile Ile Pro Asp Arg Arg Arg Tyr Ala Leu Gly Ile
            100                 105                 110

Gly Gly Leu Ser Asn Arg Ile Ser Lys Val Ile Arg Asp Met Gln Ser
        115                 120                 125

Phe Gly Val Gln Gln Ala Ile Val Asp Gly Gly Tyr Lys Gln Pro Gln
    130                 135                 140

Gly Asp Lys Gln Arg Glu Met Arg Pro Arg Phe Ser Lys Asp Asp Asp
145                 150                 155                 160

Ser Asp Phe Val Gly Leu Glu Ala Asn Val Lys Lys Leu Val Gly Tyr
                165                 170                 175

Leu Val Asp Glu Ala Asn Val Gln Val Val Ser Ile Thr Gly Met Gly
            180                 185                 190

Gly Leu Gly Lys Thr Thr Leu Ala Lys Gln Val Phe Asn His Glu Asp
        195                 200                 205

Val Lys His Gln Phe Asp Gly Leu Ser Trp Val Cys Val Ser Gln Asp
    210                 215                 220

Phe Thr Arg Met Asn Val Trp Gln Lys Ile Leu Arg Asp Leu Lys Pro
225                 230                 235                 240

Lys Glu Glu Glu Lys Lys Ile Met Glu Met Thr Gln Asp Thr Leu Gln
                245                 250                 255

Gly Glu Leu Ile Arg Leu Leu Glu Thr Ser Lys Ser Leu Ile Val Leu
            260                 265                 270

Asp Asp Ile Trp Glu Lys Glu Asp Trp Glu Leu Ile Lys Pro Ile Phe
        275                 280                 285

Pro Pro Thr Lys Gly Trp Lys Val Leu Leu Thr Ser Arg Asn Glu Ser
    290                 295                 300

Val Ala Met Arg Arg Asn Thr Ser Tyr Ile Asn Phe Lys Pro Glu Cys
305                 310                 315                 320

Leu Thr Thr Glu Asp Ser Trp Thr Leu Phe Gln Arg Ile Ala Leu Pro
                325                 330                 335

Met Lys Asp Ala Ala Glu Phe Lys Ile Asp Glu Glu Lys Glu Glu Leu
            340                 345                 350

Gly Lys Leu Met Ile Lys His Cys Gly Gly Leu Pro Leu Ala Ile Arg
        355                 360                 365

Val Leu Gly Gly Met Leu Ala Glu Lys Tyr Thr Ser His Asp Trp Arg
    370                 375                 380

Arg Leu Ser Glu Asn Ile Gly Ser His Leu Val Gly Gly Arg Thr Asn
385                 390                 395                 400

Phe Asn Asp Asp Asn Asn Asn Thr Cys Asn Tyr Val Leu Ser Leu Ser
                405                 410                 415

Phe Glu Glu Leu Pro Ser Tyr Leu Lys His Cys Phe Leu Tyr Leu Ala
            420                 425                 430

His Phe Pro Asp Asp Tyr Glu Ile Asn Val Lys Asn Leu Ser Tyr Tyr
        435                 440                 445

Trp Ala Ala Glu Gly Ile Phe Gln Pro Arg His Tyr Asp Gly Glu Ile
    450                 455                 460

Ile Arg Asp Val Gly Asp Val Tyr Ile Glu Glu Leu Val Arg Arg Asn
```

```
465                 470                 475                 480

Met Val Ile Ser Glu Arg Asp Val Lys Thr Ser Arg Phe Glu Thr Cys
                485                 490                 495

His Leu His Asp Met Met Arg Glu Val Cys Leu Leu Lys Ala Lys Glu
            500                 505                 510

Glu Asn Phe Leu Gln Ile Thr Ser Ser Arg Thr Ser Thr Gly Asn Ser
        515                 520                 525

Leu Ser Ile Val Thr Ser Arg Arg Leu Val Tyr Gln Tyr Pro Ile Thr
    530                 535                 540

Leu Asp Val Glu Lys Asp Ile Asn Asp Pro Lys Leu Arg Ser Leu Val
545                 550                 555                 560

Val Val Ala Asn Thr Tyr Met Phe Trp Gly Gly Trp Ser Trp Met Leu
                565                 570                 575

Leu Gly Ser Ser Phe Ile Arg Leu Glu Leu Leu Arg Val Leu Asp Ile
            580                 585                 590

His Arg Ala Lys Leu Lys Gly Gly Lys Leu Ala Ser Ser Ile Gly Gln
        595                 600                 605

Leu Ile His Leu Arg Tyr Leu Asn Leu Lys His Ala Glu Val Thr His
    610                 615                 620

Ile Pro Tyr Ser Leu Gly Asn Leu Lys Leu Leu Ile Tyr Leu Asn Leu
625                 630                 635                 640

Val Ile Leu Val Ser Gly Ser Thr Leu Val Pro Asn Val Leu Lys Glu
                645                 650                 655

Met Gln Gln Leu Arg Tyr Leu Ala Leu Pro Lys Asp Met Gly Arg Lys
            660                 665                 670

Thr Lys Leu Glu Leu Ser Asn Leu Val Lys Leu Glu Thr Leu Lys Asn
        675                 680                 685

Phe Ser Thr Lys Asn Cys Ser Leu Glu Asp Leu Arg Gly Met Val Arg
    690                 695                 700

Leu Arg Thr Leu Thr Ile Glu Leu Arg Lys Glu Thr Ser Leu Glu Thr
705                 710                 715                 720

Leu Ala Ala Ser Ile Gly Gly Leu Lys Tyr Leu Glu Ser Leu Thr Ile
                725                 730                 735

Thr Asp Leu Gly Ser Glu Met Arg Thr Lys Glu Ala Gly Ile Val Phe
            740                 745                 750

Asp Phe Val Tyr Leu Lys Thr Leu Thr Leu Lys Leu Tyr Met Pro Arg
        755                 760                 765

Leu Ser Lys Glu Gln His Phe Pro Ser His Leu Thr Thr Leu Tyr Leu
    770                 775                 780

Gln His Cys Arg Leu Glu Glu Asp Pro Met Pro Ile Leu Glu Lys Leu
785                 790                 795                 800

His Gln Leu Lys Glu Leu Glu Leu Arg Arg Lys Ser Phe Ser Gly Lys
                805                 810                 815

Glu Met Val Cys Ser Ser Gly Gly Phe Pro Gln Leu Gln Lys Leu Ser
            820                 825                 830

Ile Lys Gly Leu Glu Glu Trp Glu Asp Trp Lys Val Glu Glu Ser Ser
        835                 840                 845

Met Pro Val Leu His Thr Leu Asp Ile Arg Asp Cys Arg Lys Leu Lys
    850                 855                 860

Gln Leu Pro Asp Glu His Leu Pro Ser His Leu Thr Ser Ile Ser Leu
865                 870                 875                 880

Phe Phe Cys Cys Leu Glu Glu Asp Pro Met Pro Thr Leu Glu Arg Leu
                885                 890                 895
```

```
Val His Leu Lys Glu Leu Gln Leu Leu Phe Arg Ser Phe Ser Gly Arg
            900                 905                 910

Ile Met Val Cys Ala Gly Ser Gly Phe Pro Gln Leu His Lys Leu Lys
        915                 920                 925

Leu Ser Glu Leu Asp Gly Leu Glu Glu Trp Ile Val Glu Asp Gly Ser
    930                 935                 940

Met Pro Gln Leu His Thr Leu Glu Ile Arg Arg Cys Pro Lys Leu Lys
945                 950                 955                 960

Lys Leu Pro Asn Gly Phe Pro Gln Leu Gln Asn Leu Glu Leu Asn Glu
                965                 970                 975

Leu Glu Glu Trp Glu Glu Trp Ile Val Glu Asp Gly Ser Met Pro Leu
            980                 985                 990

Leu His Thr Leu Arg Ile Trp Asn  Cys Pro Lys Leu Lys  Gln Leu Pro
        995                 1000                1005

Asp Gly  Leu Arg Phe Ile Tyr  Ser Leu Lys Asn Leu  Thr Val Pro
    1010                1015                1020

Lys Arg  Trp Lys Lys Arg Leu  Ser Lys Gly Gly Glu  Asp Tyr Tyr
    1025                1030                1035

Lys Val  Gln His Ile Pro Ser  Val Glu Phe Tyr
    1040                1045
```

<210> SEQ ID NO 67
<211> LENGTH: 3757
<212> TYPE: DNA
<213> ORGANISM: Arabidopsis thaliana

<400> SEQUENCE: 67

```
cgtgtgctta tccaaagacg acgagaggag tcccaagaag tctagcggta tcaatcaaat     60

ctcttcttac tagaggagat tccttggaac catcaagagg aagcattatg gctggggaac    120

ttatttcgtt tggtatacaa aacctgtgga acctactgag tcaagaatgc gagctatttc    180

agggagtcga agatcaagta actgaactaa aaagggatct aaacttgtta agctcttttc    240

tgaaagatgc agatgcaaag aaacatacaa gtgcggtggt gaaaaactgt gttgaagaga    300

tcaaggaaat tatctatgat ggagaggata caatcgaaac atttgttctt gagcaaaacc    360

tgggaaaaac aagtggtatc aagaagagta tcagaagact tgcttgcatt attccagatc    420

gaaggagata tgcattaggt atcggaggct taagtaatag gatctccaag gtgatccgag    480

atatgcagag ttttggagtg caacaagcta tcgttgatgg tgggtataag caacctcaag    540

gtgataaaca aagggagatg cgaccaagat tttctaagga cgacgatagc gattttgtgg    600

ggttggaagc aaatgttaag aaattggttg gatatttggt ggacgaagca aacgttcaag    660

tggtttccat aaccgggatg ggtggtctag gtaaaaccac acttgctaaa caggttttta    720

accatgagga tgttaaacat cagtttgatg ggctctcatg ggtgtgtgtt tcacaagatt    780

ttacccgaat gaatgtatgg caaaagatct tgagggacct caaacccaaa gaggaagaaa    840

agaaaatcat ggagatgaca caagatacac tccaaggtga actaattcga ttgttggaaa    900

cgtctaagtc attaattgtc ctcgatgaca tatgggaaaa agaagattgg gaactaatca    960

agccaatatt tccaccgacc aaaggttgga aagtgttgct tacttctcga aacgagagtg   1020

tcgccatgcg tagaaataca tcatatatca actttaaacc agaatgccta accactgaag   1080

acagttggac actttttcag aggatagccc ttcctatgaa agatgcagct gaatttaaga   1140

ttgatgagga aaaggaagag ttgggtaagc taatgatcaa acactgtgga gggttaccat   1200

tggccatcag agtgttagga ggtatgttag ctgaaaaata cacatcgcat gattggagaa   1260
```

```
gattatctga gaatattgga tctcatctcg tgggaggaag aactaacttt aatgacgaca   1320
acaacaatac atgtaactat gtattgtctc taagctttga agaattgcca agttatttga   1380
agcattgttt cctctacttg gcccattttc cagatgatta tgagataaac gtaaagaatt   1440
tgtcatatta ctgggctgca gaaggaatat tccaacctag gcattacgat ggagaaatca   1500
ttcgagatgt tggagatgtc tacatagagg agctggtgag gaggaatatg gtcatttccg   1560
aaagagatgt aaagacttcg agatttgaaa cttgtcattt gcatgacatg atgagagaag   1620
tttgtttgtt aaaagccaaa gaagagaact tcctacagat taccagtagc cgcacttcaa   1680
ctggaaactc tctgtctatt gtcacatctc gcaggcttgt ctaccaatat cctattacat   1740
tagatgttga gaaagatata aacgatccaa aacttcgatc tctcgtggtt gttgccaata   1800
cttatatgtt ttggggaggt tggagttgga tgctgttagg ttcaagcttt ataaggttag   1860
aactactgag ggtattagat atccatagag ccaagttgaa aggagggaag ttagcttctt   1920
ccattggaca gctcatccac ttaagatact tgaacttaaa gcatgctgag gtaactcata   1980
taccttattc actaggaaat ctgaagttgt tgatctatct gaatttagtc attttagtct   2040
ccggatctac attggtgccc aatgtcttga aggagatgca acaactgaga taccttgcgt   2100
taccaaaaga tatggggagg aagacaaaac tagaattgag taatctagta aaattggaga   2160
ctttgaaaaa tttctcaaca aagaattgca gcttggagga tcttcgtggt atggtcaggc   2220
tgagaacgct caccatcgaa ttacgtaagg agacgagtct agaaactcta gctgcatcta   2280
taggcggatt gaaatacctc gaaagcctta caataactga tcttggttct gagatgagga   2340
cgaaggaagc gggaatcgta tttgatttcg tttatctcaa aacgctaacg ttgaaactgt   2400
atatgcctag gctttctaaa gaacaacact tcccttctca ccttacaacc ttatatctac   2460
aacattgtcg gttggaagag gatcccatgc cgattctaga gaagttgcat cagttgaaag   2520
agcttgaatt aaggcgtaaa tctttcagtg gaaaggaaat ggtttgctcg agcggtgggt   2580
ttcctcaatt gcagaagctt tcaataaaag gactagagga atgggaagat tggaaagtag   2640
aagaaagctc catgccagtt cttcatactc tcgatattcg ggattgtcga aaattaaagc   2700
agcttcctga tgaacacctt ccttctcacc ttacatccat atctctattt ttttgttgtt   2760
tggaggagga tccaatgccg actctagaga gattggttca cttgaaagag cttcaattat   2820
tgtttagatc tttcagtggg aggataatgg tttgcgctgg cagtgggttt cctcaactgc   2880
acaagctaaa attatctgaa ctagatgggt tggaagagtg gatagtagag gatggctcca   2940
tgccacagct tcatactctg gaaattcgtc ggtgtccaaa gttaaagaag cttcctaatg   3000
ggtttccaca attgcagaat cttgagttaa atgagctaga ggaatgggaa gagtggatag   3060
tagaggatgg ctccatgcca cttcttcata ctctaagaat ttggaattgt ccaaagttaa   3120
agcagctgcc tgatgggttg cgatttatct attcattaaa gaatttgact gtaccaaaga   3180
gatggaagaa gagattgtcg aaaggaggag aagattatta caaagtccaa cacattcctt   3240
ctgttgaatt ctactaggaa tgctctcagc aatcacagac tatgtatata tatgtacaca   3300
taaagagctg cattgatggt gttcgatgaa ttgtctaact gtgactatcc ttgacgagat   3360
atgtaatcat aagcctctgt ttccacccaa aatcaggtcg gaagatagtt gcaggtagga   3420
agctaatcaa acaagacacc ttatttttca cgacgagatg ttgaacccct gaagaatgtt   3480
ggacaccatt ttgatggata aaacattttc ataggagaaa tgatagagtc gaggtgaaaa   3540
ggtgtctagc ttttgaagct ttgctgtgta ctaagtggac aactttctta ttctctatct   3600
gtttttggtg tgtaataaga atctgaattt tatgcatggg tgaatttgta cgggttaata   3660
```

```
gagaagttca taacctaagt taagactagt ctgctaaatt cggacacaat gtgaaattct   3720

caagctcatc gtttaatcaa cagagagaat ttgattg                            3757


<210> SEQ ID NO 68
<211> LENGTH: 1049
<212> TYPE: PRT
<213> ORGANISM: Arabidopsis thaliana

<400> SEQUENCE: 68

Met Ala Gly Glu Leu Ile Ser Phe Gly Ile Gln Asn Leu Trp Asn Leu
1               5                   10                  15

Leu Ser Gln Glu Cys Glu Leu Phe Gln Gly Val Glu Asp Gln Val Thr
            20                  25                  30

Glu Leu Lys Arg Asp Leu Asn Leu Leu Ser Ser Phe Leu Lys Asp Ala
        35                  40                  45

Asp Ala Lys Lys His Thr Ser Ala Val Val Lys Asn Cys Val Glu Glu
    50                  55                  60

Ile Lys Glu Ile Ile Tyr Asp Gly Glu Asp Thr Ile Glu Thr Phe Val
65                  70                  75                  80

Leu Glu Gln Asn Leu Gly Lys Thr Ser Gly Ile Lys Lys Ser Ile Arg
                85                  90                  95

Arg Leu Ala Cys Ile Ile Pro Asp Arg Arg Arg Tyr Ala Leu Gly Ile
            100                 105                 110

Gly Gly Leu Ser Asn Arg Ile Ser Lys Val Ile Arg Asp Met Gln Ser
        115                 120                 125

Phe Gly Val Gln Gln Ala Ile Val Asp Gly Gly Tyr Lys Gln Pro Gln
    130                 135                 140

Gly Asp Lys Gln Arg Glu Met Arg Pro Arg Phe Ser Lys Asp Asp Asp
145                 150                 155                 160

Ser Asp Phe Val Gly Leu Glu Ala Asn Val Lys Lys Leu Val Gly Tyr
                165                 170                 175

Leu Val Asp Glu Ala Asn Val Gln Val Val Ser Ile Thr Gly Met Gly
            180                 185                 190

Gly Leu Gly Lys Thr Thr Leu Ala Lys Gln Val Phe Asn His Glu Asp
        195                 200                 205

Val Lys His Gln Phe Asp Gly Leu Ser Trp Val Cys Val Ser Gln Asp
    210                 215                 220

Phe Thr Arg Met Asn Val Trp Gln Lys Ile Leu Arg Asp Leu Lys Pro
225                 230                 235                 240

Lys Glu Glu Glu Lys Lys Ile Met Glu Met Thr Gln Asp Thr Leu Gln
                245                 250                 255

Gly Glu Leu Ile Arg Leu Leu Glu Thr Ser Lys Ser Leu Ile Val Leu
            260                 265                 270

Asp Asp Ile Trp Glu Lys Glu Asp Trp Glu Leu Ile Lys Pro Ile Phe
        275                 280                 285

Pro Pro Thr Lys Gly Trp Lys Val Leu Leu Thr Ser Arg Asn Glu Ser
    290                 295                 300

Val Ala Met Arg Arg Asn Thr Ser Tyr Ile Asn Phe Lys Pro Glu Cys
305                 310                 315                 320

Leu Thr Thr Glu Asp Ser Trp Thr Leu Phe Gln Arg Ile Ala Leu Pro
                325                 330                 335

Met Lys Asp Ala Ala Glu Phe Lys Ile Asp Glu Glu Lys Glu Glu Leu
            340                 345                 350

Gly Lys Leu Met Ile Lys His Cys Gly Gly Leu Pro Leu Ala Ile Arg
        355                 360                 365
```

```
Val Leu Gly Gly Met Leu Ala Glu Lys Tyr Thr Ser His Asp Trp Arg
    370                 375                 380

Arg Leu Ser Glu Asn Ile Gly Ser His Leu Val Gly Gly Arg Thr Asn
385                 390                 395                 400

Phe Asn Asp Asp Asn Asn Asn Thr Cys Asn Tyr Val Leu Ser Leu Ser
                405                 410                 415

Phe Glu Glu Leu Pro Ser Tyr Leu Lys His Cys Phe Leu Tyr Leu Ala
            420                 425                 430

His Phe Pro Asp Asp Tyr Glu Ile Asn Val Lys Asn Leu Ser Tyr Tyr
        435                 440                 445

Trp Ala Ala Glu Gly Ile Phe Gln Pro Arg His Tyr Asp Gly Glu Ile
    450                 455                 460

Ile Arg Asp Val Gly Asp Val Tyr Ile Glu Glu Leu Val Arg Arg Asn
465                 470                 475                 480

Met Val Ile Ser Glu Arg Asp Val Lys Thr Ser Arg Phe Glu Thr Cys
                485                 490                 495

His Leu His Asp Met Met Arg Glu Val Cys Leu Leu Lys Ala Lys Glu
            500                 505                 510

Glu Asn Phe Leu Gln Ile Thr Ser Ser Arg Thr Ser Thr Gly Asn Ser
        515                 520                 525

Leu Ser Ile Val Thr Ser Arg Arg Leu Val Tyr Gln Tyr Pro Ile Thr
    530                 535                 540

Leu Asp Val Glu Lys Asp Ile Asn Asp Pro Lys Leu Arg Ser Leu Val
545                 550                 555                 560

Val Val Ala Asn Thr Tyr Met Phe Trp Gly Gly Trp Ser Trp Met Leu
                565                 570                 575

Leu Gly Ser Ser Phe Ile Arg Leu Glu Leu Leu Arg Val Leu Asp Ile
            580                 585                 590

His Arg Ala Lys Leu Lys Gly Gly Lys Leu Ala Ser Ser Ile Gly Gln
        595                 600                 605

Leu Ile His Leu Arg Tyr Leu Asn Leu Lys His Ala Glu Val Thr His
    610                 615                 620

Ile Pro Tyr Ser Leu Gly Asn Leu Lys Leu Leu Ile Tyr Leu Asn Leu
625                 630                 635                 640

Val Ile Leu Val Ser Gly Ser Thr Leu Val Pro Asn Val Leu Lys Glu
                645                 650                 655

Met Gln Gln Leu Arg Tyr Leu Ala Leu Pro Lys Asp Met Gly Arg Lys
            660                 665                 670

Thr Lys Leu Glu Leu Ser Asn Leu Val Lys Leu Glu Thr Leu Lys Asn
        675                 680                 685

Phe Ser Thr Lys Asn Cys Ser Leu Glu Asp Leu Arg Gly Met Val Arg
    690                 695                 700

Leu Arg Thr Leu Thr Ile Glu Leu Arg Lys Glu Thr Ser Leu Glu Thr
705                 710                 715                 720

Leu Ala Ala Ser Ile Gly Gly Leu Lys Tyr Leu Glu Ser Leu Thr Ile
                725                 730                 735

Thr Asp Leu Gly Ser Glu Met Arg Thr Lys Glu Ala Gly Ile Val Phe
            740                 745                 750

Asp Phe Val Tyr Leu Lys Thr Leu Thr Leu Lys Leu Tyr Met Pro Arg
        755                 760                 765

Leu Ser Lys Glu Gln His Phe Pro Ser His Leu Thr Thr Leu Tyr Leu
    770                 775                 780

Gln His Cys Arg Leu Glu Glu Asp Pro Met Pro Ile Leu Glu Lys Leu
```

```
785                 790                 795                 800

His Gln Leu Lys Glu Leu Glu Leu Arg Arg Lys Ser Phe Ser Gly Lys
                805                 810                 815

Glu Met Val Cys Ser Ser Gly Gly Phe Pro Gln Leu Gln Lys Leu Ser
            820                 825                 830

Ile Lys Gly Leu Glu Glu Trp Glu Asp Trp Lys Val Glu Glu Ser Ser
        835                 840                 845

Met Pro Val Leu His Thr Leu Asp Ile Arg Asp Cys Arg Lys Leu Lys
    850                 855                 860

Gln Leu Pro Asp Glu His Leu Pro Ser His Leu Thr Ser Ile Ser Leu
865                 870                 875                 880

Phe Phe Cys Cys Leu Glu Glu Asp Pro Met Pro Thr Leu Glu Arg Leu
                885                 890                 895

Val His Leu Lys Glu Leu Gln Leu Leu Phe Arg Ser Phe Ser Gly Arg
            900                 905                 910

Ile Met Val Cys Ala Gly Ser Gly Phe Pro Gln Leu His Lys Leu Lys
        915                 920                 925

Leu Ser Glu Leu Asp Gly Leu Glu Glu Trp Ile Val Glu Asp Gly Ser
    930                 935                 940

Met Pro Gln Leu His Thr Leu Glu Ile Arg Arg Cys Pro Lys Leu Lys
945                 950                 955                 960

Lys Leu Pro Asn Gly Phe Pro Gln Leu Gln Asn Leu Glu Leu Asn Glu
                965                 970                 975

Leu Glu Glu Trp Glu Glu Trp Ile Val Glu Asp Gly Ser Met Pro Leu
            980                 985                 990

Leu His Thr Leu Arg Ile Trp Asn  Cys Pro Lys Leu Lys  Gln Leu Pro
        995                 1000                1005

Asp Gly  Leu Arg Phe Ile Tyr  Ser Leu Lys Asn Leu  Thr Val Pro
    1010                 1015                1020

Lys Arg  Trp Lys Lys Arg Leu  Ser Lys Gly Gly Glu  Asp Tyr Tyr
    1025                 1030                1035

Lys Val  Gln His Ile Pro Ser  Val Glu Phe Tyr
    1040                 1045
```

```
<210> SEQ ID NO 69
<211> LENGTH: 740
<212> TYPE: DNA
<213> ORGANISM: Arabidopsis thaliana

<400> SEQUENCE: 69

aaacatcatt attacatcaa aacaaaaaat gggaaagaga ggacaaaaac agaacaggtt     60

cttgagaatc gtcaccatgc ctcttaaagt tctatgcaaa gctcgtgatc tctacatgag    120

aagcatcaca ggttgtgcag ctcgaactca ctactcttca gccgtcgacg ccgcatccgt    180

tccatttccg agaagccgga gtacttcctc cgccttctct tcctctgcct cttctcggag    240

aagatcttcg gatttcactt tcgacgatga ttatagcgag ctgcttagag ctgcttccgt    300

taggagttta ggtcataaga atgagattga catgatcata caacaacagc aacagcagca    360

gcagcaacgg caggagaatc gcgttgcgat gggagcggtt acggttaaag gcggtttgcc    420

taagagctcg agtgttggga tgacaatggc taggattgat gaagaagatg aagaagaagg    480

atctgtaaag aatcaaaaga agggatctga tttcttatat cctcgtagca gatcacatgc    540

tgttactatt agaggatcca agttttaata tatactacta attaattgtc agttttattt    600

ttcttttgat ttaatttaaa agaatgttcc taattataca tgtttatgga attattttga    660
```

tgtaaagtta ctgtcatgga tttatacaaa aaaaaagtta ctgtcaaatt tatttcaata 720
aaaattccta tatagattaa 740

<210> SEQ ID NO 70
<211> LENGTH: 179
<212> TYPE: PRT
<213> ORGANISM: Arabidopsis thaliana

<400> SEQUENCE: 70

Met Gly Lys Arg Gly Gln Lys Gln Asn Arg Phe Leu Arg Ile Val Thr
1 5 10 15

Met Pro Leu Lys Val Leu Cys Lys Ala Arg Asp Leu Tyr Met Arg Ser
20 25 30

Ile Thr Gly Cys Ala Ala Arg Thr His Tyr Ser Ser Ala Val Asp Ala
35 40 45

Ala Ser Val Pro Phe Pro Arg Ser Arg Ser Thr Ser Ser Ala Phe Ser
50 55 60

Ser Ser Ala Ser Ser Arg Arg Arg Ser Ser Asp Phe Thr Phe Asp Asp
65 70 75 80

Asp Tyr Ser Glu Leu Leu Arg Ala Ala Ser Val Arg Ser Leu Gly His
85 90 95

Lys Asn Glu Ile Asp Met Ile Ile Gln Gln Gln Gln Gln Gln Gln Gln
100 105 110

Gln Arg Gln Glu Asn Arg Val Ala Met Gly Ala Val Thr Val Lys Gly
115 120 125

Gly Leu Pro Lys Ser Ser Ser Val Gly Met Thr Met Ala Arg Ile Asp
130 135 140

Glu Glu Asp Glu Glu Glu Gly Ser Val Lys Asn Gln Lys Lys Gly Ser
145 150 155 160

Asp Phe Leu Tyr Pro Arg Ser Arg Ser His Ala Val Thr Ile Arg Gly
165 170 175

Ser Lys Phe

<210> SEQ ID NO 71
<211> LENGTH: 1313
<212> TYPE: DNA
<213> ORGANISM: Arabidopsis thaliana

<400> SEQUENCE: 71
tggttatata acactaatca ggagtgaaat ttcatccaca aaaattcctt ataaattcac 60
gaccaaacac acacatttct ttaattccat aaaaacaaaa acaaaaatat aatgtggact 120
tctaaaacca taagcttcac tctcttcatc acaacaacac ttctcgggtc ctgcaacgca 180
tctgcaaagg ccaaaacgca accgctattc ccagcgattc taatctttgg tgattcaaca 240
gtcgacacag gcaacaataa ttacccttca caaacaatct tcagagctaa acatgttcct 300
tacggaattg atctcccaaa ccactcacct aacggaagat tctcaaacgg gaaaattttc 360
tccgacataa tcgcaaccaa actcaacatc aaacagtttg ttcctccttt cttacaacca 420
aatctcaccg accaagaaat tgtaaccgga gtctgtttcg catcagcagg tgccggttac 480
gatgaccaaa ccagtctcac gacacaagcg attcgtgtct cggaacaacc aaatatgttc 540
aagagttaca ttgctcgtct taagagtatc gtaggagaca agaaagccat gaagatcata 600
aacaatgctt tggtggttgt gagtgcaggg cctaatgatt tcatcttgaa ttattacgag 660
gttccctcat ggcgtcgcat gtatcctagc atttctgatt accaagattt tgttcttagt 720
aggcttaaca atttcgtgaa ggagctttac agcctaggtt gccggaaaat tttggtcgga 780

```
ggtttaccgc caatgggatg tttaccgatt caaatgactg ctcaattccg caacgtccta    840

aggttttgct tggaacaaga gaacagagac tctgttttat acaatcagaa acttcagaag    900

ctcttacctc agacacaagc atctcttaca ggaagcaaga tcctttactc tgatgtctat    960

gaccctatga tggagatgct ccaaaaccct agcaaatacg gatttaaaga gacgacgaga   1020

ggatgttgtg gaacagggtt cttggagacg agcttcatgt gtaatgctta ttcttccatg   1080

tgtcagaatc gctcggagtt tctgttcttt gactcgattc atccatctga agctacctac   1140

aattacattg gtaatgttct ggatactaag attcgtgggt ggcttaaggc ttaagttatc   1200

aagatttgca aagattgaac aaaattatct gtttcataat gtgactattt gtggacttcg   1260

tttgtttatc aactattaac tttggctctt actggcgctt taacttagcg aaa          1313
```

<210> SEQ ID NO 72
<211> LENGTH: 360
<212> TYPE: PRT
<213> ORGANISM: Arabidopsis thaliana

<400> SEQUENCE: 72

```
Met Trp Thr Ser Lys Thr Ile Ser Phe Thr Leu Phe Ile Thr Thr Thr
1               5                   10                  15

Leu Leu Gly Ser Cys Asn Ala Ser Ala Lys Ala Lys Thr Gln Pro Leu
            20                  25                  30

Phe Pro Ala Ile Leu Ile Phe Gly Asp Ser Thr Val Asp Thr Gly Asn
        35                  40                  45

Asn Asn Tyr Pro Ser Gln Thr Ile Phe Arg Ala Lys His Val Pro Tyr
    50                  55                  60

Gly Ile Asp Leu Pro Asn His Ser Pro Asn Gly Arg Phe Ser Asn Gly
65                  70                  75                  80

Lys Ile Phe Ser Asp Ile Ile Ala Thr Lys Leu Asn Ile Lys Gln Phe
                85                  90                  95

Val Pro Pro Phe Leu Gln Pro Asn Leu Thr Asp Gln Glu Ile Val Thr
            100                 105                 110

Gly Val Cys Phe Ala Ser Ala Gly Ala Gly Tyr Asp Asp Gln Thr Ser
        115                 120                 125

Leu Thr Thr Gln Ala Ile Arg Val Ser Glu Gln Pro Asn Met Phe Lys
    130                 135                 140

Ser Tyr Ile Ala Arg Leu Lys Ser Ile Val Gly Asp Lys Lys Ala Met
145                 150                 155                 160

Lys Ile Ile Asn Asn Ala Leu Val Val Val Ser Ala Gly Pro Asn Asp
                165                 170                 175

Phe Ile Leu Asn Tyr Tyr Glu Val Pro Ser Trp Arg Arg Met Tyr Pro
            180                 185                 190

Ser Ile Ser Asp Tyr Gln Asp Phe Val Leu Ser Arg Leu Asn Asn Phe
        195                 200                 205

Val Lys Glu Leu Tyr Ser Leu Gly Cys Arg Lys Ile Leu Val Gly Gly
    210                 215                 220

Leu Pro Pro Met Gly Cys Leu Pro Ile Gln Met Thr Ala Gln Phe Arg
225                 230                 235                 240

Asn Val Leu Arg Phe Cys Leu Glu Gln Glu Asn Arg Asp Ser Val Leu
                245                 250                 255

Tyr Asn Gln Lys Leu Gln Lys Leu Leu Pro Gln Thr Gln Ala Ser Leu
            260                 265                 270

Thr Gly Ser Lys Ile Leu Tyr Ser Asp Val Tyr Asp Pro Met Met Glu
        275                 280                 285
```

```
Met Leu Gln Asn Pro Ser Lys Tyr Gly Phe Lys Glu Thr Thr Arg Gly
    290                 295                 300

Cys Cys Gly Thr Gly Phe Leu Glu Thr Ser Phe Met Cys Asn Ala Tyr
305                 310                 315                 320

Ser Ser Met Cys Gln Asn Arg Ser Glu Phe Leu Phe Phe Asp Ser Ile
                325                 330                 335

His Pro Ser Glu Ala Thr Tyr Asn Tyr Ile Gly Asn Val Leu Asp Thr
            340                 345                 350

Lys Ile Arg Gly Trp Leu Lys Ala
        355                 360


<210> SEQ ID NO 73
<211> LENGTH: 867
<212> TYPE: DNA
<213> ORGANISM: Arabidopsis thaliana

<400> SEQUENCE: 73

atcttcttca tcaattgatc tactctgctc tgctcaagat cagaaatcgt cggtttagtt      60

ctccggttaa aagtttcgtc tctgcgggaa ttggaacttc aatggaggga ttaaagctct     120

cagaagcgga attgatgatt tttattcatc cttcccagag cagaaacgtt tttcaaggaa     180

tttgtcgcga gctcagttct cttctattcc agtataatga aacctttgat ggagttctat     240

tggcttatga tgctactgtg aaaagcaaac aagctaaaat ccttacagga cttcatcctt     300

actttggcgt cagagttaac actagactac tcttatttga tcctaagccc aagagttttg     360

tagaagggaa aattgtgaag atttctccag agtcaatcca tgttattgtt cttggtttct     420

ctgctgctgt cattacagac gttgatatcc gggaagagtt caaatacaga gtgagagatg     480

gtgaaggttc tttcgtgagc agatcgcata aacggcatgc actaaagctt ggaactatgt     540

tgcgccttca agtccaaagt tttgatgaag aggttatgca tatagctgga tctctacttc     600

cggaaaacac aggatgcgtt aagtggctcg aaaagaagtc tgaagaagct ttgcctacgg     660

atagggatca taaaaggagg aaactcgcct gaggaatttt gaaattacaa aacagtagaa     720

gactcttgaa atgaagagaa gcagctatgc tgaaattttg ttgtatcaaa tccatttatg     780

taaacccttt tttttcatca taatactaac attaatgtcc tttaaaatct gaatgttctc     840

cttaatcaaa atcaaaaagt tatgagt                                          867


<210> SEQ ID NO 74
<211> LENGTH: 196
<212> TYPE: PRT
<213> ORGANISM: Arabidopsis thaliana

<400> SEQUENCE: 74

Met Glu Gly Leu Lys Leu Ser Glu Ala Glu Leu Met Ile Phe Ile His
1               5                   10                  15

Pro Ser Gln Ser Arg Asn Val Phe Gln Gly Ile Cys Arg Glu Leu Ser
            20                  25                  30

Ser Leu Leu Phe Gln Tyr Asn Glu Thr Phe Asp Gly Val Leu Leu Ala
        35                  40                  45

Tyr Asp Ala Thr Val Lys Ser Lys Gln Ala Lys Ile Leu Thr Gly Leu
    50                  55                  60

His Pro Tyr Phe Gly Val Arg Val Asn Thr Arg Leu Leu Leu Phe Asp
65                  70                  75                  80

Pro Lys Pro Lys Ser Phe Val Glu Gly Lys Ile Val Lys Ile Ser Pro
                85                  90                  95
```

```
Glu Ser Ile His Val Ile Val Leu Gly Phe Ser Ala Ala Val Ile Thr
            100                 105                 110

Asp Val Asp Ile Arg Glu Glu Phe Lys Tyr Arg Val Arg Asp Gly Glu
        115                 120                 125

Gly Ser Phe Val Ser Arg Ser His Lys Arg His Ala Leu Lys Leu Gly
    130                 135                 140

Thr Met Leu Arg Leu Gln Val Gln Ser Phe Asp Glu Glu Val Met His
145                 150                 155                 160

Ile Ala Gly Ser Leu Leu Pro Glu Asn Thr Gly Cys Val Lys Trp Leu
                165                 170                 175

Glu Lys Lys Ser Glu Glu Ala Leu Pro Thr Asp Arg Asp His Lys Arg
            180                 185                 190

Arg Lys Leu Ala
        195


<210> SEQ ID NO 75
<211> LENGTH: 887
<212> TYPE: DNA
<213> ORGANISM: Arabidopsis thaliana

<400> SEQUENCE: 75

ttgagactgt ttaattcgaa aaccctaagc tcattctcaa aagataaaac ttgccgctat      60

atagtttctc agaagtgaag cttttttttt atatatattt atgaacagga attggaactt     120

caatggaggg attaaagctc tcagaagcgg aattgatgat tttattcat ccttcccaga     180

gcagaaacgt tttcaagga atttgtcgcg agctcagttc tcttctattc cagtataatg     240

aaacctttga tggagttcta ttggcttatg atgctactgt gaaaagcaaa caagctaaaa     300

tccttacagg acttcatcct tactttggcg tcagagttaa cactagacta ctcttatttg     360

atcctaagcc caagagtttt gtagaaggga aaattgtgaa gatttctcca gagtcaatcc     420

atgttattgt tcttggtttc tctgctgctg tcattacaga cgttgatatc cgggaagagt     480

tcaaatacag agtgagagat ggtgaaggtt ctttcgtgag cagatcgcat aaacggcatg     540

cactaaagct tggaactatg ttgcgccttc aagtccaaag ttttgatgaa gaggttatgc     600

atatagctgg atctctactt ccggaaaaca caggatgcgt taagtggctc gaaaagaagt     660

ctgaagaagc tttgcctacg gatagggatc ataaaaggag gaaactcgcc tgaggaattt     720

tgaaattaca aaacagtaga agactcttga aatgaagaga agcagctatg ctgaaatttt     780

gttgtatcaa atccatttat gtaaaccctt tttttcatc ataatactaa cattaatgtc     840

ctttaaaatc tgaatgttct ccttaatcaa aatcaaaaag ttatgag                   887


<210> SEQ ID NO 76
<211> LENGTH: 196
<212> TYPE: PRT
<213> ORGANISM: Arabidopsis thaliana

<400> SEQUENCE: 76

Met Glu Gly Leu Lys Leu Ser Glu Ala Glu Leu Met Ile Phe Ile His
1               5                   10                  15

Pro Ser Gln Ser Arg Asn Val Phe Gln Gly Ile Cys Arg Glu Leu Ser
            20                  25                  30

Ser Leu Leu Phe Gln Tyr Asn Glu Thr Phe Asp Gly Val Leu Leu Ala
        35                  40                  45

Tyr Asp Ala Thr Val Lys Ser Lys Gln Ala Lys Ile Leu Thr Gly Leu
    50                  55                  60

His Pro Tyr Phe Gly Val Arg Val Asn Thr Arg Leu Leu Leu Phe Asp
```

```
65                  70                  75                  80

Pro Lys Pro Lys Ser Phe Val Glu Gly Lys Ile Val Lys Ile Ser Pro
                85                  90                  95

Glu Ser Ile His Val Ile Val Leu Gly Phe Ser Ala Ala Val Ile Thr
            100                 105                 110

Asp Val Asp Ile Arg Glu Glu Phe Lys Tyr Arg Val Arg Asp Gly Glu
        115                 120                 125

Gly Ser Phe Val Ser Arg Ser His Lys Arg His Ala Leu Lys Leu Gly
    130                 135                 140

Thr Met Leu Arg Leu Gln Val Gln Ser Phe Asp Glu Glu Val Met His
145                 150                 155                 160

Ile Ala Gly Ser Leu Leu Pro Glu Asn Thr Gly Cys Val Lys Trp Leu
                165                 170                 175

Glu Lys Lys Ser Glu Glu Ala Leu Pro Thr Asp Arg Asp His Lys Arg
            180                 185                 190

Arg Lys Leu Ala
        195
```

<210> SEQ ID NO 77
<211> LENGTH: 2039
<212> TYPE: DNA
<213> ORGANISM: Arabidopsis thaliana

<400> SEQUENCE: 77

```
aagggaaaat cctaataaag gagaagaaaa acagatctga aatcccgctt gatactccac     60

cgactttaaa ctactggttt ttgtttgatt taagtatagt gttaatgact cctctctcca    120

ccttcctttg attctaccta tcacttccct tgccgttgct ccatcttcat cactagtcac    180

tatacaccaa tcttagatcc gggaagctaa tttctcttct ccgatcggtg aatgcagtta    240

cattgacctc ggatctaacc aagctcttct ggtttccagc tctctggaat tcaaaaaaat    300

ggaggagaaa tccaagtcaa gaggttggtg cggttggttc atcgccatta ttgtgctagc    360

ttctgttatc ctcgccgtcg tttacactgt taaattgaga acgaagaaat ccggtgacga    420

tgacggtggc ggtcccgttc ctggacctcc cggcgccatt gataagaaat acgccgacgc    480

tcttaagctc gctttgcagt tcttcgatat ccagaaatct ggtaaattgg agaacaataa    540

gataccttgg agaggagatt caggtcttaa agatggaagt gaagataatc tggatctttc    600

caaaggctta tatgatgctg gagatcatat aaagtttggt tttccaatgg ctttcactgc    660

tacagttttg tcatggtcga ttcttgagta tggtgatcaa atgaatgcag tgaaccaatt    720

ggatcctgct aaagactctc tccggtggat cactgactat cttatcaaag ctcatccttc    780

tgacaatgtc ctctatatcc aggtgggaga tccaaaagta gatcatccat gctgggagag    840

accagaggat atgaaagaga agagaccact tactaaaatt gatgtagata ctccagggac    900

agaggttgct gctgaaactg ctgcagctat ggcttcagcg tctttggtgt ttaaggatag    960

tgatcctaca tattcagcaa cgcttctgaa acatgcgaag cagttgttta attttgcaga   1020

tacaaagaga ggctcttaca gtgttaacat acctgaggtt cagaagtttt acaattcgac   1080

tggatatggt gatgagctac tatgggcagc tagttggttg tatcatgcaa cagaggataa   1140

aacttacctt gattatgtgt ctaatcatgg aaaagaattt gctagttttg gaaatcctac   1200

ttggtttagt tgggacaaca agcttgcagg aacacaggta ctattatcaa gattactctt   1260

ctttaagaaa gatttatcag gaagcaaggg acttggaaat tacaggaaca cagctaaagc   1320

tgtcatgtgt ggacttctac caaagtctcc aacatctaca gctagtagaa caaacggtgg   1380
```

```
tcttatatgg gttagtgaat ggaactcgat gcaacaatcc gtttcgtcag cgtttttagc   1440

ctcgcttttc agtgattaca tgctcacttc ccgtatccat aaaatatctt gcgacgggaa   1500

aatcttcaaa gcaacagagc ttagagattt cgccaaatcg caggctgatt acatgctggg   1560

gaagaatccg ttgggaacga gcttcgtggt gggttatgga gacaaatacc cacaatttgt   1620

gcatcataga ggagcttcga tcccggcaga tgcaacaacg ggttgcttag atggattcaa   1680

atggtttaac tcgacgaaac caaacccaaa catagcatat ggtgcactcg taggtggacc   1740

tttcttcaat gagacgttca ctgactcacg agagaaccca atgcagaacg agccaaccac   1800

ttacaacaat gcactcctcg ttggtctctt gtctagtctt gtcactacat cttctacttt   1860

acagtcgttg aagtgagctt tgcgtgtttt agccttctta ttgaaaatca cattgcttca   1920

tttttatttg taattttta aaaaaaatcg tgggtgtgtg tgtattcacg ttgtgtattg   1980

cttgatatgt tgatgcgtgt aaccaaacaa ttagttgctc tacgaatcca aaattgagg    2039
```

<210> SEQ ID NO 78
<211> LENGTH: 525
<212> TYPE: PRT
<213> ORGANISM: Arabidopsis thaliana

<400> SEQUENCE: 78

```
Met Glu Glu Lys Ser Lys Ser Arg Gly Trp Cys Gly Trp Phe Ile Ala
1               5                   10                  15

Ile Ile Val Leu Ala Ser Val Ile Leu Ala Val Val Tyr Thr Val Lys
            20                  25                  30

Leu Arg Thr Lys Lys Ser Gly Asp Asp Asp Gly Gly Gly Pro Val Pro
        35                  40                  45

Gly Pro Pro Gly Ala Ile Asp Lys Lys Tyr Ala Asp Ala Leu Lys Leu
    50                  55                  60

Ala Leu Gln Phe Phe Asp Ile Gln Lys Ser Gly Lys Leu Glu Asn Asn
65                  70                  75                  80

Lys Ile Pro Trp Arg Gly Asp Ser Gly Leu Lys Asp Gly Ser Glu Asp
                85                  90                  95

Asn Leu Asp Leu Ser Lys Gly Leu Tyr Asp Ala Gly Asp His Ile Lys
            100                 105                 110

Phe Gly Phe Pro Met Ala Phe Thr Ala Thr Val Leu Ser Trp Ser Ile
        115                 120                 125

Leu Glu Tyr Gly Asp Gln Met Asn Ala Val Asn Gln Leu Asp Pro Ala
    130                 135                 140

Lys Asp Ser Leu Arg Trp Ile Thr Asp Tyr Leu Ile Lys Ala His Pro
145                 150                 155                 160

Ser Asp Asn Val Leu Tyr Ile Gln Val Gly Asp Pro Lys Val Asp His
                165                 170                 175

Pro Cys Trp Glu Arg Pro Glu Asp Met Lys Glu Lys Arg Pro Leu Thr
            180                 185                 190

Lys Ile Asp Val Asp Thr Pro Gly Thr Glu Val Ala Ala Glu Thr Ala
        195                 200                 205

Ala Ala Met Ala Ser Ala Ser Leu Val Phe Lys Asp Ser Asp Pro Thr
    210                 215                 220

Tyr Ser Ala Thr Leu Leu Lys His Ala Lys Gln Leu Phe Asn Phe Ala
225                 230                 235                 240

Asp Thr Lys Arg Gly Ser Tyr Ser Val Asn Ile Pro Glu Val Gln Lys
                245                 250                 255

Phe Tyr Asn Ser Thr Gly Tyr Gly Asp Glu Leu Leu Trp Ala Ala Ser
            260                 265                 270
```

```
Trp Leu Tyr His Ala Thr Glu Asp Lys Thr Tyr Leu Asp Tyr Val Ser
        275                 280                 285

Asn His Gly Lys Glu Phe Ala Ser Phe Gly Asn Pro Thr Trp Phe Ser
    290                 295                 300

Trp Asp Asn Lys Leu Ala Gly Thr Gln Val Leu Leu Ser Arg Leu Leu
305                 310                 315                 320

Phe Phe Lys Lys Asp Leu Ser Gly Ser Lys Gly Leu Gly Asn Tyr Arg
                325                 330                 335

Asn Thr Ala Lys Ala Val Met Cys Gly Leu Leu Pro Lys Ser Pro Thr
            340                 345                 350

Ser Thr Ala Ser Arg Thr Asn Gly Gly Leu Ile Trp Val Ser Glu Trp
        355                 360                 365

Asn Ser Met Gln Gln Ser Val Ser Ser Ala Phe Leu Ala Ser Leu Phe
    370                 375                 380

Ser Asp Tyr Met Leu Thr Ser Arg Ile His Lys Ile Ser Cys Asp Gly
385                 390                 395                 400

Lys Ile Phe Lys Ala Thr Glu Leu Arg Asp Phe Ala Lys Ser Gln Ala
                405                 410                 415

Asp Tyr Met Leu Gly Lys Asn Pro Leu Gly Thr Ser Phe Val Val Gly
            420                 425                 430

Tyr Gly Asp Lys Tyr Pro Gln Phe Val His His Arg Gly Ala Ser Ile
        435                 440                 445

Pro Ala Asp Ala Thr Thr Gly Cys Leu Asp Gly Phe Lys Trp Phe Asn
    450                 455                 460

Ser Thr Lys Pro Asn Pro Asn Ile Ala Tyr Gly Ala Leu Val Gly Gly
465                 470                 475                 480

Pro Phe Phe Asn Glu Thr Phe Thr Asp Ser Arg Glu Asn Pro Met Gln
                485                 490                 495

Asn Glu Pro Thr Thr Tyr Asn Asn Ala Leu Leu Val Gly Leu Leu Ser
            500                 505                 510

Ser Leu Val Thr Thr Ser Ser Thr Leu Gln Ser Leu Lys
        515                 520                 525
```

<210> SEQ ID NO 79
<211> LENGTH: 677
<212> TYPE: DNA
<213> ORGANISM: Arabidopsis thaliana

<400> SEQUENCE: 79

```
gcttaagcga ttctctgcaa agcttcatac caaacaaaga gaagtcgaaa tgccagtttc      60

agctccatct ccgcctcgtc ttcattctcc gttcattcac tgtcccatca atttcactcc     120

ttcttctttc tcggcgagga atctccggtc gccgtcaaca tcttatcccc gaatcaaagc     180

tgaactcgat cccaacacgg tagtcgcgat atctgtaggc gtagcaagcg tcgcattagg     240

aatcggaatc cctgtgttct acgagactca aatcgacaat gcggctaagc gagagaatac     300

tcaaccttgt tttccctgta atggcaccgg agctcagaaa tgcagattgt gtgtgggaag     360

tggtaatgtg accgtagagc ttggtggagg agagaaagaa gtctcaaact gtatcaactg     420

tgatggtgct ggttccttaa cttgcactac ttgtcaaggc tctggtgttc aacctcgata     480

ccttgatcga agggagttca aggacgatga ctaaatacct tgctctaagg aacatttctt     540

ttcttctccc ttctcacatt tcttcattgt acaatgctgt tttgttcacc aaacatgttg     600

agagaacatc atgacatgga tattgtaatt gtgaaagaaa accaccagag ttcaatcaaa     660

tgtttcttct tgtactt                                                    677
```

<210> SEQ ID NO 80
<211> LENGTH: 154
<212> TYPE: PRT
<213> ORGANISM: Arabidopsis thaliana

<400> SEQUENCE: 80

```
Met Pro Val Ser Ala Pro Ser Pro Pro Arg Leu His Ser Pro Phe Ile
1               5                   10                  15

His Cys Pro Ile Asn Phe Thr Pro Ser Ser Phe Ser Ala Arg Asn Leu
            20                  25                  30

Arg Ser Pro Ser Thr Ser Tyr Pro Arg Ile Lys Ala Glu Leu Asp Pro
        35                  40                  45

Asn Thr Val Val Ala Ile Ser Val Gly Val Ala Ser Val Ala Leu Gly
    50                  55                  60

Ile Gly Ile Pro Val Phe Tyr Glu Thr Gln Ile Asp Asn Ala Ala Lys
65                  70                  75                  80

Arg Glu Asn Thr Gln Pro Cys Phe Pro Cys Asn Gly Thr Gly Ala Gln
                85                  90                  95

Lys Cys Arg Leu Cys Val Gly Ser Gly Asn Val Thr Val Glu Leu Gly
            100                 105                 110

Gly Gly Glu Lys Glu Val Ser Asn Cys Ile Asn Cys Asp Gly Ala Gly
        115                 120                 125

Ser Leu Thr Cys Thr Thr Cys Gln Gly Ser Gly Val Gln Pro Arg Tyr
    130                 135                 140

Leu Asp Arg Arg Glu Phe Lys Asp Asp Asp
145                 150
```

<210> SEQ ID NO 81
<211> LENGTH: 501
<212> TYPE: DNA
<213> ORGANISM: Arabidopsis thaliana

<400> SEQUENCE: 81

```
atggtgtttg gatatgcata tcctgcttat gagtgcttca aaacggtcga actcaacaag     60

cctgaaattc aacaacttca gttctggtgc cagtattgga ttattgtagc tgctttgacg    120

attttcgaaa gaattggtga tgctcttgtt tcttggttac caatgtatag cgaggcgaag    180

ttggctttct tcatttatct ctggtttcca aagactaaag gaacaacata cgtttacgat    240

tctttcttca ggccatatat agcaaagcat gaaaatgaaa ttgaccgcaa cttggtgaag    300

gtaaagacta gagctaagga tatggcaatg atatatctcc aaaaagcaat caaccaaggg    360

cagaccaaat tctttgagat cttacagtat atcacagaac aatcaacacc aaaatctaag    420

gctgaggaaa agaaagagac aacaatacct aaactcgatg atccaattct taaggtgaaa    480

gaaaacgaag tcactaaatg a                                              501
```

<210> SEQ ID NO 82
<211> LENGTH: 166
<212> TYPE: PRT
<213> ORGANISM: Arabidopsis thaliana

<400> SEQUENCE: 82

```
Met Val Phe Gly Tyr Ala Tyr Pro Ala Tyr Glu Cys Phe Lys Thr Val
1               5                   10                  15

Glu Leu Asn Lys Pro Glu Ile Gln Gln Leu Gln Phe Trp Cys Gln Tyr
            20                  25                  30

Trp Ile Ile Val Ala Ala Leu Thr Ile Phe Glu Arg Ile Gly Asp Ala
```

```
        35                  40                  45

Leu Val Ser Trp Leu Pro Met Tyr Ser Glu Ala Lys Leu Ala Phe Phe
    50                  55                  60

Ile Tyr Leu Trp Phe Pro Lys Thr Lys Gly Thr Thr Tyr Val Tyr Asp
65                  70                  75                  80

Ser Phe Phe Arg Pro Tyr Ile Ala Lys His Glu Asn Glu Ile Asp Arg
                85                  90                  95

Asn Leu Val Lys Val Lys Thr Arg Ala Lys Asp Met Ala Met Ile Tyr
            100                 105                 110

Leu Gln Lys Ala Ile Asn Gln Gly Gln Thr Lys Phe Phe Glu Ile Leu
        115                 120                 125

Gln Tyr Ile Thr Glu Gln Ser Thr Pro Lys Ser Lys Ala Glu Glu Lys
    130                 135                 140

Lys Glu Thr Thr Ile Pro Lys Leu Asp Asp Pro Ile Leu Lys Val Lys
145                 150                 155                 160

Glu Asn Glu Val Thr Lys
                165


<210> SEQ ID NO 83
<211> LENGTH: 798
<212> TYPE: DNA
<213> ORGANISM: Arabidopsis thaliana

<400> SEQUENCE: 83

atgtcttctc cactcgccgc aaaatcaaac ctaaccacga ctcgatcggc ttcgttaaac      60

attccacatt cgacacgtac caatcacaac cacgatctcc ggtatagtct ttccgctggt     120

cctcgtacga acgaagatcg accagcttct gggaacggcg tcgccggaat cctctataaa     180

tgggtaaact acggccaagg atggaaacga cggtggttcg tactccagga cggtgttttg     240

tcgtattata gaatccatgg tcccgataaa atatctctct ccgttgagat ggatcggaga     300

tctaaactga tcggcggcga atctttacgg tttatttgcc gacatagcaa acgcggtgat     360

gttcatagcc ccgggaaacc tctcggccaa attcacctca aggtttcatc gattggacaa     420

agcatatcag atggcaagag attcactgta ttcacgggca cgaagagtct gcatttacga     480

gcagcaacga gcgaggatcg tgcctcttgg atcgaagcat tgaaagctgt taaagaaacg     540

tttccaagaa tgtcaaacga agaactaatg gcatcgacga ctaatgtctc agtctcgacc     600

gataagctaa ggcagagatt aatggaagaa gaggtagatg agacaatcat caaagattgc     660

gaagacataa tgaagaacaa tttcttagca ttgcatgatg aggttatgtc tctaaaacgg     720

taccaatatc atcttataga ttctctcaag aacgtcagta actcacctat aagacccagt     780

aaccaaagtt tttcatga                                                   798


<210> SEQ ID NO 84
<211> LENGTH: 265
<212> TYPE: PRT
<213> ORGANISM: Arabidopsis thaliana

<400> SEQUENCE: 84

Met Ser Ser Pro Leu Ala Ala Lys Ser Asn Leu Thr Thr Thr Arg Ser
1               5                   10                  15

Ala Ser Leu Asn Ile Pro His Ser Thr Arg Thr Asn His Asn His Asp
            20                  25                  30

Leu Arg Tyr Ser Leu Ser Ala Gly Pro Arg Thr Asn Glu Asp Arg Pro
        35                  40                  45

Ala Ser Gly Asn Gly Val Ala Gly Ile Leu Tyr Lys Trp Val Asn Tyr
```

```
    50                  55                  60

Gly Gln Gly Trp Lys Arg Arg Trp Phe Val Leu Gln Asp Gly Val Leu
65                  70                  75                  80

Ser Tyr Tyr Arg Ile His Gly Pro Asp Lys Ile Ser Leu Ser Val Glu
                85                  90                  95

Met Asp Arg Arg Ser Lys Leu Ile Gly Gly Glu Ser Leu Arg Phe Ile
            100                 105                 110

Cys Arg His Ser Lys Arg Gly Asp Val His Ser Pro Gly Lys Pro Leu
        115                 120                 125

Gly Gln Ile His Leu Lys Val Ser Ser Ile Gly Gln Ser Ile Ser Asp
    130                 135                 140

Gly Lys Arg Phe Thr Val Phe Thr Gly Thr Lys Ser Leu His Leu Arg
145                 150                 155                 160

Ala Ala Thr Ser Glu Asp Arg Ala Ser Trp Ile Glu Ala Leu Lys Ala
                165                 170                 175

Val Lys Glu Thr Phe Pro Arg Met Ser Asn Glu Glu Leu Met Ala Ser
            180                 185                 190

Thr Thr Asn Val Ser Val Ser Thr Asp Lys Leu Arg Gln Arg Leu Met
        195                 200                 205

Glu Glu Glu Val Asp Glu Thr Ile Ile Lys Asp Cys Glu Asp Ile Met
    210                 215                 220

Lys Asn Asn Phe Leu Ala Leu His Asp Glu Val Met Ser Leu Lys Arg
225                 230                 235                 240

Tyr Gln Tyr His Leu Ile Asp Ser Leu Lys Asn Val Ser Asn Ser Pro
                245                 250                 255

Ile Arg Pro Ser Asn Gln Ser Phe Ser
            260                 265


<210> SEQ ID NO 85
<211> LENGTH: 2339
<212> TYPE: DNA
<213> ORGANISM: Arabidopsis thaliana

<400> SEQUENCE: 85

accctaatcc gtaatcgaat gccatttcga agattgtaag aagactaaga agctagggtt      60

tctctgatga gtagatgatg cgtgaaccgc ttgttagcga agaagaagaa gaagaagcta     120

ctgaagtttt actagtggag aagacgaagt tgtgtaagag acgaggagac gaagaaaaaa     180

cggaagagag aagagacgat ttgttgttac tagctttaac gccgatggta cgatcgaaat     240

ctcaaggaac tactcggcgc gtcactccca cgccacctcc tgttgacgtg gagaaaccgt     300

taccaaacgg agatctctac atgggaacgt tttccggcgg gtttcccaac ggatccggta     360

agtatttgtg gaaggatggg tgtatgtacg aaggcgagtg gaaacgtggt aaagcgagtg     420

gtaaaggcaa gttttcgtgg ccgagtggtg cgacttatga aggagagttc aaatctggga     480

gaatggaagg atctgggact tttgttggtg ttgatggtga tacttatcgt ggctcttggg     540

ttgctgatcg gaaacaaggt catggtcaga agagatatgc caacggagat tactatgaag     600

gtacatggcg gcggaatctt caggatggga gagggagata tgtttggatg aatgggaatc     660

agtatacagg agagtggaga aatggtgtga tatgtggtaa aggtgtgctt gcttggccta     720

atgggaatag atatgaaggt caatgggaaa atggtgttcc taaaggaagt ggtgtgttta     780

cttgggctga tggaagttcg tggattggtt cttggaatga gagtagtaat ctcatgagga     840

atttctttga tgggattgag aagaatgagt tgattgttgc gactaggaag agatcttcgg     900

ttgatagtgg cgctggaagt ttgactgggg agaagatttt ccctaggata tgtatttggg     960
```

```
agtctgatgg agaagctggg gatattactt gtgatattgt tgataatgtg gaagcttctg   1020

tgatatacag agataggatt tctattgata aagatgggtt tcgtcagttt aggaagaatc   1080

cttgttgttt cagcggtgag gctaagaaac ctggagagac gatatctaaa gggcataaga   1140

aatatgattt gatgctcaac ctgcagcatg gaattaggta ctctgtcggc aaacacgctt   1200

ccgttgttcg agatctcaaa cagagtgatt ttgacccaag tgaaaagttc tggacaaggt   1260

tcccaccgga gggttctaag accacaccac cgcatctatc tgtggatttc cgctggaagg   1320

actattgccc tttggtgttt agacggctta gggagctatt cacggtggat cctgccgatt   1380

acatgctagc tatctgtgga aacgatgccc ttagggaatt gtcttcgcct ggaaagagtg   1440

gaagcttttt ttacttaact caagatgaca gatttatgat caagacggtg aagaaatctg   1500

aagtcaaggt gcttctacga atgcttccaa gttactacaa acacgtctgc cagtatgaaa   1560

atacacttgt gactaggttc tatggtgtgc attgtatcaa acctgttggt ggccagaaga   1620

ctcggtttat cgttatgggg aacttgttct gctccgaata tagaatccag agaaggtttg   1680

accttaaagg gtcttcccat ggacggtata cctccaaacc tgaaggggaa attgatgaga   1740

ccactactct taaggacctt gatctcaatt ttgctttccg tcttcagaga aattggtacc   1800

aagagcttat gacgcaaatt aaacgcgact gtgagttctt ggaagctgaa agaataatgg   1860

attatagtct tttggttggc gttcacttcc gtgatgacaa cacaggagac aaaatggggt   1920

tatctccatt tgtattgaga tctggtaaga tagagtcata ccaaagcgaa aaatttatgc   1980

gtggttgtcg gttcttggag gcggaacttc aagacatgga ccgcatttta gctggcagga   2040

aaccattgat tcgattaggc gcaaacatgc ctgcaagagc agaacgaatg gcgagaagaa   2100

gcgactatga tcagtattcc tcaggaggga ccaactacca atctcatgga gaggtctacg   2160

aagtggttct atattttgga atcattgaca ttttacaaga ttacgacata agcaagaaga   2220

tcgagcatgc ttacaagtct ctacaagctg acccggcttc aatctctgcc gttgatccca   2280

aactatactc aagaaggttt agagatttca tcagcagaat cttcatcgaa gacggctaa    2339
```

```
<210> SEQ ID NO 86
<211> LENGTH: 754
<212> TYPE: PRT
<213> ORGANISM: Arabidopsis thaliana

<400> SEQUENCE: 86

Met Met Arg Glu Pro Leu Val Ser Glu Glu Glu Glu Glu Glu Ala Thr
1               5                   10                  15

Glu Val Leu Leu Val Glu Lys Thr Lys Leu Cys Lys Arg Arg Gly Asp
            20                  25                  30

Glu Glu Lys Thr Glu Glu Arg Arg Asp Asp Leu Leu Leu Leu Ala Leu
        35                  40                  45

Thr Pro Met Val Arg Ser Lys Ser Gln Gly Thr Thr Arg Arg Val Thr
    50                  55                  60

Pro Thr Pro Pro Pro Val Asp Val Glu Lys Pro Leu Pro Asn Gly Asp
65                  70                  75                  80

Leu Tyr Met Gly Thr Phe Ser Gly Gly Phe Pro Asn Gly Ser Gly Lys
                85                  90                  95

Tyr Leu Trp Lys Asp Gly Cys Met Tyr Glu Gly Glu Trp Lys Arg Gly
            100                 105                 110

Lys Ala Ser Gly Lys Gly Lys Phe Ser Trp Pro Ser Gly Ala Thr Tyr
        115                 120                 125

Glu Gly Glu Phe Lys Ser Gly Arg Met Glu Gly Ser Gly Thr Phe Val
```

```
    130                 135                 140

Gly Val Asp Gly Asp Thr Tyr Arg Gly Ser Trp Val Ala Asp Arg Lys
145                 150                 155                 160

Gln Gly His Gly Gln Lys Arg Tyr Ala Asn Gly Asp Tyr Tyr Glu Gly
                165                 170                 175

Thr Trp Arg Arg Asn Leu Gln Asp Gly Arg Gly Arg Tyr Val Trp Met
            180                 185                 190

Asn Gly Asn Gln Tyr Thr Gly Glu Trp Arg Asn Gly Val Ile Cys Gly
        195                 200                 205

Lys Gly Val Leu Ala Trp Pro Asn Gly Asn Arg Tyr Glu Gly Gln Trp
    210                 215                 220

Glu Asn Gly Val Pro Lys Gly Ser Gly Val Phe Thr Trp Ala Asp Gly
225                 230                 235                 240

Ser Ser Trp Ile Gly Ser Trp Asn Glu Ser Ser Asn Leu Met Arg Asn
                245                 250                 255

Phe Phe Asp Gly Ile Glu Lys Asn Glu Leu Ile Val Ala Thr Arg Lys
            260                 265                 270

Arg Ser Ser Val Asp Ser Gly Ala Gly Ser Leu Thr Gly Glu Lys Ile
        275                 280                 285

Phe Pro Arg Ile Cys Ile Trp Glu Ser Asp Gly Glu Ala Gly Asp Ile
    290                 295                 300

Thr Cys Asp Ile Val Asp Asn Val Glu Ala Ser Val Ile Tyr Arg Asp
305                 310                 315                 320

Arg Ile Ser Ile Asp Lys Asp Gly Phe Arg Gln Phe Arg Lys Asn Pro
                325                 330                 335

Cys Cys Phe Ser Gly Glu Ala Lys Lys Pro Gly Glu Thr Ile Ser Lys
            340                 345                 350

Gly His Lys Lys Tyr Asp Leu Met Leu Asn Leu Gln His Gly Ile Arg
        355                 360                 365

Tyr Ser Val Gly Lys His Ala Ser Val Val Arg Asp Leu Lys Gln Ser
    370                 375                 380

Asp Phe Asp Pro Ser Glu Lys Phe Trp Thr Arg Phe Pro Pro Glu Gly
385                 390                 395                 400

Ser Lys Thr Thr Pro Pro His Leu Ser Val Asp Phe Arg Trp Lys Asp
                405                 410                 415

Tyr Cys Pro Leu Val Phe Arg Arg Leu Arg Glu Leu Phe Thr Val Asp
            420                 425                 430

Pro Ala Asp Tyr Met Leu Ala Ile Cys Gly Asn Asp Ala Leu Arg Glu
        435                 440                 445

Leu Ser Ser Pro Gly Lys Ser Gly Ser Phe Phe Tyr Leu Thr Gln Asp
    450                 455                 460

Asp Arg Phe Met Ile Lys Thr Val Lys Lys Ser Glu Val Lys Val Leu
465                 470                 475                 480

Leu Arg Met Leu Pro Ser Tyr Tyr Lys His Val Cys Gln Tyr Glu Asn
                485                 490                 495

Thr Leu Val Thr Arg Phe Tyr Gly Val His Cys Ile Lys Pro Val Gly
            500                 505                 510

Gly Gln Lys Thr Arg Phe Ile Val Met Gly Asn Leu Phe Cys Ser Glu
        515                 520                 525

Tyr Arg Ile Gln Arg Arg Phe Asp Leu Lys Gly Ser Ser His Gly Arg
    530                 535                 540

Tyr Thr Ser Lys Pro Glu Gly Glu Ile Asp Glu Thr Thr Thr Leu Lys
545                 550                 555                 560
```

```
Asp Leu Asp Leu Asn Phe Ala Phe Arg Leu Gln Arg Asn Trp Tyr Gln
                565                 570                 575

Glu Leu Met Thr Gln Ile Lys Arg Asp Cys Glu Phe Leu Glu Ala Glu
            580                 585                 590

Arg Ile Met Asp Tyr Ser Leu Leu Val Gly Val His Phe Arg Asp Asp
        595                 600                 605

Asn Thr Gly Asp Lys Met Gly Leu Ser Pro Phe Val Leu Arg Ser Gly
    610                 615                 620

Lys Ile Glu Ser Tyr Gln Ser Glu Lys Phe Met Arg Gly Cys Arg Phe
625                 630                 635                 640

Leu Glu Ala Glu Leu Gln Asp Met Asp Arg Ile Leu Ala Gly Arg Lys
                645                 650                 655

Pro Leu Ile Arg Leu Gly Ala Asn Met Pro Ala Arg Ala Glu Arg Met
            660                 665                 670

Ala Arg Arg Ser Asp Tyr Asp Gln Tyr Ser Ser Gly Gly Thr Asn Tyr
        675                 680                 685

Gln Ser His Gly Glu Val Tyr Glu Val Val Leu Tyr Phe Gly Ile Ile
    690                 695                 700

Asp Ile Leu Gln Asp Tyr Asp Ile Ser Lys Lys Ile Glu His Ala Tyr
705                 710                 715                 720

Lys Ser Leu Gln Ala Asp Pro Ala Ser Ile Ser Ala Val Asp Pro Lys
                725                 730                 735

Leu Tyr Ser Arg Arg Phe Arg Asp Phe Ile Ser Arg Ile Phe Ile Glu
            740                 745                 750

Asp Gly


<210> SEQ ID NO 87
<211> LENGTH: 1318
<212> TYPE: DNA
<213> ORGANISM: Arabidopsis thaliana

<400> SEQUENCE: 87

aaactctctc tacacagctc ataacagaaa gaagaaacac aaagtgagac agaactctct      60

aattagtccc gaaggtttca aaagggtatt ttggtaaaat cgaaagagaa tcatggacgc     120

ttttgatgcg attccagatc ctgtggtcat cgacattttg aacagagtcg gtgacgtcaa     180

aacgttaata cgatgtcgtt ccgtttctaa acgattcaac tcgttagcca ctcagtctga     240

gtcgctcctt ctccaactcg atcagatcct cggagccacc gaatctgact ccgagatcga     300

ttctcctatc gctagcttct tccgatctct cttcaaatcc attcacggtc tccttcctcc     360

tatcttctcc aaaccagcta actctgacga aatcctaacc cgatctccga aaactccggc     420

tcagattctc tccggatttg aacggatccg gaatctggag gtggaattat acggtggtga     480

tgtcaagctt gagaaaggcg ccgccgttaa gtggaaggct gagttcggga aaactctcaa     540

gagctgcgtc atcgtcgctt tccgttccgc gacggttaat acttcagcag ctacggaagc     600

tgccgccgtc gtcgacggtg ttgttgagtc agattcggag tttgtttgtg gattgaagac     660

gcgcgtggtg tggacgatca gcgcgttgat ggcggcttcc acgcgtcatt acttgatgag     720

agatttggtg aaagatcaca aggagatgga gaaattgatt gtgcgtgaca gtgatggtga     780

aggtacggtg gtgatggacg cggcggggat gaaagaatac agagagacgg aggtgcgtgg     840

ggataataaa gaatcagagc gcgtggggga acgaactgtg gtacctagcg tgaggatgag     900

tatgagacac gcgccgtcgc tgatgctgaa gagcgggatt tgtctcgaag cagcgacgct     960

ggtggtcgta aggccgactg gtgtggcttc cgatgataac gatgttgagc tggtgacgga    1020
```

```
ggcgttcgcc ggagatggcg acgattgtat gtacggagaa gctgttacgg cgttgcttaa   1080

gcgtaggaga aatgtgttag agatgaattc tttctaaggc ctagtgggct tttttgggc    1140

ttccgtttgt ttggcccttt ttaatgtata tacatacgca tcgtacaaag ccaactgtac   1200

tattggcgta cgacttttgg gtcaaatgac atcaaatccg aattattcct ctaatatcat   1260

atgattacca cattaaatgc gttgcagcat ctaatattat acatagatat gattcgaa     1318


<210> SEQ ID NO 88
<211> LENGTH: 334
<212> TYPE: PRT
<213> ORGANISM: Arabidopsis thaliana

<400> SEQUENCE: 88

Met Asp Ala Phe Asp Ala Ile Pro Asp Pro Val Val Ile Asp Ile Leu
1               5                   10                  15

Asn Arg Val Gly Asp Val Lys Thr Leu Ile Arg Cys Arg Ser Val Ser
            20                  25                  30

Lys Arg Phe Asn Ser Leu Ala Thr Gln Ser Glu Ser Leu Leu Leu Gln
        35                  40                  45

Leu Asp Gln Ile Leu Gly Ala Thr Glu Ser Asp Ser Glu Ile Asp Ser
    50                  55                  60

Pro Ile Ala Ser Phe Phe Arg Ser Leu Phe Lys Ser Ile His Gly Leu
65                  70                  75                  80

Leu Pro Pro Ile Phe Ser Lys Pro Ala Asn Ser Asp Glu Ile Leu Thr
                85                  90                  95

Arg Ser Pro Lys Thr Pro Ala Gln Ile Leu Ser Gly Phe Glu Arg Ile
            100                 105                 110

Arg Asn Leu Glu Val Glu Leu Tyr Gly Gly Asp Val Lys Leu Glu Lys
        115                 120                 125

Gly Ala Ala Val Lys Trp Lys Ala Glu Phe Gly Lys Thr Leu Lys Ser
    130                 135                 140

Cys Val Ile Val Ala Phe Arg Ser Ala Thr Val Asn Thr Ser Ala Ala
145                 150                 155                 160

Thr Glu Ala Ala Ala Val Val Asp Gly Val Val Glu Ser Asp Ser Glu
                165                 170                 175

Phe Val Cys Gly Leu Lys Thr Arg Val Val Trp Thr Ile Ser Ala Leu
            180                 185                 190

Met Ala Ala Ser Thr Arg His Tyr Leu Met Arg Asp Leu Val Lys Asp
        195                 200                 205

His Lys Glu Met Glu Lys Leu Ile Val Arg Asp Ser Asp Gly Glu Gly
    210                 215                 220

Thr Val Val Met Asp Ala Ala Gly Met Lys Glu Tyr Arg Glu Thr Glu
225                 230                 235                 240

Val Arg Gly Asp Asn Lys Glu Ser Glu Arg Val Gly Glu Arg Thr Val
                245                 250                 255

Val Pro Ser Val Arg Met Ser Met Arg His Ala Pro Ser Leu Met Leu
            260                 265                 270

Lys Ser Gly Ile Cys Leu Glu Ala Ala Thr Leu Val Val Val Arg Pro
        275                 280                 285

Thr Gly Val Ala Ser Asp Asp Asn Asp Val Glu Leu Val Thr Glu Ala
    290                 295                 300

Phe Ala Gly Asp Gly Asp Asp Cys Met Tyr Gly Glu Ala Val Thr Ala
305                 310                 315                 320

Leu Leu Lys Arg Arg Arg Asn Val Leu Glu Met Asn Ser Phe
                325                 330
```

<210> SEQ ID NO 89
<211> LENGTH: 1350
<212> TYPE: DNA
<213> ORGANISM: Arabidopsis thaliana

<400> SEQUENCE: 89

```
aaaccaaaca ccaagaaaac aaaagcagac ttaaaagaag ctatgatcaa aggaaacaat     60
ggaaacagag gatcttcttc ttctggttac tctgcagatt tgttggtttg tttcccttca    120
agaacccact tagctctgac tcctaagccc atttgtagcc catctcgtcc ctcagactct    180
tccactaacc gtcgtcctca ccaccgtcgc cagctcagta aactctccgg cggcggtgga    240
ggaggacacg gtagtcctgt tttgtgggct aaacaagcaa gtagtaagaa tatgggaggt    300
gacgaaatag cagaaccaac ttctcctaaa gtaacttgcg caggtcagat caaagtccgg    360
ccaagtaaat gcggagggag aggaaagaac tggcaatcgg tgatggaaga gattgagagg    420
atacatgata atagatcgca aagcaagttt tttgggttga agaaagatgt gatgggtttc    480
ttgacttgtc ttagaaacat caaattcgat ttcaggtgtt ttggtgattt ccgacatgct    540
gatgtcacta gcgacgacga tgaggaagaa gatgatgatg atgatgagga agaagaggta    600
gtggaaggag aagaagaaga gaattcaaag actgttttct ctaaatggtt tatggtttta    660
caagaggaac agaacaacaa agatgacgac aagaacaaca acaagtgtga tgagaaacgc    720
gatcttgaag acacagagac agaaccagcg gttccgccgc caaacgcgct tttgttgatg    780
cggtgtagat cagctccagc gaagagttgg ttagaagaga gaatgaaagt aaaaacagag    840
caagaaaaga gagaagaaca aaaagaggaa aaagaaacag aggatcaaga aacgagtatg    900
aagacaaaga agaaggattt gagatcatta atggaagaag agaagatgga attggtgttg    960
atgagatacg atactgagtt ttacagactc tcttcagaca tagctaagga aacttgggtt   1020
gtcggaggaa ttcaagatcc tctgtctcgg agtcgaagct ggaaaaattg attacacaga   1080
ttcatcgtta ctcatcagta aacatcgtat tttaaaaacc taatcaagcg tttttactat   1140
aatttgatta tctgttaatt aattttgata cttacatttt tttttttttg ggtttcttga   1200
gtttttttta atggttcttc tccctttttgt ttcgtatctc aaaggttttt ttttgtttac   1260
cttctttgtt ttgtgttttt catcacaacg tttgtaatgt aatgcaaaat atgtacaggc   1320
tttttacgtt ttacgcaaat ctgcttaata                                     1350
```

<210> SEQ ID NO 90
<211> LENGTH: 342
<212> TYPE: PRT
<213> ORGANISM: Arabidopsis thaliana

<400> SEQUENCE: 90

```
Met Ile Lys Gly Asn Asn Gly Asn Arg Gly Ser Ser Ser Ser Gly Tyr
1               5                   10                  15

Ser Ala Asp Leu Leu Val Cys Phe Pro Ser Arg Thr His Leu Ala Leu
            20                  25                  30

Thr Pro Lys Pro Ile Cys Ser Pro Ser Arg Pro Ser Asp Ser Ser Thr
        35                  40                  45

Asn Arg Arg Pro His His Arg Arg Gln Leu Ser Lys Leu Ser Gly Gly
    50                  55                  60

Gly Gly Gly Gly His Gly Ser Pro Val Leu Trp Ala Lys Gln Ala Ser
65                  70                  75                  80

Ser Lys Asn Met Gly Gly Asp Glu Ile Ala Glu Pro Thr Ser Pro Lys
                85                  90                  95
```

```
Val Thr Cys Ala Gly Gln Ile Lys Val Arg Pro Ser Lys Cys Gly Gly
            100                 105                 110

Arg Gly Lys Asn Trp Gln Ser Val Met Glu Glu Ile Glu Arg Ile His
        115                 120                 125

Asp Asn Arg Ser Gln Ser Lys Phe Phe Gly Leu Lys Lys Asp Val Met
    130                 135                 140

Gly Phe Leu Thr Cys Leu Arg Asn Ile Lys Phe Asp Phe Arg Cys Phe
145                 150                 155                 160

Gly Asp Phe Arg His Ala Asp Val Thr Ser Asp Asp Asp Glu Glu Glu
                165                 170                 175

Asp Asp Asp Asp Asp Glu Glu Glu Glu Val Val Glu Gly Glu Glu Glu
            180                 185                 190

Glu Asn Ser Lys Thr Val Phe Ser Lys Trp Phe Met Val Leu Gln Glu
        195                 200                 205

Glu Gln Asn Asn Lys Asp Asp Asp Lys Asn Asn Asn Lys Cys Asp Glu
    210                 215                 220

Lys Arg Asp Leu Glu Asp Thr Glu Thr Glu Pro Ala Val Pro Pro Pro
225                 230                 235                 240

Asn Ala Leu Leu Leu Met Arg Cys Arg Ser Ala Pro Ala Lys Ser Trp
                245                 250                 255

Leu Glu Glu Arg Met Lys Val Lys Thr Glu Gln Glu Lys Arg Glu Glu
            260                 265                 270

Gln Lys Glu Glu Lys Glu Thr Glu Asp Gln Glu Thr Ser Met Lys Thr
        275                 280                 285

Lys Lys Lys Asp Leu Arg Ser Leu Met Glu Glu Glu Lys Met Glu Leu
    290                 295                 300

Val Leu Met Arg Tyr Asp Thr Glu Phe Tyr Arg Leu Ser Ser Asp Ile
305                 310                 315                 320

Ala Lys Glu Thr Trp Val Val Gly Gly Ile Gln Asp Pro Leu Ser Arg
                325                 330                 335

Ser Arg Ser Trp Lys Asn
            340
```

<210> SEQ ID NO 91
<211> LENGTH: 1593
<212> TYPE: DNA
<213> ORGANISM: Arabidopsis thaliana

<400> SEQUENCE: 91

```
atggcaaaat cgaagaaaat ttctacaggt caaatatttg gttgtgagag tctccttggg      60
tgcattttcc agagctggag ccctcgccgt cgaaaaccct ctttaccgga aaaggatcat     120
cgggcaaaag ataacttgtc ttccaagtca tcaacaaccg ttacaaaccc taaaatcctc     180
ccaagaaaat ccaccgatac ttcttctcaa ccaaagaaat ctgactccca gaaaccccaa     240
caaaagccaa aaccagatga gaatcacccg cgaaaatcat cggaatccgc cagaaaatca     300
tctgattccg caagaaaatc gatttcgtca ggctcatcaa gaacagagag caagagattc     360
tcacttaacg gcgttatggg aaacatcatc gtgaaaccac agccagccgt taaaactgac     420
gtgacacaga cgaaaagtcg gtgggagggt aaaccggtaa atcacagact cgatccagag     480
actctgaaga aaatgggaaa cgaagagtat tgtcgtggga ggtttggaca agctctcgtg     540
ttttacgaga gagccatttc agctgacccc aaaacgccga cgtattggtc taacaaatcc     600
gccgctttga tcagtctcgg tcgtcttctt gaagcttctg atgcttgtga agaagcttta     660
agactaaacc caacttacga gagagctcat cagagactag cttccctcca actcagattg     720
```

```
ggtgaggttg agaaagcttt gtgtcactat aatgaagctg gaaaatatac agagacaaaa     780

catattgaac aagttgaaga tgttgttaaa tgcttaagga ggtgtgacga agctcgaaga     840

tcaaaggaat ggaatgttgc attgaaagag actctttttg cgatatcata tggagcagat     900

tcttctcctc gggtctatgc actccaaacc gaggctttat tgcatcttca gcgacacgag     960

gaagcataca gcgtgtatca gaaaggaaca aaacgcttcg acatcgatag tttcataaag    1020

atttttggtc tttccctcac ttcttacctc ttgatggtcg gagctcaggt ctacatagca    1080

gtaggaaggt ttgaagatgc agtaacggcg tcaaggcaag cggctcgact tgatccaagc    1140

agcgaagaag taaacgcggt ggctagaaaa gcgagagcgg ttgcttctgc aagactgagt    1200

ggaaatttgc ttttcaacgc atcaaaattt gaaggggcta gcgtggttta cacggaagga    1260

cttgagaacg atccatataa tgctctcttg ctctgtaaca gagctgcttc aagattcaag    1320

cttgatctgt tcgagaaagc tattgaagat tgcacattgg ctctcagtct ccagccatcg    1380

taccggaagg cgaggcggcg cagggcagat tcttatgcca agttggagaa atggcaacac    1440

gcgattcaag attatgagtt gttgatgatg gagacacctg aagacgaaga gactagaaga    1500

gccttaactg aggtgaatgt ccggtttaag aaacagaccg gtggagatgt ccggtttaaa    1560

ggagtcggct cggaattggt tgtggctaat tga                                 1593
```

<210> SEQ ID NO 92
<211> LENGTH: 530
<212> TYPE: PRT
<213> ORGANISM: Arabidopsis thaliana

<400> SEQUENCE: 92

```
Met Ala Lys Ser Lys Lys Ile Ser Thr Gly Gln Ile Phe Gly Cys Glu
1               5                   10                  15

Ser Leu Leu Gly Cys Ile Phe Gln Ser Trp Ser Pro Arg Arg Arg Lys
            20                  25                  30

Pro Ser Leu Pro Glu Lys Asp His Arg Ala Lys Asp Asn Leu Ser Ser
        35                  40                  45

Lys Ser Ser Thr Thr Val Thr Asn Pro Lys Ile Leu Pro Arg Lys Ser
    50                  55                  60

Thr Asp Thr Ser Ser Gln Pro Lys Lys Ser Asp Ser Gln Lys Pro Gln
65                  70                  75                  80

Gln Lys Pro Lys Pro Asp Glu Asn His Pro Arg Lys Ser Ser Glu Ser
                85                  90                  95

Ala Arg Lys Ser Ser Asp Ser Ala Arg Lys Ser Ile Ser Ser Gly Ser
            100                 105                 110

Ser Arg Thr Glu Ser Lys Arg Phe Ser Leu Asn Gly Val Met Gly Asn
        115                 120                 125

Ile Ile Val Lys Pro Gln Pro Ala Val Lys Thr Asp Val Thr Gln Thr
    130                 135                 140

Lys Ser Arg Trp Glu Gly Lys Pro Val Asn His Arg Leu Asp Pro Glu
145                 150                 155                 160

Thr Leu Lys Lys Met Gly Asn Glu Glu Tyr Cys Arg Gly Arg Phe Gly
                165                 170                 175

Gln Ala Leu Val Phe Tyr Glu Arg Ala Ile Ser Ala Asp Pro Lys Thr
            180                 185                 190

Pro Thr Tyr Trp Ser Asn Lys Ser Ala Ala Leu Ile Ser Leu Gly Arg
        195                 200                 205

Leu Leu Glu Ala Ser Asp Ala Cys Glu Glu Ala Leu Arg Leu Asn Pro
    210                 215                 220
```

```
Thr Tyr Glu Arg Ala His Gln Arg Leu Ala Ser Leu Gln Leu Arg Leu
225                 230                 235                 240

Gly Glu Val Glu Lys Ala Leu Cys His Tyr Asn Glu Ala Gly Lys Tyr
                245                 250                 255

Thr Glu Thr Lys His Ile Glu Gln Val Glu Asp Val Val Lys Cys Leu
            260                 265                 270

Arg Arg Cys Asp Glu Ala Arg Arg Ser Lys Glu Trp Asn Val Ala Leu
        275                 280                 285

Lys Glu Thr Leu Phe Ala Ile Ser Tyr Gly Ala Asp Ser Ser Pro Arg
    290                 295                 300

Val Tyr Ala Leu Gln Thr Glu Ala Leu Leu His Leu Gln Arg His Glu
305                 310                 315                 320

Glu Ala Tyr Ser Val Tyr Gln Lys Gly Thr Lys Arg Phe Asp Ile Asp
                325                 330                 335

Ser Phe Ile Lys Ile Phe Gly Leu Ser Leu Thr Ser Tyr Leu Leu Met
            340                 345                 350

Val Gly Ala Gln Val Tyr Ile Ala Val Gly Arg Phe Glu Asp Ala Val
        355                 360                 365

Thr Ala Ser Arg Gln Ala Ala Arg Leu Asp Pro Ser Ser Glu Glu Val
    370                 375                 380

Asn Ala Val Ala Arg Lys Ala Arg Ala Val Ala Ser Ala Arg Leu Ser
385                 390                 395                 400

Gly Asn Leu Leu Phe Asn Ala Ser Lys Phe Glu Gly Ala Ser Val Val
                405                 410                 415

Tyr Thr Glu Gly Leu Glu Asn Asp Pro Tyr Asn Ala Leu Leu Leu Cys
            420                 425                 430

Asn Arg Ala Ala Ser Arg Phe Lys Leu Asp Leu Phe Glu Lys Ala Ile
        435                 440                 445

Glu Asp Cys Thr Leu Ala Leu Ser Leu Gln Pro Ser Tyr Arg Lys Ala
    450                 455                 460

Arg Arg Arg Arg Ala Asp Ser Tyr Ala Lys Leu Glu Lys Trp Gln His
465                 470                 475                 480

Ala Ile Gln Asp Tyr Glu Leu Leu Met Met Glu Thr Pro Glu Asp Glu
                485                 490                 495

Glu Thr Arg Arg Ala Leu Thr Glu Val Asn Val Arg Phe Lys Lys Gln
            500                 505                 510

Thr Gly Gly Asp Val Arg Phe Lys Gly Val Gly Ser Glu Leu Val Val
        515                 520                 525

Ala Asn
    530
```

<210> SEQ ID NO 93
<211> LENGTH: 1287
<212> TYPE: DNA
<213> ORGANISM: Arabidopsis thaliana

<400> SEQUENCE: 93

```
atggattggg caacactgcc aaaggatctc ttagacctga tctccaaatg tctagaatct      60

tcctttgatc tcatacagtt ccgttctgta tgttcttcat ggcgatctgc cgcggggcca     120

aagcgccttc tctgggcaca taacctcccg ttcttcccct ctgatgacaa accctttctc     180

tccaatgtaa tcctccgcgt cgcgcaccag agtattttac ttatcaagcc taatgaaccg     240

caatgcgagg cggatctgtt tggatggatt gtcaaggttt gggataacat atatgtatct     300

cgtaagatga cccttctcaa accgttgagt tcttcaagaa actactttcc tcagcattta     360
```

```
cctcgtattt tcgatatgtc taagtttacg gttcgtgaat tgtgtcggga agtcaagctc    420
tatcatcctg attactactg tgtccctgga cacacagctt tagagttgga gttggggaaa    480
actgttgtca agtacctaaa tgatgacaaa ttcgtgttgc ttacaattct tgaatatgga    540
aagttagctg tgtttaggtc ttgggatcga gaatggactg tgatcaatga ttacatacct    600
tctcgttgtc aagatttgat tatgttcgat ggacgtttct ttgctatcga ctacaatggg    660
aggactgtag ttgttgacta ctcttctttc aaattgacat tggccgctaa tcctttgatt    720
ggcggcggtg acaagaagtt tctgattgaa tcttgtggtg aaatgtttct ggtggatata    780
gagttttgcc tgaatgaaaa accggaattc acagggggtt tctattcgta ttttaatgag    840
accacggtca gttacaaatt taaattcttt aaattagtgg aaagagagaa gagatgggtt    900
gaggttgagg atcttgggga taagatgttt ttccttggtg atgactccac cttttccgct    960
tcaactgctg atattatacc tcgctgcgtg ggaactggaa gcttcgtgtt cttctacacg   1020
catgaggaat ccttggtggt gatggatgat cgaaacttgg gagtgtttga tttcaggagt   1080
gggaaaacag agctggtaaa caaactccct gaatatgcca agttgttttg gcctccacct   1140
ccatggatta ctacttctca tgaggtcagt ggtttccaat ctctcaacca cccgaataga   1200
gtagtgttga aaattatact ggagaaacat catcacaatc ccaatcttga gtttaagacc   1260
ttggagatga cacttcaact tgaatga                                       1287
```

```
<210> SEQ ID NO 94
<211> LENGTH: 428
<212> TYPE: PRT
<213> ORGANISM: Arabidopsis thaliana

<400> SEQUENCE: 94

Met Asp Trp Ala Thr Leu Pro Lys Asp Leu Leu Asp Leu Ile Ser Lys
1               5                   10                  15

Cys Leu Glu Ser Ser Phe Asp Leu Ile Gln Phe Arg Ser Val Cys Ser
            20                  25                  30

Ser Trp Arg Ser Ala Ala Gly Pro Lys Arg Leu Leu Trp Ala His Asn
        35                  40                  45

Leu Pro Phe Phe Pro Ser Asp Asp Lys Pro Phe Leu Ser Asn Val Ile
    50                  55                  60

Leu Arg Val Ala His Gln Ser Ile Leu Leu Ile Lys Pro Asn Glu Pro
65                  70                  75                  80

Gln Cys Glu Ala Asp Leu Phe Gly Trp Ile Val Lys Val Trp Asp Asn
                85                  90                  95

Ile Tyr Val Ser Arg Lys Met Thr Leu Leu Lys Pro Leu Ser Ser Ser
            100                 105                 110

Arg Asn Tyr Phe Pro Gln His Leu Pro Arg Ile Phe Asp Met Ser Lys
        115                 120                 125

Phe Thr Val Arg Glu Leu Cys Arg Glu Val Lys Leu Tyr His Pro Asp
    130                 135                 140

Tyr Tyr Cys Val Pro Gly His Thr Ala Leu Glu Leu Glu Leu Gly Lys
145                 150                 155                 160

Thr Val Val Lys Tyr Leu Asn Asp Asp Lys Phe Val Leu Leu Thr Ile
                165                 170                 175

Leu Glu Tyr Gly Lys Leu Ala Val Phe Arg Ser Trp Asp Arg Glu Trp
            180                 185                 190

Thr Val Ile Asn Asp Tyr Ile Pro Ser Arg Cys Gln Asp Leu Ile Met
        195                 200                 205
```

```
Phe Asp Gly Arg Phe Phe Ala Ile Asp Tyr Asn Gly Arg Thr Val Val
    210                 215                 220

Val Asp Tyr Ser Ser Phe Lys Leu Thr Leu Ala Ala Asn Pro Leu Ile
225                 230                 235                 240

Gly Gly Gly Asp Lys Lys Phe Leu Ile Glu Ser Cys Gly Glu Met Phe
                245                 250                 255

Leu Val Asp Ile Glu Phe Cys Leu Asn Glu Lys Pro Glu Phe Thr Gly
            260                 265                 270

Gly Phe Tyr Ser Tyr Phe Asn Glu Thr Thr Val Ser Tyr Lys Phe Lys
        275                 280                 285

Phe Phe Lys Leu Val Glu Arg Glu Lys Arg Trp Val Glu Val Glu Asp
    290                 295                 300

Leu Gly Asp Lys Met Phe Phe Leu Gly Asp Asp Ser Thr Phe Ser Ala
305                 310                 315                 320

Ser Thr Ala Asp Ile Ile Pro Arg Cys Val Gly Thr Gly Ser Phe Val
                325                 330                 335

Phe Phe Tyr Thr His Glu Glu Ser Leu Val Val Met Asp Asp Arg Asn
            340                 345                 350

Leu Gly Val Phe Asp Phe Arg Ser Gly Lys Thr Glu Leu Val Asn Lys
        355                 360                 365

Leu Pro Glu Tyr Ala Lys Leu Phe Trp Pro Pro Pro Pro Trp Ile Thr
    370                 375                 380

Thr Ser His Glu Val Ser Gly Phe Gln Ser Leu Asn His Pro Asn Arg
385                 390                 395                 400

Val Val Leu Lys Ile Ile Leu Glu Lys His His His Asn Pro Asn Leu
                405                 410                 415

Glu Phe Lys Thr Leu Glu Met Thr Leu Gln Leu Glu
            420                 425
```

<210> SEQ ID NO 95
<211> LENGTH: 979
<212> TYPE: DNA
<213> ORGANISM: Arabidopsis thaliana

<400> SEQUENCE: 95

```
gggaaaagat attgagctcc cgggttttag gttccacccg actgaggaag agcttcttga      60

tttctacctc aagaacatgg tttacggtaa gagatcgagt gtcgaagtca ttggtttcct     120

taacatatac cgtcatgatc catgggactt acctggttta tcgagaatcg gggagaggga     180

atggtacttc tttgtaccaa gggaaaggaa gcatgggaac ggtgggaggc caagcaggac     240

aactgaaaaa ggatattgga aagcaactgg atccgatcgt aaaatcataa gcttgtctga     300

gccaaaacgt gttatagggc tcaagaagac gcttgtgttc tatagaggaa gagcaccagg     360

aggaagcaag actgattggg tgatgaacga gtttcggatg cccgataatt gctccttacc     420

aaaggatgtt gtgctttgta agatatatag aaaagctact tcattgaaag tattggagca     480

aagggcagag atggaagcta agatgaatca aacatgtcct aactctcctc tttcgtcttc     540

cgagacgatt tctttcgttg gtaaagaaga aaacatgatg acttcgttcc gtgctcctca     600

agtaatagct atggaagaag caaacaagat ccaaatgcat caagaaaacg cgaaaaccga     660

agagaaacaa agagaagcag agaccaaaga accttcttca tcactgaagc taccgtttgg     720

aagtttacca gagctacaat taccaaaacc aggagtagaa tgggaccagt tgttgagtat     780

aagcccatgg ctccagaatc ttacaccaat agttaacata tattggtagg atatgtaaag     840

aacaaataca tttaaatatt cttactctcg taaaaaacag agcttgtacc aaatagtatt     900
```

```
tactaaactt ttatgtatct tttgtaattt tgtaacataa gaaaatttgt aacactattt    960

atagtcatat ttgacgatc                                                 979
```

<210> SEQ ID NO 96
<211> LENGTH: 250
<212> TYPE: PRT
<213> ORGANISM: Arabidopsis thaliana

<400> SEQUENCE: 96

```
Met Val Tyr Gly Lys Arg Ser Ser Val Glu Val Ile Gly Phe Leu Asn
1               5                   10                  15

Ile Tyr Arg His Asp Pro Trp Asp Leu Pro Gly Leu Ser Arg Ile Gly
            20                  25                  30

Glu Arg Glu Trp Tyr Phe Phe Val Pro Arg Glu Arg Lys His Gly Asn
        35                  40                  45

Gly Gly Arg Pro Ser Arg Thr Thr Glu Lys Gly Tyr Trp Lys Ala Thr
    50                  55                  60

Gly Ser Asp Arg Lys Ile Ile Ser Leu Ser Glu Pro Lys Arg Val Ile
65                  70                  75                  80

Gly Leu Lys Lys Thr Leu Val Phe Tyr Arg Gly Arg Ala Pro Gly Gly
                85                  90                  95

Ser Lys Thr Asp Trp Val Met Asn Glu Phe Arg Met Pro Asp Asn Cys
            100                 105                 110

Ser Leu Pro Lys Asp Val Val Leu Cys Lys Ile Tyr Arg Lys Ala Thr
        115                 120                 125

Ser Leu Lys Val Leu Glu Gln Arg Ala Glu Met Glu Ala Lys Met Asn
    130                 135                 140

Gln Thr Cys Pro Asn Ser Pro Leu Ser Ser Ser Glu Thr Ile Ser Phe
145                 150                 155                 160

Val Gly Lys Glu Glu Asn Met Met Thr Ser Phe Arg Ala Pro Gln Val
                165                 170                 175

Ile Ala Met Glu Glu Ala Asn Lys Ile Gln Met His Gln Glu Asn Ala
            180                 185                 190

Lys Thr Glu Glu Lys Gln Arg Glu Ala Glu Thr Lys Glu Pro Ser Ser
        195                 200                 205

Ser Leu Lys Leu Pro Phe Gly Ser Leu Pro Glu Leu Gln Leu Pro Lys
    210                 215                 220

Pro Gly Val Glu Trp Asp Gln Leu Leu Ser Ile Ser Pro Trp Leu Gln
225                 230                 235                 240

Asn Leu Thr Pro Ile Val Asn Ile Tyr Trp
                245                 250
```

<210> SEQ ID NO 97
<211> LENGTH: 735
<212> TYPE: DNA
<213> ORGANISM: Arabidopsis thaliana

<400> SEQUENCE: 97

```
atgtcagatt ctgcagagat gcaacagccg gagttactgc tgaaatccat gaataaattg     60

aatgggtatc atccacaact aatcattcca aagaagactc tcttcaagtg tgatctcgat    120

gacaaacagt cacgactcca agtttcttcc atgcatatgg aaaattcagg cttcttaacg    180

gaagatgaaa aacgaaccat agaggcacaa aagatgaaga aacgacggac ggctggtttg    240

agagtagctt ttatagatcc tgaatcgcaa cagtacgtgc ttgagttaca taagtggacc    300

aagagctatg cctttgttaa aggttggaat aaggtggttg ataagaacga caaaacgttc    360
```

```
aaggtgggcg acgttttctc tctctgggtt ttccgttgcg gaggagtgaa ccctgttcac    420

gacggcgtca atctttcggg tggccacgcc gactctgttg ttgacggttt ggagcaaggt    480

agtctctgtt ttgttctggt tcctgcaaaa gtttctgttc acgacggcaa tcttcctcaa    540

gattctggtc acgacggcca caacgacaat cttcctcaag attctgttga acctagctct    600

tttttcgacg agtcttacga gttaaaccac ctgttctttg atcaagaaga cagtcaaggc    660

tatcttcccg acgaagatga agactttggc ttcaacgatg atggctcgat tcgtgattcc    720

ggtcactacc agtga                                                      735
```

<210> SEQ ID NO 98
<211> LENGTH: 244
<212> TYPE: PRT
<213> ORGANISM: Arabidopsis thaliana

<400> SEQUENCE: 98

```
Met Ser Asp Ser Ala Glu Met Gln Gln Pro Glu Leu Leu Leu Lys Ser
1               5                   10                  15

Met Asn Lys Leu Asn Gly Tyr His Pro Gln Leu Ile Ile Pro Lys Lys
            20                  25                  30

Thr Leu Phe Lys Cys Asp Leu Asp Asp Lys Gln Ser Arg Leu Gln Val
        35                  40                  45

Ser Ser Met His Met Glu Asn Ser Gly Phe Leu Thr Glu Asp Glu Lys
    50                  55                  60

Arg Thr Ile Glu Ala Gln Lys Met Lys Lys Arg Arg Thr Ala Gly Leu
65                  70                  75                  80

Arg Val Ala Phe Ile Asp Pro Glu Ser Gln Gln Tyr Val Leu Glu Leu
                85                  90                  95

His Lys Trp Thr Lys Ser Tyr Ala Phe Val Lys Gly Trp Asn Lys Val
            100                 105                 110

Val Asp Lys Asn Asp Lys Thr Phe Lys Val Gly Asp Val Phe Ser Leu
        115                 120                 125

Trp Val Phe Arg Cys Gly Gly Val Asn Pro Val His Asp Gly Val Asn
    130                 135                 140

Leu Ser Gly Gly His Ala Asp Ser Val Val Asp Gly Leu Glu Gln Gly
145                 150                 155                 160

Ser Leu Cys Phe Val Leu Val Pro Ala Lys Val Ser Val His Asp Gly
                165                 170                 175

Asn Leu Pro Gln Asp Ser Gly His Asp Gly His Asn Asp Asn Leu Pro
            180                 185                 190

Gln Asp Ser Val Glu Pro Ser Ser Phe Phe Asp Glu Ser Tyr Glu Leu
        195                 200                 205

Asn His Leu Phe Phe Asp Gln Glu Asp Ser Gln Gly Tyr Leu Pro Asp
    210                 215                 220

Glu Asp Glu Asp Phe Gly Phe Asn Asp Asp Gly Ser Ile Arg Asp Ser
225                 230                 235                 240

Gly His Tyr Gln
```

<210> SEQ ID NO 99
<211> LENGTH: 1164
<212> TYPE: DNA
<213> ORGANISM: Arabidopsis thaliana

<400> SEQUENCE: 99

```
atgaaatcac ggcgacagaa tgtgtccgtg gctcgacaaa ccatccttgg acgcgacgaa     60

aactttgaac caatcccaat tgatctcgtt atcgagatat tctcaaggtc gcctgtgaag    120
```

```
tctatagcaa gatgtcgttg cgtatcaaag ctttgggcct ccatactccg cctaccctat    180
ttcacggagt tgtacttgac caaatcttgt gctcgcccga ggctcttgtt cgcctgccaa    240
aaacacagag agttgttctt cttctcgaca cctcagcctc ataatcctaa tgagagctcg    300
tctcctttag ctgccagttt tcatatgaaa attccctttg atggtcgctt taatattatc    360
agtcctatcg gtggccttgt ctttgttaga tatgaacaga tcttaaaggg aaggaaaact    420
ccagaatttg tctcggcgat atgtaaccct agcacgggac aatccttaac cttaccaaaa    480
cctaagacaa ggaagaggat ttggggtaca agccattttg ggtatgatcc tattgagaaa    540
caattcaagg tattgtcaat gaatataggt gatggggtct ataaagagca ttatgttctg    600
acattaggaa ctgagaacct ctcttggaga aggatcgaat gttctatacc ccatgttcat    660
ggttctaaag ggatatgcat caatggtgtt ttgtattatc gagcaaaggc tgacatgttt    720
tcaggtactt taatgatagt ttgctttgat gttaggtttg agaagttcag ctatattaaa    780
atcttgaaac ctacaacaac tctgattagc tacaacggta aattggcttc actagtgtgg    840
gaagggccta gttatatttg tggaaaacgt tttgaaatgt gggttttagg agaccccgaa    900
aaacatgaat ggttgaagca tacttacgaa ttgcgtcctc ggtggcagaa tgtacttgga    960
gaggacttgt taatttttgc tggaatgact ggtacaaatg aaattgtgtt gtcgccaaag   1020
tatccatctc accctttcta tgttttctac tacaatttgg agaggaatac tatcagaaga   1080
gttgaaatcc aaggaatggg agcgtttaag gttaatgaag attacatctt tctagaccat   1140
gtagaggatg tgaagcttat ataa                                          1164
```

<210> SEQ ID NO 100
<211> LENGTH: 387
<212> TYPE: PRT
<213> ORGANISM: Arabidopsis thaliana

<400> SEQUENCE: 100

```
Met Lys Ser Arg Arg Gln Asn Val Ser Val Ala Arg Gln Thr Ile Leu
1               5                   10                  15

Gly Arg Asp Glu Asn Phe Glu Pro Ile Pro Ile Asp Leu Val Ile Glu
            20                  25                  30

Ile Phe Ser Arg Ser Pro Val Lys Ser Ile Ala Arg Cys Arg Cys Val
        35                  40                  45

Ser Lys Leu Trp Ala Ser Ile Leu Arg Leu Pro Tyr Phe Thr Glu Leu
    50                  55                  60

Tyr Leu Thr Lys Ser Cys Ala Arg Pro Arg Leu Leu Phe Ala Cys Gln
65                  70                  75                  80

Lys His Arg Glu Leu Phe Phe Phe Ser Thr Pro Gln Pro His Asn Pro
                85                  90                  95

Asn Glu Ser Ser Ser Pro Leu Ala Ala Ser Phe His Met Lys Ile Pro
            100                 105                 110

Phe Asp Gly Arg Phe Asn Ile Ile Ser Pro Ile Gly Gly Leu Val Phe
        115                 120                 125

Val Arg Tyr Glu Gln Ile Leu Lys Gly Arg Lys Thr Pro Glu Phe Val
    130                 135                 140

Ser Ala Ile Cys Asn Pro Ser Thr Gly Gln Ser Leu Thr Leu Pro Lys
145                 150                 155                 160

Pro Lys Thr Arg Lys Arg Ile Trp Gly Thr Ser His Phe Gly Tyr Asp
                165                 170                 175

Pro Ile Glu Lys Gln Phe Lys Val Leu Ser Met Asn Ile Gly Asp Gly
            180                 185                 190
```

-continued

```
Val Tyr Lys Glu His Tyr Val Leu Thr Leu Gly Thr Glu Asn Leu Ser
        195                 200                 205

Trp Arg Arg Ile Glu Cys Ser Ile Pro His Val His Gly Ser Lys Gly
    210                 215                 220

Ile Cys Ile Asn Gly Val Leu Tyr Tyr Arg Ala Lys Ala Asp Met Phe
225                 230                 235                 240

Ser Gly Thr Leu Met Ile Val Cys Phe Asp Val Arg Phe Glu Lys Phe
                245                 250                 255

Ser Tyr Ile Lys Ile Leu Lys Pro Thr Thr Thr Leu Ile Ser Tyr Asn
            260                 265                 270

Gly Lys Leu Ala Ser Leu Val Trp Glu Gly Pro Ser Tyr Ile Cys Gly
        275                 280                 285

Lys Arg Phe Glu Met Trp Val Leu Gly Asp Pro Glu Lys His Glu Trp
    290                 295                 300

Leu Lys His Thr Tyr Glu Leu Arg Pro Arg Trp Gln Asn Val Leu Gly
305                 310                 315                 320

Glu Asp Leu Leu Ile Phe Ala Gly Met Thr Gly Thr Asn Glu Ile Val
                325                 330                 335

Leu Ser Pro Lys Tyr Pro Ser His Pro Phe Tyr Val Phe Tyr Tyr Asn
            340                 345                 350

Leu Glu Arg Asn Thr Ile Arg Arg Val Glu Ile Gln Gly Met Gly Ala
        355                 360                 365

Phe Lys Val Asn Glu Asp Tyr Ile Phe Leu Asp His Val Glu Asp Val
    370                 375                 380

Lys Leu Ile
385
```

GENERATION OF PLANTS WITH ALTERED PROTEIN, FIBER, OR OIL CONTENT

CROSS REFERENCE TO RELATED APPLICATION(S)

This application claims the benefit of U.S. Provisional Application No. 60/866,053, filed Nov. 15, 2006, the entirety of which is incorporated herein by reference.

FIELD OF THE DISCLOSURE

The present disclosure is related to transgenic plants with altered oil, protein, and/or fiber content, as well as methods of making plants having altered oil, protein, and/or fiber content and producing oil from such plants.

BACKGROUND

The ability to manipulate the composition of crop seeds, particularly the content and composition of seed oil and protein, as well as the available metabolizable energy ("AME") in the seed meal in livestock, has important applications in the agricultural industries, relating both to processed food oils and to animal feeds. Seeds of agricultural crops contain a variety of valuable constituents, including oil, protein and starch. Industrial processing can separate some or all of these constituents for individual sale in specific applications. For instance, nearly 60% of the U.S. soybean crop is crushed by the soy processing industry. Soy processing yields purified oil, which is sold at high value, while the remaining seed meal is sold for livestock feed (U.S. Soybean Board, 2001 Soy Stats). Canola seed is also crushed to produce oil and the co-product canola meal (Canola Council of Canada). Canola meal contains a high percentage of protein and a good balance of amino acids but because it has a high fiber and phytate content, it is not readily digested by livestock (Slominski, B. A., et al., 1999 Proceedings of the 10$^{th}$ International Rapeseed Congress, Can berra, Australia) and has a lower value than soybean meal.

Over 55% of the corn produced in the U.S. is used as animal feed (Iowa Corn Growers Association). The value of the corn is directly related to its ability to be digested by livestock. Thus, it is desirable to maximize both oil content of seeds and the AME of meal. For processed oilseeds such as soy and canola, increasing the absolute oil content of the seed will increase the value of such grains, while increasing the AME of meal will increase its value. For processed corn, either an increase or a decrease in oil content may be desired, depending on how the other major constituents are to be used. Decreasing oil may improve the quality of isolated starch by reducing undesired flavors associated with oil oxidation. Alternatively, when the starch is used for ethanol production, where flavor is unimportant, increasing oil content may increase overall value.

In many feed grains, such as corn and wheat, it is desirable to increase seed oil content, because oil has higher energy content than other seed constituents such as carbohydrate. Oilseed processing, like most grain processing businesses, is a capital-intensive business; thus small shifts in the distribution of products from the low valued components to the high value oil component can have substantial economic impacts for grain processors. In addition, increasing the AME of meal by adjusting seed protein and fiber content and composition, without decreasing seed oil content, can increase the value of animal feed.

Biotechnological manipulation of oils has been shown to provide compositional alteration and improvement of oil yield. Compositional alterations include high oleic acid soybean and corn oil (U.S. Pat. Nos. 6,229,033 and 6,248,939), and laurate-containing seeds (U.S. Pat. No. 5,639,790), among others. Work in compositional alteration has predominantly focused on processed oilseeds, but has been readily extendable to non-oilseed crops, including corn. While there is considerable interest in increasing oil content, the only currently practiced biotechnology in this area is High-Oil Corn (HOC) technology (DuPont, U.S. Pat. No. 5,704,160). HOC employs high oil pollinators developed by classical selection breeding along with elite (male-sterile) hybrid females in a production system referred to as TopCross. The TopCross High Oil system raises harvested grain oil content in maize from about 3.5% to about 7%, improving the energy content of the grain.

While it has been fruitful, the HOC production system has inherent limitations. First, the system of having a low percentage of pollinators responsible for an entire field's seed set contains inherent risks, particularly in drought years. Second, oil content in current HOC fields has plateaued at about 9% oil. Finally, high-oil corn is not primarily a biochemical change, but rather an anatomical mutant (increased embryo size) that has the indirect result of increasing oil content. For these reasons, an alternative high oil strategy, particularly one that derives from an altered biochemical output, would be especially valuable.

Manipulation of seed composition has identified several components that improve the nutritive quality, digestibility, and AME in seed meal. Increasing the lysine content in canola and soybean (Falco et al., 1995 *Bio/Technology* 13:577-582) increases the availability of this essential amino acid and decreases the need for nutritional supplements. Soybean varieties with increased seed protein were shown to contain considerably more metabolizable energy than conventional varieties (Edwards et al., 1999, *Poultry Sci.* 79:525-527). Decreasing the phytate content of corn seed has been shown to increase the bioavailability of amino acids in animal feeds (Douglas et al., 2000, *Poultry Sci.* 79:1586-1591) and decreasing oligosaccharide content in soybean meal increases the metabolizable energy in the meal (Parsons et al., 2000, *Poultry Sci.* 79:1127-1131).

Soybean and canola are the most obvious target crops for the processed oil and seed meal markets since both crops are crushed for oil and the remaining meal sold for animal feed. A large body of commercial work (e.g., U.S. Pat. No. 5,952,544; PCT Application No. WO9411516) demonstrates that *Arabidopsis* is an excellent model for oil metabolism in these crops. Biochemical screens of seed oil composition have identified *Arabidopsis* genes for many critical biosynthetic enzymes and have led to identification of agronomically important gene orthologs. For instance, screens using chemically mutagenized populations have identified lipid mutants whose seeds display altered fatty acid composition (Lemieux et al., 1990, *Theor. Appl. Genet.* 80, 234-240; James and Dooner, 1990, *Theor. Appl. Genet.* 80, 241-245). T-DNA mutagenesis screens (Feldmann et al., 1989, *Science* 243:1351-1354) that detected altered fatty acid composition identified the omega 3 desaturase (FAD3) and delta-12 desaturase (FAD2) genes (U.S. Pat. No. 5,952,544; Yadav et al., 1993, *Plant Physiol.* 103, 467-476; Okuley et al., 1994, *Plant Cell* 6(1): 147-158). A screen which focused on oil content rather than oil quality, analyzed chemically-induced mutants for wrinkled seeds or altered seed density, from which altered seed oil content was inferred (Focks and Benning, 1998, *Plant Physiol.* 118:91-101).

Another screen, designed to identify enzymes involved in production of very long chain fatty acids, identified a mutation in the gene encoding a diacylglycerol acyltransferase (DGAT) as being responsible for reduced triacyl glycerol accumulation in seeds (Katavic V et al., 1995, *Plant Physiol.* 108(1):399-409). It was further shown that seed-specific over-expression of the DGAT cDNA was associated with increased seed oil content (Jako et al., 2001, *Plant Physiol.* 126(2):861-74). *Arabidopsis* is also a model for understanding the accumulation of seed components that affect meal quality. For example, *Arabidopsis* contains albumin and globulin seed storage proteins found in many dicotyledonous plants including canola and soybean (Shewry 1995, *Plant Cell* 7:945-956). The biochemical pathways for synthesizing components of fiber, such as cellulose and lignin, are conserved within the vascular plants, and mutants of *Arabidopsis* affecting these components have been isolated (reviewed in Chapel and Carpita 1998, *Current Opinion in Plant Biology* 1:179-185).

Activation tagging in plants refers to a method of generating random mutations by insertion of a heterologous nucleic acid construct comprising regulatory sequences (e.g., an enhancer) into a plant genome. The regulatory sequences can act to enhance transcription of one or more native plant genes; accordingly, activation tagging is a fruitful method for generating gain-of-function, generally dominant mutants (see, e.g., Hayashi et al., 1992, *Science* 258: 1350-1353; Weigel D et al., 2000, *Plant Physiology,* 122:1003-1013). The inserted construct provides a molecular tag for rapid identification of the native plant whose mis-expression causes the mutant phenotype. Activation tagging may also cause loss-of-function phenotypes. The insertion may result in disruption of a native plant gene, in which case the phenotype is generally recessive.

Activation tagging has been used in various species, including tobacco and *Arabidopsis*, to identify many different kinds of mutant phenotypes and the genes associated with these phenotypes (Wilson et al., 1996, *Plant Cell* 8: 659-671; Schäffer et al., 1998, *Cell* 93: 1219-1229; Fridborg et al., 1999, *Plant Cell* 11: 1019-1032; Kardailsky et al., 1999, *Science* 286: 1962-1965; and Christensen S et al., 1998, 9$^{th}$ *International Conference on Arabidopsis Research*, Univ. of Wisconsin-Madison, June 24-28, Abstract 165).

SUMMARY

Provided herein are transgenic plants having an Improved Seed Quality phenotype. Transgenic plants with an Improved Seed Quality phenotype may include an improved oil quantity and/or an improved meal quality. Transgenic plants with improved meal quality have an Improved Meal Quality (IMQ) phenotype and transgenic plants with improved oil quantity have an Improved Oil Quantity (IOQ) phenotype. The IMQ phenotype in a transgenic plant may include altered protein and/or fiber content in any part of the transgenic plant, for example in the seeds. The IOQ phenotype in a transgenic plant may include altered oil content in any part of the transgenic plant, for example in the seeds. In particular embodiments, a transgenic plant may include an IOQ phenotype and/or an IMQ phenotype. In some embodiments of a transgenic plant, the IMQ phenotype may be an increase in protein content in the seed and/or a decrease in the fiber content of the seed. In other embodiments of a transgenic plant, the IOQ phenotype is an increase in the oil content of the seed (a high oil phenotype). Also provided is seed meal derived from the seeds of transgenic plants, wherein the seeds have altered protein content and/or altered fiber content. Further provided is oil derived from the seeds of transgenic plants, wherein the seeds have altered oil content. Any of these changes can lead to an increase in the AME from the seed or seed meal from transgenic plants, relative to control, non-transgenic, or wild-type plants. Also provided herein is meal, feed, or food produced from any part of the transgenic plant with an IMQ phenotype and/or IOQ phenotype.

In certain embodiments, the disclosed transgenic plants comprise a transformation vector comprising an IMQ nucleotide sequence that encodes or is complementary to a sequence that encodes an "IMQ" polypeptide. In particular embodiments, expression of an IMQ polypeptide in a transgenic plant causes an altered oil content, an altered protein content, and/or an altered fiber content in the transgenic plant. In preferred embodiments, the transgenic plant is selected from the group consisting of plants of the *Brassica* species, including canola and rapeseed, soy, corn, sunflower, cotton, cocoa, safflower, oil palm, coconut palm, flax, castor, peanut, wheat, oat and rice. Also provided is a method of producing oil or seed meal, comprising growing the transgenic plant and recovering oil and/or seed meal from said plant. The disclosure further provides feed, meal, grain, or seed comprising a nucleic acid sequence that encodes an IMQ polypeptide. The disclosure also provides feed, meal, grain, or seed comprising the IMQ polypeptide, or an ortholog thereof.

Examples of the disclosed transgenic plant are produced by a method that comprises introducing into progenitor cells of the plant a plant transformation vector comprising an IMQ nucleotide sequence that encodes, or is complementary to a sequence that encodes, an IMQ polypeptide, and growing the transformed progenitor cells to produce a transgenic plant, wherein the IMQ polynucleotide sequence is expressed, causing an IOQ phenotype and/or and IMQ phenotype in the transgenic plant. In some specific, non-limiting examples, the method produces transgenic plants wherein expression of the IMQ polypeptide causes a high (increased) oil, high (increased) protein, and/or low (decreased) fiber phenotype in the transgenic plant, relative to control, non-transgenic, or wild-type plants.

Additional methods are disclosed herein of generating a plant having an IMQ and/or an IOQ phenotype, wherein a plant is identified that has an allele in its IMQ nucleic acid sequence that results in an IMQ phenotype and/or an IOQ phenotype, compared to plants lacking the allele. The plant can generate progeny, wherein the progeny inherit the allele and have an IMQ phenotype and/or an IOQ phenotype. In some embodiments of the method, the method employs candidate gene/QTL methodology or TILLING methodology.

Also provided herein is a transgenic plant cell having an IMQ phenotype and/or an IOQ phenotype. The transgenic plant cell comprises a transformation vector comprising an IMQ nucleotide sequence that encodes or is complementary to a sequence that encodes an IMQ polypeptide. In preferred embodiments, the transgenic plant cell is selected from the group consisting of plants of the *Brassica* species, including canola and rapeseed, soy, corn, sunflower, cotton, cocoa, safflower, oil palm, coconut palm, flax, castor, peanut, wheat, oat and rice. In other embodiments, the plant cell is a seed, pollen, propagule, or embryo cell. The disclosure also provides plant cells from a plant that is the direct progeny or the indirect progeny of a plant grown from said progenitor cells.

DETAILED DESCRIPTION

Terms

Unless otherwise indicated, all technical and scientific terms used herein have the same meaning as they would to one skilled in the art of the present disclosure. Practitioners are particularly directed to Sambrook et al. (*Molecular Cloning: A Laboratory Manual* (Second Edition), Cold Spring Harbor Press, Plainview, N.Y., 1989) and Ausubel F M et al. (*Current Protocols in Molecular Biology*, John Wiley & Sons, New York, N.Y., 1993) for definitions and terms of the art. It is to be understood that this disclosure is not limited to the particular methodology, protocols, and reagents described, as these may vary.

As used herein, the term "IMQ phenotype" refers to plants, or any part of a plant (for example, seeds, or meal produced from seeds), with an altered protein and/or fiber content (phenotype). As provided herein, altered protein and/or fiber content includes either an increased or decreased level of protein and/or fiber content in plants, seeds or seed meal. Any combination of these changes can lead to an IMQ phenotype. For example, in one specific non-limiting example, an IMQ phenotype can refer to increased protein and decreased fiber content. In another specific non-limiting example, an IMQ phenotype can refer to unchanged protein and decreased fiber content. In yet another specific non-limiting example, an IMQ phenotype can refer to increased protein and unchanged fiber content. It is also provided that any combination of these changes can lead to an increase in the AME (available metabolizable energy) from the seed or meal generated from the seed. An IMQ phenotype also includes an improved seed quality (ISQ) phenotype or an improved seed meal quality phenotype.

As used herein, the term "IOQ phenotype" refers to plants, or any part of a plant (for example, seeds), with an altered oil content (phenotype). As provided herein, altered oil content includes an increased, for example a high, oil content in plants or seeds. In some embodiments, a transgenic plant can express both an IOQ phenotype and an IMQ phenotype. In specific, non-limiting examples, a transgenic plant having a combination of an IOQ phenotype and an IMQ phenotype can lead to an increase in the AME (available metabolizable energy) from the seed or meal generated from the seed. An IOQ phenotype also includes an improved seed quality (ISQ) phenotype.

As used herein, the term "available metabolizable energy" (AME) refers to the amount of energy in the feed that is able to be extracted by digestion in an animal and is correlated with the amount of digestible protein and oil available in animal meal. AME is determined by estimating the amount of energy in the feed prior to feeding and measuring the amount of energy in the excreta of the animal following consumption of the feed. In one specific, non-limiting example, a transgenic plant with an increase in AME includes transgenic plants with altered seed protein and/or fiber content and without a decrease in seed oil content (seed oil content remains unchanged or is increased), resulting in an increase in the value of animal feed derived from the seed.

As used herein, the term "content" refers to the type and relative amount of, for instance, a seed or seed meal component.

As used herein, the term "fiber" refers to non-digestible components of the plant seed including cellular components such as cellulose, hemicellulose, pectin, lignin, and phenolics.

As used herein, the term "meal" refers to seed components remaining following the extraction of oil from the seed. Examples of components of meal include protein and fiber.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

A "heterologous" nucleic acid construct or sequence has a portion of the sequence that is not native to the plant cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell by infection, transfection, microinjection, electroporation, or the like. A "heterologous" nucleic acid construct may contain a control sequence/DNA coding sequence combination that is the same as, or different from, a control sequence/DNA coding sequence combination found in the native plant. Specific, non-limiting examples of a heterologous nucleic acid sequence include an IMQ nucleic acid sequence, or a fragment, derivative (variant), or ortholog thereof.

As used herein, the term "gene" means the segment of DNA involved in producing a polypeptide chain, which may or may not include regions preceding and following the coding region, e.g. 5' untranslated (5' UTR) or "leader" sequences and 3' UTR or "trailer" sequences, as well as intervening sequences (introns) between individual coding segments (exons) and non-transcribed regulatory sequences.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed, or not expressed at all as a result of deliberate human intervention.

As used herein, the term "gene expression" refers to the process by which a polypeptide is produced based on the nucleic acid sequence of a gene. The process includes both transcription and translation; accordingly, "expression" may refer to either a polynucleotide or polypeptide sequence, or both. Sometimes, expression of a polynucleotide sequence will not lead to protein translation. "Over-expression" refers to increased expression of a polynucleotide and/or polypeptide sequence relative to its expression in a wild-type (or other reference [e.g., non-transgenic]) plant and may relate to a naturally-occurring or non-naturally occurring sequence. "Ectopic expression" refers to expression at a time, place, and/or increased level that does not naturally occur in the non-altered or wild-type plant. "Under-expression" refers to decreased expression of a polynucleotide and/or polypeptide sequence, generally of an endogenous gene, relative to its expression in a wild-type plant. The terms "mis-expression" and "altered expression" encompass over-expression, under-expression, and ectopic expression.

The term "introduced" in the context of inserting a nucleic acid sequence into a cell, includes "transfection," "transformation," and "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

As used herein, a "plant cell" refers to any cell derived from a plant, including cells from undifferentiated tissue (e.g., callus), as well as from plant seeds, pollen, propagules, and embryos.

As used herein, the terms "native" and "wild-type" relative to a given plant trait or phenotype refers to the form in which that trait or phenotype is found in the same variety of plant in nature. In one embodiment, a wild-type plant is also a control plant. In another embodiment, a wild-type plant is a non-transgenic plant.

As used herein, the term "modified" regarding a plant trait, refers to a change in the phenotype of a transgenic plant (for example, a transgenic plant with any combination of an altered oil content, an altered protein content, and/or an altered fiber content) in any part of the transgenic plant, for example the seeds, relative to a similar non-transgenic plant. As used herein, the term "altered" refers to either an increase or a decrease of a plant trait or phenotype (for example, oil content, protein content, and/or fiber content) in a transgenic plant, relative to a similar non-transgenic plant. In one specific, non-limiting example, a transgenic plant with a modified trait includes a plant with an increased oil content, increased protein content, and/or decreased fiber content relative to a similar non-transgenic plant. In another specific, non-limiting example, a transgenic plant with a modified trait includes unchanged oil content, increased protein content, and/or decreased fiber content relative to a similar non-transgenic plant. In yet another specific, non-limiting example, a transgenic plant with a modified trait includes an increased oil content, increased protein content, and/or unchanged fiber content relative to a similar non-transgenic plant. Specific, non-limiting examples of a change in phenotype include an IMQ phenotype or an IOQ phenotype.

An "interesting phenotype (trait)" with reference to a transgenic plant refers to an observable or measurable phenotype demonstrated by a T1 and/or subsequent generation plant, which is not displayed by the corresponding non-transgenic plant (i.e., a genotypically similar plant that has been raised or assayed under similar conditions). An interesting phenotype may represent an improvement in the plant (for example, increased oil content, increased protein content, and/or decreased fiber content in seeds of the plant) or may provide a means to produce improvements in other plants. An "improvement" is a feature that may enhance the utility of a plant species or variety by providing the plant with a unique and/or novel phenotype or quality. Such transgenic plants may have an improved phenotype, such as an IMQ phenotype or an IOQ phenotype.

The phrase "altered oil content phenotype" refers to a measurable phenotype of a genetically modified (transgenic) plant, where the plant displays a statistically significant increase or decrease in overall oil content (i.e., the percentage of seed mass that is oil), as compared to the similar, but non-modified (non-transgenic) plant. A high oil phenotype refers to an increase in overall oil content. The phrase "altered protein content phenotype" refers to measurable phenotype of a genetically modified plant, where the plant displays a statistically significant increase or decrease in overall protein content (i.e., the percentage of seed mass that is protein), as compared to the similar, but non-modified plant. A high protein phenotype refers to an increase in overall protein content. The phrase "altered fiber content phenotype" refers to measurable phenotype of a genetically modified plant, where the plant displays a statistically significant increase or decrease in overall fiber content (i.e., the percentage of seed mass that is fiber), as compared to the similar, but non-modified plant. A low fiber phenotype refers to decrease in overall fiber content.

As used herein, a "mutant" polynucleotide sequence or gene differs from the corresponding wild-type polynucleotide sequence or gene either in terms of sequence or expression, where the difference contributes to a modified or altered plant phenotype or trait. Relative to a plant or plant line, the term "mutant" refers to a plant or plant line which has a modified or altered plant phenotype or trait, where the modified or altered phenotype or trait is associated with the modified or altered expression of a wild-type polynucleotide sequence or gene.

As used herein, the term "T1" refers to the generation of plants from the seed of T0 plants. The T1 generation is the first set of transformed plants that can be selected by application of a selection agent, e.g., an antibiotic or herbicide, for which the transgenic plant contains the corresponding resistance gene. The term "T2" refers to the generation of plants by self-fertilization of the flowers of T1 plants, previously selected as being transgenic. T3 plants are generated from T2 plants, etc. As used herein, the "direct progeny" of a given plant derives from the seed (or, sometimes, other tissue) of that plant and is in the immediately subsequent generation; for instance, for a given lineage, a T2 plant is the direct progeny of a T1 plant. The "indirect progeny" of a given plant derives from the seed (or other tissue) of the direct progeny of that plant, or from the seed (or other tissue) of subsequent generations in that lineage; for instance, a T3 plant is the indirect progeny of a T1 plant.

As used herein, the term "plant part" includes any plant organ or tissue, including, without limitation, seeds, embryos, meristematic regions, callus tissue, leaves, roots, shoots, gametophytes, sporophytes, pollen, and microspores. Plant cells can be obtained from any plant organ or tissue and cultures prepared therefrom. Provided herein is a transgenic plant cell having an IMQ phenotype and/or an IOQ phenotype. The transgenic plant cell comprises a transformation vector comprising an IMQ nucleotide sequence that encodes or is complementary to a sequence that encodes an IMQ polypeptide. In preferred embodiments, the transgenic plant cell is selected from the group consisting of plants of the *Brassica* species, including canola and rapeseed, soy, corn, sunflower, cotton, cocoa, safflower, oil palm, coconut palm, flax, castor, peanut, wheat, oat and rice. In other embodiments, the plant cell is a seed, pollen, propagule, or embryo cell. The disclosure also provides plant cells from a plant that is the direct progeny or the indirect progeny of a plant grown from said progenitor cells. The class of plants which can be used in the methods of the present invention is generally as broad as the class of higher plants amenable to transformation techniques, including both monocotyledonous and dicotyledonous plants.

As used herein, "transgenic plant" includes a plant that comprises within its genome a heterologous polynucleotide. The heterologous polynucleotide can be either stably integrated into the genome, or can be extra-chromosomal. Preferably, the polynucleotide of the present invention is stably integrated into the genome such that the polynucleotide is passed on to successive generations. A plant cell, tissue, organ, or plant into which the heterologous polynucleotides have been introduced is considered "transformed," "transfected," or "transgenic." Direct and indirect progeny of transformed plants or plant cells that also contain the heterologous polynucleotide are also considered transgenic.

Disclosed herein are transgenic plants having an Improved Seed Quality phenotype. Transgenic plants with an Improved Seed Quality phenotype may include an improved oil quantity and/or an improved meal quality. Transgenic plants with improved meal quality have an IMQ phenotype and transgenic plants with improved oil quantity have an IOQ phenotype. The IMQ phenotype in a transgenic plant may include altered protein and/or fiber content in any part of the transgenic plant, for example in the seeds. The IOQ phenotype in a transgenic plant may include altered oil content in any part of the transgenic plant, for example in the seeds. In particular embodiments, a transgenic plant may include an IOQ phenotype and/or an IMQ phenotype. In some embodiments of a transgenic plant, the IMQ phenotype may be an increase in protein content in the seed and/or a decrease in the fiber content of the seed. In other embodiments of a transgenic plant, the IOQ phenotype is an increase in the oil content of the seed (a high oil phenotype). Also provided is seed meal derived from the seeds of transgenic plants, wherein the seeds have altered protein content and/or altered fiber content. Further provided is oil derived from the seeds of transgenic plants, wherein the seeds have altered oil content. Any of these changes can lead to an increase in the AME from the seed or seed meal from transgenic plants, relative to control, non-transgenic, or wild-type plants. Also provided herein is meal, feed, or food produced from any part of the transgenic plant with an IMQ phenotype and/or IOQ phenotype.

In certain embodiments, the disclosed transgenic plants comprise a transformation vector comprising an IMQ nucleotide sequence that encodes or is complementary to a sequence that encodes an "IMQ" polypeptide. In particular embodiments, expression of an IMQ polypeptide in a transgenic plant causes an altered oil content, an altered protein content, and/or an altered fiber content in the transgenic plant. In preferred embodiments, the transgenic plant is selected from the group consisting of plants of the *Brassica* species, including canola and rapeseed, soy, corn, sunflower, cotton, cocoa, safflower, oil palm, coconut palm, flax, castor, peanut, wheat, oat and rice. Also provided is a method of producing oil or seed meal, comprising growing the transgenic plant and recovering oil and/or seed meal from said plant. The disclosure further provides feed, meal, grain, or seed comprising a nucleic acid sequence that encodes an IMQ polypeptide. The disclosure also provides feed, meal, grain, or seed comprising the IMQ polypeptide, or an ortholog thereof.

Various methods for the introduction of a desired polynucleotide sequence encoding the desired protein into plant cells are available and known to those of skill in the art and include, but are not limited to: (1) physical methods such as microinjection, electroporation, and microprojectile mediated delivery (biolistics or gene gun technology); (2) virus mediated delivery methods; and (3) *Agrobacterium*-mediated transformation methods (see, for example, WO 2007/053482 and WO 2005/107437, which are incorporated herein by reference in their entirety).

The most commonly used methods for transformation of plant cells are the *Agrobacterium*-mediated DNA transfer process and the biolistics or microprojectile bombardment mediated process (i.e., the gene gun). Typically, nuclear transformation is desired but where it is desirable to specifically transform plastids, such as chloroplasts or amyloplasts, plant plastids may be transformed utilizing a microprojectile-mediated delivery of the desired polynucleotide.

*Agrobacterium*-mediated transformation is achieved through the use of a genetically engineered soil bacterium belonging to the genus *Agrobacterium*. A number of wild-type and disarmed strains of *Agrobacterium tumefaciens* and *Agrobacterium rhizogenes* harboring Ti or Ri plasmids can be used for gene transfer into plants. Gene transfer is done via the transfer of a specific DNA known as "T-DNA" that can be genetically engineered to carry any desired piece of DNA into many plant species.

*Agrobacterium*-mediated genetic transformation of plants involves several steps. The first step, in which the virulent *Agrobacterium* and plant cells are first brought into contact with each other, is generally called "inoculation." Following the inoculation, the *Agrobacterium* and plant cells/tissues are permitted to be grown together for a period of several hours to several days or more under conditions suitable for growth and T-DNA transfer. This step is termed "co-culture." Following co-culture and T-DNA delivery, the plant cells are treated with bactericidal or bacteriostatic agents to kill the *Agrobacterium* remaining in contact with the explant and/or in the vessel containing the explant. If this is done in the absence of any selective agents to promote preferential growth of transgenic versus non-transgenic plant cells, then this is typically referred to as the "delay" step. If done in the presence of selective pressure favoring transgenic plant cells, then it is referred to as a "selection" step. When a "delay" is used, it is typically followed by one or more "selection" steps.

With respect to microprojectile bombardment (U.S. Pat. Nos. 5,550,318; 5,538,880, 5,610,042; and PCT Publication WO 95/06128; each of which is specifically incorporated herein by reference in its entirety), particles are coated with nucleic acids and delivered into cells by a propelling force. Exemplary particles include those comprised of tungsten, platinum, and preferably, gold.

An illustrative embodiment of a method for delivering DNA into plant cells by acceleration is the Biolistics Particle Delivery System (BioRad, Hercules, Calif.), which can be used to propel particles coated with DNA or cells through a screen, such as a stainless steel or Nytex screen, onto a filter surface covered with monocot plant cells cultured in suspension.

Microprojectile bombardment techniques are widely applicable, and may be used to transform virtually any plant species. Examples of species that have been transformed by microprojectile bombardment include monocot species such as maize (PCT Publication No. WO 95/06128), barley, wheat (U.S. Pat. No. 5,563,055, incorporated herein by reference in its entirety), rice, oat, rye, sugarcane, and sorghum, as well as a number of dicots including tobacco, soybean (U.S. Pat. No. 5,322,783, incorporated herein by reference in its entirety), sunflower, peanut, cotton, tomato, and legumes in general (U.S. Pat. No. 5,563,055, incorporated herein by reference in its entirety).

To select or score for transformed plant cells regardless of transformation methodology, the DNA introduced into the cell contains a gene that functions in a regenerable plant tissue to produce a compound that confers upon the plant tissue resistance to an otherwise toxic compound. Genes of interest for use as a selectable, screenable, or scorable marker would include but are not limited to GUS, green fluorescent protein (GFP), luciferase (LUX), antibiotic or herbicide tolerance genes. Examples of antibiotic resistance genes include the penicillins, kanamycin (and neomycin, G418, bleomycin), methotrexate (and trimethoprim), chloramphenicol, and tetracycline. Polynucleotide molecules encoding proteins involved in herbicide tolerance are known in the art, and include, but are not limited to a polynucleotide molecule encoding 5-enolpyruvylshikimate-3-phosphate synthase (EPSPS) described in U.S. Pat. Nos. 5,627,061, 5,633,435, 6,040,497 and aroA described in U.S. Pat. No. 5,094,945 for glyphosate tolerance; a polynucleotide molecule encoding bromoxynil nitrilase (Bxn) described in U.S. Pat. No. 4,810,648 for Bromoxynil tolerance; a polynucleotide molecule encoding phytoene desaturase (crtI) described in Misawa et al., (*Plant J.* 4:833-840, 1993) and Misawa et al., (*Plant J.* 6:481-489, 1994) for norflurazon tolerance; a polynucleotide molecule encoding acetohydroxyacid synthase (AHAS, also known as ALS) described in Sathasiivan et al. (*Nucl. Acids Res.* 18:2188-2193, 1990) for tolerance to sulfonylurea herbicides; and the bar gene described in DeBlock, et al., (*EMBO J.* 6:2513-2519, 1987) for glufosinate and bialaphos tolerance.

The regeneration, development, and cultivation of plants from various transformed explants are well documented in the art. This regeneration and growth process typically includes the steps of selecting transformed cells and culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Cells that survive the exposure to the selective agent, or cells that have been scored positive in a screening assay, may be cultured in media that supports regeneration of plants. Developing plantlets are transferred to soil less plant growth mix, and hardened off, prior to transfer to a greenhouse or growth chamber for maturation.

The present invention can be used with any transformable cell or tissue. By transformable as used herein is meant a cell or tissue that is capable of further propagation to give rise to a plant. Those of skill in the art recognize that a number of plant cells or tissues are transformable in which after insertion of exogenous DNA and appropriate culture conditions the plant cells or tissues can form into a differentiated plant. Tissue suitable for these purposes can include but is not limited to immature embryos, scutellar tissue, suspension cell cultures, immature inflorescence, shoot meristem, nodal explants, callus tissue, hypocotyl tissue, cotyledons, roots, and leaves.

Any suitable plant culture medium can be used. Examples of suitable media would include but are not limited to MS-based media (Murashige and Skoog, Physiol. Plant, 15:473-497, 1962) or N6-based media (Chu et al., Scientia Sinica 18:659, 1975) supplemented with additional plant growth regulators including but not limited to auxins, cytokinins, ABA, and gibberellins. Those of skill in the art are familiar with the variety of tissue culture media, which when supplemented appropriately, support plant tissue growth and development and are suitable for plant transformation and regeneration. These tissue culture media can either be purchased as a commercial preparation, or custom prepared and modified. Those of skill in the art are aware that media and media supplements such as nutrients and growth regulators for use in transformation and regeneration and other culture conditions such as light intensity during incubation, pH, and incubation temperatures that can be optimized for the particular variety of interest.

One of ordinary skill will appreciate that, after an expression cassette is stably incorporated in transgenic plants and confirmed to be operable, it can be introduced into other plants by sexual crossing. Any of a number of standard breeding techniques can be used, depending upon the species to be crossed.

Identification of Plants with an Improved Oil Quantity Phenotype and/or Improved Meal Quality Phenotype An *Arabidopsis* activation tagging screen (ACTTAG) was used to identify the association between 1) ACTTAG plant lines with an altered protein, fiber and/or oil content (phenotype, for example, see columns 4, 5 and 6, respectively, of Table 1, below) and 2) the nucleic acid sequences identified in column 3 of Tables 2 and 3, wherein each nucleic acid sequence is provided with a gene alias or an IMQ designation (IMQ#; see column 1 in Tables 1, 2, and 3). Briefly, and as further described in the Examples, a large number of *Arabidopsis* plants were mutated with the pSK1015 vector, which comprises a T-DNA from the Ti plasmid of *Agrobacterium tumifaciens*, a viral enhancer element, and a selectable marker gene (Weigel et al., 2000, *Plant Physiology,* 122: 1003-1013). When the T-DNA inserts into the genome of transformed plants, the enhancer element can cause up-regulation of genes in the vicinity, generally within about nine kilobases (kb) of the enhancers. T1 plants were exposed to the selective agent in order to specifically recover transformed plants that expressed the selectable marker and therefore harbored T-DNA insertions. T1 plants were allowed to grow to maturity, self-fertilize and produce seed. T2 seed was harvested, labeled and stored. To amplify the seed stocks, about eighteen T2 were sown in soil and, after germination, exposed to the selective agent to recover transformed T2 plants. T3 seed from these plants was harvested and pooled. Oil, protein and fiber content of the seed were estimated using Near Infrared Spectroscopy (NIR) as described in the Examples.

Quantitative determination of fatty acid (FA) content (column 7, Table 1) in T2 seeds was performed using the following methods. A sample of 15 to 20 T2 seeds from each line tested. This sample generally contained plants with homozygous insertions, no insertions, and hemizygous insertions in a standard 1:1:2 ratios. The seed sample was massed on UMT-2 ultra-microbalance (Mettler-Toledo Co., Ohio, USA) and then transferred to a glass extraction vial. Lipids were extracted from the seeds and trans-esterified in 500 ul 2.5% $H_2SO_4$ in MeOH for 3 hours at 80° C., following the method of Browse et al. (*Biochem J* 235:25-31, 1986) with modifications. A known amount of heptadecanoic acid was included in the reaction as an internal standard. 750 ul of water and 400 ul of hexane were added to each vial, which was then shaken vigorously and allowed to phase separate. Reaction vials were loaded directly onto gas chromatography (GC) for analysis and the upper hexane phase was sampled by the autosampler. Gas chromatography with Flame Ionization detection was used to separate and quantify the fatty acid methyl esters. Agilent 6890 Plus GC's were used for separation with Agilent Innowax columns (30 m×0.25 mm ID, 250 um film thickness). The carrier gas was Hydrogen at a constant flow of 2.5 ml/minute. 1 ul of sample was injected in splitless mode (inlet temperature 220° C., Purge flow 15 ml/min at 1 minute). The oven was programmed for an initial temperature of 105° C., initial time 0.5 minutes, followed by a ramp of 60° C. per minute to 175° C., a 40° C./minute ramp to 260° C. with a final hold time of 2 minutes. Detection was by Flame Ionization (Temperature 275° C., Fuel flow 30.0 ml/min, Oxidizer 400.0 ml/min). Instrument control and data collection and analysis were monitored using the Millennium Chromatography Management System (Version 3.2, Waters Corporation, Milford, Mass.). Peaks were initially identified by comparison with standards. Integration and quantification were performed automatically, but all analyses were subsequently examined manually to verify correct peak identification and acceptable signal to noise ratio before inclusion of the derived results in the study.

The association of an IMQ nucleic acid sequence with an IMQ phenotype or an IOQ phenotype was discovered by analysis of the genomic DNA sequence flanking the T-DNA insertion in the ACTTAG line identified in column 3 of Table 1. An ACTTAG line is a family of plants derived from a single plant that was transformed with a T-DNA element containing four tandem copies of the CaMV 35S enhancers. Accordingly, the disclosed IMQ nucleic acid sequences and/or polypeptides may be employed in the development of transgenic plants having an improved seed quality phenotype, including an IMQ phenotype and/or an IOQ phenotype. IMQ nucleic acid sequences may be used in the generation of transgenic plants, such as oilseed crops, that provide improved oil yield from oilseed processing and result in an increase in the quantity of oil recovered from seeds of the transgenic plant. IMQ nucleic acid sequences may also be used in the generation of transgenic plants, such as feed grain crops, that provide an IMQ phenotype resulting in increased energy for animal feeding, for example, seeds or seed meal with an altered protein and/or fiber content, resulting in an increase in AME. IMQ nucleic acid sequences may further be used to increase the oil content of specialty oil crops, in order to augment yield and/or recovery of desired unusual fatty acids. Transgenic plants that have been genetically modified to express IMQ polypeptides can be used in the production of seeds, wherein the transgenic plants are grown, and oil and seed meal are obtained from plant parts (e.g. seed) using standard methods.

IMQ Nucleic Acids and Polypeptides

The IMQ designation for each of the IMQ nucleic acid sequences discovered in the activation tagging screen described herein are listed in column 1 of Tables 1-3, below. The disclosed IMQ polypeptides are listed in column 5 of Table 2 and column 4 of Table 3. As used herein, the term "IMQ polypeptide" refers to any polypeptide that when expressed in a plant causes an IMQ phenotype and/or an IOQ phenotype in any part of the plant, for example the seeds. In one embodiment, an IMQ polypeptide refers to a full-length IMQ protein, or a fragment, derivative (variant), or ortholog thereof that is "functionally active," such that the protein fragment, derivative, or ortholog exhibits one or more or the functional activities associated with one or more of the disclosed full-length IMQ polypeptides, for example, the amino acid sequences provided in the GenBank entry referenced in column 5 of Table 2, which correspond to the amino acid sequences set forth as SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, or SEQ ID NO: 100, or an ortholog thereof. In one preferred embodiment, a functionally active IMQ polypeptide causes an IMQ phenotype and/or an IOQ phenotype in a transgenic plant. In another embodiment, a functionally active IMQ polypeptide causes an altered oil, protein, and/or fiber content phenotype (for example, an altered seed meal content phenotype) when mis-expressed in a plant. In other preferred embodiments, mis-expression of the IMQ polypeptide causes a high oil (such as, increased oil), high protein (such as, increased protein), and/or low fiber (such as, decreased fiber) phenotype in a plant. In another embodiment, mis-expression of the IMQ polypeptide causes an improved AME of meal. In yet another embodiment, a functionally active IMQ polypeptide can rescue defective (including deficient) endogenous IMQ activity when expressed in a plant or in plant cells; the rescuing polypeptide may be from the same or from a different species as the species with the defective polypeptide activity. The disclosure also provides feed, meal, grain, food, or seed comprising the IMQ polypeptide, or a fragment, derivative (variant), or ortholog thereof.

In another embodiment, a functionally active fragment of a full length IMQ polypeptide (for example, a functionally active fragment of a native polypeptide having the amino acid sequence set forth as SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, or SEQ ID NO: 100, or a naturally occurring ortholog thereof) retains one or more of the biological properties associated with the full-length IMQ polypeptide, such as signaling activity, binding activity, catalytic activity, or cellular or extra-cellular localizing activity. An IMQ fragment preferably comprises an IMQ domain, such as a C- or N-terminal or catalytic domain, among others, and preferably comprises at least 10, preferably at least 20, more preferably at least 25, and most preferably at least 50 contiguous amino acids of an IMQ protein. Functional domains of IMQ genes are listed in column 8 of Table 2 and can be identified using the PFAM program (Bateman A et al., 1999, *Nucleic Acids Res.* 27:260-262) or INTERPRO (Mulder et al., 2003, *Nucleic Acids Res.* 31, 315-318) program. Functionally active variants of full-length IMQ polypeptides, or fragments thereof, include polypeptides with amino acid insertions, deletions, or substitutions that retain one of more of the biological properties associated with the full-length IMQ polypeptide. In some cases, variants are generated that change the post-translational processing of an IMQ polypeptide. For instance, variants may have altered protein transport or protein localization characteristics, or altered protein half-life, compared to the native polypeptide.

As used herein, the term "IMQ nucleic acid" refers to any polynucleotide that when expressed in a plant causes an IMQ phenotype and/or an IOQ phenotype in any part of the plant, for example the seeds. In one embodiment, an IMQ polynucleotide encompasses nucleic acids with the sequence provided in or complementary to the GenBank entry referenced in column 3 of Table 2, which correspond to nucleic acid sequences set forth as SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73 SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, or SEQ ID NO: 99, as well as functionally active fragments, derivatives, or orthologs thereof. An IMQ nucleic acid of this disclosure may be DNA, derived from genomic DNA or cDNA, or RNA. Genomic sequences of the genes listed in Table 2 are known and available in public databases such as GenBank.

In one embodiment, a functionally active IMQ nucleic acid encodes or is complementary to a nucleic acid that encodes a functionally active IMQ polypeptide. A functionally active IMQ nucleic acid also includes genomic DNA that serves as a template for a primary RNA transcript (i.e., an mRNA precursor) that requires processing, such as splicing, before encoding the functionally active IMQ polypeptide. An IMQ nucleic acid can include other non-coding sequences, which may or may not be transcribed; such sequences include 5' and 3' UTRs, polyadenylation signals and regulatory sequences that control gene expression, among others, as are known in the art. Some polypeptides require processing events, such as proteolytic cleavage, covalent modification, etc., in order to become fully active. Accordingly, functionally active nucleic acids may encode the mature or the pre-processed IMQ polypeptide, or an intermediate form. An IMQ polynucleotide can also include heterologous coding sequences, for example, sequences that encode a marker included to facilitate the purification of the fused polypeptide, or a transformation marker. In another embodiment, a functionally active IMQ nucleic acid is capable of being used in the generation of loss-of-function IMQ phenotypes, for instance, via antisense suppression, co-suppression, etc. The disclosure also provides feed, meal, grain, food, or seed comprising a nucleic acid sequence that encodes an IMQ polypeptide.

In one preferred embodiment, an IMQ nucleic acid used in the disclosed methods comprises a nucleic acid sequence that encodes, or is complementary to a sequence that encodes, an IMQ polypeptide having at least 50%, 60%, 70%, 75%, 80%, 85%, 90%, 95%, 97%, 98%, or 99% sequence identity to a disclosed IMQ polypeptide sequence, for example the amino acid sequence set forth as SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, or SEQ ID NO: 100.

In another embodiment, an IMQ polypeptide comprises a polypeptide sequence with at least 50% or 60% identity to a disclosed IMQ polypeptide sequence (for example, the amino acid sequence set forth as SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, or SEQ ID NO: 100) and may have at least 70%, 80%, 85%, 90%, 95%, 97%, 98%, or 99% sequence identity to a disclosed IMQ polypeptide sequence. In a further embodiment, an IMQ polypeptide comprises 50%, 60%, 70%, 80%, 85%, 90%, 95%, 97%, 98%, or 99% sequence identity to a disclosed IMQ polypeptide sequence, and may include a conserved protein domain of the IMQ polypeptide (such as the protein domain(s) listed in column 8 of Table 2). In another embodiment, an IMQ polypeptide comprises a polypeptide sequence with at least 50%, 60%, 70%, 80%, 85%, 90%, 95%, 97%, 98%, or 99% sequence identity to a functionally active fragment of the polypeptide referenced in column 5 of Table 2. In yet another embodiment, an IMQ polypeptide comprises a polypeptide sequence with at least 50%, 60%, 70%, 80%, 90%, 95%, 97%, 98%, or 99% identity to the polypeptide sequence of the GenBank entry referenced in column 5 of Table 2 over its entire length and comprises a conserved protein domain(s) listed in column 8 of Table 2.

In another aspect, an IMQ polynucleotide sequence is at least 50% to 60% identical over its entire length to a disclosed IMQ nucleic acid sequence, such as the nucleic acid sequence set forth as SEQ ID NO: 1, SEQ ID NO: 3, SEQ ID NO: 5, SEQ ID NO: 7, SEQ ID NO: 9, SEQ ID NO:11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73 SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO:89, SEQ ID NO:91, SEQ ID NO:93, SEQ ID NO:95, SEQ ID NO:97, or SEQ ID NO: 99, or nucleic acid sequences that are complementary to such an IMQ sequence, and may comprise at least 70%, 80%, 85%, 90%, 95%, 97%, 98%, or 99% sequence identity to the disclosed IMQ sequence, or a functionally active fragment thereof, or complementary sequences. In another embodiment, a disclosed IMQ nucleic acid comprises a nucleic acid sequence as shown in SEQ ID NO: 1, SEQ ID NO: 3, SEQ ID NO: 5, SEQ ID NO: 7, SEQ ID NO: 9, SEQ ID NO: 1, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73 SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, or SEQ ID NO: 99, or nucleic acid sequences that are complementary to such an IMQ sequence, and nucleic acid sequences that have substantial sequence homology to a such IMQ sequences. As used herein, the phrase "substantial sequence homology" refers to those nucleic acid sequences that have slight or inconsequential sequence variations from such IMQ sequences, i.e., the sequences function in substantially the same manner and encode an IMQ polypeptide.

As used herein, "percent (%) sequence identity" with respect to a specified subject sequence, or a specified portion thereof, is defined as the percentage of nucleotides or amino acids in an identified sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., *J. Mol. Biol.,* 1990, 215:403-410) with search parameters set to default values. The HSP S and HSP S2 parameters are dynamic values and are established by the program itself depending upon the composition of the particular sequence and composition of the particular database against which the sequence of interest is being searched. A "percent (%) identity value" is determined by the number of matching identical nucleotides or amino acids divided by the sequence length for which the percent identity is being reported. "Percent (%) amino acid sequence similarity" is determined by performing the same calculation as for determining % amino acid sequence identity, but including conservative amino acid substitutions in addition to identical amino acids in the computation. A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, serine, threonine, cysteine and glycine.

Derivative nucleic acid molecules of the subject nucleic acid molecules include sequences that selectively hybridize to the disclosed IMQ nucleic acid sequences (for example, the nucleic acid sequence set forth as SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73 SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, or SEQ ID NO: 99). The stringency of hybridization can be controlled by temperature, ionic strength, pH, and the presence of denaturing agents such as formamide during hybridization and washing. Conditions routinely used are well known (see, e.g., *Current Protocol in Molecular Biology*, Vol. 1, Chap. 2.10, John Wiley & Sons, Publishers (1994); Sambrook et al., 1989, Molecular Cloning: A Laboratory Manual (Second Edition), Cold Spring Harbor Press, Plainview, N.Y.).

In some embodiments, a nucleic acid molecule of the disclosure is capable of hybridizing to a nucleic acid molecule containing the disclosed nucleotide sequence under stringent hybridization conditions that are: prehybridization of filters containing nucleic acid for 8 hours to overnight at 65° C. in a solution comprising 6× single strength citrate (SSC) (1×SSC is 0.15 M NaCl, 0.015 M Na citrate; pH 7.0), 5×Denhardt's solution, 0.05% sodium pyrophosphate and 100 μg/ml herring sperm DNA; hybridization for 18-20 hours at 65° C. in a solution containing 6×SSC, 1×Denhardt's solution, 100 μg/ml yeast tRNA and 0.05% sodium pyrophosphate; and washing of filters at 65° C. for 1 h in a solution containing 0.1×SSC and 0.1% SDS (sodium dodecyl sulfate). In other embodiments, moderately stringent hybridization conditions are used that are: pretreatment of filters containing nucleic acid for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 μg/ml denatured salmon sperm DNA; hybridization for 18-20 h at 40° C. in a solution containing 35% formamide, 5×SSC, 50 mM Tris-HCl (pH 7.5), 5 mM EDTA, 0.02% PVP, 0.02% Ficoll, 0.2% BSA, 100 μg/ml salmon sperm DNA, and 10% (wt/vol) dextran sulfate; followed by washing twice for 1 hour at 55° C. in a solution containing 2×SSC and 0.1% SDS. Alternatively, low stringency conditions can be used that comprise: incubation for 8 hours to overnight at 37° C. in a solution comprising 20% formamide, 5×SSC, 50 mM sodium phosphate (pH 7.6), 5×Denhardt's solution, 10% dextran sulfate, and 20 μg/ml denatured sheared salmon sperm DNA; hybridization in the same buffer for 18 to 20 hours; and washing of filters in 1×SSC at about 37° C. for 1 hour.

As a result of the degeneracy of the genetic code, a number of polynucleotide sequences encoding an IMQ polypeptide can be produced. For example, codons may be selected to increase the rate at which expression of the polypeptide occurs in a particular host species, in accordance with the optimum codon usage dictated by the particular host organism (see, e.g., Nakamura et al., 1999, *Nucleic Acids Res.* 27:292). Such sequence variants may be used in the methods disclosed herein.

The disclosed methods may use orthologs of a disclosed *Arabidopsis* IMQ nucleic acid sequence. Representative putative orthologs of each of the disclosed *Arabidopsis* IMQ genes are identified in column 3 of Table 3, below. Methods of identifying the orthologs in other plant species are known in the art. In general, orthologs in different species retain the same function, due to presence of one or more protein motifs and/or 3-dimensional structures. In evolution, when a gene duplication event follows speciation, a single gene in one species, such as *Arabidopsis*, may correspond to multiple genes (paralogs) in another. As used herein, the term "orthologs" encompasses paralogs. When sequence data is available for a particular plant species, orthologs are generally identified by sequence homology analysis, such as BLAST analysis, usually using protein bait sequences. Sequences are assigned as a potential ortholog if the best hit sequence from the forward BLAST result retrieves the original query sequence in the reverse BLAST (Huynen M A and Bork P, 1998, *Proc. Natl. Acad. Sci.,* 95:5849-5856; Huynen M A et al., 2000, *Genome Research,* 10: 1204-1210).

Programs for multiple sequence alignment, such as CLUSTAL (Thompson J D et al., 1994, *Nucleic Acids Res.* 22:4673-4680) may be used to highlight conserved regions and/or residues of orthologous proteins and to generate phylogenetic trees. In a phylogenetic tree representing multiple homologous sequences from diverse species (e.g., retrieved through BLAST analysis), orthologous sequences from two species generally appear closest on the tree with respect to all other sequences from these two species. Structural threading or other analysis of protein folding (e.g., using software by ProCeryon, Biosciences, Salzburg, Austria) may also identify potential orthologs. Nucleic acid hybridization methods may also be used to find orthologous genes and are preferred when sequence data are not available. Degenerate PCR and screening of cDNA or genomic DNA libraries are common methods for finding related gene sequences and are well known in the art (see, e.g., Sambrook, 1989, *Molecular Cloning: A Laboratory Manual* (Second Edition), Cold Spring Harbor Press, Plainview, N.Y.; Dieffenbach and Dveksler, 1995, *PCR*

*Primer: A Laboratory Manual*, Cold Spring Harbor Laboratory Press, NY). For instance, methods for generating a cDNA library from the plant species of interest and probing the library with partially homologous gene probes are described in Sambrook et al. A highly conserved portion of the *Arabidopsis* IMQ coding sequence may be used as a probe. IMQ ortholog nucleic acids may hybridize to the nucleic acid of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73 SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, or SEQ ID NO: 99 under high, moderate, or low stringency conditions. After amplification or isolation of a segment of a putative ortholog, that segment may be cloned and sequenced by standard techniques and utilized as a probe to isolate a complete cDNA or genomic DNA clone.

Alternatively, it is possible to initiate an EST project to generate a database of sequence information for the plant species of interest. In another approach, antibodies that specifically bind known IMQ polypeptides are used for ortholog isolation (see, e.g., Harlow and Lane, 1988, 1999, *Antibodies: A Laboratory Manual*, Cold Spring Harbor Laboratory Press, New York). Western blot analysis can determine that an IMQ ortholog (i.e., a protein orthologous to a disclosed IMQ polypeptide) is present in a crude extract of a particular plant species. When reactivity is observed, the sequence encoding the candidate ortholog may be isolated by screening expression libraries representing the particular plant species. Expression libraries can be constructed in a variety of commercially available vectors, including lambda gt11, as described in Sambrook, et al., 1989. Once the candidate ortholog(s) are identified by any of these means, candidate orthologous sequence are used as bait (the "query") for the reverse BLAST against sequences from *Arabidopsis* or other species in which IMQ nucleic acid and/or polypeptide sequences have been identified.

IMQ nucleic acids and polypeptides may be obtained using any available method. For instance, techniques for isolating cDNA or genomic DNA sequences of interest by screening DNA libraries or by using polymerase chain reaction (PCR), as previously described, are well known in the art. Alternatively, nucleic acid sequence may be synthesized. Any known method, such as site directed mutagenesis (Kunkel T A et al., 1991, *Methods Enzymol.* 204:125-39), may be used to introduce desired changes into a cloned nucleic acid.

In general, the methods disclosed herein involve incorporating the desired form of the IMQ nucleic acid into a plant expression vector for transformation of plant cells, and the IMQ polypeptide is expressed in the host plant. Transformed plants and plant cells expressing an IMQ polypeptide express an IMQ phenotype and/or an IOQ phenotype and, in one specific, non-limiting example, may have high (increased) oil, high (increased) protein, and/or low (decreased) fiber content.

An "isolated" IMQ nucleic acid molecule is other than in the form or setting in which it is found in nature, and is identified and separated from least one contaminant nucleic acid molecule with which it is ordinarily associated in the natural source of the IMQ nucleic acid. However, an isolated IMQ nucleic acid molecule includes IMQ nucleic acid molecules contained in cells that ordinarily express IMQ where, for example, the nucleic acid molecule is in a chromosomal location different from that of natural cells.

Generation of Genetically Modified Plants with an Improved Oil Quantity Phenotype and/or an Improved Meal Quality Phenotype The disclosed IMQ nucleic acids and polypeptides may be used in the generation of transgenic plants having a modified or altered oil, protein, and/or fiber content phenotype. As used herein, an "altered oil content (phenotype)" may refer to altered oil content in any part of the plant. In a preferred embodiment, altered expression of the IMQ gene in a plant is used to generate plants with a high oil content (phenotype). As used herein, an "altered protein content (phenotype)" may refer to altered protein content in any part of the plant. In a preferred embodiment, altered expression of the IMQ gene in a plant is used to generate plants with a high (or increased) protein content (phenotype). As used herein, an "altered fiber content (phenotype)" may refer to altered fiber content in any part of the plant. In a preferred embodiment, altered expression of the IMQ gene in a plant is used to generate plants with a low (or decreased) fiber content (phenotype). The altered oil, protein, and/or fiber content is often observed in seeds. Examples of a transgenic plant include plants comprising a plant transformation vector with a nucleotide sequence that encodes or is complementary to a sequence that encodes an IMQ polypeptide having the amino acid sequence as set forth in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, or SEQ ID NO: 100, or an ortholog thereof.

Transgenic plants, such as corn, soybean and canola containing the disclosed nucleic acid sequences, can be used in the production of vegetable oil and meal. Vegetable oil is used in a variety of food products, while meal from seed is used as an animal feed. After harvesting seed from transgenic plants, the seed is cleaned to remove plant stalks and other material and then flaked in roller mills to break the hulls. The crushed seed is heated to 75-100° C. to denature hydrolytic enzymes, lyse the unbroken oil containing cells, and allow small oil droplets to coalesce. Most of the oil is then removed (and can be recovered) by pressing the seed material in a screw press. The remaining oil is removed from the presscake by extraction with and organic solvents, such as hexane. The solvent is removed from the meal by heating it to approximately 100° C. After drying, the meal is then granulated to a consistent form. The meal, containing the protein, digestible carbohydrate, and fiber of the seed, may be mixed with other materials prior to being used as an animal feed.

The methods described herein for generating transgenic plants are generally applicable to all plants. Although activation tagging and gene identification is carried out in *Arabidopsis*, the IMQ nucleic acid sequence (or an ortholog, variant or fragment thereof) may be expressed in any type of plant. In a preferred embodiment, oil-producing plants produce and store triacylglycerol in specific organs, primarily in seeds. Such species include soybean (*Glycine max*), rapeseed and canola (including *Brassica napus, B. campestris*), sunflower (*Helianthus annus*), cotton (*Gossypium hirsutum*), corn (*Zea mays*), cocoa (*Theobroma cacao*), safflower (*Carthamus tinctorius*), oil palm (*Elaeis guineensis*), coconut palm (*Cocos nucifera*), flax (*Linum usitatissimum*), castor (*Ricinus communis*), and peanut (*Arachis hypogaea*), as well as wheat, rice and oat. Fruit- and vegetable-bearing plants, grain-producing plants, nut-producing plants, rapid cycling *Brassica* species, alfalfa (*Medicago sativa*), tobacco (Nicotiana), turfgrass (Poaceae family), other forage crops, and wild species may also be a source of unique fatty acids. In other embodiments, any plant expressing the IMQ nucleic acid sequence can also express increased protein and/or decreased fiber content in a specific plant part or organ, such as in seeds.

The skilled artisan will recognize that a wide variety of transformation techniques exist in the art, and new techniques are continually becoming available. Any technique that is suitable for the target host plant can be employed within the scope of the present invention. For example, the constructs can be introduced in a variety of forms including, but not limited to, as a strand of DNA, in a plasmid, or in an artificial chromosome. The introduction of the constructs into the target plant cells can be accomplished by a variety of techniques, including, but not limited to, *Agrobacterium*-mediated transformation, electroporation, microinjection, microprojectile bombardment, calcium-phosphate-DNA co-precipitation, or liposome-mediated transformation of a heterologous nucleic acid. The transformation of the plant is preferably permanent, i.e. by integration of the introduced expression constructs into the host plant genome, so that the introduced constructs are passed onto successive plant generations. Depending upon the intended use, a heterologous nucleic acid construct comprising an IMQ polynucleotide may encode the entire protein or a biologically active portion thereof.

In one embodiment, binary Ti-based vector systems may be used to transfer polynucleotides. Standard *Agrobacterium* binary vectors are known to those of skill in the art, and many are commercially available (e.g., pBI121 Clontech Laboratories, Palo Alto, Calif.). A construct or vector may include a plant promoter to express the nucleic acid molecule of choice. In a preferred embodiment, the promoter is a plant promoter.

The optimal procedure for transformation of plants with *Agrobacterium* vectors will vary with the type of plant being transformed. Exemplary methods for *Agrobacterium*-mediated transformation include transformation of explants of hypocotyl, shoot tip, stem or leaf tissue, derived from sterile seedlings and/or plantlets. Such transformed plants may be reproduced sexually, or by cell or tissue culture. *Agrobacterium* transformation has been previously described for a large number of different types of plants and methods for such transformation may be found in the scientific literature. Of particular relevance are methods to transform commercially important crops, such as plants of the *Brassica* species, including canola and rapeseed, (De Block et al., 1989, *Plant Physiol.,* 91:694-701), sunflower (Everett et al., 1987, *Bio/Technology,* 5:1201), soybean (Christou et al., 1989, *Proc. Natl. Acad. Sci. USA,* 86:7500-7504; Kline et al., 1987, *Nature,* 327:70), wheat, rice and oat.

Expression (including transcription and translation) of an IMQ nucleic acid sequence may be regulated with respect to the level of expression, the tissue type(s) where expression takes place and/or developmental stage of expression. A number of heterologous regulatory sequences (e.g., promoters and enhancers) are available for controlling the expression of an IMQ nucleic acid. These include constitutive, inducible and regulatable promoters, as well as promoters and enhancers that control expression in a tissue- or temporal-specific manner. Exemplary constitutive promoters include the raspberry E4 promoter (U.S. Pat. Nos. 5,783,393 and 5,783,394), the nopaline synthase (NOS) promoter (Ebert et al., *Proc. Natl. Acad. Sci.* (*U.S.A.*) 84:5745-5749, 1987), the octopine synthase (OCS) promoter (which is carried on tumor-inducing plasmids of *Agrobacterium tumefaciens*), the caulimovirus promoters such as the cauliflower mosaic virus (CaMV) 19S promoter (Lawton et al., *Plant Mol. Biol.* 9:315-324, 1987) and the CaMV 35S promoter (Odell et al., *Nature* 313:810-812, 1985 and Jones J D et al, 1992, *Transgenic Res.,* 1:285-297), the figwort mosaic virus 35S-promoter (U.S. Pat. No. 5,378,619), the light-inducible promoter from the small subunit of ribulose-1,5-bis-phosphate carboxylase (ss-RUBISCO), the Adh promoter (Walker et al., *Proc. Natl. Acad. Sci.* (*U.S.A.*) 84:6624-6628, 1987), the sucrose synthase promoter (Yang et al., *Proc. Natl. Acad. Sci.* (*U.S.A.*) 87:4144-4148, 1990), the R gene complex promoter (Chandler et al., *The Plant Cell* 1:1175-1183, 1989), the chlorophyll a/b binding protein gene promoter, the CsVMV promoter (Verdaguer B et al., 1998, *Plant Mol. Biol.,* 37:1055-1067), and the melon actin promoter (published PCT application WO0056863). Exemplary tissue-specific promoters include the tomato E4 and E8 promoters (U.S. Pat. No. 5,859,330) and the tomato 2AII gene promoter (Van Haaren M J J et al., 1993, *Plant Mol Bio.,* 21:625-640).

In one preferred embodiment, expression of the IMQ nucleic acid sequence is under control of regulatory sequences from genes whose expression is associated with early seed and/or embryo development. Indeed, in a preferred embodiment, the promoter used is a seed-enhanced promoter. Examples of such promoters include the 5' regulatory regions from such genes as napin (Kridl et al., *Seed Sci. Res.* 1:209:219, 1991), globulin (Belanger and Kriz, *Genet.,* 129: 863-872, 1991, GenBank Accession No. L22295), gamma zein Z 27 (Lopes et al., *Mol Gen Genet.,* 247:603-613, 1995), L3 oleosin promoter (U.S. Pat. No. 6,433,252), phaseolin (Bustos et al., *Plant Cell,* 1(9):839-853, 1989), arcelin5 (U.S. Application No. 2003/0046727), a soybean 7S promoter, a 7Sα promoter (U.S. Application No. 2003/0093828), the soybean 7Sα' beta conglycinin promoter, a 7S α' promoter (Beachy et al., *EMBO J.,* 4:3047, 1985; Schuler et al., *Nucleic Acid Res.,* 10(24):8225-8244, 1982), soybean trypsin inhibitor (Riggs et al., *Plant Cell* 1(6):609-621, 1989), ACP (Baerson et al., *Plant Mol. Biol.,* 22(2):255-267, 1993), stearoyl-ACP desaturase (Slocombe et al., *Plant Physiol.* 104(4):167-176, 1994), soybean a' subunit of β-conglycinin (Chen et al., *Proc. Natl. Acad. Sci.* 83:8560-8564, 1986), *Vicia faba* USP (P-Vf.Usp, SEQ ID NO: 1, 2, and 3 in (U.S. Application No. 2003/229918) and *Zea mays* L3 oleosin promoter (Hong et al., *Plant Mol. Biol.,* 34(3):549-555, 1997). Also included are the zeins, which are a group of storage proteins found in corn endosperm. Genomic clones for zein genes have been isolated (Pedersen et al., *Cell,* 29:1015-1026, 1982; and Russell et al., *Transgenic Res.* 6(2):157-168) and the promoters from these clones, including the 15 kD, 16 kD, 19 kD, 22 kD, 27 kD and genes, could also be used. Other promoters known to function, for example, in corn include the promoters for the following genes: waxy, *Brittle, Shrunken* 2, Branching enzymes I and II, starch synthases, debranching enzymes, oleosins, glutelins and sucrose synthases. Legume genes whose promoters are associated with early seed and embryo development include *V. faba* legumin (Baumlein et al., 1991, *Mol. Gen. Genet.* 225:121-8; Baumlein et al., 1992, *Plant J.*

2:233-9), *V. faba* usp (Fiedler et al., 1993, *Plant Mol. Biol.* 22:669-79), pea *convicilin* (Bown et al., 1988, *Biochem. J.* 251:717-26), pea *lectin* (depater et al., 1993, *Plant Cell* 5:877-86), *P. vulgaris beta phaseolin* (Bustos et al., 1991, *EMBO J.* 10: 1469-79), *P. vulgaris* DLEC2 and PHS [beta] (Bobb et al., 1997, *Nucleic Acids Res.* 25:641-7), and soybean beta-Conglycinin, 7S storage protein (Chamberland et al., 1992, *Plant Mol. Biol.* 19:937-49).

Cereal genes whose promoters are associated with early seed and embryo development include rice glutelin ("GluA-3," Yoshihara and Takaiwa, 1996, *Plant Cell Physiol.* 37:107-11; "GluB-1," Takaiwa et al., 1996, *Plant Mol. Biol.* 30:1207-21; Washida et al., 1999, *Plant Mol. Biol.* 40:1-12; "Gt3," Leisy et al., 1990, *Plant Mol. Biol.* 14:41-50), rice prolamin (Zhou & Fan, 1993, *Transgenic Res.* 2:141-6), wheat prolamin (Hammond-Kosack et al., 1993, *EMBO J.* 12:545-54), maize zein (Z4, Matzke et al., 1990, *Plant Mol. Biol.* 14:323-32), and barley *B-hordeins* (Entwistle et al., 1991, *Plant Mol. Biol.* 17:1217-31).

Other genes whose promoters are associated with early seed and embryo development include oil palm GLO7A (7S globulin, Morcillo et al., 2001, *Physiol. Plant* 112:233-243), *Brassica napus napin,* 2S storage protein, and napA gene (Josefsson et al., 1987, *J. Biol. Chem.* 262:12196-201; Stalberg et al., 1993, *Plant Mol. Biol.* 1993 23:671-83; Ellerstrom et al., 1996, *Plant Mol. Biol.* 32:1019-27), *Brassica napus oleosin* (Keddie et al., 1994, *Plant Mol. Biol.* 24:327-40), *Arabidopsis oleosin* (Plant et al., 1994, *Plant Mol. Biol.* 25:193-205), *Arabidopsis* FAE1 (Rossak et al., 2001, *Plant Mol. Biol.* 46:717-25), *Canavalia gladiata* conA (Yamamoto et al., 1995, *Plant Mol. Biol.* 27:729-41), and *Catharanthus roseus* strictosidine synthase (Str, Ouwerkerk and Memelink, 1999, *Mol. Gen. Genet.* 261:635-43). In another preferred embodiment, regulatory sequences from genes expressed during oil biosynthesis are used (see, e.g., U.S. Pat. No. 5,952,544). Alternative promoters are from plant storage protein genes (Bevan et al., 1993, *Philos. Trans. R. Soc. Lond. B. Biol. Sci.* 342:209-15). Additional promoters that may be utilized are described, for example, in U.S. Pat. Nos. 5,378,619; 5,391,725; 5,428,147; 5,447,858; 5,608,144; 5,608,144; 5,614,399; 5,633,441; 5,633,435; and 4,633,436.

In yet another aspect, in some cases it may be desirable to inhibit the expression of the endogenous IMQ nucleic acid sequence in a host cell. Exemplary methods for practicing this aspect of the invention include, but are not limited to antisense suppression (Smith, et al., 1988, *Nature,* 334:724-726; van der Krol et al., 1988, *BioTechniques,* 6:958-976); co-suppression (Napoli, et al., 1990, *Plant Cell,* 2:279-289); ribozymes (PCT Publication WO 97/10328); and combinations of sense and antisense (Waterhouse, et al., 1998, *Proc. Natl. Acad. Sci. USA,* 95:13959-13964). Methods for the suppression of endogenous sequences in a host cell typically employ the transcription or transcription and translation of at least a portion of the sequence to be suppressed. Such sequences may be homologous to coding as well as non-coding regions of the endogenous sequence. Antisense inhibition may use the entire cDNA sequence (Sheehy et al., 1988, *Proc. Natl. Acad. Sci. USA,* 85:8805-8809), a partial cDNA sequence including fragments of 5' coding sequence, (Cannon et al., 1990, *Plant Mol. Biol.,* 15:39-47), or 3' non-coding sequences (Ch'ng et al., 1989, *Proc. Natl. Acad. Sci. USA,* 86:10006-10010). Cosuppression techniques may use the entire cDNA sequence (Napoli et al., 1990, *Plant Cell,* 2:279-289; van der Krol et al., 1990, *Plant Cell,* 2:291-299), or a partial cDNA sequence (Smith et al., 1990, *Mol. Gen. Genetics,* 224:477-481).

Standard molecular and genetic tests may be performed to further analyze the association between a nucleic acid sequence and an observed phenotype. Exemplary techniques are described below.

1. DNA/RNA Analysis

The stage- and tissue-specific gene expression patterns in mutant versus wild-type lines may be determined, for instance, by in situ hybridization. Analysis of the methylation status of the gene, especially flanking regulatory regions, may be performed. Other suitable techniques include over-expression, ectopic expression, expression in other plant species and gene knock-out (reverse genetics, targeted knock-out, viral induced gene silencing (VIGS; see, Baulcombe D, 1999, *Arch. Virol. Suppl.* 15:189-201).

In a preferred application expression profiling, generally by microarray analysis, is used to simultaneously measure differences or induced changes in the expression of many different genes. Techniques for microarray analysis are well known in the art (Schena M et al., *Science* 1995 270:467-470; Baldwin D et al., 1999, *Cur. Opin. Plant Biol.* 2(2):96-103; Dangond F, *Physiol Genomics* (2000) 2:53-58; van Hal N L et al., *J Biotechnol.* (2000) 78:271-280; Richmond T and Somerville S, *Curr. Opin. Plant Biol.* 2000 3:108-116). Expression profiling of individual tagged lines may be performed. Such analysis can identify other genes that are coordinately regulated as a consequence of the over-expression of the gene of interest, which may help to place an unknown gene in a particular pathway.

2. Gene Product Analysis

Analysis of gene products may include recombinant protein expression, antisera production, immunolocalization, biochemical assays for catalytic or other activity, analysis of phosphorylation status, and analysis of interaction with other proteins via yeast two-hybrid assays.

3. Pathway Analysis

Pathway analysis may include placing a gene or gene product within a particular biochemical, metabolic or signaling pathway based on its mis-expression phenotype or by sequence homology with related genes. Alternatively, analysis may comprise genetic crosses with wild-type lines and other mutant lines (creating double mutants) to order the gene in a pathway, or determining the effect of a mutation on expression of downstream "reporter" genes in a pathway.

Generation of Mutated Plants with an Improved Oil Quantity Phenotype and/or Improved Meal Quality Phenotype Additional methods are disclosed herein of generating a plant having an IMQ and/or an IOQ phenotype, wherein a plant is identified that has an allele in its IMQ nucleic acid sequence that results in an IMQ phenotype and/or an IOQ phenotype, compared to plants lacking the allele. The plant can generate progeny, wherein the progeny inherit the allele and have an IMQ phenotype and/or an IOQ phenotype. For example, provided herein is a method of identifying plants that have mutations in the endogenous IMQ nucleic acid sequence that confer an IMQ phenotype and/or an IOQ phenotype and generating progeny of these plants with an IMQ and/or IOQ phenotype that are not genetically modified. In some embodiments, the plants have an IMQ phenotype with an altered protein and/or fiber content or seed meal content, or an IOQ phenotype, with an altered oil content.

In one method, called "TILLING" (for targeting induced local lesions in genomes), mutations are induced in the seed of a plant of interest, for example, using EMS (ethylmethane sulfonate) treatment. The resulting plants are grown and self-fertilized, and the progeny are used to prepare DNA samples. PCR amplification and sequencing of the IMQ nucleic acid sequence is used to identify whether a mutated plant has a mutation in the IMQ nucleic acid sequence. Plants having IMQ mutations may then be tested for altered oil, protein, and/or fiber content, or alternatively, plants may be tested for altered oil, protein, and/or fiber content, and then PCR amplification and sequencing of the IMQ nucleic acid sequence is used to determine whether a plant having altered oil, protein, and/or fiber content has a mutated IMQ nucleic acid sequence. TILLING can identify mutations that may alter the expression of specific genes or the activity of proteins encoded by these genes (see Colbert et al., 2001, *Plant Physiol.* 126:480-484; McCallum et al., 2000, *Nature Biotechnology* 18:455-457).

In another method, a candidate gene/Quantitative Trait Locus (QTLs) approach can be used in a marker-assisted breeding program to identify alleles of or mutations in the IMQ nucleic acid sequence or orthologs of the IMQ nucleic acid sequence that may confer altered oil, protein, and/or fiber content (see Bert et al., *Theor Appl Genet.,* 2003 June; 107 (1):181-9; and Lionneton et al., *Genome,* 2002 December; 45(6):1203-15). Thus, in a further aspect of the disclosure, an IMQ nucleic acid is used to identify whether a plant having altered oil, protein, and/or fiber content has a mutation an endogenous IMQ nucleic acid sequence or has a particular allele that causes altered oil, protein, and/or fiber content.

While the disclosure has been described with reference to specific methods and embodiments, it will be appreciated that various modifications and changes may be made without departing from the disclosure. All publications cited herein are expressly incorporated herein by reference for the purpose of describing and disclosing compositions and methodologies that might be used in connection with the disclosure. All cited patents, patent applications, and sequence information in referenced public databases are also incorporated by reference.

EXAMPLES

Example 1

Generation of Plants with an IMO Phenotype and/or an 100 Phenotype by Transformation with an Activation Tagging Construct This Example describes the generation of transgenic plants with altered oil, protein, and/or fiber content.

Mutants were generated using the activation tagging "ACTTAG" vector, pSKI015 (GI#6537289; Weigel D et al., 2000, *Plant Physiology,* 122:1003-1013). Standard methods were used for the generation of *Arabidopsis* transgenic plants, and were essentially as described in published application PCT WO0183697. Briefly, T0 *Arabidopsis* (Col-0) plants were transformed with *Agrobacterium* carrying the pSKI015 vector, which comprises T-DNA derived from the *Agrobacterium* Ti plasmid, an herbicide resistance selectable marker gene, and the 4×CaMV 35S enhancer element. Transgenic plants were selected at the T1 generation based on herbicide resistance. T2 seed (from T1 plants) was harvested and sown in soil. T2 plants were exposed to the herbicide to kill plants lacking the ACTTAG vector. T2 plants were grown to maturity, allowed to self-fertilize and set seed. T3 seed (from the T2 plants) was harvested in bulk for each line.

T3 seed was analyzed by Near Infrared Spectroscopy (NIR) at the time of harvest. NIR spectra were captured using a Bruker 22 near infrared spectrometer. Bruker Software was used to estimate total seed oil, total seed protein and total seed fiber content using data from NIR analysis and reference methods according to the manufacturer's instructions. Oil content predicting calibrations were developed following the general method of AOCS Procedure Am1-92, Official Methods and Recommended Practices of the American Oil Chemists Society, 5th Ed., AOCS, Champaign, Ill. A NIR protein content predicting calibration was developed using total nitrogen content data of seed samples following the general method of Dumas Procedure AOAC 968.06 (Official Methods of Analysis of AOAC International 17$^{th}$ Edition AOAC, Gaithersburg, Md.). A fiber content predicting calibration was developed by measuring crude fiber content in a set of seed samples. Fiber content of in a known mass of seed was determined using the method of Honig and Rackis, (1979*, J. Agri. Food Chem.,* 27: 1262-1266). Digestible protein content of in a known mass of seed was determined by quantifying the individual amino acids liberated by an acid hydrolysis Steine and Moore (1958*, Anal. Chem.,* 30:1185-1190). The quantification was performed by the Amino Quant (Agilent). The undigested protein remaining associated with the non digestible fraction is measured by the same method described for the whole seed homogenate. Digestible protein content is determined by subtracting the amount of undigested protein associated with the non digestible fraction from the total amount of protein in the seed sample.

Seed oil, protein, digestible protein and fiber values in 82,274 lines were determined by NIR spectroscopy and normalized to allow comparison of seed component values in plants grown at different times. Oil, protein and fiber values were normalized by calculating the average oil, protein and fiber values in seed from all plants planted on the same day (including a large number of other ACTTAG plants, including control, wild-type, or non-transgenic plants). The seed components for each line was expressed as a "percent relative value" which was calculated by dividing the component value for each line with the average component value for all lines planted on the same day (which should approximate the value in control, wild-type, or non-transgenic plants). The "percent relative protein" and "percent relative fiber" were calculated similarly.

Inverse PCR was used to recover genomic DNA flanking the T-DNA insertion. The PCR product was subjected to sequence analysis and placed on the genome using a basic BLASTN search and/or a search of the *Arabidopsis* Information Resource (TAIR) database (available at the publicly available website). Promoters within 9 kb of the enhancers in the ACTTAG element are considered to be within "activation space." Genes with T-DNA inserts within coding sequences were not considered to be within "activation space." The ACTTAG lines with the above average oil and protein values, and below average fiber values were identified and are listed in column 3 of Table 1.

TABLE 1

| 1. Gene alias | 2. Tair | 3. ACTTAG Line | 4. Relative Seed Protein Content | 5. Relative Seed Fiber Content | 6. Relative Seed Oil Content | 7. GC FA |
|---|---|---|---|---|---|---|
| IMQ21.1 | At1g05230 | W000032537 | 114.20% | 100.35% | 79.63% | |
| IMQ21.1 | At1g05230 | W000032537 | 114.20% | 100.35% | 79.63% | |
| IMQ21.2 | At1g05240 | W000032537 | 114.20% | 100.35% | 79.63% | |
| IMQ21.3 | At1g05250 | W000032537 | 114.20% | 100.35% | 79.63% | |
| IMQ21.4 | At1g05260 | W000032537 | 114.20% | 100.35% | 79.63% | |
| IMQ22.1 | At1g10140 | W000181281 | 106.75% | 91.28% | 94.79% | |
| IMQ22.2 | At1g10150 | W000181281 | 106.75% | 91.28% | 94.79% | |
| IMQ22.3 | At1g10155 | W000181281 | 106.75% | 91.28% | 94.79% | |
| IMQ23.1 | At1g13630 | W000189711 | 156.76% | 98.48% | 62.78% | |
| IMQ23.2 | At1g13640 | W000189711 | 156.76% | 98.48% | 62.78% | |
| IMQ23.3 | At1g13650 | W000189711 | 156.76% | 98.48% | 62.78% | |
| IMQ23.3 | At1g13650 | W000189711 | 156.76% | 98.48% | 62.78% | |
| IMQ24.1 | At1g25400 | W000092974 | 113.43% | 93.89% | 92.75% | |
| IMQ24.2 | At1g25410 | W000092974 | 113.43% | 93.89% | 92.75% | |
| IMQ24.3 | At1g25420 | W000092974 | 113.43% | 93.89% | 92.75% | |
| IMQ24.3 | At1g25420 | W000092974 | 113.43% | 93.89% | 92.75% | |
| IMQ24.3 | At1g25420 | W000092974 | 113.43% | 93.89% | 92.75% | |
| IMQ25.1 | At1g27630 | W000156857 | 115.45% | 91.17% | 93.30% | |
| IMQ25.2 | At1g27640 | W000156857 | 115.45% | 91.17% | 93.30% | |
| IMQ25.3 | At1g27650 | W000156857 | 115.45% | 91.17% | 93.30% | |
| IMQ25.4 | At1g27660 | W000156857 | 115.45% | 91.17% | 93.30% | 94.87% |
| IMQ26.1 | At1g34160 | W000181882 | 106.61% | 89.49% | 95.13% | |
| IMQ26.2 | At1g34170 | W000181882 | 106.61% | 89.49% | 95.13% | |
| IMQ26.2 | At1g34170 | W000181882 | 106.61% | 89.49% | 95.13% | |
| IMQ26.3 | At1g34180 | W000181882 | 106.61% | 89.49% | 95.13% | |
| IMQ27.1 | At1g45160 | W000144884 | 99.69% | 99.35% | 106.43% | |
| IMQ27.2 | At1g45170 | W000144884 | 99.69% | 99.35% | 106.43% | |
| IMQ27.3 | At1g45180 | W000144884 | 99.69% | 99.35% | 106.43% | |
| IMQ28.1 | At1g52140 | W000160181 | 111.10% | 92.26% | 96.12% | |
| IMQ28.2 | At1g52150 | W000160181 | 111.10% | 92.26% | 96.12% | |
| IMQ28.2 | At1g52150 | W000160181 | 111.10% | 92.26% | 96.12% | |
| IMQ29.1 | At1g58410 | W000050532 | 100.73% | 91.01% | 101.59% | 108.07% |
| IMQ29.1 | At1g58410 | W000050532 | 100.73% | 91.01% | 101.59% | |
| IMQ29.1 | At1g58410 | W000050532 | 100.73% | 91.01% | 101.59% | |
| IMQ29.2 | At1g58420 | W000050532 | 100.73% | 91.01% | 101.59% | |
| IMQ29.3 | At1g58430 | W000050532 | 100.73% | 91.01% | 101.59% | |
| IMQ30.1 | At1g75670 | W000161468 | 114.49% | 91.60% | 93.46% | |
| IMQ30.1 | At1g75670 | W000161468 | 114.49% | 91.60% | 93.46% | |
| IMQ30.2 | At1g75680 | W000161468 | 114.49% | 91.60% | 93.46% | |
| IMQ30.3 | At1g75690 | W000161468 | 114.49% | 91.60% | 93.46% | |
| IMQ30.4 | At1g75700 | W000161468 | 114.49% | 91.60% | 93.46% | |
| IMQ31.1 | At1g77730 | W000032887 | 115.30% | 99.58% | 80.09% | |
| IMQ31.2 | At1g77740 | W000032887 | 115.30% | 99.58% | 80.09% | |
| IMQ32.1 | At1g78100 | W000060346 | 116.83% | 90.96% | 88.40% | |
| IMQ32.2 | At1g78110 | W000060346 | 116.83% | 90.96% | 88.40% | |
| IMQ32.3 | At1g78120 | W000060346 | 116.83% | 90.96% | 88.40% | |
| IMQ33.1 | At2g17036 | W000176513 | 138.95% | 98.90% | 78.13% | |
| IMQ33.2 | At2g17040 | W000176513 | 138.95% | 98.90% | 78.13% | |
| IMQ34.1 | At2g31460 | W000137133 | 135.45% | 89.55% | 82.65% | |
| IMQ34.2 | At2g31470 | W000137133 | 135.45% | 89.55% | 82.65% | |

TABLE 2

| 1. Gene alias | 2. Tair | 3. Nucleic Acid seq. GI# | 4. SEQ ID NO | 5. Polypeptide seq. GI# | 6. SEQ ID NO | 7. Putative biochemical function/protein name | 8. Conserved protein domain |
|---|---|---|---|---|---|---|---|
| IMQ21.1 | At1g05230 | gi\|30679180 | SEQ ID NO: 1 | gi\|30679181 | SEQ ID NO: 2 | DNA binding/ transcription factor | IPR002913 Lipid-binding START; IPR001356 Homeobox |
| IMQ21.1 | At1g05230 | gi\|30679175 | SEQ ID NO: 3 | gi\|15220448 | SEQ ID NO: 4 | DNA binding/ transcription factor | IPR002913 Lipid-binding START; IPR001356 Homeobox |
| IMQ21.2 | At1g05240 | gi\|30679186 | SEQ ID NO: 5 | gi\|18390498 | SEQ ID NO: 6 | peroxidase | IPR002016 Haem peroxidase, plant/fungal/bacterial; IPR000823 Plant peroxidase |
| IMQ21.3 | At1g05250 | gi\|30679195 | SEQ ID NO: 7 | gi\|18390500 | SEQ ID NO: 8 | peroxidase | IPR002016 Haem peroxidase, plant/fungal/bacterial; |

TABLE 2-continued

| 1. Gene alias | 2. Tair | 3. Nucleic Acid seq. GI# | 4. SEQ ID NO | 5. Polypeptide seq. GI# | 6. SEQ ID NO | 7. Putative biochemical function/protein name | 8. Conserved protein domain |
|---|---|---|---|---|---|---|---|
| IMQ21.4 | At1g05260 | gi\|30679199 | SEQ ID NO: 9 | gi\|15220463 | SEQ ID NO: 10 | RCI3 (RARE COLD INDUCIBLE GENE 3); peroxidase | IPR000823 Plant peroxidase IPR002016 Haem peroxidase, plant/fungal/bacterial; IPR000823 Plant peroxidase |
| IMQ22.1 | At1g10140 | gi\|42561890 | SEQ ID NO: 11 | gi\|18391115 | SEQ ID NO: 12 | unknown protein | |
| IMQ22.2 | At1g10150 | gi\|42561891 | SEQ ID NO: 13 | gi\|18391117 | SEQ ID NO: 14 | ATPP2-A10 | |
| IMQ22.3 | At1g10155 | gi\|22329463 | SEQ ID NO: 15 | gi\|22329464 | SEQ ID NO: 16 | unknown protein | |
| IMQ23.1 | At1g13630 | gi\|18394018 | SEQ ID NO: 17 | gi\|15222912 | SEQ ID NO: 18 | unknown protein | IPR002885 Pentatricopeptide repeat |
| IMQ23.2 | At1g13640 | gi\|30683391 | SEQ ID NO: 19 | gi\|18394020 | SEQ ID NO: 20 | inositol or phosphatidylinositol kinase/ phosphotransferase, alcohol group as acceptor | IPR000403 Phosphatidylinositol 3- and 4-kinase, catalytic; IPR000626 Ubiquitin |
| IMQ23.3 | At1g13650 | gi\|30683401 | SEQ ID NO: 21 | gi\|30683402 | SEQ ID NO: 22 | unknown protein | |
| IMQ23.3 | At1g13650 | gi\|30683399 | SEQ ID NO: 23 | gi\|15222916 | SEQ ID NO: 24 | unknown protein | |
| IMQ24.1 | At1g25400 | gi\|30689203 | SEQ ID NO: 25 | gi\|18395663 | SEQ ID NO: 26 | unknown protein | |
| IMQ24.2 | At1g25410 | gi\|18395666 | SEQ ID NO: 27 | gi\|15222583 | SEQ ID NO: 28 | ATIPT6; ATP binding/ adenylate dimethylallyltransferase/ tRNA isopentenyltransferase | IPR002648 Isopentenyl transferase; IPR002627 tRNA isopentenyltransferase; IPR011593 Isopentenyl transferase-like |
| IMQ24.3 | At1q25420 | gi\|42571640 | SEQ ID NO: 29 | gi\|42571641 | SEQ ID NO: 30 | expressed protein | IPR005061 Protein of unknown function DUF292, eukaryotic |
| IMQ24.3 | At1g25420 | gi\|42571638 | SEQ ID NO: 31 | gi\|42571639 | SEQ ID NO: 32 | expressed protein | IPR005061 Protein of unknown function DUF292, eukaryotic |
| IMQ24.3 | At1g25420 | gi\|30689214 | SEQ ID NO: 33 | gi\|18395668 | SEQ ID NO: 34 | expressed protein | IPR005061 Protein of unknown function DUF292, eukaryotic |
| IMQ25.1 | At1g27630 | gi\|30690014 | SEQ ID NO: 35 | gi\|15217663 | SEQ ID NO: 36 | cyclin-dependent protein kinase | IPR005258 Cyclin ccl1; IPR006671 Cyclin, N-terminal |
| IMQ25.2 | At1g27640 | gi\|18396427 | SEQ ID NO: 37 | gi\|15217664 | SEQ ID NO: 38 | unknown protein | |
| IMQ25.3 | At1g27650 | gi\|30690022 | SEQ ID NO: 39 | gi\|15217666 | SEQ ID NO: 40 | RNA binding/nucleic acid binding | IPR000571 Zinc finger, CCCH-type; IPR000504 RNA-binding region RNP-1 (RNA recognition motif); IPR009145 U2 auxiliary factor small subunit |
| IMQ25.4 | At1g27660 | gi\|42562353 | SEQ ID NO: 41 | gi\|15217667 | SEQ ID NO: 42 | transcription factor | IPR001092 Basic helix-loop-helix dimerisation region bHLH |
| IMQ26.1 | At1g34160 | gi\|18399159 | SEQ ID NO: 43 | gi\|15218513 | SEQ ID NO: 44 | unknown protein | IPR002885 Pentatricopeptide repeat |
| IMQ26.2 | At1g34170 | gi\|79356538 | SEQ ID NO: 45 | gi\|79356539 | SEQ ID NO: 46 | ARF13; transcription factor | IPR010525 Auxin response factor; IPR003340 Transcriptional factor B3 |
| IMQ26.2 | At1g34170 | gi\|79319168 | SEQ ID NO: 47 | gi\|79319169 | SEQ ID NO: 48 | ARF13 | IPR010525 Auxin response factor; IPR003340 Transcriptional factor B3 |

TABLE 2-continued

| 1. Gene alias | 2. Tair | 3. Nucleic Acid seq. GI# | 4. SEQ ID NO | 5. Polypeptide seq. GI# | 6. SEQ ID NO | 7. Putative biochemical function/protein name | 8. Conserved protein domain |
|---|---|---|---|---|---|---|---|
| IMQ26.3 | At1g34180 | gi\|30693015 | SEQ ID NO: 49 | gi\|18399166 | SEQ ID NO: 50 | ANAC016; transcription factor | IPR003441 No apical meristem (NAM) protein |
| IMQ27.1 | At1g45160 | gi\|30693922 | SEQ ID NO: 51 | gi\|15219539 | SEQ ID NO: 52 | kinase | IPR000719 Protein kinase; IPR008271 Serine/threonine protein kinase, active site; IPR000687 Protein of unknown function RIO1 |
| IMQ27.2 | At1g45170 | gi\|79360074 | SEQ ID NO: 53 | gi\|79360075 | SEQ ID NO: 54 | unknown protein | |
| IMQ27.3 | At1q45180 | gi\|30693927 | SEQ ID NO: 55 | gi\|15220067 | SEQ ID NO: 56 | protein binding/ ubiquitin-protein ligase/ zinc ion binding | IPR001841 Zinc finger, RING-type; IPR001 965 Zinc finger, PHD-type |
| IMQ28.1 | At1g52140 | gi\|30695146 | SEQ ID NO: 57 | gi\|18403871 | SEQ ID NO: 58 | unknown protein | |
| IMQ28.2 | At1g52150 | gi\|30695148 | SEQ ID NO: 59 | gi\|30695149 | SEQ ID NO: 60 | ATHB-15 (INCURVATA 4); DNA binding/ transcription factor | IPR002913 Lipid-binding START; IPR001356 Homeobox; IPR004827 Basic-leucine zipper (bZIP) transcription factor |
| IMQ28.2 | At1g52150 | gi\|30695147 | SEQ ID NO: 61 | gi\|15218158 | SEQ ID NO: 62 | ATHB-15 (INCURVATA 4); DNA binding/ transcription factor | IPR002913 Lipid-binding START; IPR001356 Homeobox; IPR004827 Basic-leucine zipper (bZIP) transcription factor |
| IMQ29.1 | At1g58410 | gi\|18406289 | SEQ ID NO: 63 | gi\|15217959 | SEQ ID NO: 64 | ATP binding | IPR000767 Disease resistance protein; IPR001611 Leucine-rich repeat; IPR002182 NB-ARC; IPR011072 Protein kinase PKN/PRK1, effector |
| IMQ29.1 | At1g58410 | gi\|79583692 | SEQ ID NO: 65 | gi\|79583693 | SEQ ID NO: 66 | ATP binding | IPR000767 Disease resistance protein; IPR001611 Leucine-rich repeat; IPR002182 NB-ARC |
| IMQ29.1 | At1g58410 | gi\|79320239 | SEQ ID NO: 67 | gi\|79320240 | SEQ ID NO: 68 | ATP binding | IPR000767 Disease resistance protein; IPR001611 Leucine-rich repeat; IPR002182 NB-ARC |
| IMQ29.2 | At1g58420 | gi\|30696259 | SEQ ID NO: 69 | gi\|18406291 | SEQ ID NO: 70 | unknown protein | |
| IMQ29.3 | At1g58430 | gi\|30696261 | SEQ ID NO: 71 | gi\|15217963 | SEQ ID NO: 72 | RXF26; carboxylic ester hydrolase/hydrolase, acting on ester bonds | IPR001087 Lipolytic enzyme, G-D-S-L |
| IMQ30.1 | At1g75670 | gi\|42572114 | SEQ ID NO: 73 | gi\|42572115 | SEQ ID NO: 74 | unknown protein | IPR007830 RNA polymerase Rpa43 subunit |
| IMQ30.1 | At1g75670 | gi\|30699111 | SEQ ID NO: 75 | gi\|18410907 | SEQ ID NO: 76 | unknown protein | IPR007830 RNA polymerase Rpa43 subunit |
| IMQ30.2 | At1g75680 | gi\|30699112 | SEQ ID NO: 77 | gi\|15222328 | SEQ ID NO: 78 | hydrolase, hydrolyzing O-glycosyl compounds | IPR001701 Glycoside hydrolase, family 9 |
| IMQ30.3 | At1g75690 | gi\|30699113 | SEQ ID NO: 79 | gi\|15222330 | SEQ ID NO: 80 | unknown protein | IPR001305 DnaJ central region |
| IMQ30.4 | At1g75700 | gi\|18410915 | SEQ ID NO: 81 | gi\|15222332 | SEQ ID NO: 82 | unknown protein | IPR004345 TB2/DP1 and HVA22 related protein; IPR005296 IBV 3C protein |
| IMQ31.1 | At1g77730 | gi\|18411662 | SEQ ID NO: 83 | gi\|15217449 | SEQ ID NO: 84 | unknown protein | IPR001849 Pleckstrin-like; IPR000648 Oxysterol-binding protein |

TABLE 2-continued

| 1. Gene alias | 2. Tair | 3. Nucleic Acid seq. GI# | 4. SEQ ID NO | 5. Polypeptide seq. GI# | 6. SEQ ID NO | 7. Putative biochemical function/protein name | 8. Conserved protein domain |
|---|---|---|---|---|---|---|---|
| IMQ31.2 | At1g77740 | gi\|18411668 | SEQ ID NO: 85 | gi\|15217451 | SEQ ID NO: 86 | 1-phosphatidylinositol-4-phosphate 5-kinase | IPR002498 Phosphatidylinositol-4-phosphate 5-kinase; IPR003409 MORN motif |
| IMQ32.1 | At1g78100 | gi\|30699306 | SEQ ID NO: 87 | gi\|18411823 | SEQ ID NO: 88 | unknown protein | IPR001810 Cyclin-like F-box |
| IMQ32.2 | At1g78110 | gi\|42563307 | SEQ ID NO: 89 | gi\|15218227 | SEQ ID NO: 90 | unknown protein | |
| IMQ32.3 | At1g78120 | gi\|18411834 | SEQ ID NO: 91 | gi\|15218228 | SEQ ID NO: 92 | unknown protein | IPR001440 TPR repeat; IPR005687 Mitochondrial import translocase, subunit Tom70 |
| IMQ33.1 | At2g17036 | gi\|18398290 | SEQ ID NO: 93 | gi\|18398291 | SEQ ID NO: 94 | unknown protein | IPR001810 Cyclin-like F-box; IPR005174 Protein of unknown function DUF295 |
| IMQ33.2 | At2g17040 | gi\|30679858 | SEQ ID NO: 95 | gi\|18398293 | SEQ ID NO: 96 | ANAC036; transcription factor | IPR003441 No apical meristem (NAM) protein |
| IMQ34.1 | At2g31460 | gi\|18402675 | SEQ ID NO: 97 | gi\|15225088 | SEQ ID NO: 98 | unknown protein | IPR005508 Protein of unknown function DUF313 |
| IMQ34.2 | At2g31470 | gi\|18402677 | SEQ ID NO: 99 | gi\|15225089 | SEQ ID NO: 100 | unknown protein | IPR006527 F-box protein interaction domain; IPR001810 Cyclin-like F-box |

TABLE 3

| 1. Gene alias | 2. Tair | 3. Nucleic Acid seq. GI# | 4. Polypeptide seq. GI# | 5. Orthologous Genes: Nucleic Acid/Polypeptide seq. GI# Nucleic Acid GI# | Polypeptide GI# | Species |
|---|---|---|---|---|---|---|
| IMQ21.1 | At1g05230 | gi\|30679180 | gi\|30679181 | gi\|30679175 | gi\|15220448 | *Arabidopsis thaliana* |
| | | | | gi\|42567019 | gi\|22328861 | *Arabidopsis thaliana* |
| | | | | gi\|1173621 | gi\|1173622 | *Phalaenopsis* sp. SM9108 |
| | | | | gi\|50928892 | gi\|50928893 | *Oryza sativa* (*japonica* cultivar-group) |
| IMQ21.1 | At1g05230 | gi\|30679175 | gi\|15220448 | gi\|30679180 | gi\|30679181 | *Arabidopsis thaliana* |
| | | | | gi\|42567019 | gi\|22328861 | *Arabidopsis thaliana* |
| | | | | gi\|1173621 | gi\|1173622 | *Phalaenopsis* sp. SM9108 |
| | | | | gi\|50928892 | gi\|50928893 | *Oryza sativa* (*japonica* cultivar-group) |
| IMQ21.2 | At1g05240 | gi\|30679186 | gi\|18390498 | gi\|30679195 | gi\|18390500 | *Arabidopsis thaliana* |
| | | | | gi\|30685217 | gi\|15242237 | *Arabidopsis thaliana* |
| | | | | gi\|30678297 | gi\|15232058 | *Arabidopsis thaliana* |
| | | | | gi\|7259218 | gi\|7259219 | *Spinacia oleracea* |
| IMQ21.3 | At1g05250 | gi\|30679195 | gi\|18390500 | gi\|30679186 | gi\|18390498 | *Arabidopsis thaliana* |
| | | | | gi\|30685217 | gi\|15242237 | *Arabidopsis thaliana* |
| | | | | gi\|30678297 | gi\|15232058 | *Arabidopsis thaliana* |
| | | | | gi\|7259218 | gi\|7259219 | *Spinacia oleracea* |
| IMQ21.4 | At1g05260 | gi\|30679199 | gi\|15220463 | gi\|50261254 | gi\|50261255 | *Capsella bursa-pastoris* |
| | | | | gi\|30686383 | gi\|15233153 | *Arabidopsis thaliana* |
| | | | | gi\|30681721 | gi\|15237128 | *Arabidopsis thaliana* |
| IMQ22.1 | At1g10140 | gi\|42561890 | gi\|18391115 | gi\|30696259 | gi\|18406291 | *Arabidopsis thaliana* |
| | | | | gi\|50933830 | gi\|50933831 | *Oryza sativa* (*japonica* cultivar-group) |
| | | | | gi\|45860990 | gi\|50872457 | *Oryza sativa* (*japonica* cultivar-group) |
| IMQ22.2 | At1g10150 | gi\|42561891 | gi\|18391117 | gi\|30696298 | gi\|18406365 | *Arabidopsis thaliana* |
| | | | | gi\|50933834 | gi\|50933835 | *Oryza sativa* (*japonica* cultivar-group) |
| | | | | gi\|37514985 | gi\|40539064 | *Oryza sativa* (*japonica* cultivar-group) |
| IMQ22.3 | At1g10155 | gi\|22329463 | gi\|22329464 | gi\|18397840 | gi\|15221633 | *Arabidopsis thaliana* |
| | | | | gi\|6850933 | gi\|6850934 | *Cicer arietinum* |
| | | | | gi\|4995204 | gi\|4995205 | *Glycine max* |
| IMQ23.1 | At1g13630 | gi\|18394018 | gi\|15222912 | gi\|37535403 | gi\|37535404 | *Oryza sativa* (*japonica* cultivar-group) |
| | | | | gi\|18403403 | gi\|15228763 | *Arabidopsis thaliana* |
| | | | | gi\|18391375 | gi\|15221282 | *Arabidopsis thaliana* |
| IMQ23.2 | At1g13640 | gi\|30683391 | gi\|18394020 | gi\|30678087 | gi\|18395629 | *Arabidopsis thaliana* |
| | | | | gi\|30689401 | gi\|18395825 | *Arabidopsis thaliana* |
| | | | | gi\|42570678 | gi\|42570679 | *Arabidopsis thaliana* |

TABLE 3-continued

| 1. Gene alias | 2. Tair | 3. Nucleic Acid seq. GI# | 4. Polypeptide seq. GI# | 5. Orthologous Genes: Nucleic Acid/Polypeptide seq. GI# Nucleic Acid GI# | Polypeptide GI# | Species |
|---|---|---|---|---|---|---|
| IMQ23.3 | At1g13650 | gi\|30683401 | gi\|30683402 | gi\|30683399 | gi\|15222916 | *Arabidopsis thaliana* |
| | | | | gi\|30678078 | gi\|30678079 | *Arabidopsis thaliana* |
| | | | | gi\|42570676 | gi\|42570677 | *Arabidopsis thaliana* |
| | | | | gi\|23496321 | gi\|23496344 | *Plasmodium falciparum* 3D7 |
| IMQ23.3 | At1g13650 | gi\|30683399 | gi\|15222916 | gi\|30683401 | gi\|30683402 | *Arabidopsis thaliana* |
| | | | | gi\|30678078 | gi\|30678079 | *Arabidopsis thaliana* |
| | | | | gi\|42570676] | gi\|42570677 | *Arabidopsis thaliana* |
| | | | | gi\|23496321 | gi\|23496344 | *Plasmodium falciparum* 3D7 |
| IMQ24.1 | At1g25400 | gi\|30689203 | gi\|18395663 | gi\|30697678 | gi\|18409031 | *Arabidopsis thaliana* |
| IMQ24.2 | At1g25410 | gi\|18395666 | gi\|15222583 | gi\|18409036 | gi\|15221410 | *Arabidopsis thaliana* |
| | | | | gi\|74038586 | gi\|74038587 | *Brassica rapa* subsp. *pekinensis* |
| | | | | gi\|18402143 | gi\|15230294 | *Arabidopsis thaliana* |
| IMQ24.3 | At1g25420 | gi\|42571640 | gi\|42571641 | gi\|42571638 | gi\|42571639 | *Arabidopsis thaliana* |
| | | | | gi\|30689214 | gi\|18395668 | *Arabidopsis thaliana* |
| | | | | gi\|34911297 | gi\|34911298 | *Oryza sativa* (*japonica* cultivar-group) |
| | | | | gi\|16191725 | gi\|56784451 | *Oryza sativa* (*japonica* cultivar-group) |
| IMQ24.3 | At1g25420 | gi\|42571638 | gi\|42571639 | gi\|42571640 | gi\|42571641 | *Arabidopsis thaliana* |
| | | | | gi\|30689214 | gi\|18395668 | *Arabidopsis thaliana* |
| | | | | gi\|34911297 | gi\|34911298 | *Oryza sativa* (*japonica* cultivar-group) |
| | | | | gi\|16191725 | gi\|56784451 | *Oryza sativa* (*japonica* cultivar-group) |
| IMQ24.3 | At1g25420 | gi\|30689214 | gi\|18395668 | gi\|42571640 | gi\|42571641 | *Arabidopsis thaliana* |
| | | | | gi\|42571638 | gi\|42571639 | *Arabidopsis thaliana* |
| | | | | gi\|16191725 | gi\|56784451 | *Oryza sativa* (*japonica* cultivar-group) |
| | | | | gi\|42571740 | gi\|42571741 | *Arabidopsis thaliana* |
| IMQ25.1 | At1g27630 | gi\|30690014 | gi\|15217663 | gi\|30694714 | gi\|30694715 | *Arabidopsis thaliana* |
| | | | | gi\|77548247 | gi\|77548754 | *Oryza sativa* (*japonica* cultivar-group) |
| | | | | gi\|30684821 | gi\|30684822 | *Arabidopsis thaliana* |
| IMQ25.2 | At1g27640 | gi\|18396427 | gi\|15217664 | gi\|214833 | gi\|214834 | *Xenopus laevis* |
| IMQ25.3 | At1g27650 | gi\|30690022 | gi\|15217666 | gi\|30694150 | gi\|15239067 | *Arabidopsis thaliana* |
| | | | | gi\|42573546 | gi\|42573547 | *Arabidopsis thaliana* |
| | | | | gi\|13278054 | gi\|13278055 | *Mus musculus* |
| | | | | gi\|3850815 | gi\|3850816 | *Oryza sativa* |
| IMQ25.4 | At1g27660 | gi\|42562353 | gi\|15217667 | gi\|55769700 | gi\|55769701 | *Oryza sativa* (*japonica* cultivar-group) |
| | | | | gi\|58532108 | gi\|21741062 | *Oryza sativa* (*japonica* cultivar-group) |
| | | | | gi\|30696593 | gi\|18407276 | *Arabidopsis thaliana* |
| IMQ26.1 | At1g34160 | gi\|18399159 | gi\|15218513 | gi\|77552765 | gi\|77554579 | *Oryza sativa* (*japonica* cultivar-group) |
| | | | | gi\|54695179 | gi\|54695180 | *Physcomitrella patens* |
| | | | | gi\|45935109 | gi\|45935146 | *Ipomoea trifida* |
| IMQ26.2 | At1g34170 | gi\|79356538 | gi\|79356539 | gi\|42562509 | gi\|42562510 | *Arabidopsis thaliana* |
| | | | | gi\|18399246 | gi\|15218610 | *Arabidopsis thaliana* |
| | | | | gi\|18399735 | gi\|15219635 | *Arabidopsis thaliana* |
| IMQ26.2 | At1g34170 | gi\|79319168 | gi\|79319169 | gi\|42562509 | gi\|42562510 | *Arabidopsis thaliana* |
| | | | | gi\|18399735 | gi\|15219635 | *Arabidopsis thaliana* |
| | | | | gi\|18399246 | gi\|15218610 | *Arabidopsis thaliana* |
| IMQ26.3 | At1g34180 | gi\|30693015 | gi\|18399166 | gi\|30693016 | gi\|18399168 | *Arabidopsis thaliana* |
| | | | | gi\|21105741 | gi\|21105742 | *Petunia* x *hybrida* |
| | | | | gi\|21105739 | gi\|21105740 | *Petunia* x *hybrida* |
| IMQ27.1 | At1g45160 | gi\|30693922 | gi\|15219539 | gi\|30684701 | gi\|30684702 | *Arabidopsis thaliana* |
| | | | | gi\|50918242 | gi\|50918243 | *Oryza sativa* (*japonica* cultivar-group) |
| | | | | gi\|30697658 | gi\|15241795 | *Arabidopsis thaliana* |
| IMQ27.2 | At1g45170 | gi\|79360074 | gi\|79360075 | gi\|42562572 | gi\|42562573 | *Arabidopsis thaliana* |
| | | | | gi\|30694183 | gi\|18422277 | *Arabidopsis thaliana* |
| | | | | gi\|2764573 | gi\|2764574 | *Pisum sativum* |
| IMQ27.3 | At1g45180 | gi\|30693927 | gi\|15220067 | gi\|22327533 | gi\|15239131 | *Arabidopsis thaliana* |
| | | | | gi\|42569056 | gi\|15226553 | *Arabidopsis thaliana* |
| | | | | gi\|42570792 | gi\|42570793 | *Arabidopsis thaliana* |
| | | | | gi\|50929180 | gi\|50929181 | *Oryza sativa* (*japonica* cultivar-group) |
| IMQ28.1 | At1g52140 | gi\|30695146 | gi\|18403871 | gi\|30684002 | gi\|15228179 | *Arabidopsis thaliana* |
| | | | | gi\|12003387 | gi\|12003388 | *Nicotiana tabacum* |
| | | | | gi\|18417331 | gi\|15233454 | *Arabidopsis thaliana* |
| IMQ28.2 | At1g52150 | gi\|30695148 | gi\|30695149 | gi\|30695147 | gi\|15218158 | *Arabidopsis thaliana* |
| | | | | gi\|60327628 | gi\|60327629 | *Populus trichocarpa* |
| | | | | gi\|60327630 | gi\|60327631 | *Populus trichocarpa* |
| IMQ28.2 | At1g52150 | gi\|30695147 | gi\|15218158 | gi\|30695148 | gi\|30695149 | *Arabidopsis thaliana* |
| | | | | gi\|60327628 | gi\|60327629 | *Populus trichocarpa* |
| | | | | gi\|60327630 | gi\|60327631 | *Populus trichocarpa* |
| IMQ29.1 | At1g58410 | gi\|18406289 | gi\|15217959 | gi\|18406284 | gi\|15217957 | *Arabidopsis thaliana* |
| | | | | gi\|42562806 | gi\|15218003 | *Arabidopsis thaliana* |
| | | | | gi\|79320239 | gi\|79320240 | *Arabidopsis thaliana* |
| | | | | gi\|79583692 | gi\|79583693 | *Arabidopsis thaliana* |
| | | | | gi\|18406280 | gi\|15217954 | *Arabidopsis thaliana* |
| IMQ29.1 | At1g58410 | gi\|79583692 | gi\|79583693 | gi\|42562806 | gi\|15218003 | *Arabidopsis thaliana* |
| | | | | gi\|79320239 | gi\|79320240 | *Arabidopsis thaliana* |
| | | | | gi\|30696274 | gi\|22330316 | *Arabidopsis thaliana* |

TABLE 3-continued

| 1. Gene alias | 2. Tair | 3. Nucleic Acid seq. GI# | 4. Polypeptide seq. GI# | 5. Orthologous Genes: Nucleic Acid/Polypeptide seq. GI# Nucleic Acid GI# | Polypeptide GI# | Species |
|---|---|---|---|---|---|---|
| | | | | gi\|22330305 | gi\|22330306 | *Arabidopsis thaliana* |
| | | | | gi\|30696285 | gi\|30696286 | *Arabidopsis thaliana* |
| IMQ29.1 | At1g58410 | gi\|79320239 | gi\|79320240 | gi\|42562806 | gi\|15218003 | *Arabidopsis thaliana* |
| | | | | gi\|79583692 | gi\|79583693 | *Arabidopsis thaliana* |
| | | | | gi\|30696274 | gi\|22330316 | *Arabidopsis thaliana* |
| | | | | gi\|22330305 | gi\|22330306 | *Arabidopsis thaliana* |
| | | | | gi\|30696285 | gi\|30696286 | *Arabidopsis thaliana* |
| IMQ29.2 | At1g58420 | gi\|30696259 | gi\|18406291 | gi\|42561890 | gi\|18391115 | *Arabidopsis thaliana* |
| | | | | gi\|50933830 | gi\|50933831 | *Oryza sativa* (*japonica* cultivar-group) |
| | | | | gi\|30698165 | gi\|30698166 | *Arabidopsis thaliana* |
| IMQ29.3 | At1g58430 | gi\|30696261 | gi\|15217963 | gi\|18402698 | gi\|15225096 | *Arabidopsis thaliana* |
| | | | | gi\|18402315 | gi\|15227734 | *Arabidopsis thaliana* |
| | | | | gi\|18402293 | gi\|15227723 | *Arabidopsis thaliana* |
| IMQ30.1 | At1g75670 | gi\|42572114 | gi\|42572115 | gi\|30699111 | gi\|18410907 | *Arabidopsis thaliana* |
| | | | | gi\|55741413 | gi\|55741414 | *Oryza sativa* (*japonica* cultivar-group) |
| | | | | gi\|34898425 | gi\|34898426 | *Oryza sativa* (*japonica* cultivar-group) |
| | | | | gi\|66828550 | gi\|66828551 | *Dictyostelium discoideum* |
| IMQ30.1 | At1g75670 | gi\|30699111 | gi\|18410907 | gi\|42572114 | gi\|42572115 | *Arabidopsis thaliana* |
| | | | | gi\|55741413 | gi\|55741414 | *Oryza sativa* (*japonica* cultivar-group) |
| | | | | gi\|34898425 | gi\|34898426 | *Oryza sativa* (*japonica* cultivar-group) |
| | | | | gi\|66828550 | gi\|66828551 | *Dictyostelium discoideum* |
| IMQ30.2 | At1g75680 | gi\|30699112 | gi\|15222328 | gi\|18394803 | gi\|15223718 | *Arabidopsis thaliana* |
| | | | | gi\|50725787 | gi\|50725801 | *Oryza sativa* (*japonica* cultivar-group) |
| | | | | gi\|46849602 | gi\|53791781 | *Oryza sativa* (*japonica* cultivar-group) |
| IMQ30.3 | At1g75690 | gi\|30699113 | gi\|15222330 | gi\|4732090 | gi\|4732091 | *Zea mays* |
| | | | | gi\|68433925 | gi\|68433926 | *Danio rerio* |
| | | | | gi\|13430173 | gi\|13430174 | *Castanea sativa* |
| IMQ30.4 | At1g75700 | gi\|18410915 | gi\|15222332 | gi\|18394804 | gi\|18394805 | *Arabidopsis thaliana* |
| | | | | gi\|30694082 | gi\|18422223 | *Arabidopsis thaliana* |
| | | | | gi\|50919650 | gi\|50919651 | *Oryza sativa* (*japonica* cultivar-group) |
| IMQ31.1 | At1g77730 | gi\|18411662 | gi\|15217449 | gi\|42572842 | gi\|42572843 | *Arabidopsis thaliana* |
| | | | | gi\|42570130 | gi\|42570131 | *Arabidopsis thaliana* |
| | | | | gi\|30680661 | gi\|30680662 | *Arabidopsis thaliana* |
| IMQ31.2 | At1g77740 | gi\|18411668 | gi\|15217451 | gi\|30687626 | gi\|15219152 | *Arabidopsis thaliana* |
| | | | | gi\|50918122 | gi\|50918123 | *Oryza sativa* (*japonica* cultivar-group) |
| | | | | gi\|8885991 | gi\|8885992 | *Nicotiana rustica* |
| IMQ32.1 | At1g78100 | gi\|30699306 | gi\|18411823 | gi\|42562235 | gi\|15219845 | *Arabidopsis thaliana* |
| | | | | gi\|18844754 | gi\|55297493 | *Oryza sativa* (*japonica* cultivar-group) |
| | | | | gi\|50931860 | gi\|50931861 | *Oryza sativa* (*japonica* cultivar-group) |
| IMQ32.2 | At1g78110 | gi\|42563307 | gi\|15218227 | gi\|18395090 | gi\|15219847 | *Arabidopsis thaliana* |
| | | | | gi\|50899793 | gi\|50899794 | *Oryza sativa* (*japonica* cultivar-group) |
| | | | | gi\|50912868 | gi\|50912869 | *Oryza sativa* (*japonica* cultivar-group) |
| IMQ32.3 | At1g78120 | gi\|18411834 | gi\|15218228 | gi\|42568787 | gi\|15238361 | *Arabidopsis thaliana* |
| | | | | gi\|18416178 | gi\|15238058 | *Arabidopsis thaliana* |
| | | | | gi\|37694873 | gi\|72255609 | *Brassica rapa* |
| IMQ33.1 | At2g17036 | gi\|18398290 | gi\|18398291 | gi\|42569091 | gi\|18398287 | *Arabidopsis thaliana* |
| | | | | gi\|18424314 | gi\|15238601 | *Arabidopsis thaliana* |
| | | | | gi\|42562951 | gi\|42562952 | *Arabidopsis thaliana* |
| IMQ33.2 | At2g17040 | gi\|30679858 | gi\|18398293 | gi\|66394519 | gi\|66394520 | *Glycine max* |
| | | | | gi\|54291125 | gi\|54291129 | *Oryza sativa* (*japonica* cultivar-group) |
| | | | | gi\|30678001 | gi\|30678002 | *Arabidopsis thaliana* |
| IMQ34.1 | At2g31460 | gi\|18402675 | gi\|15225088 | gi\|18401417 | gi\|15225878 | *Arabidopsis thaliana* |
| | | | | gi\|18402662 | gi\|15224674 | *Arabidopsis thaliana* |
| | | | | gi\|18408901 | gi\|15229174 | *Arabidopsis thaliana* |
| IMQ34.2 | At2g31470 | gi\|18402677 | gi\|15225089 | gi\|18403984 | gi\|15229553 | *Arabidopsis thaliana* |
| | | | | gi\|18424999 | gi\|15239182 | *Arabidopsis thaliana* |
| | | | | gi\|18408857 | gi\|15229145 | *Arabidopsis thaliana* |

Example 2

Analysis of the *Arabidopsis* IMO Sequence

Sequence analyses were performed with BLAST (Altschul et al., 1990, *J. Mol. Biol.* 215:403-410), PFAM (Bateman et al., 1999, *Nucleic Acids Res.* 27:260-262), INTERPRO (Mulder et al. 2003 *Nucleic Acids Res.* 31, 315-318.), PSORT (Nakai K, and Horton P, 1999, *Trends Biochem. Sci.* 24:34-6), and/or CLUSTAL (Thompson J D et al., 1994, *Nucleic Acids Res.* 22:4673-4680). Conserved domains for each protein are listed in column 8 of Table 2.

Example 3

To test whether over-expression of the genes identified in Tables 1-3 alter the seed composition phenotype, protein, digestible protein, oil and fiber content in seeds from transgenic plants expressing these genes was compared with protein, digestible protein, oil and fiber content in seeds from non-transgenic control plants. To do this, the genes were cloned into plant transformation vectors behind the strong constitutive CsVMV promoter and the seed specific PRU promoter. These constructs were transformed into *Arabidopsis* plants using the floral dip method. The plant transformation vector contains a gene, which provides resistance to a toxic compound, and serves as a selectable marker. Seed from the transformed plants were plated on agar medium containing the toxic compound. After 7 days, transgenic plants were identified as healthy green plants and transplanted to soil. Non-transgenic control plants were germinated on agar medium, allowed to grow for 7 days and then transplanted to soil. Transgenic seedlings and non-transgenic control plants were transplanted to two inch pots that were placed in random positions in a 10 inch by 20 inch tray. The plants were grown to maturity, allowed to self-fertilize and set seed. Seed was harvested from each plant and its oil content estimated by Near Infrared (NIR) Spectroscopy using methods previously described. The effect of each construct on seed composition was examined in at least two experiments.

Table 4 lists constructs tested for causing a significant increase in oil, protein, digestible protein or a significant decrease in fiber were identified by a two-way Analysis of Variance (ANOVA) test at a p-value ≦0.05. The ANOVA p-values for Protein, Oil, Digestible Protein and Fiber are listed in columns 4-7, respectively. Those with a significant p-value are listed in bold. The Average values for Protein, Oil, Digestible Protein and Fiber are listed in columns 8-11, respectively and were calculated by averaging the average values determined for the transgenic plants in each experiment.

petri plate, treated with *Agrobacterium* Z707S or LBA4404 strain containing pDAB721. The *Agrobacterium* is grown overnight at 28° C. in the dark on a shaker at 150 rpm and subsequently re-suspended in the culture medium.

After 30 minute treatment of the hypocotyl segments with *Agrobacterium*, these are placed back on the callus induction medium for 3 days. Following co-cultivation, the segments are placed on K1D1TC (callus induction medium containing 250 mg/l Carbenicillin and 300 mg/l Timentin) for one week of recovery. Alternately, the segments are placed directly on selection medium K1D1H1 (above medium with 1 mg/l selection agent, for example an herbicide). Carbenicillin and Timentin are antibiotics used to kill the *Agrobacterium*. The selection agent is used to allow the growth of the transformed cells.

Callus samples from independent events are tested by PCR. All the samples tested are positive for the presence of the transformed gene, whereas the non-transformed controls are negative. Callus samples are confirmed to express the appropriate protein as determined by ELISA.

Callused hypocotyl segments are then placed on B3Z1H1 (MS medium, 3 mg/l benzylamino purine, 1 mg/l Zeatin, 0.5 gm/l MES [2-(N-morpholino) ethane sulfonic acid], 5 mg/l

TABLE 4

| 1. Gene | 2. TAIR | 3. Construct | 4. ANOVA Protein | 5. ANOVA Oil | 6. ANOVA Digestible Protein | 7. ANOVA Fiber | 8. Protein | 9. Oil | 10. Digestible Protein | 11. Fiber |
|---|---|---|---|---|---|---|---|---|---|---|
| IMQ25.3 | At1g27650 | CsVMV::At1g27650 | **0.000** | **0.052** | **0.010** | **0.003** | 89.8% | 103.7% | 95.9% | 105.1% |
| IMQ25.3 | At1g27650 | Pru::At1g27650 | **0.004** | 0.126 | **0.024** | 0.266 | 94.0% | 102.4% | 98.0% | 100.9% |
| IMQ29.1 | At1g58410 | CsVMV::At1g58410 | **0.012** | **0.005** | 0.279 | 0.775 | 104.4% | 96.7% | 101.2% | 99.7% |
| IMQ29.1 | At1g58410 | Pru::At1g58410 | 0.993 | 0.805 | 0.090 | **0.025** | 100.1% | 99.6% | 101.5% | 97.9% |
| IMQ29.2 | At1g58420 | CsVMV::At1g58420 | **0.000** | **0.011** | 0.689 | 0.145 | 95.93% | 103.73% | 99.60% | 98.73% |
| IMQ30.3 | At1g75690 | Pru::At1g75690 | 0.051 | **0.007** | 0.851 | 0.326 | 96.0% | 104.9% | 99.9% | 99.0% |

Example 4

To test whether over-expression of the genes identified in Tables 1-4 alter the seed composition phenotype, protein, digestible protein, oil, and fiber content in seeds from transgenic plants expressing these genes is compared with protein, digestible protein, oil and fiber content in seeds from non-transgenic control plants. Any one of the genes identified in Tables 1-4 is used to transform *Brassica napus* (canola). To do this, the genes are cloned into plant transformation vectors behind the strong constitutive CsVMV promoter and the seed specific phaseolin promoter. These constructs (which include a gene encoding a selection agent) are transformed into canola plants.

Transformation of canola is accomplished via *Agrobacterium*-mediated transformation. Seeds are surface-sterilized with 10% commercial bleach for 10 minutes and rinsed 3 times with sterile distilled water. The seeds are then placed on one half concentration of MS basal medium (Murashige and Skoog, *Physiol. Plant.* 15:473-497, 1962) and maintained under growth regime set at 25° C., and a photoperiod of 16 hrs light/8 hrs dark.

Hypocotyl segments (3-5 mm) are excised from 5-7 day old seedlings and placed on callus induction medium KIDI (MS medium with 1 mg/l kinetin and 1 mg/l 2,4-D) for 3 days as pre-treatment. The segments are then transferred into a silver nitrate, 1 mg/l selection agent, Carbenicillin and Timentin) shoot regeneration medium. After shoots start to regenerate (approximately 3 weeks), hypocotyl segments along with the shoots are transferred to B3Z1H3 medium (MS medium, 3 mg/l benzylamino purine, 1 mg/l Zeatin, 0.5 gm/l MES [2-(N-morpholino) ethane sulfonic acid], 5 mg/l silver nitrate, 3 mg/l selection agent, Carbenicillin and Timentin) for 3 weeks.

Shoots are excised from the hypocotyl segments and transferred to shoot elongation medium MESH10 (MS, 0.5 gm/l MES, 10 mg/l selection agent, Carbenicillin, Timentin) for 2-4 weeks. The elongated shoots are cultured for root induction on MSI.1 (MS with 0.1 mg/l Indolebutyric acid). Once the plants have a well established root system, these are transplanted into soil. The plants are acclimated under controlled environmental conditions in the Conviron for 1-2 weeks before transfer to the greenhouse. The transformed T0 plants self-pollinate in the greenhouse to obtain T1 seed. Transgenic plants are selected at the T1 generation based on resistance to a selection agent. T2 seed (from T1 plants) is harvested and sown in soil. T2 plants are grown to maturity, allowed to self-fertilize and set seed. T3 seed (from the T2 plants) is harvested in bulk for each line. Seed oil, protein, digestible protein, and fiber values are measured as discussed in Example 1.

It is claimed:

1. A method of producing an improved meal quality phenotype in a plant, said method comprising:

a) introducing into progenitor cells of the plant a plant transformation vector comprising a nucleotide sequence that encodes or is complementary to a sequence that encodes an IMQ polypeptide comprising an amino acid sequence at least 95% identical to the amino acid sequence set forth in SEQ ID NO: 80;

b) growing the transformed progenitor cells to produce a transgenic plant, wherein the nucleotide sequence is expressed, and the transgenic plant exhibits an improved meal quality phenotype relative to control plants, wherein oil content is increased relative to control plants; and c) measuring the improved meal quality phenotype in the transgenic plant, relative to control plants, thereby producing the improved meal quality phenotype in the plant.

2. A method of generating a plant having an improved meal quality phenotype comprising identifying a plant that has an allele in its ortholog of the A. thaliana IMQ gene, where the wild-type A. thaliana IMQ gene has the nucleic acid sequence set forth as SEQ ID NO: 79, which allele results in improved meal quality phenotype compared to a control plant lacking the allele; and Generating progeny of said identified plant, wherein the generated progeny inherit the allele and have improved meal quality phenotype and increased oil content; and Measuring the improved meal quality phenotype in the progeny comprising the allele, relative to the control plant lacking the allele, Thereby generating a plant having an improved meal quality phenotype.

3. The method of claim 2 that employs candidate gene/QTL methodology to identify the plant.

4. The method of claim 2 that employs TILLING methodology to identify the plant.

5. The method of claim 1, wherein the IMQ polypeptide comprises an amino acid sequence at least 98% identical to the amino acid sequence set forth in SEQ ID NO: 80.

6. The method of claim 5, wherein the IMQ polypeptide comprises an amino acid sequence at least 99% identical to the amino acid sequence set forth in SEQ ID NO: 80.

7. The method of claim 6, wherein the IMQ polypeptide comprises the amino acid sequence set forth in SEQ ID NO: 80.

8. The method of claim 7, wherein the IMQ polypeptide consists of the amino acid sequence set forth in SEQ ID NO: 80.

9. The method of claim 1, wherein the plant transformation vector comprises a nucleotide sequence at least 95% identical to the nucleic acid sequence set forth as SEQ ID NO: 79.

10. The method of claim 9, wherein the plant transformation vector comprises a nucleotide sequence at least 98% identical to the nucleic acid sequence set forth as SEQ ID NO: 79.

11. The method of claim 10, wherein the plant transformation vector comprises a nucleotide sequence at least 99% identical to the nucleic acid sequence set forth as SEQ ID NO: 79.

12. The method of claim 11, wherein the plant transformation vector comprises the nucleic acid sequence set forth as SEQ ID NO: 79.

13. The method of claim 1, wherein the nucleotide sequence is operably linked to a constitutive, inducible, or regulatable promoter sequence.

* * * * *

UNITED STATES PATENT AND TRADEMARK OFFICE

CERTIFICATE OF CORRECTION

PATENT NO. : 8,106,253 B2
APPLICATION NO. : 11/940248
DATED : January 31, 2012
INVENTOR(S) : Davies et al.

It is certified that error appears in the above-identified patent and that said Letters Patent is hereby corrected as shown below:

Column 1, line 40 "Can berra" should read --Canberra--

Column 12, line 2 "pSK1015" should read --pSKI015--

Column 16, line 43 "SEQ ID NO: 1" should read --SEQ ID NO: 11--

Column 25, line 44 "IMO" should read --IMQ--

Column 25, line 44 "100" should read --IOQ--

Column 29, line 40 (in Table 2) "At1q25420" should read --At1g25420--

Column 31, line 18 (in Table 2) "At1q45180" should read --At1g45180--

Column 37, line 58 "IMO" should read --IMQ--

Column 39, line 65 "KIDI" should read --K1D1--

Signed and Sealed this
Twenty-fifth Day of September, 2012

David J. Kappos
*Director of the United States Patent and Trademark Office*